(12) United States Patent
Asberom et al.

(10) Patent No.: US 8,759,337 B2
(45) Date of Patent: Jun. 24, 2014

(54) GAMMA SECRETASE MODULATORS

(75) Inventors: Theodros Asberom, West Orange, NJ (US); Xianhai Huang, Warren, NJ (US); Zhaoning Zhu, Plainsboro, NJ (US); John W. Clader, Milton, VT (US); Dmitri A. Pissarnitski, Scotch Plains, NJ (US); Hubert B. Josien, Jersey City, NJ (US); Hongmei Li, Warren, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 240 days.

(21) Appl. No.: 13/140,987

(22) PCT Filed: Dec. 18, 2009

(86) PCT No.: PCT/US2009/068684
§ 371 (c)(1),
(2), (4) Date: Aug. 2, 2011

(87) PCT Pub. No.: WO2010/075203
PCT Pub. Date: Jul. 1, 2010

(65) Prior Publication Data
US 2011/0294784 A1 Dec. 1, 2011

Related U.S. Application Data

(60) Provisional application No. 61/139,665, filed on Dec. 22, 2008.

(51) Int. Cl.
*A61K 31/553* (2006.01)
*C07D 498/04* (2006.01)

(52) U.S. Cl.
USPC ..................... 514/211.09; 540/552

(58) Field of Classification Search
USPC ..................... 514/211.09; 540/552
See application file for complete search history.

(56) References Cited

U.S. PATENT DOCUMENTS

2007/0117839 A1    5/2007   Kimura et al.

FOREIGN PATENT DOCUMENTS

| EP | 1 953 154 | 8/2008 |
|---|---|---|
| EP | 1 992 618 | 11/2008 |
| WO | WO 2008/137139 | 11/2008 |

OTHER PUBLICATIONS

PCT International Search Report dated Feb. 17, 2010, mailed on Mar. 1, 2010 for related International Application No. PCT/US2009/068684.

*Primary Examiner* — Brenda Coleman
(74) *Attorney, Agent, or Firm* — J. Eric Thies; John C. Todaro

(57) ABSTRACT

This invention provides novel compounds that are modulators of gamma secretase. The compounds have the formula (Chemical formula should be inserted here as it appears on abstract in paper form). Also disclosed are methods of modulating gamma secretase activity and methods of treating Alzheimer's Disease using the compounds of formula (I).

10 Claims, No Drawings

GAMMA SECRETASE MODULATORS

CROSS REFERENCE TO RELATED APPLICATION

This application is entered into national stage examination under 37 U.S.C. 371 and stems from international patent application No. PCT/US2009/068684 filed on Dec. 18, 2009, which claims priority to application No. 61/139,665 filed Dec. 22, 2008.

FIELD OF THE INVENTION

The present invention relates to certain heterocyclic compounds useful as gamma secretase modulators (including inhibitors, antagonists and the like), pharmaceutical compositions comprising the compounds, and methods of treating various diseases using the compounds and compositions. Examples of the diseases and conditions include, for example, Alzheimers disease, mild cognitive impairment (MCI), Downs Syndrome, Glaucoma, Cerebral amyloid angiopathy, stroke or dementia, Microgliosis and brain inflammation, and Olfactory function loss.

BACKGROUND OF THE INVENTION

Alzheimer's disease is a disease characterized by degeneration and loss of neurons and also by the formation of senile plaques and neurofibrillary change. Presently, treatment of Alzheimer's disease is limited to symptomatic therapies with a symptom-improving agent represented by an acetylcholinesterase inhibitor, and the basic remedy which prevents progress of the disease has not been developed. A method of controlling the cause of onset of pathologic conditions needs to be developed for creation of the basic remedy of Alzheimer's disease.

Aβ protein, which is a metabolite of amyloid precursor protein (hereinafter referred to as APP), is considered to be greatly involved in degeneration and loss of neurons as well as onset of dementia conditions (for example, see Klein W L, et al *Proceeding National Academy of Science USA*, Sep. 2, 2003, 100(18), p. 10417-22, suggest a molecular basis for reversible memory loss.

Nitsch R M, and 16 others, *Antibodies against β-amyloid slow cognitive decline in Alzheimer's disease*, Neuron, May 22, 2003, 38(4), p. 547-554) suggest that the main components of Aβ protein are Aβ40 consisting of 40 amino acids and Aβ42 having two additional amino acids at the C-terminal. The Aβ40 and Aβ42 tend to aggregate (for example, see Jarrell J T et al, *The carboxy terminus of the β amyloid protein is critical for the seeding of amyloid formation: implications for the pathogenesis of Alzheimer's disease*, Biochemistry, May 11, 1993, 32(18), p. 4693-4697) and constitute the main components of senile plaques (for example, (Glenner G G, et al, *Alzheimer's disease: initial report of the purification and characterization of a novel cerebrovascular amyloid protein*, Biochemical and Biophysical Research Communications, May 16, 1984, 120(3), p. 885-90. See also Masters C L, et al, *Amyloid plaque core protein in Alzheimer disease and Down syndrome*, Proceeding National Academy of Science USA, June 1985, 82(12), p. 4245-4249).

Furthermore, it is known that mutations of APP and presenelin genes, which is are observed in familial Alzheimer's disease, increase production of Aβ40 and Aβ42 (for example, see Gouras G K, et al, *Intraneuronal Aβ142 accumulation in human brain*, American Journal of Pathology, January 2000, 156(1), p. 15-20. Also, see Scheuner D, et al, Nature Medicine, August 1996, 2(8), p. 864-870; and Forman M S, et al, *Differential effects of the Swedish mutant amyloid precursor protein on β-amyloid accumulation and secretion in neurons and nonneuronal cells*, Journal of Biological Chemistry, Dec. 19, 1997, 272(51), p. 32247-32253). Therefore, compounds which reduce production of Aβ40 and Aβ42 are expected to be agents for controlling progress of Alzheimer's disease or for preventing the disease.

These Aβs are produced when APP is cleaved by beta secretase and subsequently cleaved by gamma secretase. In consideration of this, creation of inhibitors of γ-secretase and β-secretase has been attempted for the purpose of reducing production of Aβs. Many of these known secretase inhibitors are peptides or peptidomimetics such as L-685,458. L-685, 458, an aspartyl protease transition state mimic, is a potent inhibitor of γ-secretase activity, Biochemistry, Aug. 1, 2000, 39(30), p. 8698-8704).

Also of interest in connection with the present invention are: US 2007/0117798 (Eisai, published May 24, 2007); US 2007/0117839 (Eisai, published May 24, 2007); US 2006/0004013 (Eisai, published Jan. 5, 2006); WO 2005/110422 (Boehringer Ingelheim, published Nov. 24, 2005); WO 2006/045554 (Cellzone AG, published May 4, 2006); WO 2004/110350 (Neurogenetics, published Dec. 23, 2004); WO 2004/071431 (Myriad Genetics, published Aug. 26, 2004); US 2005/0042284 (Myriad Genetics, published Feb. 23, 2005) and WO 2006/001877 (Myriad Genetics, published Jan. 5, 2006).

There is a need for new compounds, formulations, treatments and therapies to treat diseases and disorders associated with Aβ. It is, therefore, an object of this invention to provide compounds useful in the treatment or prevention or amelioration of such diseases and disorders.

SUMMARY OF THE INVENTION

In its many embodiments, the present invention provides a novel class of compounds as gamma secretase modulators (including inhibitors, antagonists and the like), methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with the Aβ using such compounds or pharmaceutical compositions.

This invention provides novel compounds that are gamma secretase modulators, of the formula:

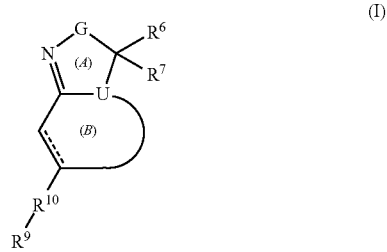

(I)

or a pharmaceutically acceptable salt, ester, or solvate thereof, wherein all substituents are defined below, and all substituents are independently selected.

This invention also provides compounds of formula (I).

This invention also includes the compounds of formula I in all its isolated forms.

This invention also provides compounds of formula (I) in pure and isolated form.

This invention also provides compounds of formula (I) selected from the group consisting of: compounds 2A, 3A, 4A, 5A, 6A, 7A, 8A, 2B, 3B, 4B, 5B, 6B, 7B, 8B, 2C, 3C, 4C, 5C, 6C, 7C, 8C, 2D, 3D, 4D, 5D, 6D, 7D, 8D, 2E, 3E, 4E, 5E, 2F, 3F, 4F, 5F, 2G, 3G, 4G, 5G, 2H, 3H, 4H, 5H, 2I, 3I, 4I, 5I, 2J, 3J, 4J, 5J, 2K, 3K, 4K, 5K, 2L, 3L, 4LH, 5L, 2M, 3M, 4M, 5M, 2N, 3N, 4N, 5N, 2O, 3O, 4O, 5O, 2P, 3P, 4P, 5P and compounds 9, and 15 to 26.

This invention also provides compounds of formula (I) selected from the group consisting of: compounds 2A, 3A, 4A, 5A, 6A, 7A, 8A, 2B, 3B, 4B, 5B, 6B, 7B, 8B, 2C, 3C, 4C, 5C, 6C, 7C, 8C, 2D, 3D, 4D, 5D, 6D, 7D, 8D, 2E, 3E, 4E, 5E, 2F, 3F, 4F, 5F, 2G, 3G, 4G, 5G, 2H, 3H, 4H, 5H, 2I, 3I, 4I, 5I, 2J, 3J, 4J, 5J, 2K, 3K, 4K, 5K, 2L, 3L, 4LH, 5L, 2M, 3M, 4M, 5M, 2N, 3N, 4N, 5N, 2O, 3O, 4O, 5O, 2P, 3P, 4P, and 5P.

This invention also provides compounds of formula (I) selected from the group consisting of compounds 9, and 15 to 26.

This invention also provides pharmaceutical compositions comprising an effective amount of one or more (e.g., one) compounds of formula (I), or a pharmaceutically acceptable salt, ester or solvate thereof, and a pharmaceutically acceptable carrier.

This invention also provides pharmaceutical compositions comprising an effective amount of one or more (e.g., one) compounds of formula (I), or a pharmaceutically acceptable salt, ester or solvate thereof, and an effective amount of one or more (e.g., one) other pharmaceutically active ingredients (e.g., drugs), and a pharmaceutically acceptable carrier.

The compounds of Formula (I) can be useful as gamma secretase modulators and can be useful in the treatment and prevention of diseases such as, for example, central nervous system disorders such as Alzheimers disease and Downs Syndrome.

Thus, this invention also provides methods for: (1) method for modulating (including inhibiting, antagonizing and the like) gamma-secretase; (2) treating one or more neurodegenerative diseases; (3) inhibiting the deposition of amyloid protein (e.g., amyloid beta protein) in, on or around neurological tissue (e.g., the brain); (4) Alzheimer's disease; and (5) treating Downs syndrome; wherein each method comprises administering an effective amount of one or more (e.g., one) compounds of formula (I) to a patient in need of such treatment.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of an effective amount of one or more (e.g. one) compounds of formula (I) and the administration of an effective amount of one or more (e.g., one) other pharmaceutical active ingredients (e.g., drugs).

This invention also provides methods for: (1) treating mild cognitive impairment; (2) treating glaucoma; (3) treating cerebral amyloid angiopathy; (4) treating stroke; (5) treating dementia; (6) treating microgliosis; (7) treating brain inflammation; and (8) treating olfactory function loss; wherein each method comprises administering an effective amount of one or more (e.g., one) compounds of formula (I) to a patient in need of such treatment.

This invention also provides a kit comprising, in separate containers, in a single package, pharmaceutical compositions for use in combination, wherein one container comprises an effective amount of a compound of formula (I) in a pharmaceutically acceptable carrier, and another container (i.e., a second container) comprises an effective amount of another pharmaceutically active ingredient (as described below), the combined quantities of the compound of formula (I) and the other pharmaceutically active ingredient being effective to treat the diseases or conditions mentioned in any of the above methods.

This invention also provides any of the above mentioned methods, pharmaceutical compositions or kit wherein the compound of formula (I) is selected from the group consisting of: 2A, 3A, 4A, 5A, 6A, 7A, 8A, 2B, 3B, 4B, 5B, 6B, 7B, 8B, 2C, 3C, 4C, 5C, 6C, 7C, 8C, 2D, 3D, 4D, 5D, 6D, 7D, 8D, 2E, 3E, 4E, 5E, 2F, 3F, 4F, 5F, 2G, 3G, 4G, 5G, 2H, 3H, 4H, 5H, 2I, 3I, 4I, 5I, 2J, 3J, 4J, 5J, 2K, 3K, 4K, 5K, 2L, 3L, 4LH, 5L, 2M, 3M, 4M, 5M, 2N, 3N, 4N, 5N, 2O, 3O, 4O, 5O, 2P, 3P, 4P, and 5P This invention also provides any of the above mentioned methods, pharmaceutical compositions or kit wherein the compound of formula (I) is selected from the group consisting of: compounds 9, and 15 to 26.

DETAILED DESCRIPTION OF THE INVENTION

This invention provides compounds, useful as gamma secretase modulators, of formula (I):

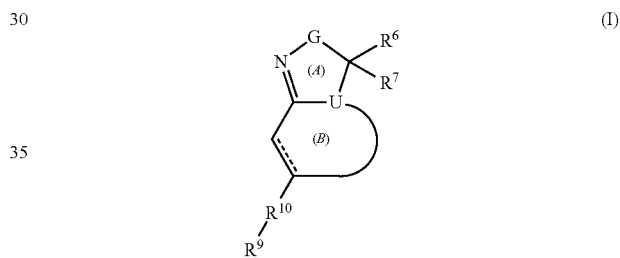

or a pharmaceutically acceptable salt, ester, or solvate thereof, wherein:

G, U, $R^6$, $R^7$, $R^9$, and $R^{10}$, are independently selected;

letters (A) and (B) in formula (I) are reference letters to identify the rings present in formula (I);

G is selected from the group consisting of: $N(R^{14})$, $C(O)$, O and S;

U is $CR^5$ or N;

the dotted line in Ring (B) represents an optional bond;

Ring (B) is a 5 to 8 membered ring (including the atoms common to Ring (A)), and: (1) when U is $CR^5$ said Ring (B) optionally comprising 1 to 2 heteroatoms independently selected from the group consisting of O, $NR^2$ and S, and (2) when U is N said Ring (B) optionally comprises 1 to 2 additional heteroatoms independently selected from the group consisting of O, $NR^2$ and S; and said Ring (B) is optionally substituted with 1 to 5 independently selected $R^{21}$ groups;

Each $R^2$ is independently selected from the group consisting of: H, —OH, —O-alkyl (i.e., alkoxy), —O-(halo substituted alky) (such as, for example, —O-fluoroalkyl), —NH($R^4$), —N($R^4$)$_2$ (wherein each $R^4$ is independently selected), —NH$_2$, —S(O)$R^4$, —S(O)(O$R^4$), —S(O)$_2R^4$, —S(O)$_2$(O$R^4$), —S(O)NH$R^4$, —S(O)N($R^4$)$_2$, —S(O)NH$_2$, —S(O)$_2$NH$R^4$, —S(O)$_2$N($R^4$)$_2$, —S(O)$_2$NH$_2$, —CN, —C(O)$_2R^4$, —C(O)NH$R^4$, —C(O)N($R^4$)$_2$, —C(O)NH$_2$, —C(O)$R^4$, unsubstituted aryl, substituted aryl, unsubstituted heteroaryl, substituted heteroaryl, unsubstituted alkyl, substituted alkyl, unsubstituted arylalkyl-, substituted arylalkyl-, unsubstituted heteroarylalkyl-, substituted heteroarylalkyl-, unsubstituted alkenyl, substituted alkenyl, unsubstituted alkynyl, substituted alkynyl, unsubstituted cycloalkyl, and substituted cycloalkyl, wherein said substituted aryl, heteroaryl, alkyl, arylalkyl-, heteroarylalkyl-, alkenyl, alkynyl and cycloalkyl groups are substituted with 1 to 5 independently selected $R^{21}$ groups;

each $R^4$ is independently selected from the group consisting of: unsubstituted aryl, substituted aryl, unsubstituted heteroaryl, substituted heteroaryl, unsubstituted alkyl, substituted alkyl, unsubstituted arylalkyl-, substituted arylalkyl-, unsubstituted heteroarylalkyl-, substituted heteroarylalkyl-, unsubstituted alkenyl, substituted alkenyl, unsubstituted alkynyl, substituted alkynyl, unsubstituted cycloalkyl, and substituted cycloalkyl, wherein said substituted aryl, heteroaryl, alkyl, arylalkyl-, heteroarylalkyl-, alkenyl, alkynyl and cycloalkyl groups are substituted with 1 to 5 independently selected $R^{21}$ groups;

$R^5$ is selected from the group consisting of: H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclyalkyl-; and wherein each of said $R^5$ alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclyalkyl- groups are optionally substituted with 1-5 independently selected $R^{21}$ substituents;

$R^6$ and $R^7$ are each independently selected from the group consisting of: H, —C(O)$R^{15}$, —C(O)O$R^{15}$, —C(O)N($R^{15}$)($R^{16}$), —C(=NO$R^{15}$)$R^{16}$, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclyalkyl-, benzofusedcycloalkyl (i.e., fused benzocycloalkyl), fused benzoheterocycloalkyl, fused heteroarylcycloalkyl, fused heteroarylheterocycloalkyl; and wherein each of said $R^6$ and $R^7$ alkyl-, alkenyl-, alkynyl-, aryl-, arylalkyl-, alkylaryl-, cycloalkyl-, cycloalkylalkyl-, heteroaryl-, heteroarylalkyl-, heterocyclyl-, heterocyclyalkyl-, benzofusedcycloalkyl, fused benzoheterocycloalkyl, fused heteroarylcycloalkyl, and fused heteroarylheterocycloalkyl group is optionally substituted with 1-5 independently selected $R^{21}$ substituents; or $R^6$ and $R^7$, taken together with the carbon atom to which they are bound, form a spirocyclic carbocyclic moiety or a spirocyclic heterocyclic moiety, and:
(a) optionally, said spirocyclic carbocyclic moiety is substituted with 1-4 independently selected $R^{21}$ substituents,
(b) optionally, said spirocyclic heterocyclic moiety is substituted with 1-4 independently selected $R^{21}$ substituents,
(c) optionally, said spirocyclic carbocyclic moiety is fused with an aryl, heteroaryl, cycloalkyl, or heterocycloalkyl ring to form a fused ring moiety, and optionally, each ring of said fused ring moiety is substituted with 1-4 independently selected $R^{21}$ substituents;
(d) optionally, said spirocyclic heterocyclic moiety is fused with an aryl, heteroaryl, cycloalkyl, or heterocycloalkyl ring to form a fused ring moiety, and optionally, each ring of said fused ring moiety is substituted with 1-4 independently selected $R^{21}$ substituents;

$R^9$ is selected from the group consisting of: alkyl-, alkenyl-, alkynyl-, aryl-, arylalkyl-, alkylaryl-, cycloalkyl-, cycloalkylalkyl-, heteroaryl-, heteroarylalkyl-, heterocyclyl- and heterocyclyalkyl-, and, optionally, each $R^9$ group is substituted with 1-3 independently selected $R^{21}$ groups;

$R^{10}$ is selected from the group consisting of a bond, alkyl-, alkenyl-, alkynyl-, aryl-, arylalkyl-, alkylaryl-, cycloalkyl-, cycloalkylalkyl-, heteroaryl-, heteroarylalkyl-, heterocyclyl-, heterocyclyalkyl-,

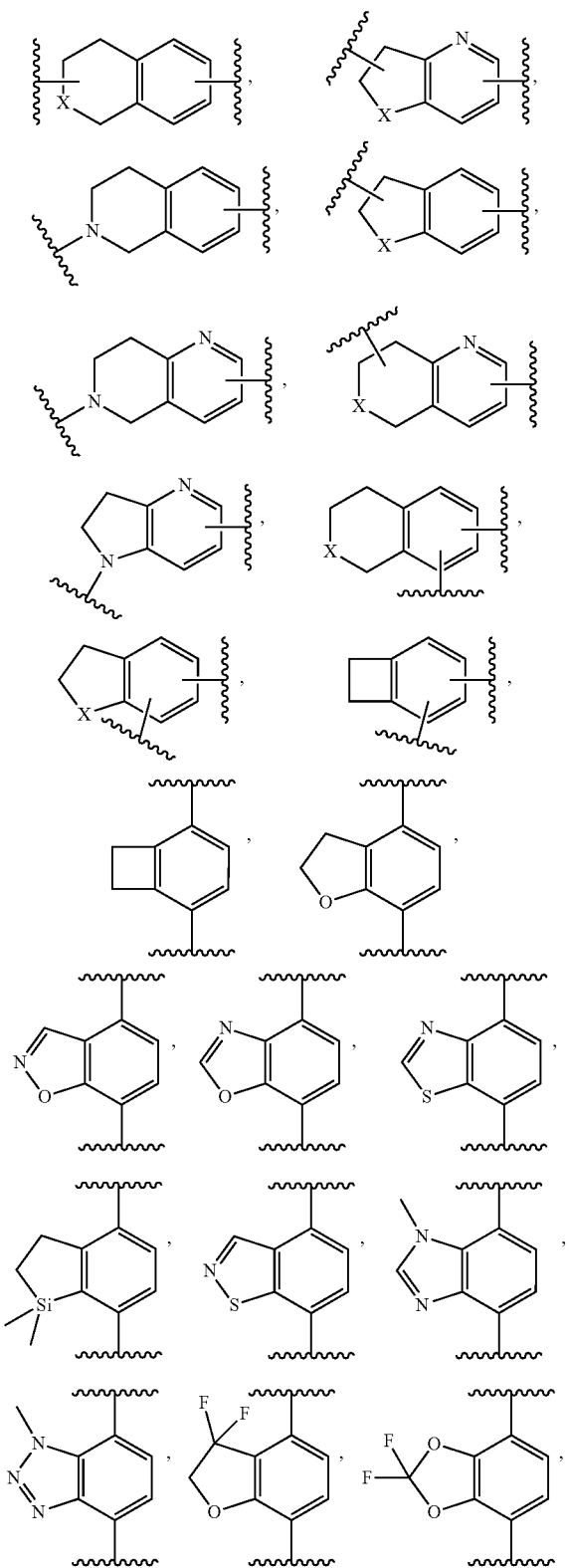

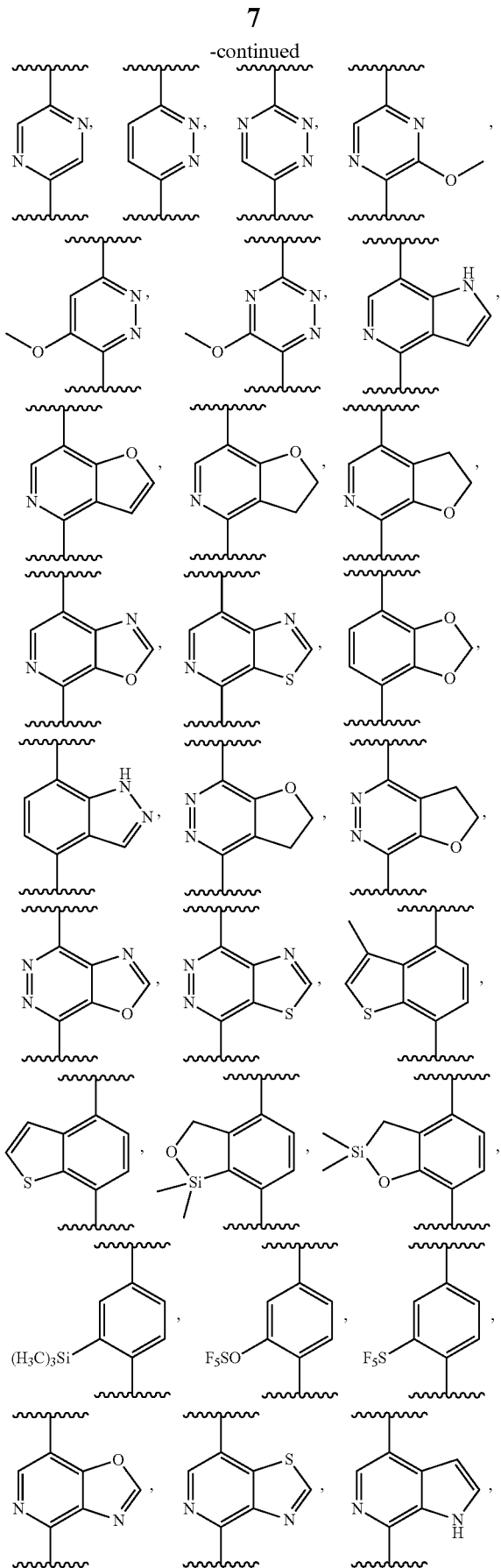
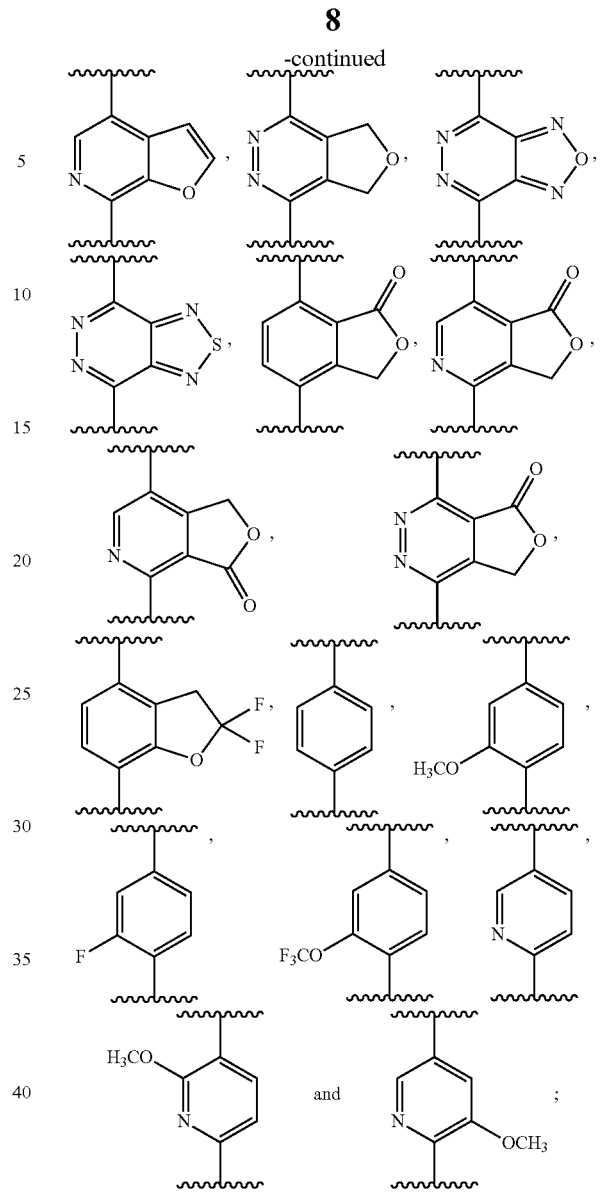

wherein X is selected from the group consisting of: O, N(R$^{14}$) or S; and, optionally, each of said R$^{10}$ groups are substituted with 1-3 independently selected R$^{21}$ substitutents;

R$^9$ is selected from the group consisting of alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclyalkyl-, wherein each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclyalkyl- can be unsubstituted or optionally independently substituted with 1-3 substituents which can be the same or different, each substituent being independently selected from the group consisting of the moieties shown below, R$^{14}$ is selected from the group consisting of H, alkyl, alkenyl, alkynyl, cycloalkyl, cycloalkylalkyl, cycloalkenyl, heterocyclyl, heterocyclenyl, heterocyclylalkyl, heterocyclyalkenyl-, aryl, arylalkyl, heteroaryl, heteroarylalkyl, —CN, —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), C(=NOR$^{15}$)R$^{16}$, and —P(O)(OR$^{15}$)(OR$^{16}$), and wherein each of the alkyl, alkenyl, alkynyl, cycloalkyl, cycloalkylalkyl, cycloalkenyl, heterocyclyl, heterocyclenyl, heterocyclylalkyl, heterocyclyalkenyl-, aryl, arylalkyl, heteroaryl, and heteroarylalkyl groups in are independently unsubstituted or substituted by 1 to 5 $R^{21}$ group;

Each $R^{15A}$ is independently selected from the group consisting of alkyl, alkenyl, alkynyl, cycloalkyl, cycloalkylalkyl, heterocyclyl, heterocyclylalkyl, aryl, arylalkyl, heteroaryl, heteroarylalkyl, arylcycloalkyl, arylheterocyclyl, $(R^{18})_{1-5}$-alkyl, $(R^{18})_{1-5}$-cycloalkyl, $(R^{18})_{1-5}$-cycloalkylalkyl, $(R^{18})_{1-5}$-heterocyclyl, $(R^{18})_{1-5}$-heterocyclylalkyl, $(R^{18})_{1-5}$-aryl, $(R^{18})_{1-5}$-arylalkyl, $(R^{18})_{1-5}$-heteroaryl and $(R^{18})_{1-5}$-heteroarylalkyl; and wherein each $R^{18}$ in each group can be on any substitutable atom;

Each $R^{16A}$ is independently selected from the group consisting of alkyl, alkenyl, alkynyl, cycloalkyl, cycloalkylalkyl, heterocyclyl, heterocyclylalkyl, aryl, arylalkyl, heteroaryl, heteroarylalkyl, arylcycloalkyl, arylheterocyclyl, $(R^{18})_{1-5}$-alkyl, $(R^{18})_{1-5}$-cycloalkyl, $(R^{18})_{1-5}$-cycloalkylalkyl, $(R^{18})_{1-5}$-heterocyclyl, $(R^{18})_{1-5}$-heterocyclylalkyl, $(R^{18})_{1-5}$-aryl, $(R^{18})_{1-5}$-arylalkyl, $(R^{18})_{1-5}$-heteroaryl and $(R^{18})_{1-5}$-heteroarylalkyl; and wherein each $R^{18}$ in each group can be on any substitutable atom;

$R^{15}$, $R^{16}$ and $R^{17}$ are independently selected from the group consisting of H, alkyl, alkenyl, alkynyl, cycloalkyl, cycloalkylalkyl, heterocyclyl, heterocyclylalkyl, aryl, arylalkyl, heteroaryl, heteroarylalkyl, arylcycloalkyl, arylheterocyclyl, $(R^{18})_{1-5}$-alkyl, $(R^{18})_{1-5}$-cycloalkyl, $(R^{18})_{1-5}$-cycloalkylalkyl, $(R^{18})_{1-5}$-heterocyclyl, $(R^{18})_{1-5}$-heterocyclylalkyl, $(R^{18})_{1-5}$-aryl, $(R^{18})_{1-5}$-arylalkyl, $(R^{18})_{1-5}$-heteroaryl and $(R^{18})_{1-5}$-heteroarylalkyl; and wherein each $R^{18}$ in each group can be on any substitutable atom;

Each $R^{18}$ is independently selected from the group consisting of alkyl, alkenyl, alkynyl, aryl, arylalkyl, arylalkenyl, arylalkynyl, $-NO_2$, halo, heteroaryl, HO-alkyoxyalkyl, $-CF_3$, $-CN$, alkyl-CN, $-C(O)R^{19}$, $-C(O)OH$, $-C(O)OR^{19}$, $-C(O)NHR^{20}$, $-C(O)NH_2$, $-C(O)NH_2-C(O)N(alkyl)_2$, $-C(O)N(alkyl)(aryl)$, $-C(O)N(alkyl)(heteroaryl)$, $-SR^{19}$, $-S(O)_2R^{20}$, $-S(O)NH_2$, $-S(O)NH(alkyl)$, $-S(O)N(alkyl)(alkyl)$, $-S(O)NH(aryl)$, $-S(O)_2NH_2$, $-S(O)_2NHR^{19}$, $-S(O)_2NH(heterocyclyl)$, $-S(O)_2N(alkyl)_2$, $-S(O)_2N(alkyl)(aryl)$, $-OCF_3$, $-OH$, $-OR^{20}$, $-O$-heterocyclyl, $-O$-cycloalkylalkyl, $-O$-heterocyclylalkyl, $-NH_2$, $-NHR^{20}$, $-N(alkyl)_2$, $-N(arylalkyl)_2$, $-N(arylalkyl)-(heteroarylalkyl)$, $-NHC(O)R^{20}$, $-NHC(O)NH_2$, $-NHC(O)NH(alkyl)$, $-NHC(O)N(alkyl)(alkyl)$, $-N(alkyl)C(O)NH(alkyl)$, $-N(alkyl)C(O)N(alkyl)(alkyl)$, $-NHS(O)_2R^{20}$, $-NHS(O)_2NH(alkyl)$, $-NHS(O)_2N(alkyl)(alkyl)$, $-N(alkyl)S(O)_2NH(alkyl)$ and $-N(alkyl)S(O)_2N(alkyl)(alkyl)$;

or, two $R^{18}$ moieties on adjacent carbons can be taken together with the atoms to which they are bound to form:

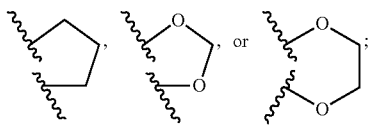

$R^{19}$ is selected from the group consisting of: alkyl, cycloalkyl, aryl, arylalkyl and heteroarylalkyl;

$R^{20}$ is selected from the group consisting of: alkyl, cycloalkyl, aryl, halo substituted aryl, arylalkyl, heteroaryl and heteroarylalkyl;

Each $R^{21}$ is independently selected from the group consisting of alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, halo, $-CN$, $-OR^{15}$, $-C(O)R^{15}$, $-C(O)OR^{15}$, $-C(O)N(R^{15})(R^{16})$, $-SF_5$, $-OSF_5$, $-Si(R^{15A})_3$ wherein each $R^{15A}$ is independently selected, $-SR^{15}$, $-S(O)N(R^{15})(R^{16})$, $-CH(R^{15})(R^{16})$, $-S(O)_2N(R^{15})(R^{16})$, $-C(=NOR^{15})R^{16}$, $-P(O)(OR^{15})(OR^{16})$, $-N(R^{15})(R^{16})$, -alkyl-$N(R^{15})(R^{16})$, $-N(R^{15})C(O)R^{16}$, $-CH_2-N(R^{15})C(O)R^{16}$, $-CH_2-N(R^{15})C(O)N(R^{16})(R^{17})$, $-CH_2-R^{15}$; $-CH_2N(R^{15})(R^{16})$, $-N(R^{15})S(O)R^{16A}$, $-N(R^{15})S(O)_2R^{16A}$, $-CH_2-N(R^{15})S(O)_2R^{16A}$, $-N(R^{15})S(O)_2N(R^{16})(R^{17})$, $-N(R^{15})S(O)N(R^{16})(R^{17})$, $-N(R^{15})C(O)N(R^{16})(R^{17})$, $-CH_2-N(R^{15})C(O)N(R^{16})(R^{17})$, $-N(R^{15})C(O)OR^{16}$, $-CH_2-N(R^{15})C(O)OR^{16}$ $(R^{17})$, $-N(R^{15})C(O)OR^{16}$, $-CH_2-N(R^{15})C(O)OR^{16}$, $-S(O)R^{16A}$, $-N_3$, $-NO_2$ and $-S(O)_2R^{15A}$; and, optionally, each of said alkyl, cycloalkenyl, cycloalkyl, cycloalkylalkyl, heterocycloalkyl, heterocycloalkylalkyl, aryl, arylalkyl, heteroaryl, heteroarylalkyl, alkenyl and alkynyl $R^{21}$ groups are substituted with 1 to 5 independently selected $R^{22}$ groups; and Each $R^{22}$ is independently selected from the group consisting of: alkyl, cycloalkyl, cycloalkenyl, heterocycloalkyl, aryl, heteroaryl, halo, $-CF_3$, $-CN$, $-OR^{15}$, $-C(O)R^{15}$, $-C(O)OR^{15}$, -alkyl-$C(O)OR^{15}$, $C(O)N(R^{15})(R^{16}))$, $-SF_5$, $-OSF_5$, $-Si(R^{15A})_3$ wherein each $R^{15A}$ is independently selected, $-SR^{15}$, $-S(O)N(R^{15})(R^{16})$, $-S(O)_2N(R^{15})(R^{16})$, $-C(=NOR^{15})R^{16}$, $-P(O)(OR^{15})(OR^{16})$, $-N(R^{15})(R^{16})$, -alkyl-$N(R^{15})(R^{16})$, $-N(R^{15})C(O)R^{16}$, $-CH_2-N(R^{15})C(O)R^{16}$, $-N(R^{15})S(O)R^{16A}$, $-N(R^{15})S(O)_2R^{16A}$, $-CH_2-N(R^{15})S(O)_2R^{16A}$, $-N(R^{15})S(O)_2N(R^{16})(R^{17})$, $-N(R^{15})S(O)N(R^{16})(R^{17})$, $-N(R^{15})C(O)N(R^{16})(R^{17})$, $-CH_2-N(R^{15})C(O)N(R^{16})(R^{17})$, $-N(R^{15})C(O)OR^{16}$, $-CH_2-N(R^{15})C(O)OR^{16}$, $-N_3$, $=NOR^{15}$, $-NO_2$, $-S(O)R^{15A}$ and $-S(O)_2R^{15A}$.

Those skilled in the art will appreciate that the moiety:

can have the stereochemistry

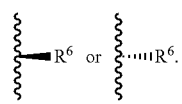

The moiety

can have the stereochemistry

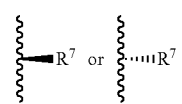

Thus, in one embodiment of this invention the $R^6$ and $R^7$ moieties can have the stereochemistry:

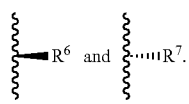

And in another embodiment of this invention the $R^6$ and $R^7$ moieties can have the stereochemistry:

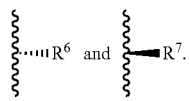

The $R^6$ and $R^7$ benzofusedcycloalkyl (i.e., fused benzocycloalkyl), fused benzoheterocycloalkyl, fused heteroarylcycloalkyl, and fused heteroarylheterocycloalkyl groups, can be optionally substituted with 1-5 independently selected $R^{21}$ groups. In one example, the $R^{21}$ groups are halo (e.g., F).

Examples of the fused ring $R^6$ and $R^7$ groups include, but are not limited to:

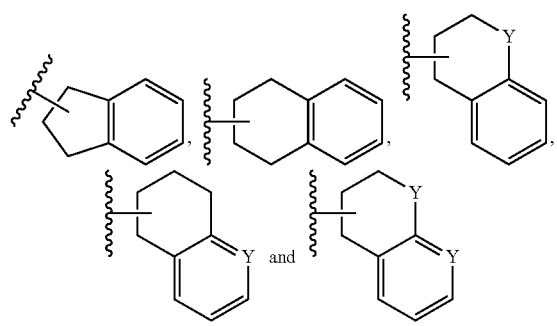

wherein each Y is independently selected from the group consisting of: —O—, —NR$^{14}$— and —C(R$^{21}$)$_q$— (wherein q is 0, 1 or 2 and each $R^{21}$ is independently selected), and wherein $R^{14}$ and $R^{21}$ are as defined for formula (I). Examples of these fused ring $R^6$ and $R^7$ groups include, for example:

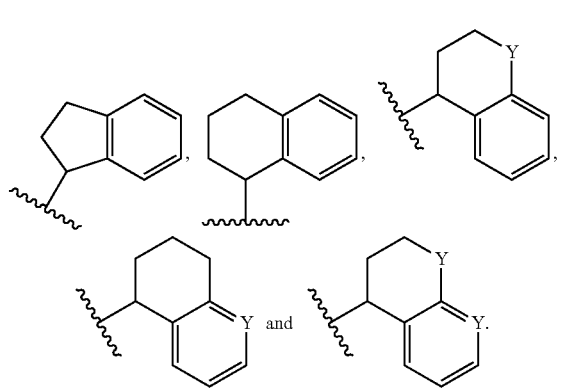

The compounds of this invention are useful for treating central nervous system disorders such as, for example, neurodegenerative diseases such as Alzheimer's disease and other diseases relating to the deposition of amyloid protein. They are especially useful for reducing Amyloid beta (hereinafter referred to as Aβ) production which is effective in the treatment of diseases caused by Aβ such as, for example, Alzheimers and Down Syndrome.

Thus, for example, the compounds of this invention can be used to treat the following diseases or conditions: Alzheimers disease, mild cognitive impairment (MCI), Downs Syndrome, Glaucoma (Guo et. al., Proc. Natl. Acad. Sci. USA 104, 13444-13449 (2007)), Cerebral amyloid angiopathy, stroke or dementia (Frangione et al., Amyloid: J. Protein folding Disord. 8, suppl. 1, 36-42 (2001), Microgliosis and brain inflammation (M P Lamber, Proc. Natl. Acad. Sci. USA 95, 6448-53 (1998)), and Olfactory function loss (Getchell, et. al. Neurobiology of Aging, 663-673, 24, 2003).

In one embodiment $R^{10}$ is selected from the group consisting of a bond, alkyl-, alkenyl-, alkynyl-, aryl-, arylalkyl-, alkylaryl-, cycloalkyl-, cycloalkylalkyl-, heteroaryl-, heteroarylalkyl-, heterocyclyl-, heterocyclyalkyl-,

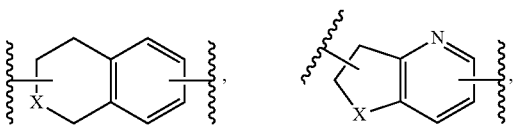

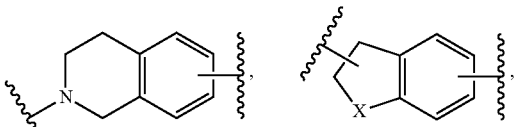

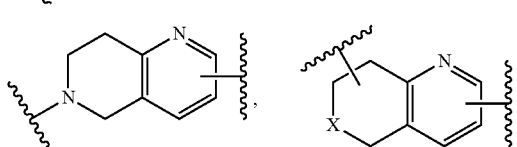

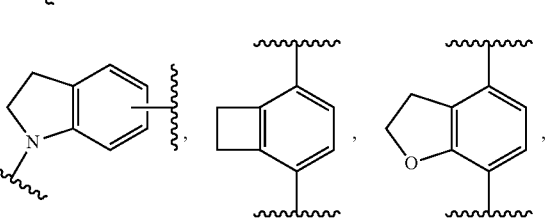

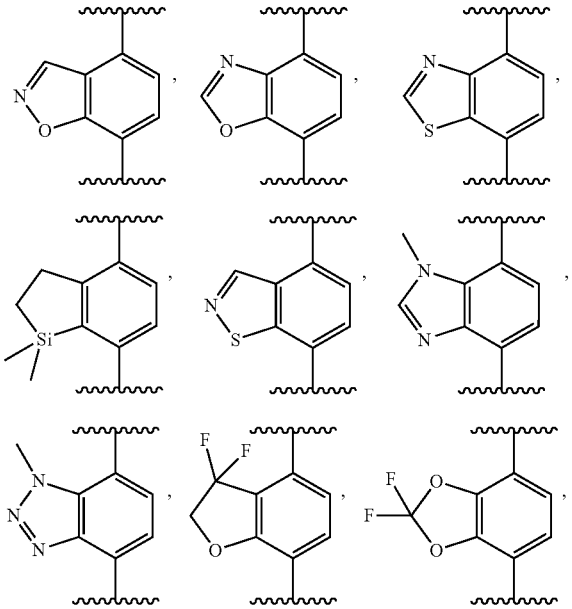

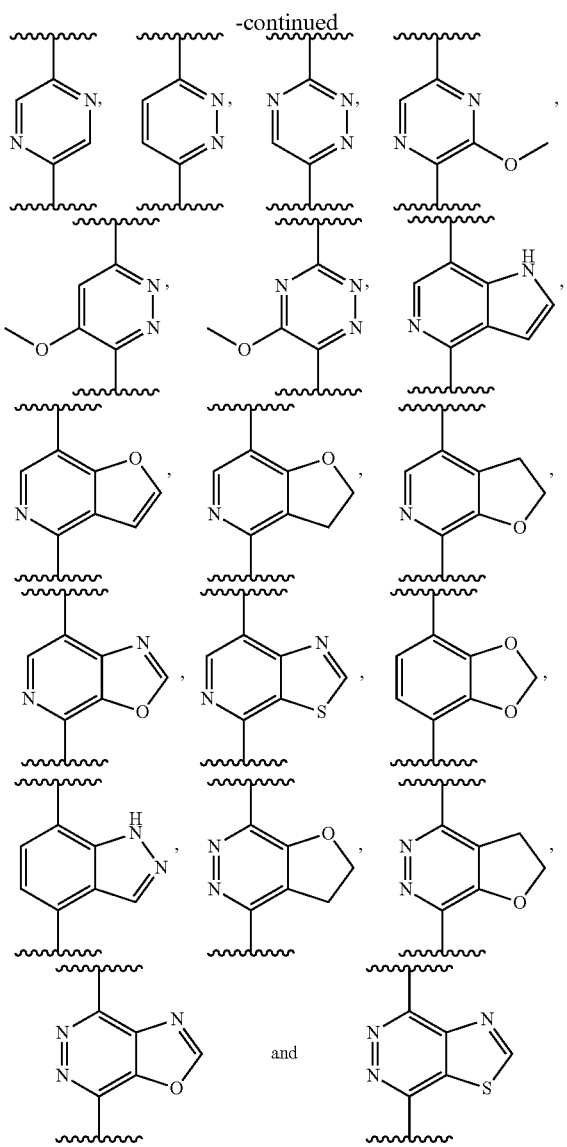

wherein X is selected from the group consisting of: O, N($R^{14}$) or S; and, optionally, each of said $R^{10}$ groups are substituted with 1-3 independently selected $R^{21}$ substitutents.

In one embodiment of this invention U is $CR^5$.
In another embodiment of this invention U is N.
In one embodiment of this invention B is a five membered ring.
In another embodiment of this invention B is a five membered ring and the optional bond is present.
In another embodiment of this invention B is a five membered ring and the optional bond is absent.
In one embodiment of this invention B is a six membered ring.
In another embodiment of this invention B is a six membered ring and the optional bond is present.
In another embodiment of this invention B is a six membered ring and the optional bond is absent.
In one embodiment of this invention B is a seven membered ring.
In another embodiment of this invention B is a seven membered ring and the optional bond is present.
In another embodiment of this invention B is a seven membered ring and the optional bond is absent.

In one embodiment of this invention B is an eight membered ring.
In another embodiment of this invention B is an eight membered ring and the optional bond is present.
In another embodiment of this invention B is an eight membered ring and the optional bond is absent.
In one embodiment of this invention B is a five membered ring and U is $CR^5$.
In another embodiment of this invention B is a five membered ring, U is $CR^5$, and the optional bond is present.
In another embodiment of this invention B is a five membered ring, U is $CR^5$, and the optional bond is absent.
In one embodiment of this invention B is a six membered ring, and U is $CR^5$.
In another embodiment of this invention B is a six membered ring, U is $CR^5$, and the optional bond is present.
In another embodiment of this invention B is a six membered ring, U is $CR^5$, and the optional bond is absent.
In one embodiment of this invention B is a seven membered ring, and U is $CR^5$.
In another embodiment of this invention B is a seven membered ring, U is $CR^5$, and the optional bond is present.
In another embodiment of this invention B is a seven membered ring, U is $CR^5$, and the optional bond is absent.
In one embodiment of this invention B is an eight membered ring, and U is $CR^5$.
In another embodiment of this invention B is an eight membered ring, U is $CR^5$, and the optional bond is present.
In another embodiment of this invention B is an eight membered ring, U is $CR^5$, and the optional bond is absent.
In one embodiment of this invention B is a five membered ring and U is N.
In another embodiment of this invention B is a five membered ring, U is N, and the optional bond is present.
In another embodiment of this invention B is a five membered ring, U is N, and the optional bond is absent.
In one embodiment of this invention B is a six membered ring, and U is N.
In another embodiment of this invention B is a six membered ring, U is N, and the optional bond is present.
In another embodiment of this invention B is a six membered ring, U is N, and the optional bond is absent.
In one embodiment of this invention B is a seven membered ring, and U is N.
In another embodiment of this invention B is a seven membered ring, U is N, and the optional bond is present.
In another embodiment of this invention B is a seven membered ring, U is N, and the optional bond is absent.
In one embodiment of this invention B is an eight membered ring, and U is N.
In another embodiment of this invention B is an eight membered ring, U is N, and the optional bond is present.
In another embodiment of this invention B is an eight membered ring, U is N, and the optional bond is absent.
In one embodiment of this invention B is a five membered ring, U is $CR^5$, and there are 1 or 2 heteroatoms present in ring B.
In another embodiment of this invention B is a five membered ring, U is $CR^5$, there are 1 or 2 heteroatoms present in ring B, and the optional bond is present.
In another embodiment of this invention B is a five membered ring, U is $CR^5$, there are 1 or 2 heteroatoms present in ring B, and the optional bond is absent.
In one embodiment of this invention B is a six membered ring, and U is $CR^5$, and there are 1 or 2 heteroatoms present in ring B.

In another embodiment of this invention B is a six membered ring, U is CR$^5$, there are 1 or 2 heteroatoms present in ring B, and the optional bond is present.

In another embodiment of this invention B is a six membered ring, U is CR$^5$, there are 1 or 2 heteroatoms present in ring B, and the optional bond is absent.

In one embodiment of this invention B is a seven membered ring, U is CR$^5$, and there are 1 or 2 heteroatoms present in ring B.

In another embodiment of this invention B is a seven membered ring, U is CR$^5$, there are 1 or 2 heteroatoms present in ring B, and the optional bond is present.

In another embodiment of this invention B is a seven membered ring, U is CR$^5$, there are 1 or 2 heteroatoms present in ring B, and the optional bond is absent.

In one embodiment of this invention B is an eight membered ring, U is CR$^5$, and there are 1 or 2 heteroatoms present in ring B.

In another embodiment of this invention B is an eight membered ring, U is CR$^5$, there are 1 or 2 heteroatoms present in ring B, and the optional bond is present.

In another embodiment of this invention B is an eight membered ring, U is CR$^5$, there are 1 or 2 heteroatoms present in ring B, and the optional bond is absent.

In one embodiment of this invention B is a five membered ring, U is N, and there are 1 or 2 additional heteroatoms present in ring B.

In another embodiment of this invention B is a five membered ring, U is N, there are 1 or 2 additional heteroatoms present in ring B, and the optional bond is present.

In another embodiment of this invention B is a five membered ring, U is N, there are 1 or 2 additional heteroatoms present in ring B, and the optional bond is absent.

In one embodiment of this invention B is a six membered ring, U is N, and there are 1 or 2 additional heteroatoms present in ring B.

In another embodiment of this invention B is a six membered ring, U is N, and the optional bond is present.

In another embodiment of this invention B is a six membered ring, U is N, there are 1 or 2 additional heteroatoms present in ring B, and the optional bond is absent.

In one embodiment of this invention B is a seven membered ring, U is N, and there are 1 or 2 additional heteroatoms present in ring B.

In another embodiment of this invention B is a seven membered ring, U is N, there are 1 or 2 additional heteroatoms present in ring B, and the optional bond is present.

In another embodiment of this invention B is a seven membered ring, U is N, there are 1 or 2 additional heteroatoms present in ring B, and the optional bond is absent.

In one embodiment of this invention B is an eight membered ring, U is N, and there are 1 or 2 additional heteroatoms present in ring B In another embodiment of this invention B is an eight membered ring, U is N, there are 1 or 2 additional heteroatoms present in ring B, and the optional bond is present.

In another embodiment of this invention B is an eight membered ring, U is N, there are 1 or 2 additional heteroatoms present in ring B, and the optional bond is absent.

In one embodiment of this invention G is O.

In another embodiment of this invention G is O and U is CR$^5$.

In another embodiment of this invention G is O and U is N.

In another embodiment of this invention G is S.

In another embodiment of this invention G is S and U is CR$^5$.

In another embodiment of this invention G is S and U is N.

In one embodiment of this invention G is C(O).

In another embodiment of this invention G is C(O) and U is CR$^5$.

In another embodiment of this invention G is C(O) and U is N.

In another embodiment of this invention G is C(O).

In another embodiment of this invention G is C(O) and U is CR$^5$.

In another embodiment of this invention G is C(O) and U is N.

In one embodiment of this invention G is N(R$^{14}$).

In another embodiment of this invention G is N(R$^{14}$) and U is CR$^5$.

In another embodiment of this invention G is N(R$^{14}$) and U is N.

In one embodiment of this invention G is N(R$^{14}$), and R$^{14}$ is H (i.e. G is NH).

In another embodiment of this invention G is N(R$^{14}$), R$^{14}$ is H (i.e. G is NH), and U is CR$^5$.

In another embodiment of this invention G is N(R$^{14}$), R$^{14}$ is H (i.e. G is NH), and U is N.

In one embodiment of this invention B is a five membered ring, and G is O.

In another embodiment of this invention B is a five membered ring, G is O, and the optional bond is present.

In another embodiment of this invention B is a five membered ring, G is O, and the optional bond is absent.

In one embodiment of this invention B is a six membered ring, and G is O.

In another embodiment of this invention B is a six membered ring, G is O and the optional bond is present.

In another embodiment of this invention B is a six membered ring, G is O, and the optional bond is absent.

In one embodiment of this invention B is a seven membered ring, and G is O.

In another embodiment of this invention B is a seven membered ring, G is O, and the optional bond is present.

In another embodiment of this invention B is a seven membered ring, G is O, and the optional bond is absent.

In one embodiment of this invention B is an eight membered ring, and G is O.

In another embodiment of this invention B is an eight membered ring, G is O, and the optional bond is present.

In another embodiment of this invention B is an eight membered ring, G is O, and the optional bond is absent.

In one embodiment of this invention B is a five membered ring, G is O, and U is CR$^5$.

In another embodiment of this invention B is a five membered ring, G is O, U is CR$^5$, and the optional bond is present.

In another embodiment of this invention B is a five membered ring, G is O, U is CR$^5$, and the optional bond is absent.

In one embodiment of this invention B is a six membered ring, G is O, and U is CR$^5$.

In another embodiment of this invention B is a six membered ring, G is O, U is CR$^5$, and the optional bond is present.

In another embodiment of this invention B is a six membered ring, G is O, U is CR$^5$, and the optional bond is absent.

In one embodiment of this invention B is a seven membered ring, G is O, and U is CR$^5$.

In another embodiment of this invention B is a seven membered ring, G is O, U is CR$^5$, and the optional bond is present.

In another embodiment of this invention B is a seven membered ring, G is O, U is CR$^5$, and the optional bond is absent.

In one embodiment of this invention B is an eight membered ring, G is O, and U is CR$^5$.

In another embodiment of this invention B is an eight membered ring, G is O, U is CR$^5$, and the optional bond is present.

In another embodiment of this invention B is an eight membered ring, G is O, U is CR$^5$, and the optional bond is absent.

In one embodiment of this invention B is a five membered ring, G is O, and U is N.

In another embodiment of this invention B is a five membered ring, G is O, U is N, and the optional bond is present.

In another embodiment of this invention B is a five membered ring, G is O, U is N, and the optional bond is absent.

In one embodiment of this invention B is a six membered ring, G is O, and U is N.

In another embodiment of this invention B is a six membered ring, G is O, U is N, and the optional bond is present.

In another embodiment of this invention B is a six membered ring, G is O, U is N, and the optional bond is absent.

In one embodiment of this invention B is a seven membered ring, G is O, and U is N.

In another embodiment of this invention B is a seven membered ring, G is O, U is N, and the optional bond is present.

In another embodiment of this invention B is a seven membered ring, G is O, U is N, and the optional bond is absent.

In one embodiment of this invention B is an eight membered ring, G is O, and U is N.

In another embodiment of this invention B is an eight membered ring, G is O, U is N, and the optional bond is present.

In another embodiment of this invention B is an eight membered ring, G is O, U is N, and the optional bond is absent.

In one embodiment of this invention B is a five membered ring, G is O, U is CR$^5$, and there are 1 or 2 heteroatoms present in ring B.

In another embodiment of this invention B is a five membered ring, G is O, U is CR$^5$, there are 1 or 2 heteroatoms present in ring B, and the optional bond is present.

In another embodiment of this invention B is a five membered ring, G is O, U is CR$^5$, there are 1 or 2 heteroatoms present in ring B, and the optional bond is absent.

In one embodiment of this invention B is a six membered ring, G is O, and U is CR$^5$, and there are 1 or 2 heteroatoms present in ring B.

In another embodiment of this invention B is a six membered ring, G is O, U is CR$^5$, there are 1 or 2 heteroatoms present in ring B, and the optional bond is present.

In another embodiment of this invention B is a six membered ring, G is O, U is CR$^5$, there are 1 or 2 heteroatoms present in ring B, and the optional bond is absent.

In one embodiment of this invention B is a seven membered ring, G is O, U is CR$^5$, and there are 1 or 2 heteroatoms present in ring B.

in another embodiment of this invention B is a seven membered ring, G is O, U is CR$^5$, there are 1 or 2 heteroatoms present in ring B, and the optional bond is present.

In another embodiment of this invention B is a seven membered ring, G is O, U is CR$^5$, there are 1 or 2 heteroatoms present in ring B, and the optional bond is absent.

In one embodiment of this invention B is an eight membered ring, G is O, U is CR$^5$, and there are 1 or 2 heteroatoms present in ring B.

In another embodiment of this invention B is an eight membered ring, G is O, U is CR$^5$, there are 1 or 2 heteroatoms present in ring B, and the optional bond is present.

In another embodiment of this invention B is an eight membered ring, G is O, U is CR$^5$, there are 1 or 2 heteroatoms present in ring B, and the optional bond is absent.

In one embodiment of this invention B is a five membered ring, G is O, U is N, and there are 1 or 2 additional heteroatoms present in ring B.

In another embodiment of this invention B is a five membered ring, G is O, U is N, there are 1 or 2 additional heteroatoms present in ring B, and the optional bond is present.

In another embodiment of this invention B is a five membered ring, G is O, U is N, there are 1 or 2 additional heteroatoms present in ring B, and the optional bond is absent.

In one embodiment of this invention B is a six membered ring, G is O, U is N, and there are 1 or 2 additional heteroatoms present in ring B.

In another embodiment of this invention B is a six membered ring, G is O, U is N, and the optional bond is present.

In another embodiment of this invention B is a six membered ring, G is O, U is N, there are 1 or 2 additional heteroatoms present in ring B, and the optional bond is absent.

In one embodiment of this invention B is a seven membered ring, G is O, U is N, and there are 1 or 2 additional heteroatoms present in ring B.

In another embodiment of this invention B is a seven membered ring, G is O, U is N, there are 1 or 2 additional heteroatoms present in ring B, and the optional bond is present.

In another embodiment of this invention B is a seven membered ring, G is O, U is N, there are 1 or 2 additional heteroatoms present in ring B, and the optional bond is absent.

In one embodiment of this invention B is an eight membered ring, G is O, U is N, and there are 1 or 2 additional heteroatoms present in ring B In another embodiment of this invention B is an eight membered ring, G is O, U is N, there are 1 or 2 additional heteroatoms present in ring B, and the optional bond is present.

In another embodiment of this invention B is an eight membered ring, G is O, U is N, there are 1 or 2 additional heteroatoms present in ring B, and the optional bond is absent.

In one embodiment of this invention B is a five membered ring, and G is S.

In another embodiment of this invention B is a five membered ring, G is S, and the optional bond is present.

In another embodiment of this invention B is a five membered ring, G is S, and the optional bond is absent.

In one embodiment of this invention B is a six membered ring, and G is S.

In another embodiment of this invention B is a six membered ring, G is S and the optional bond is present.

In another embodiment of this invention B is a six membered ring, G is S, and the optional bond is absent.

In one embodiment of this invention B is a seven membered ring, and G is S.

In another embodiment of this invention B is a seven membered ring, G is S, and the optional bond is present.

In another embodiment of this invention B is a seven membered ring, G is S, and the optional bond is absent.

In one embodiment of this invention B is an eight membered ring, and G is S.

In another embodiment of this invention B is an eight membered ring, G is S, and the optional bond is present.

In another embodiment of this invention B is an eight membered ring, G is S, and the optional bond is absent.

In one embodiment of this invention B is a five membered ring, G is S, and U is CR$^5$.

In another embodiment of this invention B is a five membered ring, G is S, U is CR$^5$, and the optional bond is present.

In another embodiment of this invention B is a five membered ring, G is S, U is CR$^5$, and the optional bond is absent.

In one embodiment of this invention B is a six membered ring, G is S, and U is CR$^5$.

In another embodiment of this invention B is a six membered ring, G is S, U is CR$^5$, and the optional bond is present.

In another embodiment of this invention B is a six membered ring, G is S, U is CR$^5$, and the optional bond is absent.

In one embodiment of this invention B is a seven membered ring, G is S, and U is CR$^5$.

In another embodiment of this invention B is a seven membered ring, G is S, U is CR$^5$, and the optional bond is present.

In another embodiment of this invention B is a seven membered ring, G is S, U is CR$^5$, and the optional bond is absent.

In one embodiment of this invention B is an eight membered ring, G is S, and U is CR$^5$.

In another embodiment of this invention B is an eight membered ring, G is S, U is CR$^5$, and the optional bond is present.

In another embodiment of this invention B is an eight membered ring, G is S, U is CR$^5$, and the optional bond is absent.

In one embodiment of this invention B is a five membered ring, G is S, and U is N.

In another embodiment of this invention B is a five membered ring, G is S, U is N, and the optional bond is present.

In another embodiment of this invention B is a five membered ring, G is S, U is N, and the optional bond is absent.

In one embodiment of this invention B is a six membered ring, G is S, and U is N.

In another embodiment of this invention B is a six membered ring, G is S, U is N, and the optional bond is present.

In another embodiment of this invention B is a six membered ring, G is S, U is N, and the optional bond is absent.

In one embodiment of this invention B is a seven membered ring, G is S, and U is N.

In another embodiment of this invention B is a seven membered ring, G is S, U is N, and the optional bond is present.

In another embodiment of this invention B is a seven membered ring, G is S, U is N, and the optional bond is absent.

In one embodiment of this invention B is an eight membered ring, G is S, and U is N.

In another embodiment of this invention B is an eight membered ring, G is S, U is N, and the optional bond is present.

In another embodiment of this invention B is an eight membered ring, G is S, U is N, and the optional bond is absent.

In one embodiment of this invention B is a five membered ring, G is S, U is CR$^5$, and there are 1 or 2 heteroatoms present in ring B.

In another embodiment of this invention B is a five membered ring, G is S, U is CR$^5$, there are 1 or 2 heteroatoms present in ring B, and the optional bond is present.

In another embodiment of this invention B is a five membered ring, G is S, U is CR$^5$, there are 1 or 2 heteroatoms present in ring B, and the optional bond is absent.

In one embodiment of this invention B is a six membered ring, G is S, and U is CR$^5$, and there are 1 or 2 heteroatoms present in ring B.

In another embodiment of this invention B is a six membered ring, G is S, U is CR$^5$, there are 1 or 2 heteroatoms present in ring B, and the optional bond is present.

In another embodiment of this invention B is a six membered ring, G is S, U is CR$^5$, there are 1 or 2 heteroatoms present in ring B, and the optional bond is absent.

In one embodiment of this invention B is a seven membered ring, G is S, U is CR$^5$, and there are 1 or 2 heteroatoms present in ring B.

In another embodiment of this invention B is a seven membered ring, G is S, U is CR$^5$, there are 1 or 2 heteroatoms present in ring B, and the optional bond is present.

In another embodiment of this invention B is a seven membered ring, G is S, U is CR$^5$, there are 1 or 2 heteroatoms present in ring B, and the optional bond is absent.

In one embodiment of this invention B is an eight membered ring, G is S, U is CR$^5$, and there are 1 or 2 heteroatoms present in ring B.

In another embodiment of this invention B is an eight membered ring, G is S, U is CR$^5$, there are 1 or 2 heteroatoms present in ring B, and the optional bond is present.

In another embodiment of this invention B is an eight membered ring, G is S, U is CR$^5$, there are 1 or 2 heteroatoms present in ring B, and the optional bond is absent.

In one embodiment of this invention B is a five membered ring, G is S, U is N, and there are 1 or 2 additional heteroatoms present in ring B.

In another embodiment of this invention B is a five membered ring, G is S, U is N, there are 1 or 2 additional heteroatoms present in ring B, and the optional bond is present.

In another embodiment of this invention B is a five membered ring, G is S, U is N, there are 1 or 2 additional heteroatoms present in ring B, and the optional bond is absent.

In one embodiment of this invention B is a six membered ring, G is S, U is N, and there are 1 or 2 additional heteroatoms present in ring B.

In another embodiment of this invention B is a six membered ring, G is S, U is N, and the optional bond is present.

In another embodiment of this invention B is a six membered ring, G is S, U is N, there are 1 or 2 additional heteroatoms present in ring B, and the optional bond is absent.

In one embodiment of this invention B is a seven membered ring, G is S, U is N, and there are 1 or 2 additional heteroatoms present in ring B.

In another embodiment of this invention B is a seven membered ring, G is S, U is N, there are 1 or 2 additional heteroatoms present in ring B, and the optional bond is present.

In another embodiment of this invention B is a seven membered ring, G is S, U is N, there are 1 or 2 additional heteroatoms present in ring B, and the optional bond is absent.

In one embodiment of this invention B is an eight membered ring, G is S, U is N, and there are 1 or 2 additional heteroatoms present in ring B In another embodiment of this invention B is an eight membered ring, G is S, U is N, there are 1 or 2 additional heteroatoms present in ring B, and the optional bond is present.

In another embodiment of this invention B is an eight membered ring, G is S, U is N, there are 1 or 2 additional heteroatoms present in ring B, and the optional bond is absent.

In one embodiment of this invention B is a five membered ring, and G is C(O).

In another embodiment of this invention B is a five membered ring, G is C(O), and the optional bond is present.

In another embodiment of this invention B is a five membered ring, G is C(O), and the optional bond is absent.

In one embodiment of this invention B is a six membered ring, and G is C(O).

In another embodiment of this invention B is a six membered ring, G is C(O) and the optional bond is present.

In another embodiment of this invention B is a six membered ring, G is C(O), and the optional bond is absent.

In one embodiment of this invention B is a seven membered ring, and G is C(O).

In another embodiment of this invention B is a seven membered ring, G is C(O), and the optional bond is present.

In another embodiment of this invention B is a seven membered ring, G is C(O), and the optional bond is absent.

In one embodiment of this invention B is an eight membered ring, and G is C(O).

In another embodiment of this invention B is an eight membered ring, G is C(O), and the optional bond is present.

In another embodiment of this invention B is an eight membered ring, G is C(O), and the optional bond is absent.

In one embodiment of this invention B is a five membered ring, G is C(O), and U is $CR^5$.

In another embodiment of this invention B is a five membered ring, G is C(O), U is $CR^5$, and the optional bond is present.

In another embodiment of this invention B is a five membered ring, G is C(O), U is $CR^5$, and the optional bond is absent.

In one embodiment of this invention B is a six membered ring, G is C(O), and U is $CR^5$.

In another embodiment of this invention B is a six membered ring, G is C(O), U is $CR^5$, and the optional bond is present.

In another embodiment of this invention B is a six membered ring, G is C(O), U is $CR^5$, and the optional bond is absent.

In one embodiment of this invention B is a seven membered ring, G is C(O), and U is $CR^5$.

In another embodiment of this invention B is a seven membered ring, G is C(O), U is $CR^5$, and the optional bond is present.

In another embodiment of this invention B is a seven membered ring, G is C(O), U is $CR^5$, and the optional bond is absent.

In one embodiment of this invention B is an eight membered ring, G is C(O), and U is $CR^5$.

In another embodiment of this invention B is an eight membered ring, G is C(O), U is $CR^5$, and the optional bond is present.

In another embodiment of this invention B is an eight membered ring, G is C(O), U is $CR^5$, and the optional bond is absent.

In one embodiment of this invention B is a five membered ring, G is C(O), and U is N.

In another embodiment of this invention B is a five membered ring, G is C(O), U is N, and the optional bond is present.

In another embodiment of this invention B is a five membered ring, G is C(O), U is N, and the optional bond is absent.

In one embodiment of this invention B is a six membered ring, G is C(O), and U is N.

In another embodiment of this invention B is a six membered ring, G is C(O), U is N, and the optional bond is present.

In another embodiment of this invention B is a six membered ring, G is C(O), U is N, and the optional bond is absent.

In one embodiment of this invention B is a seven membered ring, G is C(O), and U is N.

In another embodiment of this invention B is a seven membered ring, G is C(O), U is N, and the optional bond is present.

In another embodiment of this invention B is a seven membered ring, G is C(O), U is N, and the optional bond is absent.

In one embodiment of this invention B is an eight membered ring, G is C(O), and U is N.

In another embodiment of this invention B is an eight membered ring, G is C(O), U is N, and the optional bond is present.

In another embodiment of this invention B is an eight membered ring, G G is C(O), U is N, and the optional bond is absent.

In one embodiment of this invention B is a five membered ring, G is C(O), U is $CR^5$, and there are 1 or 2 heteroatoms present in ring B.

In another embodiment of this invention B is a five membered ring, G is C(O), U is $CR^5$, there are 1 or 2 heteroatoms present in ring B, and the optional bond is present.

In another embodiment of this invention B is a five membered ring, G is C(O), U is $CR^5$, there are 1 or 2 heteroatoms present in ring B, and the optional bond is absent.

In one embodiment of this invention B is a six membered ring, G is C(O), and U is $CR^5$, and there are 1 or 2 heteroatoms present in ring B.

In another embodiment of this invention B is a six membered ring, G is C(O), U is $CR^5$, there are 1 or 2 heteroatoms present in ring B, and the optional bond is present.

In another embodiment of this invention B is a six membered ring, G is C(O), U is $CR^5$, there are 1 or 2 heteroatoms present in ring B, and the optional bond is absent.

In one embodiment of this invention B is a seven membered ring, G is C(O), U is $CR^5$, and there are 1 or 2 heteroatoms present in ring B.

In another embodiment of this invention B is a seven membered ring, G is C(O), U is $CR^5$, there are 1 or 2 heteroatoms present in ring B, and the optional bond is present.

In another embodiment of this invention B is a seven membered ring, G is C(O), U is $CR^5$, there are 1 or 2 heteroatoms present in ring B, and the optional bond is absent.

In one embodiment of this invention B is an eight membered ring, G is C(O), U is $CR^5$, and there are 1 or 2 heteroatoms present in ring B.

In another embodiment of this invention B is an eight membered ring, G is C(O), U is $CR^5$, there are 1 or 2 heteroatoms present in ring B, and the optional bond is present.

In another embodiment of this invention B is an eight membered ring, G is C(O), U is $CR^5$, there are 1 or 2 heteroatoms present in ring B, and the optional bond is absent.

In one embodiment of this invention B is a five membered ring, G is C(O), U is N, and there are 1 or 2 additional heteroatoms present in ring B.

In another embodiment of this invention B is a five membered ring, G is C(O), U is N, there are 1 or 2 additional heteroatoms present in ring B, and the optional bond is present.

In another embodiment of this invention B is a five membered ring, G is C(O), U is N, there are 1 or 2 additional heteroatoms present in ring B, and the optional bond is absent.

In one embodiment of this invention B is a six membered ring, G is C(O), U is N, and there are 1 or 2 additional heteroatoms present in ring B.

In another embodiment of this invention B is a six membered ring, G is C(O), U is N, and the optional bond is present.

In another embodiment of this invention B is a six membered ring, G is C(O), U is N, there are 1 or 2 additional heteroatoms present in ring B, and the optional bond is absent.

In one embodiment of this invention B is a seven membered ring, G is C(O), U is N, and there are 1 or 2 additional heteroatoms present in ring B.

In another embodiment of this invention B is a seven membered ring, G is C(O), U is N, there are 1 or 2 additional heteroatoms present in ring B, and the optional bond is present.

In another embodiment of this invention B is a seven membered ring, G is C(O), U is N, there are 1 or 2 additional heteroatoms present in ring B, and the optional bond is absent.

In one embodiment of this invention B is an eight membered ring, G is C(O), U is N, and there are 1 or 2 additional heteroatoms present in ring B In another embodiment of this invention B is an eight membered ring, G is C(O), U is N, there are 1 or 2 additional heteroatoms present in ring B, and the optional bond is present.

In another embodiment of this invention B is an eight membered ring, G is C(O), U is N, there are 1 or 2 additional heteroatoms present in ring B, and the optional bond is absent.

In one embodiment of this invention B is a five membered ring, and G is $N(R^{14})$.

In another embodiment of this invention B is a five membered ring, G is $N(R^{14})$, and the optional bond is present.

In another embodiment of this invention B is a five membered ring, G is $N(R^{14})$, and the optional bond is absent.

In one embodiment of this invention B is a six membered ring, and G is $N(R^{14})$.

In another embodiment of this invention B is a six membered ring, G is $N(R^{14})$ and the optional bond is present.

In another embodiment of this invention B is a six membered ring, G is $N(R^{14})$, and the optional bond is absent.

In one embodiment of this invention B is a seven membered ring, and G is $N(R^{14})$.

In another embodiment of this invention B is a seven membered ring, G is $N(R^{14})$, and the optional bond is present.

In another embodiment of this invention B is a seven membered ring, G is $N(R^{14})$, and the optional bond is absent.

In one embodiment of this invention B is an eight membered ring, and G is $N(R^{14})$.

In another embodiment of this invention B is an eight membered ring, G is $N(R^{14})$, and the optional bond is present.

In another embodiment of this invention B is an eight membered ring, G is $N(R^{14})$, and the optional bond is absent.

In one embodiment of this invention B is a five membered ring, G is $N(R^{14})$, and U is $CR^5$.

In another embodiment of this invention B is a five membered ring, G is $N(R^{14})$, U is $CR^5$, and the optional bond is present.

In another embodiment of this invention B is a five membered ring, G is $N(R^{14})$, U is $CR^5$, and the optional bond is absent.

In one embodiment of this invention B is a six membered ring, G is $N(R^{14})$, and U is $CR^5$.

In another embodiment of this invention B is a six membered ring, G is $N(R^{14})$, U is $CR^5$, and the optional bond is present.

In another embodiment of this invention B is a six membered ring, G is $N(R^{14})$, U is $CR^5$, and the optional bond is absent.

In one embodiment of this invention B is a seven membered ring, G is $N(R^{14})$, and U is $CR^5$.

In another embodiment of this invention B is a seven membered ring, G is $N(R^{14})$, U is $CR^5$, and the optional bond is present.

In another embodiment of this invention B is a seven membered ring, G is $N(R^{14})$, U is $CR^5$, and the optional bond is absent.

In one embodiment of this invention B is an eight membered ring, G is $N(R^{14})$, and U is $CR^5$.

In another embodiment of this invention B is an eight membered ring, G is $N(R^{14})$, U is $CR^5$, and the optional bond is present.

In another embodiment of this invention B is an eight membered ring, G is $N(R^{14})$, U is $CR^5$, and the optional bond is absent.

In one embodiment of this invention B is a five membered ring, G is $N(R^{14})$, and U is N.

In another embodiment of this invention B is a five membered ring, G is $N(R^{14})$, U is N, and the optional bond is present.

In another embodiment of this invention B is a five membered ring, G is $N(R^{14})$, U is N, and the optional bond is absent.

In one embodiment of this invention B is a six membered ring, G is $N(R^{14})$, and U is N.

In another embodiment of this invention B is a six membered ring, G is $N(R^{14})$, U is N, and the optional bond is present.

In another embodiment of this invention B is a six membered ring, G is $N(R^{14})$, U is N, and the optional bond is absent.

In one embodiment of this invention B is a seven membered ring, G is $N(R^{14})$, and U is N.

In another embodiment of this invention B is a seven membered ring, G is $N(R^{14})$, U is N, and the optional bond is present.

In another embodiment of this invention B is a seven membered ring, G is $N(R^{14})$, U is N, and the optional bond is absent.

In one embodiment of this invention B is an eight membered ring, G is $N(R^{14})$, and U is N.

In another embodiment of this invention B is an eight membered ring, G is $N(R^{14})$, U is N, and the optional bond is present.

In another embodiment of this invention B is an eight membered ring, G is $N(R^{14})$, U is N, and the optional bond is absent.

In one embodiment of this invention B is a five membered ring, G is $N(R^{14})$, U is $CR^5$, and there are 1 or 2 heteroatoms present in ring B.

In another embodiment of this invention B is a five membered ring, G is $N(R^{14})$, U is $CR^5$, there are 1 or 2 heteroatoms present in ring B, and the optional bond is present.

In another embodiment of this invention B is a five membered ring, G is $N(R^{14})$, U is $CR^5$, there are 1 or 2 heteroatoms present in ring B, and the optional bond is absent.

In one embodiment of this invention B is a six membered ring, G is $N(R^{14})$, and U is $CR^5$, and there are 1 or 2 heteroatoms present in ring B.

In another embodiment of this invention B is a six membered ring, G is $N(R^{14})$, U is $CR^5$, there are 1 or 2 heteroatoms present in ring B, and the optional bond is present.

In another embodiment of this invention B is a six membered ring, G is $N(R^{14})$, U is $CR^5$, there are 1 or 2 heteroatoms present in ring B, and the optional bond is absent.

In one embodiment of this invention B is a seven membered ring, G is $N(R^{14})$, U is $CR^5$, and there are 1 or 2 heteroatoms present in ring B.

In another embodiment of this invention B is a seven membered ring, G is $N(R^{14})$, U is $CR^5$, there are 1 or 2 heteroatoms present in ring B, and the optional bond is present.

In another embodiment of this invention B is a seven membered ring, G is $N(R^{14})$, U is $CR^5$, there are 1 or 2 heteroatoms present in ring B, and the optional bond is absent.

In one embodiment of this invention B is an eight membered ring, G is $N(R^{14})$, U is $CR^5$, and there are 1 or 2 heteroatoms present in ring B.

In another embodiment of this invention B is an eight membered ring, G is $N(R^{14})$, U is $CR^5$, there are 1 or 2 heteroatoms present in ring B, and the optional bond is present.

In another embodiment of this invention B is an eight membered ring, G is $N(R^{14})$, U is $CR^5$, there are 1 or 2 heteroatoms present in ring B, and the optional bond is absent.

In one embodiment of this invention B is a five membered ring, G is $N(R^{14})$, U is N, and there are 1 or 2 additional heteroatoms present in ring B.

In another embodiment of this invention B is a five membered ring, G is $N(R^{14})$, U is N, there are 1 or 2 additional heteroatoms present in ring B, and the optional bond is present.

In another embodiment of this invention B is a five membered ring, G is $N(R^{14})$, U is N, there are 1 or 2 additional heteroatoms present in ring B, and the optional bond is absent.

In one embodiment of this invention B is a six membered ring, G is $N(R^{14})$, U is N, and there are 1 or 2 additional heteroatoms present in ring B.

In another embodiment of this invention B is a six membered ring, G is $N(R^{14})$, U is N, and the optional bond is present.

In another embodiment of this invention B is a six membered ring, G is $N(R^{14})$, U is N, there are 1 or 2 additional heteroatoms present in ring B, and the optional bond is absent.

In one embodiment of this invention B is a seven membered ring, G is $N(R^{14})$, U is N, and there are 1 or 2 additional heteroatoms present in ring B.

In another embodiment of this invention B is a seven membered ring, G is $N(R^{14})$, U is N, there are 1 or 2 additional heteroatoms present in ring B, and the optional bond is present.

In another embodiment of this invention B is a seven membered ring, G is $N(R^{14})$, U is N, there are 1 or 2 additional heteroatoms present in ring B, and the optional bond is absent.

In one embodiment of this invention B is an eight membered ring, G is $N(R^{14})$, U is N, and there are 1 or 2 additional heteroatoms present in ring B In another embodiment of this invention B is an eight membered ring, G is $N(R^{14})$, U is N, there are 1 or 2 additional heteroatoms present in ring B, and the optional bond is present.

In another embodiment of this invention B is an eight membered ring, G is $N(R^{14})$, U is N, there are 1 or 2 additional heteroatoms present in ring B, and the optional bond is absent.

In one embodiment of this invention B is a five membered ring, G is O, U is $CR^5$, and there is 1 heteroatom present in ring B.

In another embodiment of this invention B is a five membered ring, G is O, U is $CR^5$, there is 1 heteroatom present in ring B, and the optional bond is present.

In another embodiment of this invention B is a five membered ring, G is O, U is $CR^5$, there is 1 heteroatom present in ring B, and the optional bond is absent.

In one embodiment of this invention B is a six membered ring, G is O, and U is $CR^5$, and there is 1 heteroatom present in ring B.

In another embodiment of this invention B is a six membered ring, G is O, U is $CR^5$, there is 1 heteroatom present in ring B, and the optional bond is present.

In another embodiment of this invention B is a six membered ring, G is O, U is $CR^5$, there is 1 heteroatom present in ring B, and the optional bond is absent.

In one embodiment of this invention B is a seven membered ring, G is O, U is $CR^5$, and there is 1 heteroatom present in ring B.

In another embodiment of this invention B is a seven membered ring, G is O, U is $CR^5$, there is 1 heteroatom present in ring B, and the optional bond is present.

In another embodiment of this invention B is a seven membered ring, G is O, U is $CR^5$, there is 1 heteroatom present in ring B, and the optional bond is absent.

In one embodiment of this invention B is an eight membered ring, G is O, U is $CR^5$, and there is 1 heteroatom present in ring B.

In another embodiment of this invention B is an eight membered ring, G is O, U is $CR^5$, there is 1 heteroatom present in ring B, and the optional bond is present.

In another embodiment of this invention B is an eight membered ring, G is O, U is $CR^5$, there is 1 heteroatom present in ring B, and the optional bond is absent.

In one embodiment of this invention B is a five membered ring, G is O, U is N, and there is 1 additional heteroatom present in ring B.

In another embodiment of this invention B is a five membered ring, G is O, U is N, there is 1 additional heteroatom present in ring B, and the optional bond is present.

In another embodiment of this invention B is a five membered ring, G is O, U is N, there is 1 additional heteroatom present in ring B, and the optional bond is absent.

In one embodiment of this invention B is a six membered ring, G is O, U is N, and there is 1 additional heteroatom present in ring B.

In another embodiment of this invention B is a six membered ring, G is O, U is N, there is 1 additional heteroatom present in ring B, and the optional bond is absent.

In one embodiment of this invention B is a seven membered ring, G is O, U is N, and there is 1 additional heteroatom present in ring B.

In another embodiment of this invention B is a seven membered ring, G is O, U is N, there is 1 additional heteroatom present in ring B, and the optional bond is present.

In another embodiment of this invention B is a seven membered ring, G is O, U is N, there is 1 additional heteroatom present in ring B, and the optional bond is absent.

In one embodiment of this invention B is an eight membered ring, G is O, U is N, and there is 1 additional heteroatom present in ring B In another embodiment of this invention B is an eight membered ring, G is O, U is N, there is 1 additional heteroatom present in ring B, and the optional bond is present.

In another embodiment of this invention B is an eight membered ring, G is O, U is N, there is 1 additional heteroatom present in ring B, and the optional bond is absent.

In one embodiment of this invention B is a five membered ring, G is S, U is $CR^5$, and there is 1 heteroatom present in ring B.

In another embodiment of this invention B is a five membered ring, G is S, U is $CR^5$, there is 1 heteroatom present in ring B, and the optional bond is present.

In another embodiment of this invention B is a five membered ring, G is S, U is $CR^5$, there is 1 heteroatom present in ring B, and the optional bond is absent.

In one embodiment of this invention B is a six membered ring, G is S, and U is $CR^5$, and there is 1 heteroatom present in ring B.

In another embodiment of this invention B is a six membered ring, G is S, U is $CR^5$, there is 1 heteroatom present in ring B, and the optional bond is present.

In another embodiment of this invention B is a six membered ring, G is S, U is $CR^5$, there is 1 heteroatom present in ring B, and the optional bond is absent.

In one embodiment of this invention B is a seven membered ring, G is S, U is $CR^5$, and there is 1 heteroatom present in ring B.

In another embodiment of this invention B is a seven membered ring, G is S, U is $CR^5$, there is 1 heteroatom present in ring B, and the optional bond is present.

In another embodiment of this invention B is a seven membered ring, G is S, U is $CR^5$, there is 1 heteroatom present in ring B, and the optional bond is absent.

In one embodiment of this invention B is an eight membered ring, G is S, U is $CR^5$, and there is 1 heteroatom present in ring B.

In another embodiment of this invention B is an eight membered ring, G is S, U is $CR^5$, there is 1 heteroatom present in ring B, and the optional bond is present.

In another embodiment of this invention B is an eight membered ring, G is S, U is $CR^5$, there is 1 heteroatom present in ring B, and the optional bond is absent.

In one embodiment of this invention B is a five membered ring, G is S, U is N, and there is 1 additional heteroatom present in ring B.

In another embodiment of this invention B is a five membered ring, G is S, U is N, there is 1 additional heteroatom present in ring B, and the optional bond is present.

In another embodiment of this invention B is a five membered ring, G is S, U is N, there is 1 additional heteroatom present in ring B, and the optional bond is absent.

In one embodiment of this invention B is a six membered ring, G is S, U is N, and there is 1 additional heteroatom present in ring B.

In another embodiment of this invention B is a six membered ring, G is S, U is N, there is 1 additional heteroatom present in ring B, and the optional bond is absent.

In one embodiment of this invention B is a seven membered ring, G is S, U is N, and there is 1 additional heteroatom present in ring B.

In another embodiment of this invention B is a seven membered ring, G is S, U is N, there is 1 additional heteroatom present in ring B, and the optional bond is present.

In another embodiment of this invention B is a seven membered ring, G is S, U is N, there is 1 additional heteroatom present in ring B, and the optional bond is absent.

In one embodiment of this invention B is an eight membered ring, G is S, U is N, and there is 1 additional heteroatom present in ring B In another embodiment of this invention B is an eight membered ring, G is S, U is N, there is 1 additional heteroatom present in ring B, and the optional bond is present.

In another embodiment of this invention B is an eight membered ring, G is S, U is N, there is 1 additional heteroatom present in ring B, and the optional bond is absent.

In one embodiment of this invention B is a five membered ring, G is $N(R^{14})$, U is $CR^5$, and there is 1 heteroatom present in ring B.

In another embodiment of this invention B is a five membered ring, G is $N(R^{14})$, U is $CR^5$, there is 1 heteroatom present in ring B, and the optional bond is present.

In another embodiment of this invention B is a five membered ring, G is $N(R^{14})$, U is $CR^5$, there is 1 heteroatom present in ring B, and the optional bond is absent.

In one embodiment of this invention B is a six membered ring, G is $N(R^{14})$, and U is $CR^5$, and there is 1 heteroatom present in ring B.

In another embodiment of this invention B is a six membered ring, G is $N(R^{14})$, U is $CR^5$, there is 1 heteroatom present in ring B, and the optional bond is present.

In another embodiment of this invention B is a six membered ring, G is $N(R^{14})$, U is $CR^5$, there is 1 heteroatom present in ring B, and the optional bond is absent.

In one embodiment of this invention B is a seven membered ring, G is $N(R^{14})$, U is $CR^5$, and there is 1 heteroatom present in ring B.

In another embodiment of this invention B is a seven membered ring, G is $N(R^{14})$, U is $CR^5$, there is 1 heteroatom present in ring B, and the optional bond is present.

In another embodiment of this invention B is a seven membered ring, G is $N(R^{14})$, U is $CR^5$, there is 1 heteroatom present in ring B, and the optional bond is absent.

In one embodiment of this invention B is an eight membered ring, G is $N(R^{14})$, U is $CR^5$, and there is 1 heteroatom present in ring B.

In another embodiment of this invention B is an eight membered ring, G is $N(R^{14})$, U is $CR^5$, there is 1 heteroatom present in ring B, and the optional bond is present.

In another embodiment of this invention B is an eight membered ring, G is $N(R^{14})$, U is $CR^5$, there is 1 heteroatom present in ring B, and the optional bond is absent.

In one embodiment of this invention B is a five membered ring, G is $N(R^{14})$, U is N, and there is 1 additional heteroatom present in ring B.

In another embodiment of this invention B is a five membered ring, G is $N(R^{14})$, U is N, there is 1 additional heteroatom present in ring B, and the optional bond is present.

In another embodiment of this invention B is a five membered ring, G is $N(R^{14})$, U is N, there is 1 additional heteroatom present in ring B, and the optional bond is absent.

In one embodiment of this invention B is a six membered ring, G is $N(R^{14})$, U is N, and there is 1 additional heteroatom present in ring B.

In another embodiment of this invention B is a six membered ring, G is $N(R^{14})$, U is N, there is 1 additional heteroatom present in ring B, and the optional bond is absent.

In one embodiment of this invention B is a seven membered ring, G is $N(R^{14})$, U is N, and there is 1 additional heteroatom present in ring B.

In another embodiment of this invention B is a seven membered ring, G is $N(R^{14})$, U is N, there is 1 additional heteroatom present in ring B, and the optional bond is present.

In another embodiment of this invention B is a seven membered ring, G is $N(R^{14})$, U is N, there is 1 additional heteroatom present in ring B, and the optional bond is absent.

In one embodiment of this invention B is an eight membered ring, G is $N(R^{14})$, U is N, and there is 1 additional heteroatom present in ring B In another embodiment of this invention B is an eight membered ring, G is $N(R^{14})$, U is N, there is 1 additional heteroatom present in ring B, and the optional bond is present.

In another embodiment of this invention B is an eight membered ring, G is $N(R^{14})$, U is N, there is 1 additional heteroatom present in ring B, and the optional bond is absent.

In one embodiment of this invention B is a five membered ring, G is C(O), U is $CR^5$, and there is 1 heteroatom present in ring B.

In another embodiment of this invention B is a five membered ring, G is C(O), U is $CR^5$, there is 1 heteroatom present in ring B, and the optional bond is present.

In another embodiment of this invention B is a five membered ring, G is C(O), U is $CR^5$, there is 1 heteroatom present in ring B, and the optional bond is absent.

In one embodiment of this invention B is a six membered ring, G is C(O), and U is $CR^5$, and there is 1 heteroatom present in ring B.

In another embodiment of this invention B is a six membered ring, G is C(O), U is $CR^5$, there is 1 heteroatom present in ring B, and the optional bond is present.

In another embodiment of this invention B is a six membered ring, G is C(O), U is $CR^5$, there is 1 heteroatom present in ring B, and the optional bond is absent.

In one embodiment of this invention B is a seven membered ring, G is C(O), U is $CR^5$, and there is 1 heteroatom present in ring B.

In another embodiment of this invention B is a seven membered ring, G is C(O), U is $CR^5$, there is 1 heteroatom present in ring B, and the optional bond is present.

In another embodiment of this invention B is a seven membered ring, G is C(O), U is $CR^5$, there is 1 heteroatom present in ring B, and the optional bond is absent.

In one embodiment of this invention B is an eight membered ring, G is C(O), U is $CR^5$, and there is 1 heteroatom present in ring B.

In another embodiment of this invention B is an eight membered ring, G is C(O), U is $CR^5$, there is 1 heteroatom present in ring B, and the optional bond is present.

In another embodiment of this invention B is an eight membered ring, G is C(O), U is $CR^5$, there is 1 heteroatom present in ring B, and the optional bond is absent.

In one embodiment of this invention B is a five membered ring, G is C(O), U is N, and there is 1 additional heteroatom present in ring B.

In another embodiment of this invention B is a five membered ring, G is C(O), U is N, there is 1 additional heteroatom present in ring B, and the optional bond is present.

In another embodiment of this invention B is a five membered ring, G is C(O), U is N, there is 1 additional heteroatom present in ring B, and the optional bond is absent.

In one embodiment of this invention B is a six membered ring, G is C(O), U is N, and there is 1 additional heteroatom present in ring B.

In another embodiment of this invention B is a six membered ring, G is C(O), U is N, there is 1 additional heteroatom present in ring B, and the optional bond is absent.

In one embodiment of this invention B is a seven membered ring, G is C(O), U is N, and there is 1 additional heteroatom present in ring B.

In another embodiment of this invention B is a seven membered ring, G is C(O), U is N, there is 1 additional heteroatom present in ring B, and the optional bond is present.

In another embodiment of this invention B is a seven membered ring, G is C(O), U is N, there is 1 additional heteroatom present in ring B, and the optional bond is absent.

In one embodiment of this invention B is an eight membered ring, G is C(O), U is N, and there is 1 additional heteroatom present in ring B In another embodiment of this invention B is an eight membered ring, G is C(O), U is N, there is 1 additional heteroatom present in ring B, and the optional bond is present.

In another embodiment of this invention B is an eight membered ring, G is C(O), U is N, there is 1 additional heteroatom present in ring B, and the optional bond is absent.

In one embodiment of this invention B is a five membered ring, G is $N(R^{14})$, U is $CR^5$, and there is 1 heteroatom present in ring B.

In another embodiment of this invention B is a five membered ring, G is $N(R^{14})$, U is $CR^5$, there is 1 heteroatom present in ring B, and the optional bond is present.

In another embodiment of this invention B is a five membered ring, G is $N(R^{14})$, U is $CR^5$, there is 1 heteroatom present in ring B, and the optional bond is absent.

In one embodiment of this invention B is a six membered ring, G is $N(R^{14})$, and U is $CR^5$, there is 1 heteroatom present in ring B.

In another embodiment of this invention B is a six membered ring, G is $N(R^{14})$, U is $CR^5$, there is 1 heteroatom present in ring B, and the optional bond is present.

In another embodiment of this invention B is a six membered ring, G is $N(R^{14})$, U is $CR^5$, there is 1 heteroatom present in ring B, and the optional bond is absent.

In one embodiment of this invention B is a seven membered ring, G is $N(R^{14})$, U is $CR^5$, and there is 1 heteroatom present in ring B.

In another embodiment of this invention B is a seven membered ring, G is $N(R^{14})$, U is $CR^5$, there is 1 heteroatom present in ring B, and the optional bond is present.

In another embodiment of this invention B is a seven membered ring, G is $N(R^{14})$, U is $CR^5$, there is 1 heteroatom present in ring B, and the optional bond is absent.

In one embodiment of this invention B is an eight membered ring, G is $N(R^{14})$, U is $CR^5$, and there is 1 heteroatom present in ring B.

In another embodiment of this invention B is an eight membered ring, G is $N(R^{14})$, U is $CR^5$, there is 1 heteroatom present in ring B, and the optional bond is present.

In another embodiment of this invention B is an eight membered ring, G is $N(R^{14})$, U is $CR^5$, there is 1 heteroatom present in ring B, and the optional bond is absent.

In one embodiment of this invention B is a five membered ring, G is $N(R^{14})$, U is N, and there is 1 additional heteroatom present in ring B.

In another embodiment of this invention B is a five membered ring, G is $N(R^{14})$, U is N, there is 1 additional heteroatom present in ring B, and the optional bond is present.

In another embodiment of this invention B is a five membered ring, G is $N(R^{14})$, U is N, there is 1 additional heteroatom present in ring B, and the optional bond is absent.

In one embodiment of this invention B is a six membered ring, G is $N(R^{14})$, U is N, and there is 1 additional heteroatom present in ring B.

In another embodiment of this invention B is a six membered ring, G is $N(R^{14})$, U is N, there is 1 additional heteroatom present in ring B, and the optional bond is absent.

In one embodiment of this invention B is a seven membered ring, G is $N(R^{14})$, U is N, and there is 1 additional heteroatom present in ring B.

In another embodiment of this invention B is a seven membered ring, G is $N(R^{14})$, U is N, there is 1 additional heteroatom present in ring B, and the optional bond is present.

In another embodiment of this invention B is a seven membered ring, G is $N(R^{14})$, U is N, there is 1 additional heteroatom present in ring B, and the optional bond is absent.

In one embodiment of this invention B is an eight membered ring, G is $N(R^{14})$, U is N, and there is 1 additional heteroatom present in ring B In another embodiment of this invention B is an eight membered ring, G is $N(R^{14})$, U is N, there is 1 additional heteroatom present in ring B, and the optional bond is present.

In another embodiment of this invention B is an eight membered ring, G is $N(R^{14})$, U is N, there is 1 additional heteroatom present in ring B, and the optional bond is absent.

Other embodiments of this invention are directed to any one of the above embodiments wherein G is $N(R^{14})$, wherein $R^{14}$ is H (i.e. G is NH).

In one embodiment $R^2$ (of the $NR^2$ moiety) is H.

In another embodiment $R^2$ (of the $NR^2$ moiety) is alkyl, such as, for example, methyl, ethyl or isopropyl.

In another embodiment $R^2$ (of the $NR^2$ moiety) is aryl, such as, for example, phenyl.

In another embodiment $R^2$ (of the $NR^2$ moiety) is substituted aryl, such as, for example, substituted phenyl.

In another embodiment $R^2$ (of the $NR^2$ moiety) is —C(O)$R^4$ wherein $R^4$ is alkyl (such as, for example, methyl, ethyl or isopropyl).

In another embodiment $R^2$ (of the $NR^2$ moiety) is —C(O)$R^4$ wherein $R^4$ is aryl, such as, for example, phenyl.

In another embodiment $R^2$ (of the $NR^2$ moiety) is —C(O)$R^4$ wherein $R^4$ is substituted aryl, such as, for example, substituted phenyl.

In another embodiment of this invention $R^5$ is H.

Another embodiment of this invention is directed to any one of the embodiments above directed to ring (B) wherein U is $CR^5$ wherein $R^5$ is H.

In another embodiment of this invention ring (B) is not substituted with any $R^{21}$ groups.

In another embodiment of this invention, there are 1 to 5 $R^{21}$ groups present in formula (I), and at least one (e.g., 1 to 2) $R^{21}$ is selected from the group consisting of: —SF$_5$, —OSF$_5$ and —Si($R^{15A}$)$_3$, wherein each $R^{15A}$ is independently selected.

In another embodiment of this invention, there are 1 to 5 $R^{21}$ groups present in formula (I), and at least one $R^{21}$ is selected from the group consisting of: —SF$_5$ and —Si($R^{15A}$)$_3$, and each $R^{15A}$ is the same or different alkyl group.

In another embodiment of this invention, there are 1 to 5 $R^{21}$ groups present in formula (I), and at least one $R^{21}$ is selected from the group consisting of: —SF$_5$, —OSF$_5$ and —Si(CH$_3$)$_3$.

In another embodiment of this invention, there are 1 to 5 $R^{21}$ groups present in formula (I), and one of the $R^{21}$ groups is selected from the group consisting of: —SF$_5$, OSF$_5$ and —Si($R^{15A}$)$_3$.

In another embodiment of this invention, there are 1 to 5 $R^{21}$ groups present in formula (I), and one of the $R^{21}$ groups is selected from the group consisting of: —SF$_5$, OSF$_5$ and —Si($R^{15A}$)$_3$, and each $R^{15A}$ is the same or different alkyl group.

In another embodiment of this invention, there are 1 to 5 $R^{21}$ groups present in formula (I), and one of the $R^{21}$ groups is selected from the group consisting of: —SF$_5$, —OSF$_5$ and —Si(CH$_3$)$_3$.

In another embodiment of this invention, there are 2 to 5 $R^{21}$ groups present in formula (I), and two of the $R^{21}$ groups are selected from the group consisting of: —SF$_5$, OSF$_5$ and —Si($R^{15A}$)$_3$, wherein each $R^{15A}$ is independently selected.

In another embodiment of this invention, there are 2 to 5 $R^{21}$ groups present in formula (I), and two of the $R^{21}$ groups are selected from the group consisting of: —SF$_5$, OSF$_5$ and —Si($R^{15A}$)$_3$, and each $R^{15A}$ is the same or different alkyl group.

In another embodiment of this invention, there are 2 to 5 $R^{21}$ groups present in formula (I), and two of the $R^{21}$ groups are selected from the group consisting of: —SF$_5$, —OSF$_5$ and —Si(CH$_3$)$_3$.

In another embodiment of this invention, there are 1 to 5 $R^{21}$ groups present in formula (I), and at least one (e.g., 1 to 2) $R^{21}$ is selected from the group consisting of: —SF$_5$ and —Si($R^{15A}$)$_3$, wherein each $R^{15A}$ is independently selected.

In another embodiment of this invention, there are 1 to 5 $R^{21}$ groups present in formula (I), and at least one $R^{21}$ is selected from the group consisting of: —SF$_5$ and —Si($R^{15A}$)$_3$, and each $R^{15A}$ is the same or different alkyl group.

In another embodiment of this invention, there are 1 to 5 $R^{21}$ groups present in formula (I), and at least one $R^{21}$ is selected from the group consisting of: —SF$_5$ and —Si(CH$_3$)$_3$.

In another embodiment of this invention, there are 1 to 5 $R^{21}$ groups present in formula (I), and one of the $R^{21}$ groups is selected from the group consisting of: —SF$_5$ and —Si($R^{15A}$)$_3$.

In another embodiment of this invention, there are 1 to 5 $R^{21}$ groups present in formula (I), and one of the $R^{21}$ groups is selected from the group consisting of: —SF$_5$ and —Si($R^{15A}$)$_3$, and each $R^{15A}$ is the same or different alkyl group.

In another embodiment of this invention, there are 1 to 5 $R^{21}$ groups present in formula (I), and one of the $R^{21}$ groups is selected from the group consisting of: —SF$_5$ and —Si(CH$_3$)$_3$.

In another embodiment of this invention, there are 2 to 5 $R^{21}$ groups present in formula (I), and two of the $R^{21}$ groups are selected from the group consisting of: —SF$_5$ and —Si($R^{15A}$)$_3$, wherein each $R^{15A}$ is independently selected.

In another embodiment of this invention, there are 2 to 5 $R^{21}$ groups present in formula (I), and two of the $R^{21}$ groups are selected from the group consisting of: —SF$_5$ and —Si($R^{15A}$)$_3$, and each $R^{15A}$ is the same or different alkyl group.

In another embodiment of this invention, there are 2 to 5 $R^{21}$ groups present in formula (I), and two of the $R^{21}$ groups are selected from the group consisting of: —SF$_5$ and —Si(CH$_3$)$_3$.

In another embodiment of this invention, there are 1 to 5 $R^{21}$ groups present in formula (I), and one of the $R^{21}$ groups is —SF$_5$.

In another embodiment of this invention, there are 2 to 5 $R^{21}$ groups present in formula (I), and two of the $R^{21}$ groups are —SF$_5$.

In another embodiment of this invention, there are 1 to 5 $R^{21}$ groups present in formula (I), and one of the $R^{21}$ groups is —OSF$_5$.

In another embodiment of this invention, there are 2 to 5 $R^{21}$ groups present in formula (I), and two of the $R^{21}$ groups are —OSF$_5$.

In another embodiment of this invention, there are 1 to 5 $R^{21}$ groups present in formula (I), and one of the $R^{21}$ groups is —Si($R^{15A}$)$_3$.

In another embodiment of this invention, there are 1 to 5 $R^{21}$ groups present in formula (I), and one of the $R^{21}$ groups is —Si($R^{15A}$)$_3$ and each $R^{15A}$ is the same or different alkyl group.

In another embodiment of this invention, there are 1 to 5 $R^{21}$ groups present in formula (I), and one of the $R^{21}$ groups is —Si(CH$_3$)$_3$.

In another embodiment of this invention, there are 2 to 5 $R^{21}$ groups present in formula (I), and two of the $R^{21}$ groups are the same or different —Si($R^{15A}$)$_3$, wherein each $R^{15A}$ is independently selected.

In another embodiment of this invention, there are 2 to 5 $R^{21}$ groups present in formula (I), and two of the $R^{21}$ groups are the same or different —Si($R^{15A}$)$_3$ and each $R^{15A}$ is the same or different alkyl group.

In another embodiment of this invention, there are 2 to 5 $R^{21}$ groups present in formula (I), and two of the $R^{21}$ groups are —Si(CH$_3$)$_3$.

In another embodiment of this invention $R^7$ is substituted with $R^{21}$ groups, and at least one (e.g. 1 to 2) of the $R^{21}$ groups is selected from the group consisting of: —SF$_5$, —OSF$_5$ and —Si($R^{15A}$)$_3$, wherein each $R^{15A}$ is independently selected.

In another embodiment of this invention $R^7$ is substituted with $R^{21}$ groups, and at least one (e.g. 1 to 2) of the $R^{21}$ groups is selected from the group consisting of: —SF$_5$, —OSF$_5$ and —Si($R^{15A}$)$_3$, and each $R^{15A}$ is the same or different alkyl group.

In another embodiment of this invention $R^7$ is substituted with $R^{21}$ groups, and at least one (e.g. 1 to 2) of the $R^{21}$ groups is selected from the group consisting of: —$SF_5$, —$OSF_5$ and —$Si(CH_3)_3$.

In another embodiment of this invention $R^7$ is substituted with $R^{21}$ groups, and one $R^{21}$ group is selected from the group consisting of: —$SF_5$, —$OSF_5$ and —$Si(R^{15A})_3$, wherein each $R^{15A}$ is independently selected.

In another embodiment of this invention $R^7$ is substituted with $R^{21}$ groups, and one $R^{21}$ group is selected from the group consisting of: —$SF_5$, —$OSF_5$ and —$Si(R^{15A})_3$, and each $R^{15A}$ is the same or different alkyl group.

In another embodiment of this invention $R^7$ is substituted with $R^{21}$ groups, and one $R^{21}$ group is selected from the group consisting of: —$SF_5$, —$OSF_5$ and —$Si(CH_3)_3$.

In another embodiment of this invention $R^7$ is substituted with $R^{21}$ groups, and two $R^{21}$ groups are selected from the group consisting of: —$SF_5$, —$OSF_5$ and —$Si(R^{15A})_3$, wherein each $R^{15A}$ is independently selected.

In another embodiment of this invention $R^7$ is substituted with $R^{21}$ groups, and two $R^{21}$ groups are selected from the group consisting of: —$SF_5$, —$OSF_5$ and —$Si(R^{15A})_3$, and each $R^{15A}$ is the same or different alkyl group.

In another embodiment of this invention $R^7$ is substituted with $R^{21}$ groups, and two $R^{21}$ groups are selected from the group consisting of: —$SF_5$, —$OSF_5$ and —$Si(CH_3)_3$.

In another embodiment of this invention $R^7$ is substituted with $R^{21}$ groups, and one $R^{21}$ group is —$SF_5$.

In another embodiment of this invention $R^7$ is substituted with $R^{21}$ groups, and two $R^{21}$ groups are —$SF_5$.

In another embodiment of this invention $R^7$ is substituted with $R^{21}$ groups, and one $R^{21}$ group is —$OSF_5$.

In another embodiment of this invention $R^7$ is substituted with $R^{21}$ groups, and two $R^{21}$ groups are —$OSF_5$.

In another embodiment of this invention $R^7$ is substituted with $R^{21}$ groups, and one $R^{21}$ group is —$Si(R^{15A})_3$, wherein each $R^{15A}$ is independently selected.

In another embodiment of this invention $R^7$ is substituted with $R^{21}$ groups, and one $R^{21}$ group is —$Si(R^{15A})_3$ and each $R^{15A}$ is the same or different alkyl group.

In another embodiment of this invention $R^7$ is substituted with $R^{21}$ groups, and one $R^{21}$ group is —$Si(CH_3)_3$.

In another embodiment of this invention $R^7$ is substituted with $R^{21}$ groups, and two of the $R^{21}$ groups are the same or different —$Si(R^{15A})_3$, wherein each $R^{15A}$ is independently selected.

In another embodiment of this invention $R^7$ is substituted with $R^{21}$ groups, and two of the $R^{21}$ groups are the same or different —$Si(R^{15})_3$ group, and each $R^{15A}$ is the same or different alkyl group.

In another embodiment of this invention $R^7$ is substituted with $R^{21}$ groups, and two of the $R^{21}$ group are —$Si(CH_3)_3$.

In another embodiment of this invention $R^7$ is an aryl group substituted with $R^{21}$ groups, and at least one (e.g., 1 to 2) $R^{21}$ group is selected from the group consisting of: —$SF_5$, —$OSF_5$ and —$Si(R^{15A})_3$, wherein each $R^{15A}$ is independently selected.

In another embodiment of this invention $R^7$ is an aryl group substituted with $R^{21}$ groups, and at least one (e.g., 1 to 2) $R^{21}$ group is selected from the group consisting of: —$SF_5$, —$OSF_5$ and —$Si(R^{15A})_3$, and each $R^{15A}$ is the same or different alkyl group.

In another embodiment of this invention $R^7$ is an aryl group substituted with $R^{21}$ groups, and at least one (e.g., 1 to 2) $R^{21}$ group is selected from the group consisting of: —$SF_5$, —$OSF_5$ and —$Si(CH_3)_3$.

In another embodiment of this invention $R^7$ is an aryl group substituted with $R^{21}$ groups, and said aryl moiety is phenyl, and at least one (e.g., 1 to 2) $R^{21}$ group is selected from the group consisting of: —$SF_5$, —$OSF_5$ and —$Si(R^{15A})_3$, wherein each $R^{15A}$ is independently selected.

In another embodiment of this invention $R^7$ is an aryl group substituted with $R^{21}$ groups, and said aryl moiety is phenyl, and at least one (e.g., 1 to 2) $R^{21}$ group is selected from the group consisting of: —$SF_5$, —$OSF_5$ and —$Si(R^{15A})_3$, and each $R^{15A}$ is the same or different alkyl group.

In another embodiment of this invention $R^7$ is an aryl group substituted with $R^{21}$ groups, and said aryl moiety is phenyl, and at least one (e.g., 1 to 2) $R^{21}$ group is selected from the group consisting of: —$SF_5$, —$OSF_5$ and —$Si(CH_3)_3$.

In another embodiment of this invention $R^7$ is an aryl group substituted with $R^{21}$ groups, and said aryl moiety is phenyl, and said phenyl is substituted with at least one (e.g., 1 to 3, or 1 to 2) $R^{21}$ group, and at least one (e.g., 1 or 2) $R^{21}$ group on said phenyl is selected from the group consisting of: —$SF_5$, —$OSF_5$ and —$Si(R^{15A})_3$, wherein each $R^{15A}$ is independently selected.

In another embodiment of this invention $R^7$ is an aryl group substituted with $R^{21}$ groups, and said aryl moiety is phenyl, and said phenyl is substituted with at least one (e.g., 1 to 3, or 1 to 2) $R^{21}$ group, and at least one (e.g., 1 or 2) $R^{21}$ group on said phenyl is selected from the group consisting of: —$SF_5$, —$OSF_5$ and —$Si(R^{15A})_3$, and each $R^{15A}$ is the same or different alkyl group.

In another embodiment of this invention $R^7$ is an aryl group substituted with $R^{21}$ groups, and said aryl moiety is phenyl, and said phenyl is substituted with at least one (e.g., 1 to 3, or 1 to 2) $R^{21}$ group, and at least one (e.g., 1 or 2) $R^{21}$ group on said phenyl is selected from the group consisting of: —$SF_5$, —$OSF_5$ and —$Si(CH_3)_3$.

In another embodiment of this invention $R^7$ is an aryl group substituted with $R^{21}$ groups, and said aryl moiety is phenyl, and said phenyl is substituted with at least one (e.g., 1 to 3, or 1 to 2) $R^{21}$ group, and one $R^{21}$ group on said phenyl is selected from the group consisting of: —$SF_5$, —$OSF_5$ and —$Si(R^{15A})_3$, wherein each $R^{15A}$ is independently selected.

In another embodiment of this invention $R^7$ is an aryl group substituted with $R^{21}$ groups, and said aryl moiety is phenyl, and said phenyl is substituted with at least one (e.g., 1 to 3, or 1 to 2) $R^{21}$ group, and one $R^{21}$ group on said phenyl is selected from the group consisting of: —$SF_5$, —$OSF_5$ and —$Si(R^{15A})_3$, and each $R^{15A}$ is the same or different alkyl group.

In another embodiment of this invention $R^7$ is an aryl group substituted with $R^{21}$ groups, and said aryl moiety is phenyl, and said phenyl is substituted with at least one (e.g., 1 to 3, or 1 to 2) $R^{21}$ group, and one $R^{21}$ group on said phenyl is selected from the group consisting of: —$SF_5$, —$OSF_5$ and —$Si(CH_3)_3$.

In another embodiment of this invention $R^7$ is an aryl group substituted with $R^{21}$ groups, and said aryl moiety is phenyl, and said phenyl is substituted with at least two (e.g., 2 to 3, or 2, or 3) $R^{21}$ groups, and two $R^{21}$ groups on said phenyl is selected from the group consisting of: —$SF_5$, —$OSF_5$ and —$Si(R^{15A})_3$, wherein each $R^{15A}$ is independently selected.

In another embodiment of this invention $R^7$ is an aryl group substituted with $R^{21}$ groups, and said aryl moiety is phenyl, and said phenyl is substituted with at least two (e.g., 2 to 3, or 2, or 3) $R^{21}$ groups, and two $R^{21}$ groups on said phenyl is selected from the group consisting of: —$SF_5$, —$OSF_5$ and —$Si(R^{15A})_3$, and each $R^{15A}$ is the same or different alkyl group.

In another embodiment of this invention $R^7$ is an aryl group substituted with $R^{21}$ groups, and said aryl moiety is phenyl, and said phenyl is substituted with at least two (e.g., 2 to 3, or 2, or 3) $R^{21}$ groups, and two $R^{21}$ groups on said phenyl is selected from the group consisting of: —$SF_5$, —$OSF_5$ and —$Si(CH_3)_3$.

In another embodiment of this invention $R^7$ is an aryl group substituted with $R^{21}$ groups, and said aryl moiety is phenyl, and said phenyl is substituted with at least one (e.g., 1 to 3, or 1 to 2) $R^{21}$ group, and one $R^{21}$ group on said phenyl is —$SF_5$.

In another embodiment of this invention $R^7$ is an aryl group substituted with $R^{21}$ groups, and said aryl moiety is phenyl, and said phenyl is substituted with at least one (e.g., 1 to 3, or 1 to 2) $R^{21}$ group, and one $R^{21}$ group on said phenyl is —$OSF_5$.

In another embodiment of this invention $R^7$ is an aryl group substituted with $R^{21}$ groups, and said aryl moiety is phenyl, and said phenyl is substituted with at least one (e.g., 1 to 3, or 1 to 2) $R^{21}$ group, and one $R^{21}$ group on said phenyl is —Si$(R^{15A})_3$, wherein each $R^{15A}$ is independently selected.

In another embodiment of this invention $R^7$ is an aryl group substituted with $R^{21}$ groups, and said aryl moiety is phenyl, and said phenyl is substituted with at least one (e.g., 1 to 3, or 1 to 2) $R^{21}$ group, and one $R^{21}$ group on said phenyl is —Si$(R^{15A})_3$, and each $R^{15A}$ is the same or different alkyl group.

In another embodiment of this invention $R^7$ is an aryl group substituted with $R^{21}$ groups, and said aryl moiety is phenyl, and said phenyl is substituted with at least one (e.g., 1 to 3, or 1 to 2) $R^{21}$ group, and one $R^{21}$ group on said phenyl is —Si$(CH_3)_3$.

In another embodiment of this invention $R^7$ is an aryl group substituted with $R^{21}$ groups, and said aryl moiety is phenyl, and said phenyl is substituted with at least two (e.g., 2 to 3) $R^{21}$ groups, and two of the $R^{21}$ groups on said phenyl are —$SF_5$.

In another embodiment of this invention $R^7$ is an aryl group substituted with $R^{21}$ groups, and said aryl moiety is phenyl, and said phenyl is substituted with at least two (e.g., 2 to 3) $R^{21}$ groups, and two of the $R^{21}$ groups on said phenyl are —$OSF_5$.

In another embodiment of this invention $R^7$ is an aryl group substituted with $R^{21}$ groups, and said aryl moiety is phenyl, and said phenyl is substituted with at least two (e.g., 2 to 3) $R^{21}$ groups, and two of the $R^{21}$ groups on said phenyl are —Si$(R^{15A})_3$, wherein each $R^{15A}$ is independently selected.

In another embodiment of this invention $R^7$ is an aryl group substituted with $R^{21}$ groups, and said aryl moiety is phenyl, and said phenyl is substituted with at least two (e.g., 2 to 3) $R^{21}$ groups, and two of the $R^{21}$ groups on said phenyl are —Si$(R^{15A})_3$, and each $R^{15A}$ is the same or different alkyl group.

In another embodiment of this invention $R^7$ is an aryl group substituted with $R^{21}$ groups, and said aryl moiety is phenyl, and said phenyl is substituted with at least two (e.g., 2 to 3) $R^{21}$ groups, and two of the $R^{21}$ groups on said phenyl are —Si$(CH_3)_3$.

In another embodiment of this invention $R^6$ is alkyl.
In another embodiment of this invention $R^6$ is a $C_1$ to $C_3$ alkyl group.
In another embodiment of this invention $R^6$ is methyl.
In another embodiment of this invention $R^6$ is ethyl.
In another embodiment of this invention $R^6$ is a $C_3$ alkyl group.
In another embodiment of this invention $R^6$ is isopropyl.
In another embodiment $R^6$ is —C(O)O$R^{15}$.
In another embodiment $R^6$ is —C(O)O$R^{15}$ wherein $R^{15}$ is alkyl.
In another embodiment $R^6$ is —C(O)O$R^{15}$ wherein $R^{15}$ is methyl.

In another embodiment $R^6$ is alkyl substituted with 1-5 $R^{21}$ groups.
In another embodiment $R^6$ is alkyl substituted with one $R^{21}$ group.
In another embodiment $R^6$ is alkyl substituted with one $R^{21}$ group, and said $R^{21}$ group is —O$R^{15}$.
In another embodiment $R^6$ is alkyl substituted with one $R^{21}$ group, and said $R^{21}$ group is —O$R^{15}$, and said $R^{15}$ is alkyl.
In another embodiment $R^6$ is alkyl substituted with one $R^{21}$ group, and said $R^{21}$ group is —O$R^{15}$, and said $R^{15}$ is methyl.
In another embodiment $R^6$ is —$CH_2R^{21}$ (i.e. alkyl substituted with one $R^{21}$ group, wherein said alkyl is —$CH_2$—).
In another embodiment $R^6$ is —$CH_2OR^{15}$ (i.e. alkyl substituted with one $R^{21}$ group, wherein said alkyl is —$CH_2$—, and said $R^{21}$ group is —O$R^{15}$).
In another embodiment $R^6$ is —$CH_2OR^{15}$ (i.e. alkyl substituted with one $R^{21}$ group, wherein said alkyl is —$CH_2$—, and said $R^{21}$ group is —O$R^{15}$), wherein said $R^{15}$ group is alkyl.
In another embodiment $R^6$ is —$CH_2OR^{15}$ (i.e. alkyl substituted with one $R^{21}$ group, wherein said alkyl is —$CH_2$—, and said $R^{21}$ group is —O$R^{15}$), wherein said $R^{15}$ group is methyl.
In another embodiment $R^6$ is —C(O)N$R^{15}R^{16}$.
In another embodiment $R^6$ is —C(O)N$R^{15}R^{16}$ wherein $R^{15}$ and $R^{16}$ are each independently selected from the group consisting of: H and alkyl.
In another embodiment $R^6$ is —C(O)N$R^{15}R^{16}$ wherein $R^{15}$ and $R^{16}$ are the same or different alkyl.
In another embodiment $R^6$ is —C(O)N$R^{15}R^{16}$ wherein $R^{15}$ and $R^{16}$ are each independently selected from the group consisting of: H and methyl.
In another embodiment $R^6$ is —C(O)N$R^{15}R^{16}$ wherein $R^{15}$ and $R^{16}$ are each methyl.

Other embodiments of this invention are directed to any one of the embodiments above directed to Ring (B) wherein $R^6$ is alkyl. In one such embodiment $R^6$ is a $C_1$ to $C_3$ alkyl group. In another embodiment $R^6$ is methyl. In another embodiment $R^6$ is ethyl. In another embodiment $R^6$ is a $C_3$ alkyl group. In another embodiment $R^6$ is isopropyl.

In another embodiment of this invention $R^7$ is an unsubstituted aryl group (e.g., an unsubstituted phenyl group). Thus, in another embodiment $R^7$ is phenyl.

In another embodiment of this invention $R^7$ is a substituted aryl group (e.g., a substituted phenyl group). Thus, in another embodiment $R^7$ is a substituted phenyl group.

In another embodiment of this invention $R^7$ is an aryl group substituted with 1 to 3 independently selected $R^{21}$ groups.

In another embodiment of this invention $R^7$ is an aryl group substituted with one to 3 $R^{21}$ groups, and each $R^{21}$ group is the same or different halo.

In another embodiment of this invention $R^7$ is an aryl group substituted with one to 3 $R^{21}$ groups, and each $R^{21}$ group is F.

In another embodiment of this invention $R^7$ is phenyl, and said phenyl is substituted with one or more independently selected $R^{21}$ groups.

In another embodiment of this invention $R^7$ is phenyl, and said phenyl is substituted with 1 to 3 independently selected $R^{21}$ groups.

In another embodiment of this invention $R^7$ is phenyl, and said phenyl is substituted with 1 or 2 independently selected $R^{21}$ groups.

In another embodiment of this invention $R^7$ is phenyl, and said phenyl is substituted with 1 $R^{21}$ group.

In another embodiment of this invention $R^7$ is phenyl, and said phenyl is substituted with 1 to 3 $R^{21}$ groups, and each $R^{21}$ group is the same or different halo.

In another embodiment of this invention $R^7$ is phenyl, and said phenyl is substituted with three $R^{21}$ halo groups, and each $R^{21}$ group is the same or different halo.

In another embodiment of this invention $R^7$ is phenyl, and said phenyl is substituted with two $R^{21}$ halo groups, and each $R^{21}$ group is the same or different halo.

In another embodiment of this invention $R^7$ is phenyl, and said phenyl is substituted with one $R^{21}$ halo group.

In another embodiment of this invention $R^7$ is phenyl, and said phenyl is substituted with 1 to 3 F (i.e., said phenyl is substituted with 1 to 3 $R^{21}$ groups, and said $R^{21}$ groups are halo, and said halo is F).

In another embodiment of this invention $R^7$ is phenyl, and said phenyl is substituted with one F (i.e., said phenyl is substituted with one $R^{21}$ group, and said $R^{21}$ group is halo, and said halo is F).

In another embodiment of this invention $R^7$ is phenyl, and said phenyl is substituted with two F atoms (i.e., said phenyl is substituted with two $R^{21}$ groups, and said $R^{21}$ groups are halo, and said halo is F).

In another embodiment of this invention $R^7$ is phenyl, and said phenyl is substituted with three F atoms (i.e., said phenyl is substituted with three $R^{21}$ groups, and said $R^{21}$ groups are halo, and said halo is F).

In another embodiment of this invention $R^7$ is phenyl, and said phenyl is substituted with one —CN group.

In another embodiment of this invention $R^7$ is phenyl, and said phenyl is substituted with one or two $R^{21}$ alkyl groups (e.g. methyl groups), wherein each $R^{21}$ group is substituted with 1 to 3 $R^{22}$ halo groups (e.g. F groups).

In another embodiment of this invention $R^7$ is phenyl, and said phenyl is substituted with one or two —$CF_3$ groups (i.e. there are one or two $R^{21}$ alkyl groups (i.e. methyl groups) each substituted with 3 $R^{22}$ halo (i.e. F) groups).

In another embodiment of this invention $R^7$ is selected from the group consisting of:

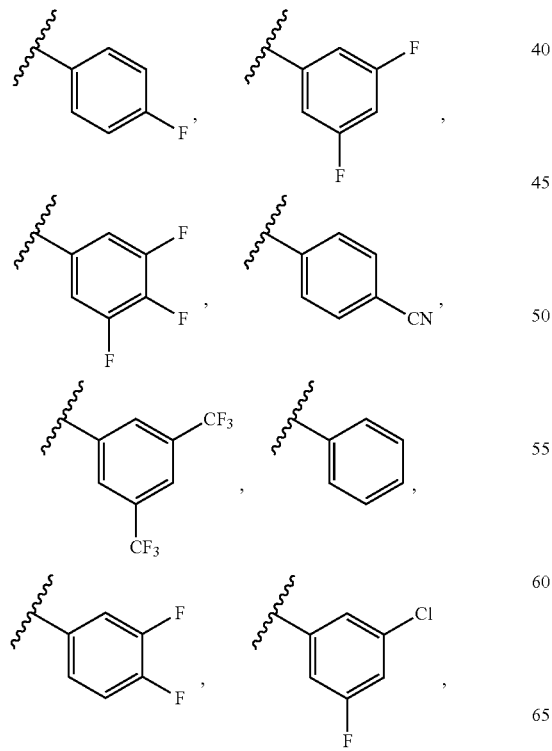

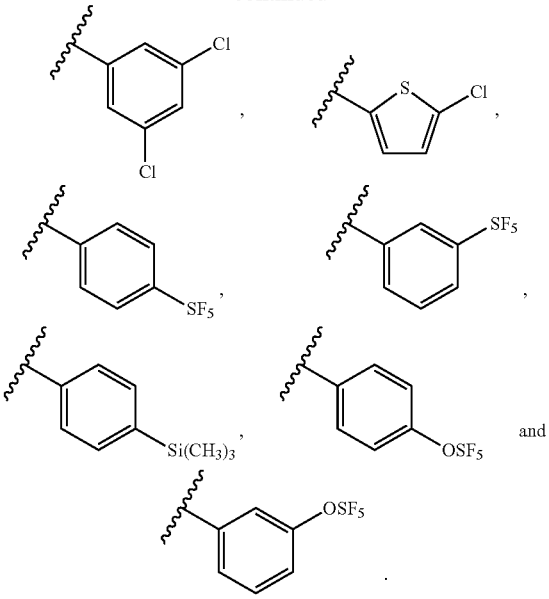

In another embodiment of this invention $R^7$ is:

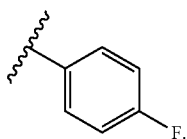

In another embodiment of this invention $R^7$ is:

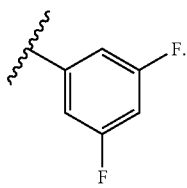 [SMILES: *c1cc(F)cc(F)c1]

In another embodiment of this invention $R^7$ is:

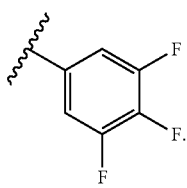 [SMILES: *c1cc(F)c(F)c(F)c1]

In another embodiment of this invention $R^7$ is:

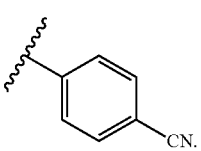 [SMILES: *c1ccc(C#N)cc1]

In another embodiment of this invention R⁷ is:

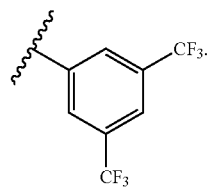

In another embodiment of this invention R⁷ is:

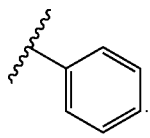 [SMILES: *c1ccccc1]

In another embodiment of this invention R⁷ is:

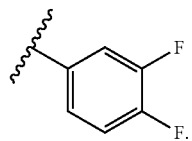 [SMILES: *c1ccc(F)c(F)c1]

In another embodiment of this invention R⁷ is:

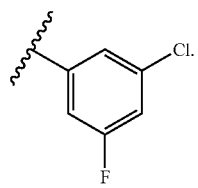 [SMILES: *c1cc(F)cc(Cl)c1]

In another embodiment of this invention R⁷ is:

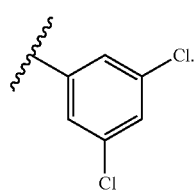 [SMILES: *c1cc(Cl)cc(Cl)c1]

In another embodiment of this invention R⁷ is:

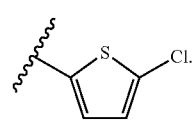

In another embodiment of this invention R⁷ is:

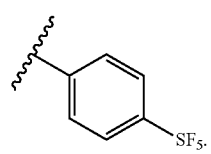

In another embodiment of this invention R⁷ is:

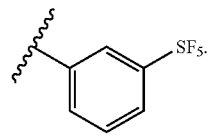

In another embodiment of this invention R⁷ is:

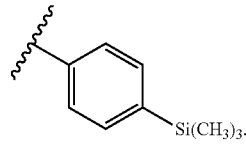

In another embodiment of this invention R⁷ is:

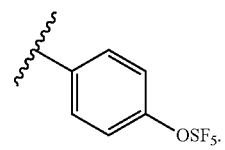

In another embodiment of this invention R⁷ is:

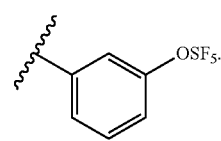

Other embodiments of this invention are directed to any one of the embodiments above directed to Ring (B) wherein:
(a) R⁶ is:
(1) alkyl, or
(2) $C_1$ to $C_3$ alkyl, or
(3) methyl, or
(4) ethyl, or
(5) a $C_3$ alkyl group, or
(6) isopropyl, or
(7) —C(O)OR¹⁵, or
(8) —C(O)OR¹⁵ wherein R¹⁵ is alkyl, or
(9) —C(O)OR¹⁵ wherein R¹⁵ is methyl, or
(10) alkyl substituted with 1-5 R²¹ groups, or
(11) alkyl substituted with one R²¹ group, or
(12) alkyl substituted with one R²¹ group, and said R²¹ group is —OR¹⁵, or
(13) alkyl substituted with one R²¹ group, and said R²¹ group is —OR¹⁵, and said R¹⁵ is alkyl, or
(14) alkyl substituted with one R²¹ group, and said R²¹ group is —OR¹⁵, and said R¹⁵ is methyl, or
(15) —CH₂R²¹ (i.e. alkyl substituted with one R²¹ group, wherein said alkyl is —CH₂—), or
(16) —CH₂OR¹⁵ (i.e. alkyl substituted with one R²¹ group, wherein said alkyl is —CH₂—, and said R²¹ group is —OR¹⁵), or
(17) —CH₂OR¹⁵ (i.e. alkyl substituted with one R²¹ group, wherein said alkyl is —CH₂—, and said R²¹ group is —OR¹⁵), wherein said R¹⁵ group is alkyl, or

(18) —CH$_2$OR$^{15}$ (i.e. alkyl substituted with one R$^{21}$ group, wherein said alkyl is —CH$_2$—, and said R$^{21}$ group is —OR$^{15}$), wherein said R$^{15}$ group is methyl, or

(19) —C(O)NR$^{15}$R$^{16}$, or

(20) —C(O)NR$^{15}$R$^{16}$ wherein R$^{15}$ and R$^{16}$ are each independently selected from the group consisting of: H and alkyl, or

(21) —C(O)NR$^{15}$R$^{16}$ wherein R$^{15}$ and R$^{16}$ are the same or different alkyl, or

(22) —C(O)NR$^{15}$R$^{16}$ wherein R$^{15}$ and R$^{16}$ are each independently selected from the group consisting of: H and methyl, or

(23) —C(O)NR$^{15}$R$^{16}$ wherein R$^{15}$ and R$^{16}$ are each methyl; and (b) R$^7$ is as defined in any one of the embodiments above that are directed to R$^7$.

Other embodiments of this invention are directed to any one of the embodiments above directed to Ring (B) wherein:

(a) R$^6$ is:
(1) alkyl, or
(2) C$_1$ to C$_3$ alkyl, or
(3) methyl, or
(4) ethyl, or
(5) a C$_3$ alkyl group, or
(6) isopropyl, or
(7) —C(O)OR$^{15}$, or
(8) —C(O)OR$^{15}$ wherein R$^{15}$ is alkyl, or
(9) —C(O)OR$^{15}$ wherein R$^{15}$ is methyl, or
(10) alkyl substituted with 1-5 R$^{21}$ groups, or
(11) alkyl substituted with one R$^{21}$ group, or
(12) alkyl substituted with one R$^{21}$ group, and said R$^{21}$ group is —OR$^{15}$, or
(13) alkyl substituted with one R$^{21}$ group, and said R$^{21}$ group is —OR$^{15}$, and said R$^{15}$ is alkyl, or
(14) alkyl substituted with one R$^{21}$ group, and said R$^{21}$ group is —OR$^{15}$, and said R$^{15}$ is methyl, or
(15) —CH$_2$R$^{21}$ (i.e. alkyl substituted with one R$^{21}$ group, wherein said alkyl is —CH$_2$—), or
(16) —CH$_2$OR$^{15}$ (i.e. alkyl substituted with one R$^{21}$ group, wherein said alkyl is —CH$_2$—, and said R$^{21}$ group is —OR$^{15}$), or
(17) —CH$_2$OR$^{15}$ (i.e. alkyl substituted with one R$^{21}$ group, wherein said alkyl is —CH$_2$—, and said R$^{21}$ group is —OR$^{15}$), wherein said R$^{15}$ group is alkyl, or
(18) —CH$_2$OR$^{15}$ (i.e. alkyl substituted with one R$^{21}$ group, wherein said alkyl is —CH$_2$—, and said R$^{21}$ group is —OR$^{15}$), wherein said R$^{15}$ group is methyl, or
(19) —C(O)NR$^{15}$R$^{16}$, or
(20) —C(O)NR$^{15}$R$^{16}$ wherein R$^{15}$ and R$^{16}$ are each independently selected from the group consisting of: H and alkyl, or
(21) —C(O)NR$^{15}$R$^{16}$ wherein R$^{15}$ and R$^{16}$ are the same or different alkyl, or
(22) —C(O)NR$^{15}$R$^{16}$ wherein R$^{15}$ and R$^{16}$ are each independently selected from the group consisting of: H and methyl, or
(23) —C(O)NR$^{15}$R$^{16}$ wherein R$^{15}$ and R$^{16}$ are each methyl; and (b) R$^7$ is selected from the group consisting of:

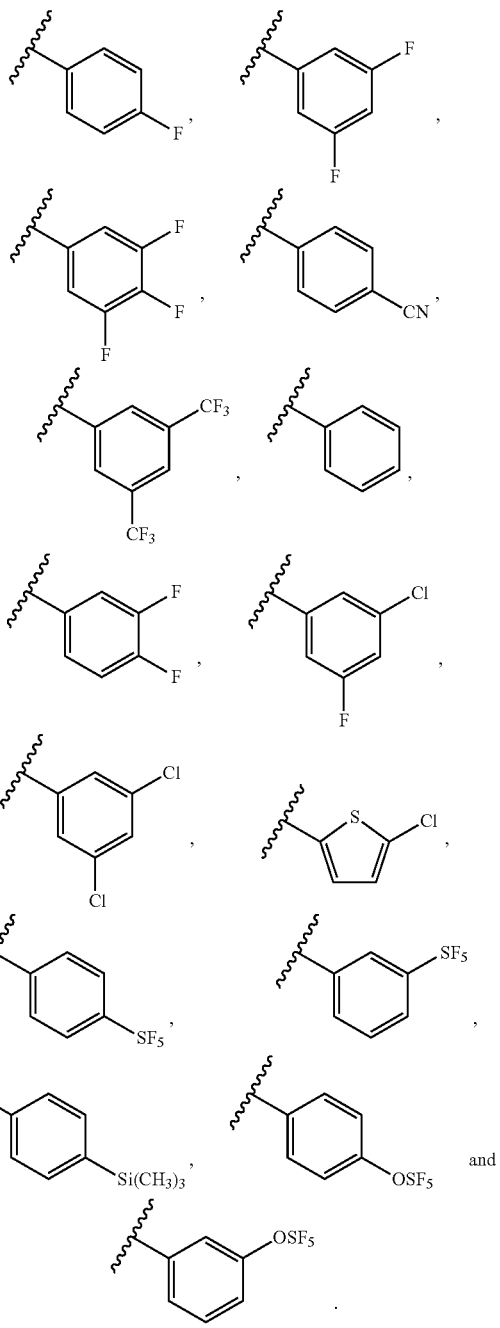

Other embodiments of this invention are directed to any one of the embodiments above directed to Ring (B) wherein:

(a) R$^6$ is:
(1) alkyl, or
(2) C$_1$ to C$_3$ alkyl, or
(3) methyl, or
(4) ethyl, or
(5) a C$_3$ alkyl group, or
(6) isopropyl, or
(7) —C(O)OR$^{15}$, or
(8) —C(O)OR$^{15}$ wherein R$^{15}$ is alkyl, or
(9) —C(O)OR$^{15}$ wherein R$^{15}$ is methyl, or
(10) alkyl substituted with 1-5 R$^{21}$ groups, or

(11) alkyl substituted with one $R^{21}$ group, or
(12) alkyl substituted with one $R^{21}$ group, and said $R^{21}$ group is —$OR^{15}$, or
(13) alkyl substituted with one $R^{21}$ group, and said $R^{21}$ group is —$OR^{15}$, and said $R^{15}$ is alkyl, or
(14) alkyl substituted with one $R^{21}$ group, and said $R^{21}$ group is —$OR^{15}$, and said $R^{15}$ is methyl, or
(15) —$CH_2R^{21}$ (i.e. alkyl substituted with one $R^{21}$ group, wherein said alkyl is —$CH_2$—), or
(16) —$CH_2OR^{15}$ (i.e. alkyl substituted with one $R^{21}$ group, wherein said alkyl is —$CH_2$—, and said $R^{21}$ group is —$OR^{15}$), or
(17) —$CH_2OR^{15}$ (i.e. alkyl substituted with one $R^{21}$ group, wherein said alkyl is —$CH_2$—, and said $R^{21}$ group is —$OR^{15}$), wherein said $R^{15}$ group is alkyl, or
(18) —$CH_2OR^{15}$ (i.e. alkyl substituted with one $R^{21}$ group, wherein said alkyl is —$CH_2$—, and said $R^{21}$ group is —$OR^{15}$), wherein said $R^{15}$ group is methyl, or
(19) —$C(O)NR^{15}R^{16}$, or
(20) —$C(O)NR^{15}R^{16}$ wherein $R^{15}$ and $R^{16}$ are each independently selected from the group consisting of: H and alkyl, or
(21) —$C(O)NR^{15}R^{16}$ wherein $R^{15}$ and $R^{16}$ are the same or different alkyl, or
(22) —$C(O)NR^{15}R^{16}$ wherein $R^{15}$ and $R^{16}$ are each independently selected from the group consisting of: H and methyl, or
(23) —$C(O)NR^{15}R^{16}$ wherein $R^{15}$ and $R^{16}$ are each methyl; and
(b) $R^7$ is selected from the group consisting of:

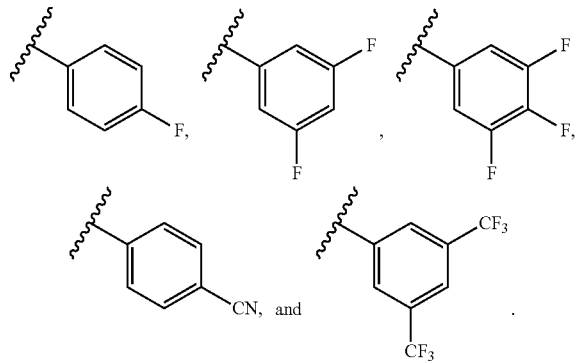

Other embodiments of this invention are directed to any one of the embodiments above directed to Ring (B) wherein $R^6$ is alkyl and $R^7$ is as defined in any one of the above embodiments directed to $R^7$. In one such embodiment $R^6$ is a $C_1$ to $C_3$ alkyl group. In another embodiment $R^6$ is methyl. In another embodiment $R^6$ is ethyl. In another embodiment $R^6$ is a $C_3$ alkyl group. In another embodiment $R^6$ is isopropyl.

In another embodiment of this invention $R^{10}$ is selected from the group consisting of aryl and aryl substituted with one or more $R^{21}$ groups.

In another embodiment of this invention $R^9$ is selected from the group consisting of heteroaryl and heteroaryl substituted with one or more $R^{21}$ groups, and wherein each $R^{21}$ is independently selected.

In another embodiment of this invention $R^{10}$ is selected from the group consisting of aryl and aryl substituted with one or more $R^{21}$ groups, and $R^9$ is selected from the group consisting of heteroaryl and heteroaryl substituted with one or more $R^{21}$ groups, and wherein each $R^{21}$ is independently selected.

Other embodiments of this invention are directed to any one of the embodiments above directed to Ring (B) wherein $R^6$ is alkyl, $R^7$ is as defined in any one of the above embodiments directed to $R^7$, $R^{10}$ is selected from the group consisting of aryl and aryl substituted with one or more independently selected $R^{21}$ groups, and $R^9$ is selected from the group consisting of heteroaryl and heteroaryl substituted with one or more independently selected $R^{21}$ groups. In one such embodiment $R^6$ is a $C_1$ to $C_3$ alkyl group. In another embodiment $R^6$ is methyl. In another embodiment $R^6$ is ethyl. In another embodiment $R^6$ is a $C_3$ alkyl group. In another embodiment $R^6$ is isopropyl.

In another embodiment of this invention $R^{10}$ is heteroaryl (e.g. pyridyl).

In another embodiment of this invention $R^{10}$ is heteroaryl substituted with one or more $R^{21}$ groups (e.g. pyridyl substituted with one or more $R^{21}$ groups).

In another embodiment of this invention $R^{10}$ is selected from the group consisting of heteroaryl and heteroaryl substituted with one or more $R^{21}$ groups, and $R^9$ group is selected from the group consisting of heteroaryl and heteroaryl substituted with one or more $R^{21}$ groups, and wherein each $R^{21}$ is independently selected.

Other embodiments of this invention are directed to the compounds of formula (I) wherein $R^{10}$ is heteroaryl or heteroaryl substituted with one or more $R^{21}$ groups, and $R^9$ is heteroaryl (e.g., imidazolyl) or heteroaryl (e.g., imidazolyl) substituted with one or more (e.g., one or two, or one) $R^{21}$ groups (e.g., alkyl, such as, for example, methyl).

Other embodiments of this invention are directed to any one of the embodiments above directed to Ring (B) wherein $R^6$ is alkyl, $R^7$ is as defined in any one of the above embodiments directed to $R^7$, $R^{10}$ is selected from the group consisting of heteroaryl and heteroaryl substituted with one or more independently selected $R^{21}$ groups, and $R^9$ is selected from the group consisting of heteroaryl and heteroaryl substituted with one or more independently selected $R^{21}$ groups. In one such embodiment $R^6$ is a $C_1$ to $C_3$ alkyl group. In another embodiment $R^6$ is methyl. In another embodiment $R^6$ is ethyl. In another embodiment $R^6$ is a $C_3$ alkyl group. In another embodiment $R^6$ is isopropyl.

In another embodiment of this invention $R^{10}$ is aryl.

In another embodiment of this invention $R^{10}$ aryl is aryl and said aryl is phenyl.

In another embodiment of this invention $R^{10}$ is aryl substituted with one or more $R^{21}$ groups.

In another embodiment of this invention $R^{10}$ is aryl substituted with one or more $R^{21}$ groups, and said aryl is phenyl, i.e., said $R^{10}$ group is phenyl substituted with one or more $R^{21}$ groups.

In another embodiment of this invention $R^{10}$ is phenyl substituted with one or more $R^{21}$ groups, and each $R^{21}$ group is the same or different —$OR^{15}$ group.

In another embodiment of this invention $R^{10}$ is phenyl substituted with one or more $R^{21}$ groups, and each $R^{21}$ group is the same or different —$OR^{15}$ group, and said $R^{15}$ is alkyl, and each alkyl is independently selected.

In another embodiment of this invention $R^{10}$ is phenyl substituted with one $R^{21}$ group, and said $R^{21}$ group is —$OR^{15}$, and said $R^{15}$ is alkyl.

In another embodiment of this invention $R^{10}$ is phenyl substituted with one $R^{21}$ group, and said $R^{21}$ group is —$OR^{15}$, and said $R^{15}$ is alkyl, and said alkyl is methyl.

In another embodiment of this invention $R^{10}$ is phenyl substituted with one or more (e.g., one or two, or one) independently selected $R^{21}$ halo groups.

In another embodiment of this invention $R^{10}$ is phenyl substituted with one $R^{21}$ group, and said $R^{21}$ group is halo.

In another embodiment of this invention $R^{10}$ is phenyl substituted with one $R^{21}$ group, and said $R^{21}$ group is F.

In another embodiment of this invention $R^{10}$ is phenyl substituted with one $R^{21}$ group and said $R^{21}$ is an —$OR^{15}$ group, and $R^{15}$ is an $(R^{18})_n$alkyl group, and $R^{18}$ is halo, and n is 1 to 3, and each halo is independently selected.

In another embodiment of this invention $R^{10}$ is phenyl substituted with one $R^{21}$ group and said $R^{21}$ is an —$OR^{15}$ group, and $R^{15}$ is an $(R^{18})_n$alkyl group, and $R^{18}$ is F, and n is 3.

In another embodiment of this invention $R^{10}$ is phenyl substituted with one $R^{21}$ group and said $R^{21}$ is an —$OR^{15}$ group, and $R^{15}$ is an $(R^{18})_n$alkyl group, and $R^{18}$ is F, and n is 3, and the alkyl is methyl (i.e., the $R^{21}$ substituent is —$OCF_3$).

In another embodiment of this invention $R^9$ is heteroaryl.

In another embodiment of this invention $R^9$ is heteroaryl substituted with one or more $R^{21}$ groups.

In another embodiment of this invention $R^9$ is heteroaryl substituted with one or more $R^{21}$ groups, and said $R^{21}$ groups are the same or different alkyl.

In another embodiment of this invention $R^9$ is heteroaryl substituted with one $R^{21}$ group, and said $R^{21}$ is alkyl.

In another embodiment of this invention $R^9$ is heteroaryl substituted with one $R^{21}$ group, and said $R^{21}$ is alkyl, and said alkyl is methyl.

In another embodiment of this invention $R^9$ is and said heteroaryl is imidazoyl.

In another embodiment of this invention $R^9$ is imidazolyl substituted with one or more $R^{21}$ groups.

In another embodiment of this invention $R^9$ is imidazolyl substituted with one or more $R^{21}$ groups, and said $R^{21}$ groups are the same or different alkyl.

In another embodiment of this invention $R^9$ is imidazolyl substituted with one $R^{21}$ group, and said $R^{21}$ is alkyl.

In another embodiment of this invention $R^9$ is imidazolyl substituted with one $R^{21}$ group, and said $R^{21}$ is alkyl, and said alkyl is methyl.

In another embodiment of this invention $R^{10}$ is selected from the group consisting of aryl and aryl substituted with one or more $R^{21}$ groups, and said $R^9$ group is selected from the group consisting of heteroaryl and heteroaryl substituted with one or more $R^{21}$ groups, wherein each $R^{21}$ is independently selected.

In another embodiment of this invention $R^{10}$ is phenyl substituted with one or more $R^{21}$ groups, and said $R^9$ is imidazolyl substituted with one or more $R^{21}$ groups, wherein each $R^{21}$ is independently selected.

In another embodiment of this invention $R^{10}$ is phenyl substituted with one $R^{21}$ group, and said $R^9$ is imidazolyl substituted with one $R^{21}$ group, wherein each $R^{21}$ is independently selected.

In another embodiment of this invention $R^{10}$ is phenyl substituted with one or more independently selected —$OR^{15}$ groups, and said $R^9$ is imidazolyl substituted with one or more independently selected alkyl groups.

In another embodiment of this invention $R^{10}$ is phenyl substituted with one or more independently selected —$OR^{15}$ groups, and said $R^9$ is imidazolyl substituted with one or more independently selected alkyl groups, and each $R^{15}$ is the same or different alkyl group.

In another embodiment of this invention $R^{10}$ is phenyl substituted with one —$OR^{15}$ group, and said $R^9$ is imidazolyl substituted with one alkyl group.

In another embodiment of this invention $R^{10}$ is phenyl substituted with one —$OR^{15}$ group, and said $R^9$ is imidazolyl substituted with one alkyl group, and $R^{15}$ is alkyl, and wherein the $R^{15}$ alkyl group, and the alkyl group on said imidazolyl are independently selected.

In another embodiment of this invention $R^{10}$ is phenyl substituted with one —$OR^{15}$ group, and said $R^9$ is imidazolyl substituted with one methyl group, and $R^{15}$ is methyl, and wherein the $R^{15}$ alkyl group, and the alkyl group on said imidazolyl are independently selected.

Other embodiments of the compounds of formula (I) are directed to any one of the above embodiments wherein $R^9$ is:

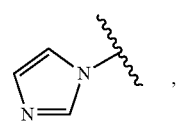

1i

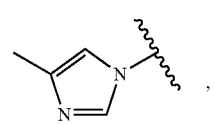

2i

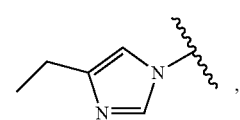

3i

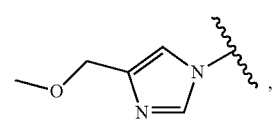

4i

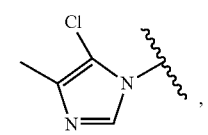

5i

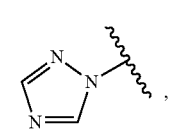

6i

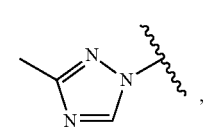

7i

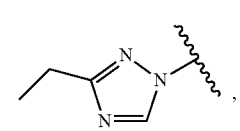

8i

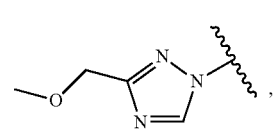

9i

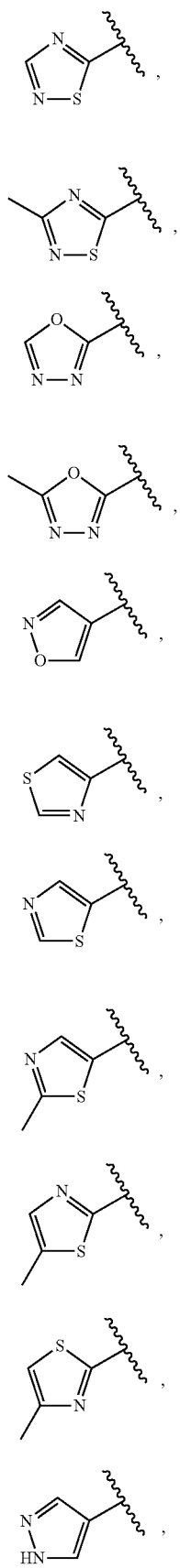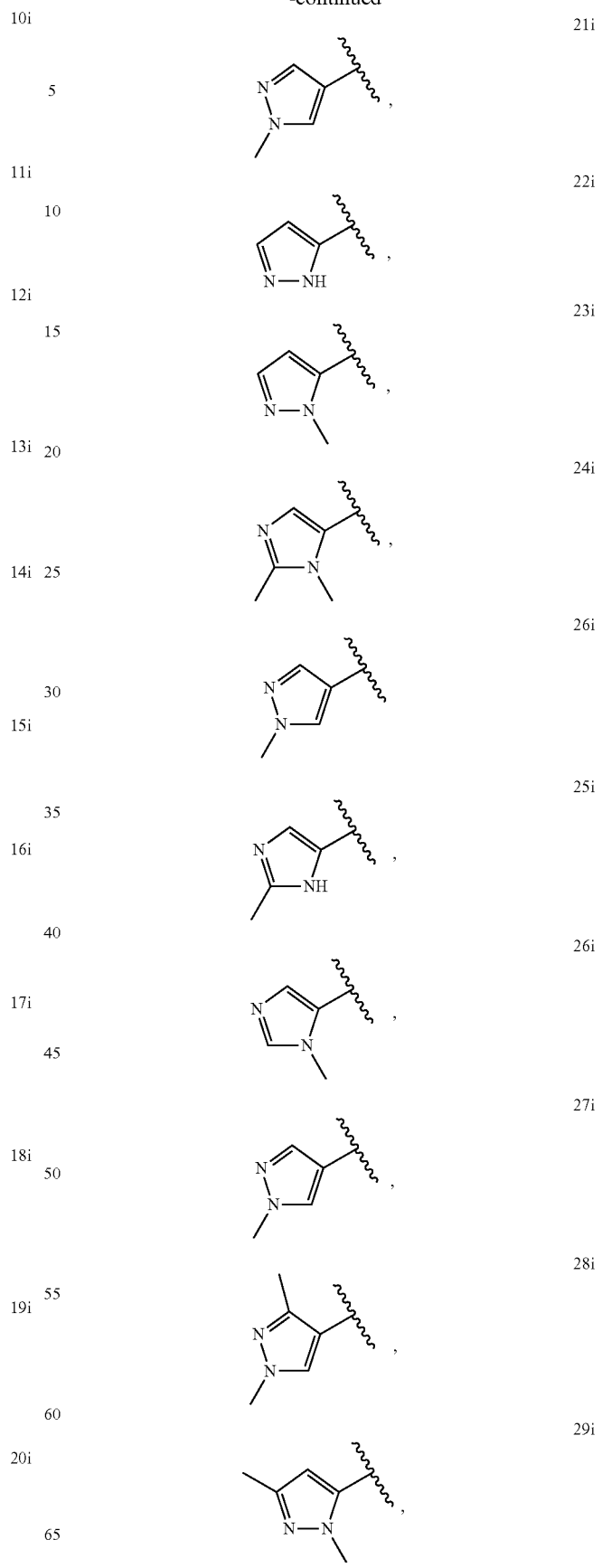

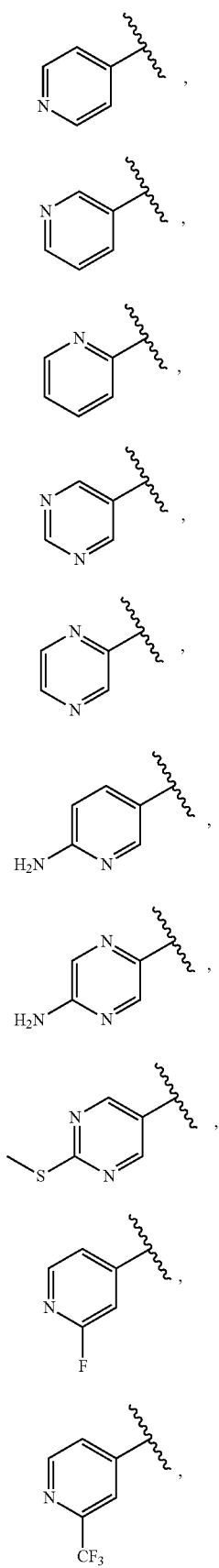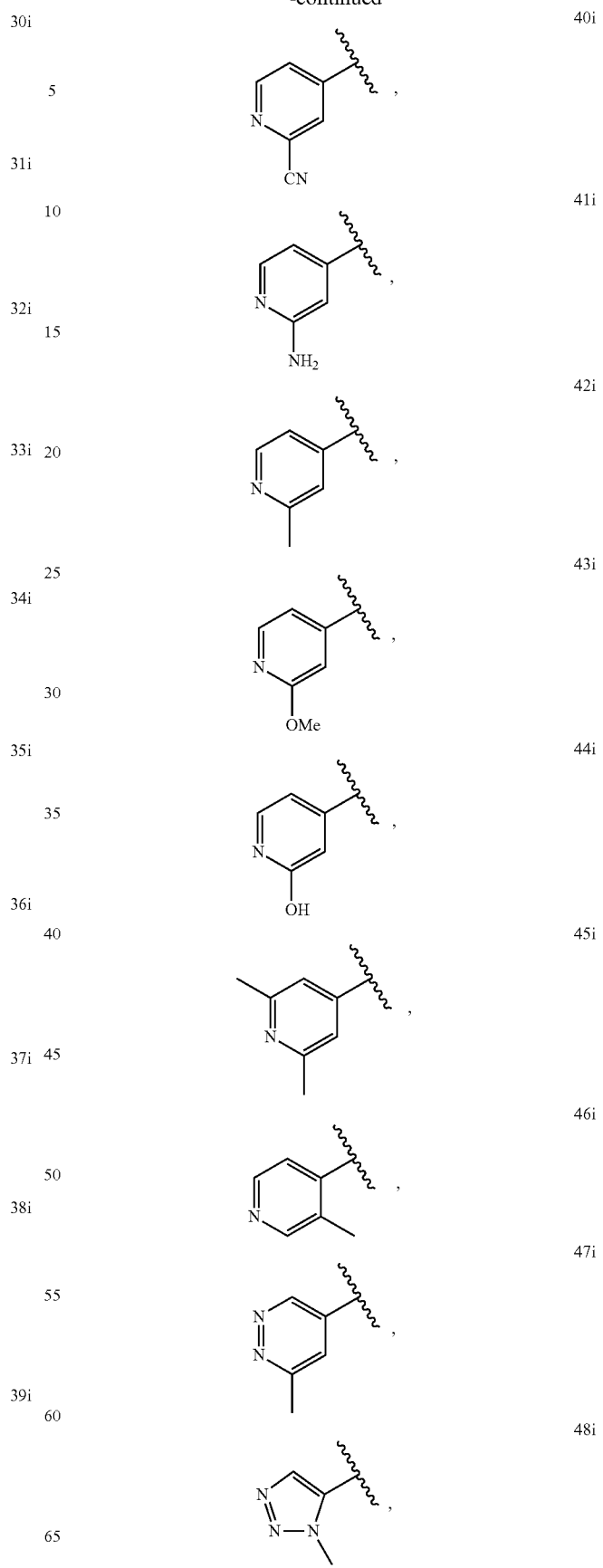

-continued

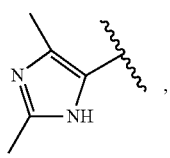 49i

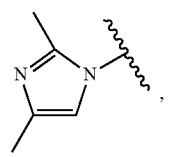 50i

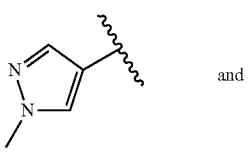 and 51i

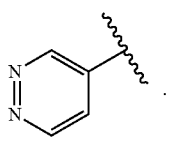 . 52i

Other embodiments of the compounds of formula (I) are directed to any one of the above embodiments wherein $R^9$ is:

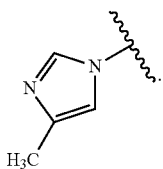

Other embodiments of the compounds of formula (I) are directed to any one of the above embodiments wherein $R^{10}$ is:

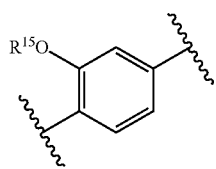

(wherein the —$OR^{15}$ is ortho to the carbon to which $R^9$ is bound to, i.e., the $R^9$—$R^{10}$— moiety is:

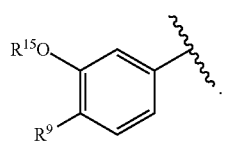

Other embodiments for the compounds of formula (I) are directed to any one of the above embodiments wherein $R^{10}$ is:

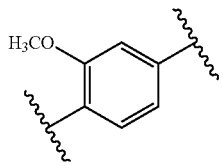 [SMILES: *c1ccc(*)c(OC)c1]

(wherein the —$OCH_3$ is ortho to the carbon to which $R^9$ is bound to, i.e., the $R^9$—$R^{10}$— moiety is:

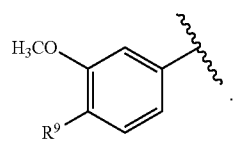

In another embodiment of this invention the $R^9$—$R^{10}$— moiety is:

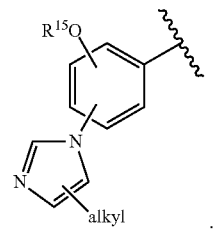

In another embodiment of this invention the $R^9$—$R^{10}$— moiety is:

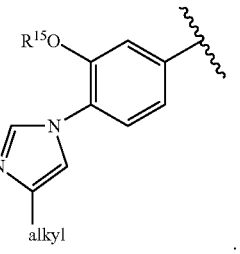

In another embodiment of this invention the $R^9$—$R^{10}$— moiety is:

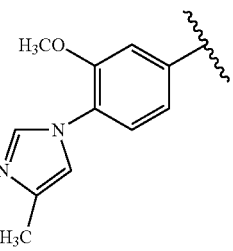

In another embodiment of this invention the $R^9$—$R^{10}$—moiety is:

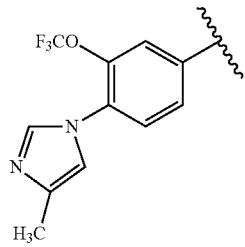

In another embodiment of this invention the $R^9$—$R^{10}$—moiety is:

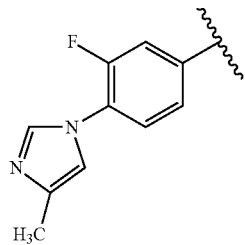

In another embodiment of this invention the $R^9$—$R^{10}$—moiety is:

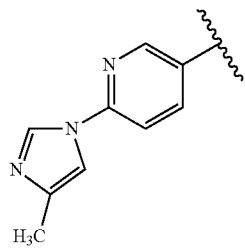

In another embodiment of this invention the $R^9$—$R^{10}$—moiety is:

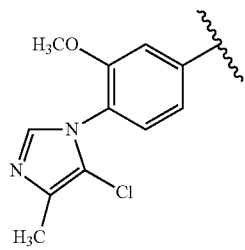

In another embodiment of this invention the $R^9$—$R^{10}$—moiety is:

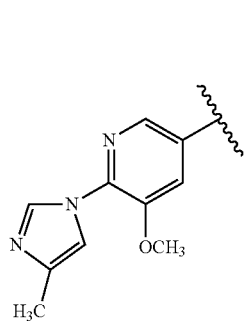

In another embodiment of this invention $R^7$ is selected from the group consisting of:

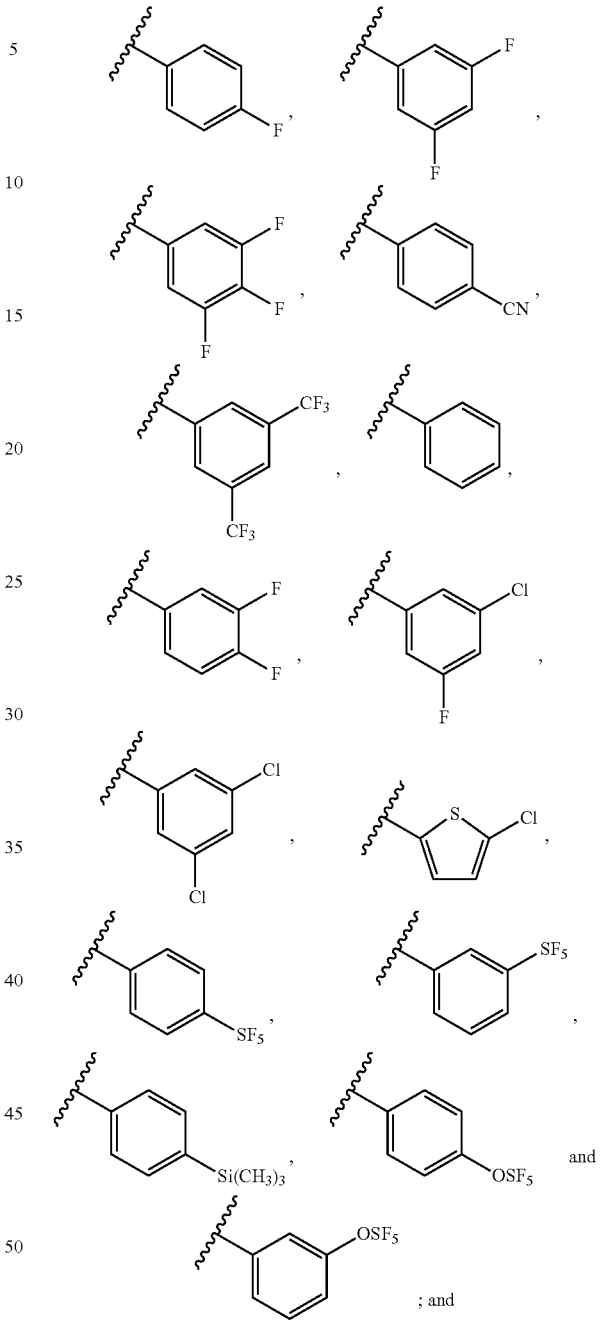

; and the $R^9$—$R^{10}$— moiety is selected from the group consisting of:

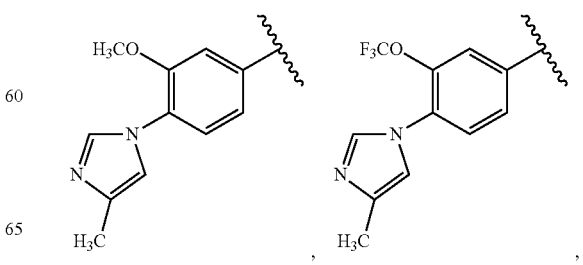

-continued
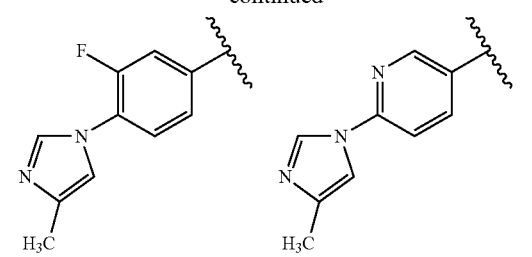
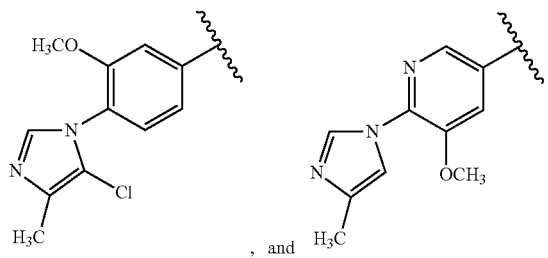
, and
In another embodiment of this invention $R^7$ is selected from the group consisting of:
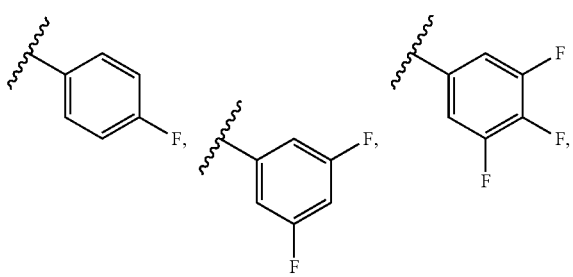
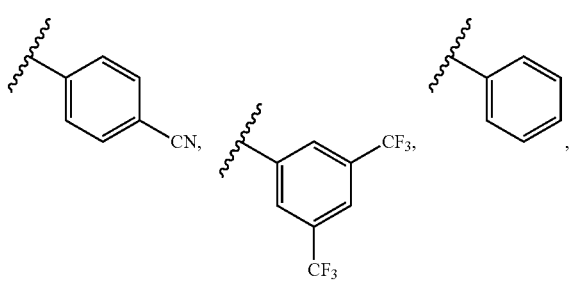
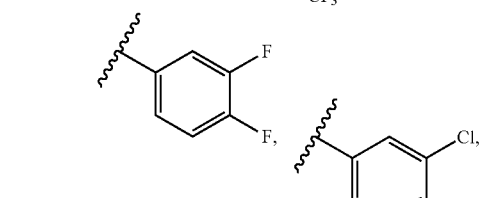
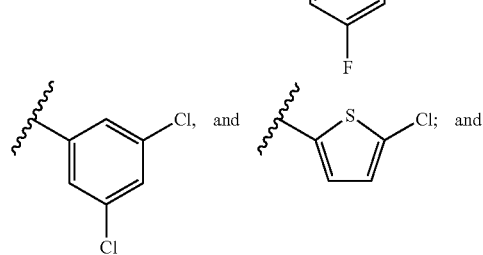
the $R^9$—$R^{10}$— moiety is selected from the group consisting of:
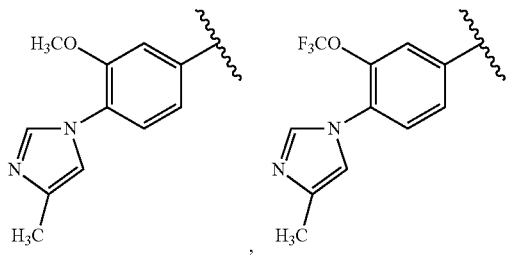
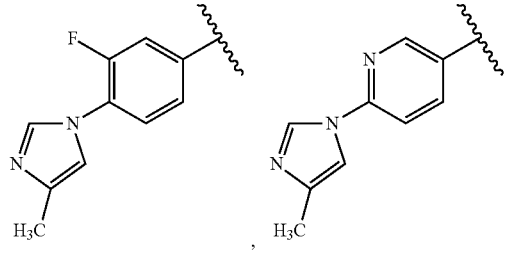
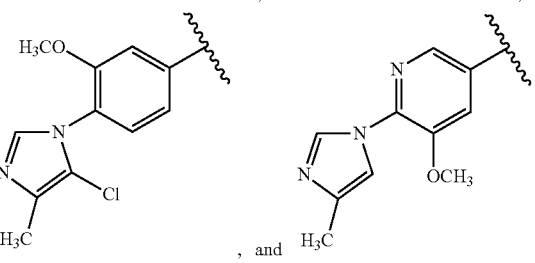
, and
In another embodiment of this invention $R^7$ is selected from the group consisting of:
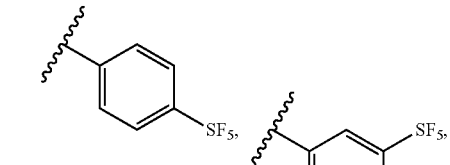
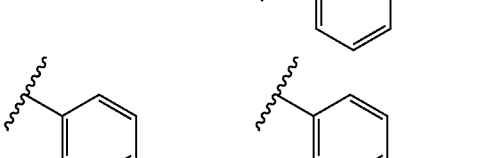
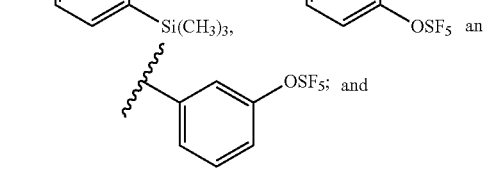; and
the $R^9$—$R^{10}$— moiety is selected from the group consisting of:
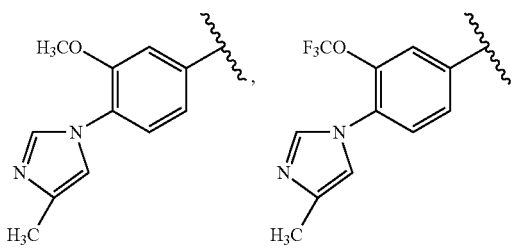

-continued
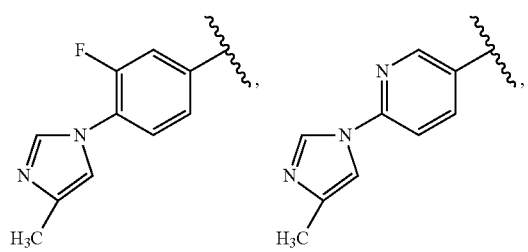
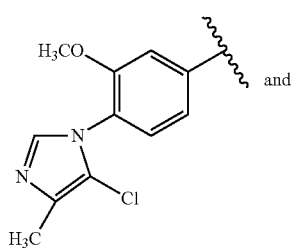
In another embodiment of this invention R⁷ is selected from the group consisting of:
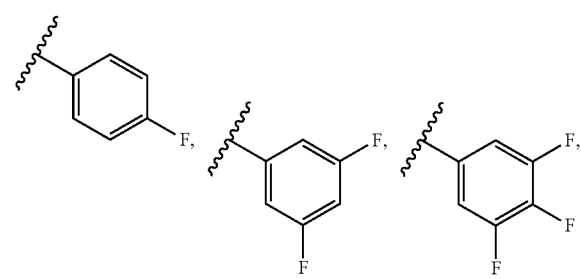
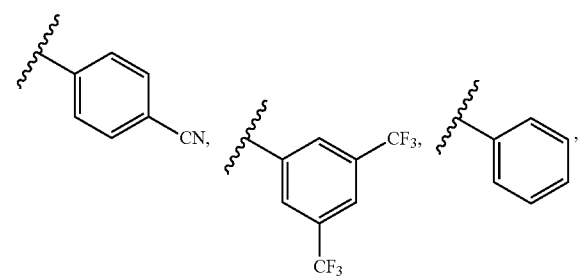
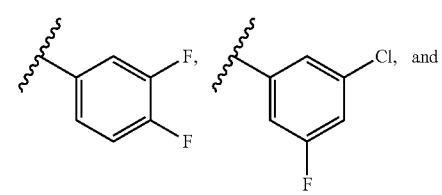
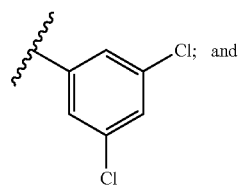
the R⁹—R¹⁰— moiety is selected from the group consisting of:
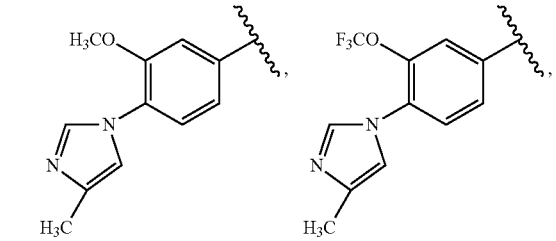
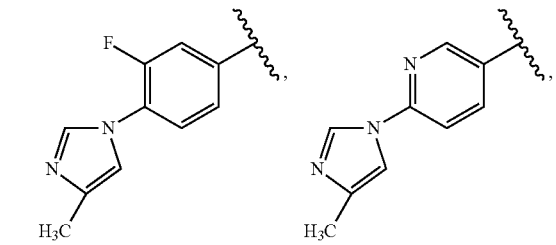
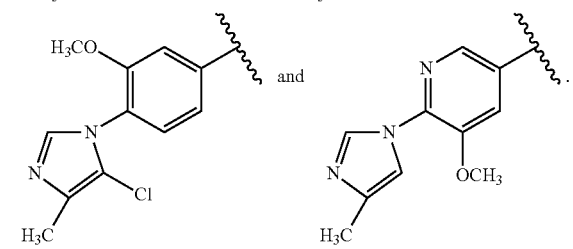
In another embodiment of this invention R⁷ is selected from the group consisting of:
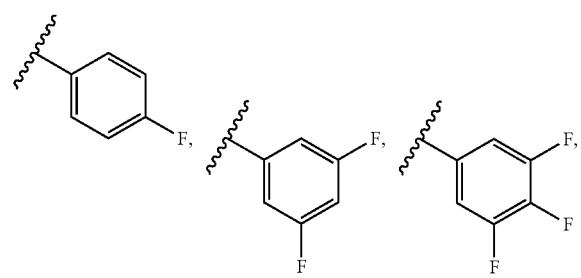
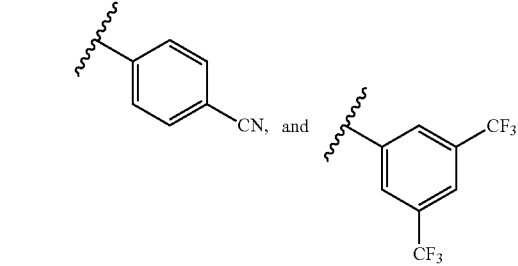
the R⁹—R¹⁰— moiety is selected from the group consisting of:
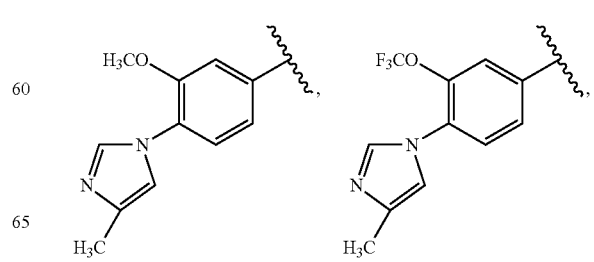

-continued
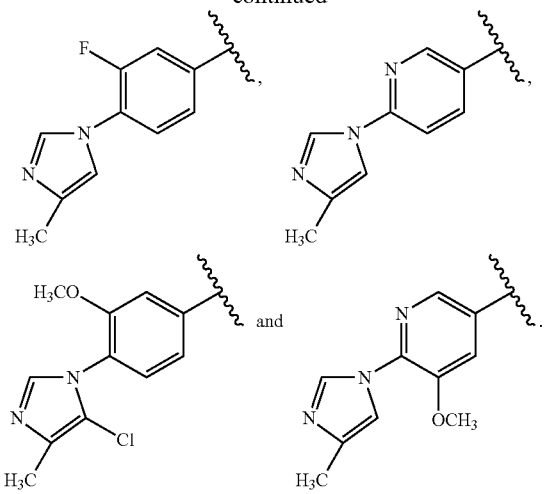
In another embodiment of this invention R$^7$ is selected from the group consisting of:
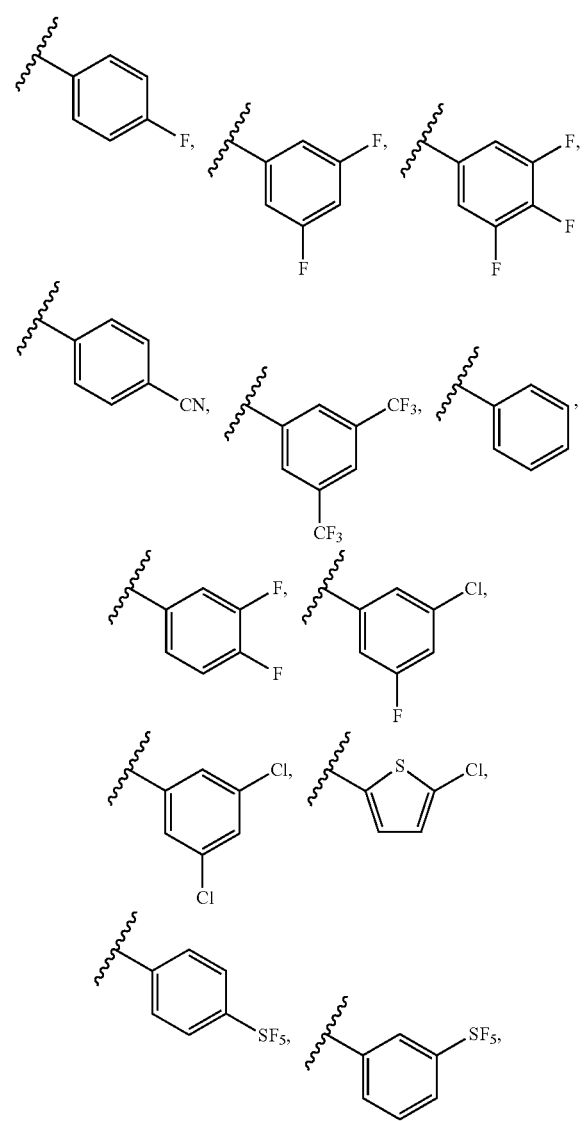
-continued
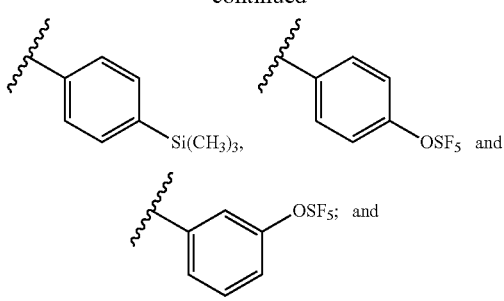
the R$^9$—R$^{10}$— moiety is:
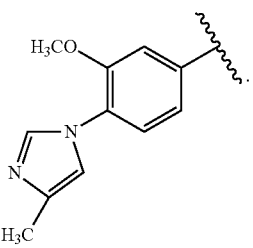
In another embodiment of this invention R$^7$ is selected from the group consisting of:

the R$^9$—R$^{10}$— moiety is:
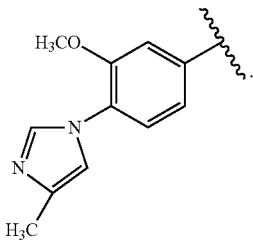
In another embodiment of this invention R$^7$ is selected from the group consisting of:
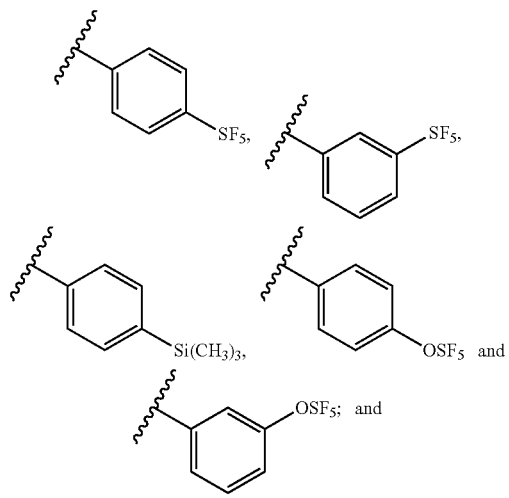
the R$^9$—R$^{10}$— moiety is:
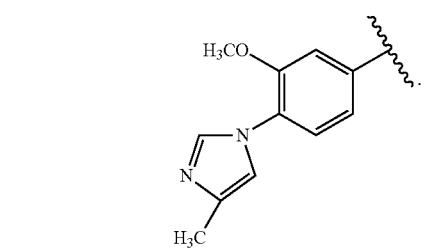 [SMILES: *c1ccc(-n2cnc(C)c2)c(OC)c1]
In another embodiment of this invention R$^7$ is selected from the group consisting of:
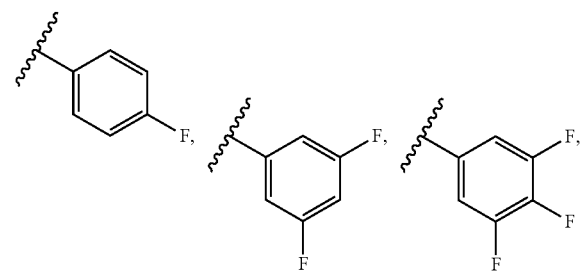
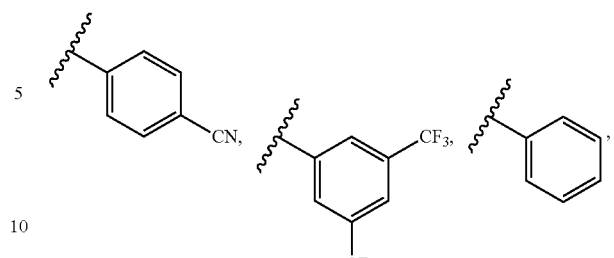
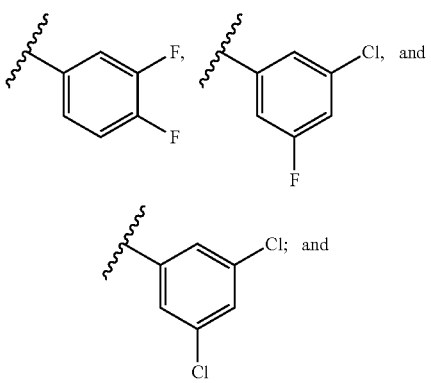
the R$^9$—R$^{10}$— moiety is:
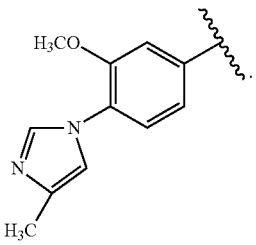 [SMILES: *c1ccc(-n2cnc(C)c2)c(OC)c1]
In another embodiment of this invention R$^7$ is selected from the group consisting of:
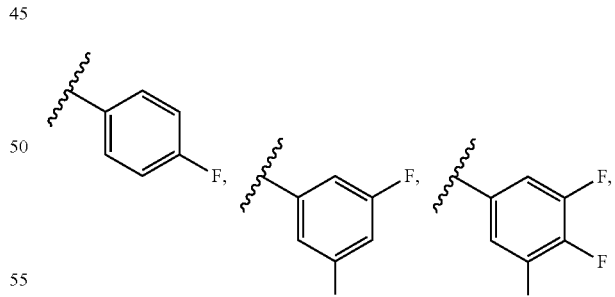
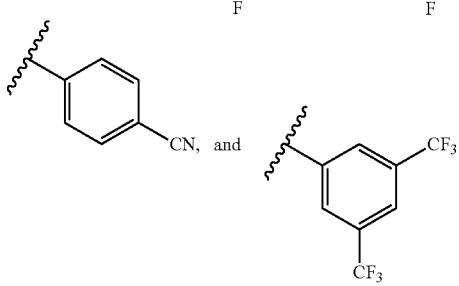

the R$^9$—R$^{10}$— moiety is:

[chemical structure: benzene ring with H$_3$CO substituent, connected to an N-linked imidazole bearing an H$_3$C group]

In another embodiment of this invention: (a) R$^6$ is alkyl (e.g., methyl), (b) R$^7$ is an aryl group, or R$^7$ is an aryl group substituted with 1 to 3 independently selected R$^{21}$ groups, (c) R$^{10}$ is selected from the group consisting of aryl and aryl substituted with one or more independently selected R$^{21}$ groups, and (d) R$^9$ is selected from the group consisting of heteroaryl and heteroaryl substituted with one or more independently selected R$^{21}$ groups.

In another embodiment of this invention: (a) R$^6$ is alkyl (e.g., methyl), (b) R$^7$ is phenyl, or R$^7$ is phenyl substituted with 1 to 3 independently selected R$^{21}$ groups, (c) R$^{10}$ is selected from the group consisting of aryl and aryl substituted with one or more independently selected R$^{21}$ groups, and (d) R$^9$ is selected from the group consisting of heteroaryl and heteroaryl substituted with one or more independently selected R$^{21}$ groups.

In another embodiment of this invention: (a) R$^6$ is alkyl (e.g., methyl), (b) R$^7$ is phenyl, or R$^7$ is phenyl substituted with 1 to 3 independently selected R$^{21}$ groups, (c) R$^{10}$ is selected from the group consisting of phenyl and phenyl substituted with one or more independently selected R$^{21}$ groups, and (d) R$^9$ is selected from the group consisting of imidazolyl and imidazolyl substituted with one or more independently selected R$^{21}$ groups.

In another embodiment of this invention: (a) R$^6$ is alkyl (e.g., methyl), (b) R$^7$ is phenyl, or R$^7$ is phenyl substituted with 1 to 3 independently selected R$^{21}$ halo groups, (c) R$^{10}$ is selected from the group consisting of phenyl and phenyl substituted with one or more independently selected —OR$^{15}$ groups, and (d) R$^9$ is selected from the group consisting of imidazolyl and imidazolyl substituted with one or more independently selected alkyl groups.

In another embodiment of this invention: (a) R$^6$ is alkyl (e.g., methyl), (b) R$^7$ is phenyl, or R$^7$ is phenyl substituted with 1 to 2 independently selected R$^{21}$ halo groups, (c) R$^{10}$ is selected from the group consisting of phenyl and phenyl substituted with one or two independently selected —OR$^{15}$ groups, wherein R$^{15}$ is alkyl, and (d) R$^9$ is selected from the group consisting of imidazolyl and imidazolyl substituted with one or two independently selected alkyl groups.

In another embodiment of this invention: (a) R$^6$ is alkyl (e.g., methyl), (b) R$^7$ is phenyl, or R$^7$ is phenyl substituted with 1 R$^{21}$ halo group, (c) R$^{10}$ is selected from the group consisting of phenyl and phenyl substituted with one or two independently selected —OR$^{15}$ groups, wherein R$^{15}$ is alkyl, and (d) R$^9$ is selected from the group consisting of imidazolyl and imidazolyl substituted with one or two independently selected alkyl groups.

In another embodiment of this invention: (a) R$^6$ is alkyl (e.g., methyl), (b) R$^7$ is phenyl, or R$^7$ is phenyl, substituted with 1 to 3 F (i.e., R$^7$ is phenyl substituted with 1 to 3 R$^{21}$ groups, and said R$^{21}$ groups are halo, and said halo is F), (c) R$^{10}$ is selected from the group consisting of phenyl and phenyl substituted with one or two independently selected —OR$^{15}$ groups, wherein R$^{15}$ is methyl, and (d) R$^9$ is selected from the group consisting of imidazolyl and imidazolyl substituted with one or two independently selected methyl groups.

In another embodiment of this invention: (a) R$^6$ is alkyl (e.g., methyl), (b) R$^7$ is phenyl, or R$^7$ is phenyl, substituted with 1 to 2 F (i.e., R$^7$ is phenyl substituted with 1 to 2 R$^{21}$ groups, and said R$^{21}$ groups are halo, and said halo is F), (c) R$^{10}$ is selected from the group consisting of phenyl and phenyl substituted with one or two independently selected —OR$^{15}$ groups, wherein R$^{15}$ is methyl, and (d) R$^9$ is selected from the group consisting of imidazolyl and imidazolyl substituted with one or two independently selected methyl groups.

In another embodiment of this invention: (a) R$^6$ is alkyl (e.g., methyl), (b) R$^7$ is phenyl, or R$^7$ is phenyl, substituted with 1 F (i.e., R$^7$ is phenyl substituted with 1 R$^{21}$ group, and said R$^{21}$ group is halo, and said halo is F), (b) R$^{10}$ is selected from the group consisting of phenyl and phenyl substituted with one or two independently selected —OR$^{15}$ groups, wherein R$^{15}$ is methyl, and (d) R$^9$ is selected from the group consisting of imidazolyl and imidazolyl substituted with one or two independently selected methyl groups.

In another embodiment of this invention: (a) R$^6$ is alkyl (e.g., methyl), (b) R$^7$ is phenyl substituted with 1 to 3 independently selected R$^{21}$ groups, (c) R$^{10}$ is selected from the group consisting of aryl and aryl substituted with one or more independently selected R$^{21}$ groups, and (d) R$^9$ is selected from the group consisting of heteroaryl and heteroaryl substituted with one or more independently selected R$^{21}$ groups.

In another embodiment of this invention: (a) R$^6$ is alkyl (e.g., methyl), (b) R$^7$ is phenyl substituted with 1 to 3 independently selected R$^{21}$ groups, (c) R$^{10}$ is selected from the group consisting of phenyl and phenyl substituted with one or more independently selected R$^{21}$ groups, and (d) R$^9$ is selected from the group consisting of imidazolyl and imidazolyl substituted with one or more independently selected R$^{21}$ groups.

In another embodiment of this invention: (a) R$^6$ is alkyl (e.g., methyl), (b) R$^7$ is phenyl substituted with 1 to 3 independently selected R$^{21}$ halo groups, (c) R$^{10}$ is selected from the group consisting of phenyl and phenyl substituted with one or more independently selected —OR$^{15}$ groups, and (d) R$^9$ is selected from the group consisting of imidazolyl and imidazolyl substituted with one or more independently selected alkyl groups.

In another embodiment of this invention: (a) R$^6$ is alkyl (e.g., methyl), (b) R$^7$ is phenyl substituted with 1 to 2 independently selected R$^{21}$ halo groups, (c) R$^{10}$ is selected from the group consisting of phenyl and phenyl substituted with one or two independently selected —OR$^{15}$ groups, wherein R$^{15}$ is alkyl, and (d) R$^9$ is selected from the group consisting of imidazolyl and imidazolyl substituted with one or two independently selected alkyl groups.

In another embodiment of this invention: (a) R$^6$ is alkyl (e.g., methyl), (b) R$^7$ is phenyl substituted with 1 R$^{21}$ halo group, (c) R$^{10}$ is selected from the group consisting of phenyl and phenyl substituted with one or two independently selected —OR$^{15}$ groups, wherein R$^{15}$ is alkyl, and (d) R$^9$ is selected from the group consisting of imidazolyl and imidazolyl substituted with one or two independently selected alkyl groups.

In another embodiment of this invention: (a) R$^6$ is alkyl (e.g., methyl), (b) R$^7$ is phenyl, substituted with 1 to 3 F (i.e., R$^7$ is phenyl substituted with 1 to 3 R$^{21}$ groups, and said R$^{21}$ groups are halo, and said halo is F), (c) R$^{10}$ is selected from the group consisting of phenyl and phenyl substituted with one or two independently selected —OR$^{15}$ groups, wherein R$^{15}$ is methyl, and (d) R$^9$ is selected from the group consisting of imidazolyl and imidazolyl substituted with one or two independently selected methyl groups.

In another embodiment of this invention: (a) R$^6$ is alkyl (e.g., methyl), (b) R$^7$ is phenyl, substituted with 1 to 2 F (i.e., R$^7$ is phenyl substituted with 1 to 2 R$^{21}$ groups, and said R$^{21}$ groups are halo, and said halo is F), (c) R$^{10}$ is selected from the group consisting of phenyl and phenyl substituted with one or two independently selected —OR$^{15}$ groups, wherein R$^{15}$ is methyl, and (d) R$^9$ is selected from the group consisting of imidazolyl and imidazolyl substituted with one or two independently selected methyl groups.

In another embodiment of this invention: (a) R$^6$ is alkyl (e.g., methyl), (b) R$^7$ is phenyl, substituted with 1 F (i.e., R$^7$ is phenyl substituted with 1 R$^{21}$ group, and said R$^{21}$ group is halo, and said halo is F), (b) R$^{10}$ is selected from the group consisting of phenyl and phenyl substituted with one or two independently selected —OR$^{15}$ groups, wherein R$^{15}$ is methyl, and (d) R$^9$ is selected from the group consisting of imidazolyl and imidazolyl substituted with one or two independently selected methyl groups.

In another embodiment of this invention: (a) R$^6$ is alkyl (e.g., methyl), (b) R$^7$ is phenyl, (c) R$^{10}$ is selected from the group consisting of aryl and aryl substituted with one or more independently selected R$^{21}$ groups, and (d) R$^9$ is selected from the group consisting of heteroaryl and heteroaryl substituted with one or more independently selected R$^{21}$ groups.

In another embodiment of this invention: (a) R$^6$ is alkyl (e.g., methyl), (b) R$^7$ is phenyl, (c) R$^{10}$ is selected from the group consisting of phenyl and phenyl substituted with one or more independently selected R$^{21}$ groups, and (d) R$^9$ is selected from the group consisting of imidazolyl and imidazolyl substituted with one or more independently selected R$^{21}$ groups.

In another embodiment of this invention: (a) R$^6$ is alkyl (e.g., methyl), (b) R$^7$ is phenyl, (c) R$^{10}$ is selected from the group consisting of phenyl and phenyl substituted with one or more independently selected —OR$^{15}$ groups, and (d) R$^9$ is selected from the group consisting of imidazolyl and imidazolyl substituted with one or more independently selected alkyl groups.

In another embodiment of this invention: (a) R$^6$ is alkyl (e.g., methyl), (b) R$^7$ is phenyl, (c) R$^{10}$ is selected from the group consisting of phenyl and phenyl substituted with one or two independently selected —OR$^{15}$ groups, wherein R$^{15}$ is alkyl, and (d) R$^9$ is selected from the group consisting of imidazolyl and imidazolyl substituted with one or two independently selected alkyl groups.

In another embodiment of this invention: (a) R$^6$ is alkyl (e.g., methyl), (b) R$^7$ is phenyl, (c) R$^{10}$ is selected from the group consisting of phenyl and phenyl substituted with one or two independently selected —OR$^{15}$ groups, wherein R$^{15}$ is alkyl, and (d) R$^9$ is selected from the group consisting of imidazolyl and imidazolyl substituted with one or two independently selected alkyl groups.

In another embodiment of this invention: (a) R$^6$ is alkyl (e.g., methyl), (b) R$^7$ is phenyl, (c) R$^{10}$ is selected from the group consisting of phenyl and phenyl substituted with one or two independently selected —OR$^{15}$ groups, wherein R$^{15}$ is methyl, and (d) R$^9$ is selected from the group consisting of imidazolyl and imidazolyl substituted with one or two independently selected methyl groups.

In another embodiment of this invention: (a) R$^6$ is alkyl (e.g., methyl), (b) R$^7$ is phenyl, (c) R$^{10}$ is selected from the group consisting of phenyl and phenyl substituted with one or two independently selected —OR$^{15}$ groups, wherein R$^{15}$ is methyl, and (d) R$^9$ is selected from the group consisting of imidazolyl and imidazolyl substituted with one or two independently selected methyl groups.

In another embodiment of this invention: (a) R$^6$ is alkyl (e.g., methyl), (b) R$^7$ is phenyl, (b) R$^{10}$ is selected from the group consisting of phenyl and phenyl substituted with one or two independently selected —OR$^{15}$ groups, wherein R$^{15}$ is methyl, and (d) R$^9$ is selected from the group consisting of imidazolyl and imidazolyl substituted with one or two independently selected methyl groups.

In another embodiment of this invention: (a) R$^6$ is alkyl (e.g., methyl), (b) R$^7$ is an aryl group, or R$^7$ is an aryl group substituted with 1 to 3 independently selected R$^{21}$ groups, (c) R$^{10}$ is selected from the group consisting of aryl and aryl substituted with one or more independently selected R$^{21}$ groups, (d) R$^9$ is selected from the group consisting of heteroaryl and heteroaryl substituted with one or more independently selected R$^{21}$ groups, and (e) G is O.

In another embodiment of this invention: (a) R$^6$ is alkyl (e.g., methyl), (b) R$^7$ is phenyl, or R$^7$ is phenyl substituted with 1 to 3 independently selected R$^{21}$ groups, (c) R$^{10}$ is selected from the group consisting of aryl and aryl substituted with one or more independently selected R$^{21}$ groups, (d) R$^9$ is selected from the group consisting of heteroaryl and heteroaryl substituted with one or more independently selected R$^{21}$ groups, and (e) G is O.

In another embodiment of this invention: (a) R$^6$ is alkyl (e.g., methyl), (b) R$^7$ is phenyl, or R$^7$ is phenyl substituted with 1 to 3 independently selected R$^{21}$ groups, (c) R$^{10}$ is selected from the group consisting of phenyl and phenyl substituted with one or more independently selected R$^{21}$ groups, (d) R$^9$ is selected from the group consisting of imidazolyl and imidazolyl substituted with one or more independently selected R$^{21}$ groups, and (e) G is O.

In another embodiment of this invention: (a) R$^6$ is alkyl (e.g., methyl), (b) R$^7$ is phenyl, or R$^7$ is phenyl substituted with 1 to 3 independently selected R$^{21}$ halo groups, (c) R$^{10}$ is selected from the group consisting of phenyl and phenyl substituted with one or more independently selected —OR$^{15}$ groups, (d) R$^9$ is selected from the group consisting of imidazolyl and imidazolyl substituted with one or more independently selected alkyl groups, and (e) G is O.

In another embodiment of this invention: (a) R$^6$ is alkyl (e.g., methyl), (b) R$^7$ is phenyl, or R$^7$ is phenyl substituted with 1 to 2 independently selected R$^{21}$ halo groups, (c) R$^{10}$ is selected from the group consisting of phenyl and phenyl substituted with one or two independently selected —OR$^{15}$ groups, wherein R$^{15}$ is alkyl, (d) R$^9$ is selected from the group consisting of imidazolyl and imidazolyl substituted with one or two independently selected alkyl groups, (e) and G is O.

In another embodiment of this invention: (a) R$^6$ is alkyl (e.g., methyl), (b) R$^7$ is phenyl, or R$^7$ is phenyl substituted with 1 R$^{21}$ halo group, (c) R$^{10}$ is selected from the group consisting of phenyl and phenyl substituted with one or two independently selected —OR$^{15}$ groups, wherein R$^{15}$ is alkyl, (d) R$^9$ is selected from the group consisting of imidazolyl and imidazolyl substituted with one or two independently selected alkyl groups, and (e) G is O.

In another embodiment of this invention: (a) R$^6$ is alkyl (e.g., methyl), (b) R$^7$ is phenyl, or R$^7$ is phenyl, substituted with 1 to 3 F (i.e., R$^7$ is phenyl substituted with 1 to 3 R$^{21}$ groups, and said R$^{21}$ groups are halo, and said halo is F), (c) R$^{10}$ is selected from the group consisting of phenyl and phenyl substituted with one or two independently selected —OR$^{15}$ groups, wherein R$^{15}$ is methyl, (d) R$^9$ is selected from the group consisting of imidazolyl and imidazolyl substituted with one or two independently selected methyl groups, and (e) G is O.

In another embodiment of this invention: (a) $R^6$ is alkyl (e.g., methyl), (b) $R^7$ is phenyl, or $R^7$ is phenyl, substituted with 1 to 2 F (i.e., $R^7$ is phenyl substituted with 1 to 2 $R^{21}$ groups, and said $R^{21}$ groups are halo, and said halo is F), (c) $R^{10}$ is selected from the group consisting of phenyl and phenyl substituted with one or two independently selected —$OR^{15}$ groups, wherein $R^{15}$ is methyl, (d) $R^9$ is selected from the group consisting of imidazolyl and imidazolyl substituted with one or two independently selected methyl groups, and (e) G is O.

In another embodiment of this invention: (a) $R^6$ is alkyl (e.g., methyl), (b) $R^7$ is phenyl, or $R^7$ is phenyl, substituted with 1 F (i.e., $R^7$ is phenyl substituted with 1 $R^{21}$ group, and said $R^{21}$ group is halo, and said halo is F), (b) $R^{10}$ is selected from the group consisting of phenyl and phenyl substituted with one or two independently selected —$OR^{15}$ groups, wherein $R^{15}$ is methyl, (d) $R^9$ is selected from the group consisting of imidazolyl and imidazolyl substituted with one or two independently selected methyl groups, and (e) G is O.

In another embodiment of this invention: (a) $R^6$ is alkyl (e.g., methyl), (b) $R^7$ is phenyl substituted with 1 to 3 independently selected $R^{21}$ groups, (c) $R^{10}$ is selected from the group consisting of aryl and aryl substituted with one or more independently selected $R^{21}$ groups, (d) $R^9$ is selected from the group consisting of heteroaryl and heteroaryl substituted with one or more independently selected $R^{21}$ groups, and (e) G is O.

In another embodiment of this invention: (a) $R^6$ is alkyl (e.g., methyl), (b) $R^7$ is phenyl substituted with 1 to 3 independently selected $R^{21}$ groups, (c) $R^{10}$ is selected from the group consisting of phenyl and phenyl substituted with one or more independently selected $R^{21}$ groups, (d) $R^9$ is selected from the group consisting of imidazolyl and imidazolyl substituted with one or more independently selected $R^{21}$ groups, and (e) G is O.

In another embodiment of this invention: (a) $R^6$ is alkyl (e.g., methyl), (b) $R^7$ is phenyl substituted with 1 to 3 independently selected $R^{21}$ halo groups, (c) $R^{10}$ is selected from the group consisting of phenyl and phenyl substituted with one or more independently selected —$OR^{15}$ groups, (d) $R^9$ is selected from the group consisting of imidazolyl and imidazolyl substituted with one or more independently selected alkyl groups, and (e) G is O.

In another embodiment of this invention: (a) $R^6$ is alkyl (e.g., methyl), (b) $R^7$ is phenyl substituted with 1 to 2 independently selected $R^{21}$ halo groups, (c) $R^{10}$ is selected from the group consisting of phenyl and phenyl substituted with one or two independently selected —$OR^{15}$ groups, wherein $R^{15}$ is alkyl, (d) $R^9$ is selected from the group consisting of imidazolyl and imidazolyl substituted with one or two independently selected alkyl groups, and (e) G is O.

In another embodiment of this invention: (a) $R^6$ is alkyl (e.g., methyl), (b) $R^7$ is phenyl substituted with 1 $R^{21}$ halo group, (c) $R^{10}$ is selected from the group consisting of phenyl and phenyl substituted with one or two independently selected —$OR^{15}$ groups, wherein $R^{15}$ is alkyl, (d) $R^9$ is selected from the group consisting of imidazolyl and imidazolyl substituted with one or two independently selected alkyl groups groups, and (e) G is O.

In another embodiment of this invention: (a) $R^6$ is alkyl (e.g., methyl), (b) $R^7$ is phenyl, substituted with 1 to 3 F (i.e., $R^7$ is phenyl substituted with 1 to 3 $R^{21}$ groups, and said $R^{21}$ groups are halo, and said halo is F), (c) $R^{10}$ is selected from the group consisting of phenyl and phenyl substituted with one or two independently selected —$OR^{15}$ groups, wherein $R^{15}$ is methyl, (d) $R^9$ is selected from the group consisting of imidazolyl and imidazolyl substituted with one or two independently selected methyl groups, and (e) G is O.

In another embodiment of this invention: (a) $R^6$ is alkyl (e.g., methyl), (b) $R^7$ is phenyl, substituted with 1 to 2 F (i.e., $R^7$ is phenyl substituted with 1 to 2 $R^{21}$ groups, and said $R^{21}$ groups are halo, and said halo is F), (c) $R^{10}$ is selected from the group consisting of phenyl and phenyl substituted with one or two independently selected —$OR^{15}$ groups, wherein $R^{15}$ is methyl, (d) $R^9$ is selected from the group consisting of imidazolyl and imidazolyl substituted with one or two independently selected methyl groups, and (e) G is O.

In another embodiment of this invention: (a) $R^6$ is alkyl (e.g., methyl), (b) $R^7$ is phenyl, substituted with 1 F (i.e., $R^7$ is phenyl substituted with 1 $R^{21}$ group, and said $R^{21}$ group is halo, and said halo is F), (b) $R^{10}$ is selected from the group consisting of phenyl and phenyl substituted with one or two independently selected —$OR^{15}$ groups, wherein $R^{15}$ is methyl, (d) $R^9$ is selected from the group consisting of imidazolyl and imidazolyl substituted with one or two independently selected methyl groups, and (e) G is O.

In another embodiment of this invention: (a) $R^6$ is alkyl (e.g., methyl), (b) $R^7$ is phenyl, (c) $R^{10}$ is selected from the group consisting of aryl and aryl substituted with one or more independently selected $R^{21}$ groups, (d) $R^9$ is selected from the group consisting of heteroaryl and heteroaryl substituted with one or more independently selected $R^{21}$ groups, and (e) G is O.

In another embodiment of this invention: (a) $R^6$ is alkyl (e.g., methyl), (b) $R^7$ is phenyl, (c) $R^{10}$ is selected from the group consisting of phenyl and phenyl substituted with one or more independently selected $R^{21}$ groups, (d) $R^9$ is selected from the group consisting of imidazolyl and imidazolyl substituted with one or more independently selected $R^{21}$ groups, and (e) G is O.

In another embodiment of this invention: (a) $R^6$ is alkyl (e.g., methyl), (b) $R^7$ is phenyl, (c) $R^{10}$ is selected from the group consisting of phenyl and phenyl substituted with one or more independently selected —$OR^{15}$ groups, (d) $R^9$ is selected from the group consisting of imidazolyl and imidazolyl substituted with one or more independently selected alkyl groups, and (e) G is O.

In another embodiment of this invention: (a) $R^6$ is alkyl (e.g., methyl), (b) $R^7$ is phenyl, (c) $R^{10}$ is selected from the group consisting of phenyl and phenyl substituted with one or two independently selected —$OR^{15}$ groups, wherein $R^{15}$ is alkyl, (d) $R^9$ is selected from the group consisting of imidazolyl and imidazolyl substituted with one or two independently selected alkyl groups, and (e) G is O.

In another embodiment of this invention: (a) $R^6$ is alkyl (e.g., methyl), (b) $R^7$ is phenyl, (c) $R^{10}$ is selected from the group consisting of phenyl and phenyl substituted with one or two independently selected —$OR^{15}$ groups, wherein $R^{15}$ is alkyl, (d) $R^9$ is selected from the group consisting of imidazolyl and imidazolyl substituted with one or two independently selected alkyl groups, and (e) G is O.

In another embodiment of this invention: (a) $R^6$ is alkyl (e.g., methyl), (b) $R^7$ is phenyl, (c) $R^{10}$ is selected from the group consisting of phenyl and phenyl substituted with one or two independently selected —$OR^{15}$ groups, wherein $R^{15}$ is methyl, (d) $R^9$ is selected from the group consisting of imidazolyl and imidazolyl substituted with one or two independently selected methyl groups, and (e) G is O.

In another embodiment of this invention: (a) $R^6$ is alkyl (e.g., methyl), (b) $R^7$ is phenyl, (c) $R^{10}$ is selected from the group consisting of phenyl and phenyl substituted with one or two independently selected —OR$^{15}$ groups, wherein R$^{15}$ is methyl, (d) R$^9$ is selected from the group consisting of imidazolyl and imidazolyl substituted with one or two independently selected methyl groups, and (e) G is O.

In another embodiment of this invention: (a) R$^6$ is alkyl (e.g., methyl), (b) R$^7$ is phenyl, (b) R$^{10}$ is selected from the group consisting of phenyl and phenyl substituted with one or two independently selected —OR$^{15}$ groups, wherein R$^{15}$ is methyl, (d) R$^9$ is selected from the group consisting of imidazolyl and imidazolyl substituted with one or two independently selected methyl groups, and (e) G is O.

In another embodiment of this invention: (a) R$^6$ is alkyl (e.g., methyl), (b) R$^7$ is an aryl group, or R$^7$ is an aryl group substituted with 1 to 3 independently selected R$^{21}$ groups, (c) R$^{10}$ is selected from the group consisting of aryl and aryl substituted with one or more independently selected R$^{21}$ groups, (d) R$^9$ is selected from the group consisting of heteroaryl and heteroaryl substituted with one or more independently selected R$^{21}$ groups, and (e) G is S.

In another embodiment of this invention: (a) R$^6$ is alkyl (e.g., methyl), (b) R$^7$ is phenyl, or R$^7$ is phenyl substituted with 1 to 3 independently selected R$^{21}$ groups, (c) R$^{10}$ is selected from the group consisting of aryl and aryl substituted with one or more independently selected R$^{21}$ groups, (d) R$^9$ is selected from the group consisting of heteroaryl and heteroaryl substituted with one or more independently selected R$^{21}$ groups, and (e) G is S.

In another embodiment of this invention: (a) R$^6$ is alkyl (e.g., methyl), (b) R$^7$ is phenyl, or R$^7$ is phenyl substituted with 1 to 3 independently selected R$^{21}$ groups, (c) R$^{10}$ is selected from the group consisting of phenyl and phenyl substituted with one or more independently selected R$^{21}$ groups, (d) R$^9$ is selected from the group consisting of imidazolyl and imidazolyl substituted with one or more independently selected R$^{21}$ groups, and (e) G is S.

In another embodiment of this invention: (a) R$^6$ is alkyl (e.g., methyl), (b) R$^7$ is phenyl, or R$^7$ is phenyl substituted with 1 to 3 independently selected R$^{21}$ halo groups, (c) R$^{10}$ is selected from the group consisting of phenyl and phenyl substituted with one or more independently selected —OR$^{15}$ groups, (d) R$^9$ is selected from the group consisting of imidazolyl and imidazolyl substituted with one or more independently selected alkyl groups, and (e) G is S.

In another embodiment of this invention: (a) R$^6$ is alkyl (e.g., methyl), (b) R$^7$ is phenyl, or R$^7$ is phenyl substituted with 1 to 2 independently selected R$^{21}$ halo groups, (c) R$^{10}$ is selected from the group consisting of phenyl and phenyl substituted with one or two independently selected —OR$^{15}$ groups, wherein R$^{15}$ is alkyl, (d) R$^9$ is selected from the group consisting of imidazolyl and imidazolyl substituted with one or two independently selected alkyl groups, (e) and G is S.

In another embodiment of this invention: (a) R$^6$ is alkyl (e.g., methyl), (b) R$^7$ is phenyl, or R$^7$ is phenyl substituted with 1 R$^{21}$ halo group, (c) R$^{10}$ is selected from the group consisting of phenyl and phenyl substituted with one or two independently selected —OR$^{15}$ groups, wherein R$^{15}$ is alkyl, (d) R$^9$ is selected from the group consisting of imidazolyl and imidazolyl substituted with one or two independently selected alkyl groups, and (e) G is S.

In another embodiment of this invention: (a) R$^6$ is alkyl (e.g., methyl), (b) R$^7$ is phenyl, or R$^7$ is phenyl, substituted with 1 to 3 F (i.e., R$^7$ is phenyl substituted with 1 to 3 R$^{21}$ groups, and said R$^{21}$ groups are halo, and said halo is F), (c) R$^{10}$ is selected from the group consisting of phenyl and phenyl substituted with one or two independently selected —OR$^{15}$ groups, wherein R$^{15}$ is methyl, (d) R$^9$ is selected from the group consisting of imidazolyl and imidazolyl substituted with one or two independently selected methyl groups, and (e) G is S.

In another embodiment of this invention: (a) R$^6$ is alkyl (e.g., methyl), (b) R$^7$ is phenyl, or R$^7$ is phenyl, substituted with 1 to 2 F (i.e., R$^7$ is phenyl substituted with 1 to 2 R$^{21}$ groups, and said R$^{21}$ groups are halo, and said halo is F), (c) R$^{10}$ is selected from the group consisting of phenyl and phenyl substituted with one or two independently selected —OR$^{15}$ groups, wherein R$^{15}$ is methyl, (d) R$^9$ is selected from the group consisting of imidazolyl and imidazolyl substituted with one or two independently selected methyl groups, and (e) G is S.

In another embodiment of this invention: (a) R$^6$ is alkyl (e.g., methyl), (b) R$^7$ is phenyl, or R$^7$ is phenyl, substituted with 1 F (i.e., R$^7$ is phenyl substituted with 1 R$^{21}$ group, and said R$^{21}$ group is halo, and said halo is F), (b) R$^{10}$ is selected from the group consisting of phenyl and phenyl substituted with one or two independently selected —OR$^{15}$ groups, wherein R$^{15}$ is methyl, (d) R$^9$ is selected from the group consisting of imidazolyl and imidazolyl substituted with one or two independently selected methyl groups, and (e) G is S.

In another embodiment of this invention: (a) R$^6$ is alkyl (e.g., methyl), (b) R$^7$ is phenyl substituted with 1 to 3 independently selected R$^{21}$ groups, (c) R$^{10}$ is selected from the group consisting of aryl and aryl substituted with one or more independently selected R$^{21}$ groups, (d) R$^9$ is selected from the group consisting of heteroaryl and heteroaryl substituted with one or more independently selected R$^{21}$ groups, and (e) G is S.

In another embodiment of this invention: (a) R$^6$ is alkyl (e.g., methyl), (b) R$^7$ is phenyl substituted with 1 to 3 independently selected R$^{21}$ groups, (c) R$^{10}$ is selected from the group consisting of phenyl and phenyl substituted with one or more independently selected R$^{21}$ groups, (d) R$^9$ is selected from the group consisting of imidazolyl and imidazolyl substituted with one or more independently selected R$^{21}$ groups, and (e) G is S.

In another embodiment of this invention: (a) R$^6$ is alkyl (e.g., methyl), (b) R$^7$ is phenyl substituted with 1 to 3 independently selected R$^{21}$ halo groups, (c) R$^{10}$ is selected from the group consisting of phenyl and phenyl substituted with one or more independently selected —OR$^{15}$ groups, (d) R$^9$ is selected from the group consisting of imidazolyl and imidazolyl substituted with one or more independently selected alkyl groups, and (e) G is S.

In another embodiment of this invention: (a) R$^6$ is alkyl (e.g., methyl), (b) R$^7$ is phenyl substituted with 1 to 2 independently selected R$^{21}$ halo groups, (c) R$^{10}$ is selected from the group consisting of phenyl and phenyl substituted with one or two independently selected —OR$^{15}$ groups, wherein R$^{15}$ is alkyl, (d) R$^9$ is selected from the group consisting of imidazolyl and imidazolyl substituted with one or two independently selected alkyl groups, and (e) G is S.

In another embodiment of this invention: (a) R$^6$ is alkyl (e.g., methyl), (b) R$^7$ is phenyl substituted with 1 R$^{21}$ halo group, (c) R$^{10}$ is selected from the group consisting of phenyl and phenyl substituted with one or two independently selected —OR$^{15}$ groups, wherein R$^{15}$ is alkyl, (d) R$^9$ is selected from the group consisting of imidazolyl and imidazolyl substituted with one or two independently selected alkyl groups groups, and (e) G is S.

In another embodiment of this invention: (a) R$^6$ is alkyl (e.g., methyl), (b) R$^7$ is phenyl, substituted with 1 to 3 F (i.e., R$^7$ is phenyl substituted with 1 to 3 R$^{21}$ groups, and said R$^{21}$ groups are halo, and said halo is F), (c) R$^{10}$ is selected from the group consisting of phenyl and phenyl substituted with one or two independently selected —OR$^{15}$ groups, wherein R$^{15}$ is methyl, (d) R$^9$ is selected from the group consisting of imidazolyl and imidazolyl substituted with one or two independently selected methyl groups, and (e) G is S.

In another embodiment of this invention: (a) R$^6$ is alkyl (e.g., methyl), (b) R$^7$ is phenyl, substituted with 1 to 2 F (i.e., R$^7$ is phenyl substituted with 1 to 2 R$^{21}$ groups, and said R$^{21}$ groups are halo, and said halo is F), (c) R$^{10}$ is selected from the group consisting of phenyl and phenyl substituted with one or two independently selected —OR$^{15}$ groups, wherein R$^{15}$ is methyl, (d) R$^9$ is selected from the group consisting of imidazolyl and imidazolyl substituted with one or two independently selected methyl groups, and (e) G is S.

In another embodiment of this invention: (a) R$^6$ is alkyl (e.g., methyl), (b) R$^7$ is phenyl, substituted with 1 F (i.e., R$^7$ is phenyl substituted with 1 R$^{21}$ group, and said R$^{21}$ group is halo, and said halo is F), (b) R$^{10}$ is selected from the group consisting of phenyl and phenyl substituted with one or two independently selected —OR$^{15}$ groups, wherein R$^{15}$ is methyl, (d) R$^9$ is selected from the group consisting of imidazolyl and imidazolyl substituted with one or two independently selected methyl groups, and (e) G is S.

In another embodiment of this invention: (a) R$^6$ is alkyl (e.g., methyl), (b) R$^7$ is phenyl, (c) R$^{10}$ is selected from the group consisting of aryl and aryl substituted with one or more independently selected R$^{21}$ groups, (d) R$^9$ is selected from the group consisting of heteroaryl and heteroaryl substituted with one or more independently selected R$^{21}$ groups, and (e) G is S.

In another embodiment of this invention: (a) R$^6$ is alkyl (e.g., methyl), (b) R$^7$ is phenyl, (c) R$^{10}$ is selected from the group consisting of phenyl and phenyl substituted with one or more independently selected R$^{21}$ groups, (d) R$^9$ is selected from the group consisting of imidazolyl and imidazolyl substituted with one or more independently selected R$^{21}$ groups, and (e) G is S.

In another embodiment of this invention: (a) R$^6$ is alkyl (e.g., methyl), (b) R$^7$ is phenyl, (c) R$^{10}$ is selected from the group consisting of phenyl and phenyl substituted with one or more independently selected —OR$^{15}$ groups, (d) R$^9$ is selected from the group consisting of imidazolyl and imidazolyl substituted with one or more independently selected alkyl groups, and (e) G is S.

In another embodiment of this invention: (a) R$^6$ is alkyl (e.g., methyl), (b) R$^7$ is phenyl, (c) R$^{10}$ is selected from the group consisting of phenyl and phenyl substituted with one or two independently selected —OR$^{15}$ groups, wherein R$^{15}$ is alkyl, (d) R$^9$ is selected from the group consisting of imidazolyl and imidazolyl substituted with one or two independently selected alkyl groups, and (e) G is S.

In another embodiment of this invention: (a) R$^6$ is alkyl (e.g., methyl), (b) R$^7$ is phenyl, (c) R$^{10}$ is selected from the group consisting of phenyl and phenyl substituted with one or two independently selected —OR$^{15}$ groups, wherein R$^{15}$ is alkyl, (d) R$^9$ is selected from the group consisting of imidazolyl and imidazolyl substituted with one or two independently selected alkyl groups, and (e) G is S.

In another embodiment of this invention: (a) R$^6$ is alkyl (e.g., methyl), (b) R$^7$ is phenyl, (c) R$^{10}$ is selected from the group consisting of phenyl and phenyl substituted with one or two independently selected —OR$^{15}$ groups, wherein R$^{15}$ is methyl, (d) R$^9$ is selected from the group consisting of imidazolyl and imidazolyl substituted with one or two independently selected methyl groups, and (e) G is S.

In another embodiment of this invention: (a) R$^6$ is alkyl (e.g., methyl), (b) R$^7$ is phenyl, (c) R$^{10}$ is selected from the group consisting of phenyl and phenyl substituted with one or two independently selected —OR$^{15}$ groups, wherein R$^{15}$ is methyl, (d) R$^9$ is selected from the group consisting of imidazolyl and imidazolyl substituted with one or two independently selected methyl groups, and (e) G is S.

In another embodiment of this invention: (a) R$^6$ is alkyl (e.g., methyl), (b) R$^7$ is phenyl, (b) R$^{10}$ is selected from the group consisting of phenyl and phenyl substituted with one or two independently selected —OR$^{15}$ groups, wherein R$^{15}$ is methyl, (d) R$^9$ is selected from the group consisting of imidazolyl and imidazolyl substituted with one or two independently selected methyl groups, and (e) G is S.

In another embodiment of this invention: (a) R$^6$ is alkyl (e.g., methyl), (b) R$^7$ is an aryl group, or R$^7$ is an aryl group substituted with 1 to 3 independently selected R$^{21}$ groups, (c) R$^{10}$ is selected from the group consisting of aryl and aryl substituted with one or more independently selected R$^{21}$ groups, (d) R$^9$ is selected from the group consisting of heteroaryl and heteroaryl substituted with one or more independently selected R$^{21}$ groups, and (e) G is C(O).

In another embodiment of this invention: (a) R$^6$ is alkyl (e.g., methyl), (b) R$^7$ is phenyl, or R$^7$ is phenyl substituted with 1 to 3 independently selected R$^{21}$ groups, (c) R$^{10}$ is selected from the group consisting of aryl and aryl substituted with one or more independently selected R$^{21}$ groups, (d) R$^9$ is selected from the group consisting of heteroaryl and heteroaryl substituted with one or more independently selected R$^{21}$ groups, and (e) G is C(O).

In another embodiment of this invention: (a) R$^6$ is alkyl (e.g., methyl), (b) R$^7$ is phenyl, or R$^7$ is phenyl substituted with 1 to 3 independently selected R$^{21}$ groups, (c) R$^{10}$ is selected from the group consisting of phenyl and phenyl substituted with one or more independently selected R$^{21}$ groups, (d) R$^9$ is selected from the group consisting of imidazolyl and imidazolyl substituted with one or more independently selected R$^{21}$ groups, and (e) G is C(O).

In another embodiment of this invention: (a) R$^6$ is alkyl (e.g., methyl), (b) R$^7$ is phenyl, or R$^7$ is phenyl substituted with 1 to 3 independently selected R$^{21}$ halo groups, (c) R$^{10}$ is selected from the group consisting of phenyl and phenyl substituted with one or more independently selected —OR$^{15}$ groups, (d) R$^9$ is selected from the group consisting of imidazolyl and imidazolyl substituted with one or more independently selected alkyl groups, and (e) G is C(O).

In another embodiment of this invention: (a) R$^6$ is alkyl (e.g., methyl), (b) R$^7$ is phenyl, or R$^7$ is phenyl substituted with 1 to 2 independently selected R$^{21}$ halo groups, (c) R$^{10}$ is selected from the group consisting of phenyl and phenyl substituted with one or two independently selected —OR$^{15}$ groups, wherein R$^{15}$ is alkyl, (d) R$^9$ is selected from the group consisting of imidazolyl and imidazolyl substituted with one or two independently selected alkyl groups, (e) and G is C(O).

In another embodiment of this invention: (a) R$^6$ is alkyl (e.g., methyl), (b) R$^7$ is phenyl, or R$^7$ is phenyl substituted with 1 R$^{21}$ halo group, (c) R$^{10}$ is selected from the group consisting of phenyl and phenyl substituted with one or two independently selected —OR$^{15}$ groups, wherein R$^{15}$ is alkyl, (d) R$^9$ is selected from the group consisting of imidazolyl and imidazolyl substituted with one or two independently selected alkyl groups, and (e) G is C(O).

In another embodiment of this invention: (a) R$^6$ is alkyl (e.g., methyl), (b) R$^7$ is phenyl, or R$^7$ is phenyl, substituted with 1 to 3 F (i.e., R$^7$ is phenyl substituted with 1 to 3 R$^{21}$ groups, and said R$^{21}$ groups are halo, and said halo is F), (c) R$^{10}$ is selected from the group consisting of phenyl and phenyl substituted with one or two independently selected —OR$^{15}$ groups, wherein R$^{15}$ is methyl, (d) R$^9$ is selected from the group consisting of imidazolyl and imidazolyl substituted with one or two independently selected methyl groups, and (e) G is C(O).

In another embodiment of this invention: (a) $R^6$ is alkyl (e.g., methyl), (b) $R^7$ is phenyl, or $R^7$ is phenyl, substituted with 1 to 2 F (i.e., $R^7$ is phenyl substituted with 1 to 2 $R^{21}$ groups, and said $R^{21}$ groups are halo, and said halo is F), (c) $R^{10}$ is selected from the group consisting of phenyl and phenyl substituted with one or two independently selected —$OR^{15}$ groups, wherein $R^{15}$ is methyl, (d) $R^9$ is selected from the group consisting of imidazolyl and imidazolyl substituted with one or two independently selected methyl groups, and (e) G is C(O).

In another embodiment of this invention: (a) $R^6$ is alkyl (e.g., methyl), (b) $R^7$ is phenyl, or $R^7$ is phenyl, substituted with 1 F (i.e., $R^7$ is phenyl substituted with 1 $R^{21}$ group, and said $R^{21}$ group is halo, and said halo is F), (b) $R^{10}$ is selected from the group consisting of phenyl and phenyl substituted with one or two independently selected —$OR^{15}$ groups, wherein $R^{15}$ is methyl, (d) $R^9$ is selected from the group consisting of imidazolyl and imidazolyl substituted with one or two independently selected methyl groups, and (e) G is C(O).

In another embodiment of this invention: (a) $R^6$ is alkyl (e.g., methyl), (b) $R^7$ is phenyl substituted with 1 to 3 independently selected $R^{21}$ groups, (c) $R^{10}$ is selected from the group consisting of aryl and aryl substituted with one or more independently selected $R^{21}$ groups, (d) $R^9$ is selected from the group consisting of heteroaryl and heteroaryl substituted with one or more independently selected $R^{21}$ groups, and (e) G is C(O).

In another embodiment of this invention: (a) $R^6$ is alkyl (e.g., methyl), (b) $R^7$ is phenyl substituted with 1 to 3 independently selected $R^{21}$ groups, (c) $R^{10}$ is selected from the group consisting of phenyl and phenyl substituted with one or more independently selected $R^{21}$ groups, (d) $R^9$ is selected from the group consisting of imidazolyl and imidazolyl substituted with one or more independently selected $R^{21}$ groups, and (e) G is C(O).

In another embodiment of this invention: (a) $R^6$ is alkyl (e.g., methyl), (b) $R^7$ is phenyl substituted with 1 to 3 independently selected $R^{21}$ halo groups, (c) $R^{10}$ is selected from the group consisting of phenyl and phenyl substituted with one or more independently selected —$OR^{15}$ groups, (d) $R^9$ is selected from the group consisting of imidazolyl and imidazolyl substituted with one or more independently selected alkyl groups, and (e) G is C(O).

In another embodiment of this invention: (a) $R^6$ is alkyl (e.g., methyl), (b) $R^7$ is phenyl substituted with 1 to 2 independently selected $R^{21}$ halo groups, (c) $R^{10}$ is selected from the group consisting of phenyl and phenyl substituted with one or two independently selected —$OR^{15}$ groups, wherein $R^{15}$ is alkyl, (d) $R^9$ is selected from the group consisting of imidazolyl and imidazolyl substituted with one or two independently selected alkyl groups, and (e) G is C(O).

In another embodiment of this invention: (a) $R^6$ is alkyl (e.g., methyl), (b) $R^7$ is phenyl substituted with 1 $R^{21}$ halo group, (c) $R^{10}$ is selected from the group consisting of phenyl and phenyl substituted with one or two independently selected —$OR^{15}$ groups, wherein $R^{15}$ is alkyl, (d) $R^9$ is selected from the group consisting of imidazolyl and imidazolyl substituted with one or two independently selected alkyl groups groups, and (e) G is C(O).

In another embodiment of this invention: (a) $R^6$ is alkyl (e.g., methyl), (b) $R^7$ is phenyl, substituted with 1 to 3 F (i.e., $R^7$ is phenyl substituted with 1 to 3 $R^{21}$ groups, and said $R^{21}$ groups are halo, and said halo is F), (c) $R^{10}$ is selected from the group consisting of phenyl and phenyl substituted with one or two independently selected —$OR^{15}$ groups, wherein $R^{15}$ is methyl, (d) $R^9$ is selected from the group consisting of imidazolyl and imidazolyl substituted with one or two independently selected methyl groups, and (e) G is C(O).

In another embodiment of this invention: (a) $R^6$ is alkyl (e.g., methyl), (b) $R^7$ is phenyl, substituted with 1 to 2 F (i.e., $R^7$ is phenyl substituted with 1 to 2 $R^{21}$ groups, and said $R^{21}$ groups are halo, and said halo is F), (c) $R^{10}$ is selected from the group consisting of phenyl and phenyl substituted with one or two independently selected —$OR^{15}$ groups, wherein $R^{15}$ is methyl, (d) $R^9$ is selected from the group consisting of imidazolyl and imidazolyl substituted with one or two independently selected methyl groups, and (e) G is C(O).

In another embodiment of this invention: (a) $R^6$ is alkyl (e.g., methyl), (b) $R^7$ is phenyl, substituted with 1 F (i.e., $R^7$ is phenyl substituted with 1 $R^{21}$ group, and said $R^{21}$ group is halo, and said halo is F), (b) $R^{10}$ is selected from the group consisting of phenyl and phenyl substituted with one or two independently selected —$OR^{15}$ groups, wherein $R^{15}$ is methyl, (d) $R^9$ is selected from the group consisting of imidazolyl and imidazolyl substituted with one or two independently selected methyl groups, and (e) G is C(O).

In another embodiment of this invention: (a) $R^6$ is alkyl (e.g., methyl), (b) $R^7$ is phenyl, (c) $R^{10}$ is selected from the group consisting of aryl and aryl substituted with one or more independently selected $R^{21}$ groups, (d) $R^9$ is selected from the group consisting of heteroaryl and heteroaryl substituted with one or more independently selected $R^{21}$ groups, and (e) G is C(O).

In another embodiment of this invention: (a) $R^6$ is alkyl (e.g., methyl), (b) $R^7$ is phenyl, (c) $R^{10}$ is selected from the group consisting of phenyl and phenyl substituted with one or more independently selected $R^{21}$ groups, (d) $R^9$ is selected from the group consisting of imidazolyl and imidazolyl substituted with one or more independently selected $R^{21}$ groups, and (e) G is C(O).

In another embodiment of this invention: (a) $R^6$ is alkyl (e.g., methyl), (b) $R^7$ is phenyl, (c) $R^{10}$ is selected from the group consisting of phenyl and phenyl substituted with one or more independently selected —$OR^{15}$ groups, (d) $R^9$ is selected from the group consisting of imidazolyl and imidazolyl substituted with one or more independently selected alkyl groups, and (e) G is C(O).

In another embodiment of this invention: (a) $R^6$ is alkyl (e.g., methyl), (b) $R^7$ is phenyl, (c) $R^{10}$ is selected from the group consisting of phenyl and phenyl substituted with one or two independently selected —$OR^{15}$ groups, wherein $R^{15}$ is alkyl, (d) $R^9$ is selected from the group consisting of imidazolyl and imidazolyl substituted with one or two independently selected alkyl groups, and (e) G is C(O).

In another embodiment of this invention: (a) $R^6$ is alkyl (e.g., methyl), (b) $R^7$ is phenyl, (c) $R^{10}$ is selected from the group consisting of phenyl and phenyl substituted with one or two independently selected —$OR^{15}$ groups, wherein $R^{15}$ is alkyl, (d) $R^9$ is selected from the group consisting of imidazolyl and imidazolyl substituted with one or two independently selected alkyl groups, and (e) G is C(O).

In another embodiment of this invention: (a) $R^6$ is alkyl (e.g., methyl), (b) $R^7$ is phenyl, (c) $R^{10}$ is selected from the group consisting of phenyl and phenyl substituted with one or two independently selected —$OR^{15}$ groups, wherein $R^{15}$ is methyl, (d) $R^9$ is selected from the group consisting of imidazolyl and imidazolyl substituted with one or two independently selected methyl groups, and (e) G is C(O).

In another embodiment of this invention: (a) $R^6$ is alkyl (e.g., methyl), (b) $R^7$ is phenyl, (c) $R^{10}$ is selected from the group consisting of phenyl and phenyl substituted with one or two independently selected —OR$^{15}$ groups, wherein R$^{15}$ is methyl, (d) R$^9$ is selected from the group consisting of imidazolyl and imidazolyl substituted with one or two independently selected methyl groups, and (e) G is C(O).

In another embodiment of this invention: (a) R$^6$ is alkyl (e.g., methyl), (b) R$^7$ is phenyl, (b) R$^{10}$ is selected from the group consisting of phenyl and phenyl substituted with one or two independently selected —OR$^{15}$ groups, wherein R$^{15}$ is methyl, (d) R$^9$ is selected from the group consisting of imidazolyl and imidazolyl substituted with one or two independently selected methyl groups, and (e) G is C(O).

In another embodiment of this invention: (a) R$^6$ is alkyl (e.g., methyl), (b) R$^7$ is an aryl group, or R$^7$ is an aryl group substituted with 1 to 3 independently selected R$^{21}$ groups, (c) R$^{10}$ is selected from the group consisting of aryl and aryl substituted with one or more independently selected R$^{21}$ groups, (d) R$^9$ is selected from the group consisting of heteroaryl and heteroaryl substituted with one or more independently selected R$^{21}$ groups, and (e) G is N(R$^{14}$) (and in one example G is NH).

In another embodiment of this invention: (a) R$^6$ is alkyl (e.g., methyl), (b) R$^7$ is phenyl, or R$^7$ is phenyl substituted with 1 to 3 independently selected R$^{21}$ groups, (c) R$^{10}$ is selected from the group consisting of aryl and aryl substituted with one or more independently selected R$^{21}$ groups, (d) R$^9$ is selected from the group consisting of heteroaryl and heteroaryl substituted with one or more independently selected R$^{21}$ groups, and (e) G is N(R$^{14}$) (and in one example G is NH).

In another embodiment of this invention: (a) R$^6$ is alkyl (e.g., methyl), (b) R$^7$ is phenyl, or R$^7$ is phenyl substituted with 1 to 3 independently selected R$^{21}$ groups, (c) R$^{10}$ is selected from the group consisting of phenyl and phenyl substituted with one or more independently selected R$^{21}$ groups, (d) R$^9$ is selected from the group consisting of imidazolyl and imidazolyl substituted with one or more independently selected R$^{21}$ groups, and (e) G is N(R$^{14}$) (and in one example G is NH).

In another embodiment of this invention: (a) R$^6$ is alkyl (e.g., methyl), (b) R$^7$ is phenyl, or R$^7$ is phenyl substituted with 1 to 3 independently selected R$^{21}$ halo groups, (c) R$^{10}$ is selected from the group consisting of phenyl and phenyl substituted with one or more independently selected —OR$^{15}$ groups, (d) R$^9$ is selected from the group consisting of imidazolyl and imidazolyl substituted with one or more independently selected alkyl groups, and (e) G is N(R$^{14}$) (and in one example G is NH).

In another embodiment of this invention: (a) R$^6$ is alkyl (e.g., methyl), (b) R$^7$ is phenyl, or R$^7$ is phenyl substituted with 1 to 2 independently selected R$^{21}$ halo groups, (c) R$^{10}$ is selected from the group consisting of phenyl and phenyl substituted with one or two independently selected —OR$^{15}$ groups, wherein R$^{15}$ is alkyl, (d) R$^9$ is selected from the group consisting of imidazolyl and imidazolyl substituted with one or two independently selected alkyl groups, (e) and G is N(R$^{14}$) (and in one example G is NH).

In another embodiment of this invention: (a) R$^6$ is alkyl (e.g., methyl), (b) R$^7$ is phenyl, or R$^7$ is phenyl substituted with 1 R$^{21}$ halo group, (c) R$^{10}$ is selected from the group consisting of phenyl and phenyl substituted with one or two independently selected —OR$^{15}$ groups, wherein R$^{15}$ is alkyl, (d) R$^9$ is selected from the group consisting of imidazolyl and imidazolyl substituted with one or two independently selected alkyl groups, and (e) G is N(R$^{14}$) (and in one example G is NH).

In another embodiment of this invention: (a) R$^6$ is alkyl (e.g., methyl), (b) R$^7$ is phenyl, or R$^7$ is phenyl, substituted with 1 to 3 F (i.e., R$^7$ is phenyl substituted with 1 to 3 R$^{21}$ groups, and said R$^{21}$ groups are halo, and said halo is F), (c) R$^{10}$ is selected from the group consisting of phenyl and phenyl substituted with one or two independently selected —OR$^{15}$ groups, wherein R$^{15}$ is methyl, (d) R$^9$ is selected from the group consisting of imidazolyl and imidazolyl substituted with one or two independently selected methyl groups, and (e) G is N(R$^{14}$) (and in one example G is NH).

In another embodiment of this invention: (a) R$^6$ is alkyl (e.g., methyl), (b) R$^7$ is phenyl, or R$^7$ is phenyl, substituted with 1 to 2 F (i.e., R$^7$ is phenyl substituted with 1 to 2 R$^{21}$ groups, and said R$^{21}$ groups are halo, and said halo is F), (c) R$^{10}$ is selected from the group consisting of phenyl and phenyl substituted with one or two independently selected —OR$^{15}$ groups, wherein R$^{15}$ is methyl, (d) R$^9$ is selected from the group consisting of imidazolyl and imidazolyl substituted with one or two independently selected methyl groups, and (e) G is N(R$^{14}$) (and in one example G is NH).

In another embodiment of this invention: (a) R$^6$ is alkyl (e.g., methyl), (b) R$^7$ is phenyl, or R$^7$ is phenyl, substituted with 1 F (i.e., R$^7$ is phenyl substituted with 1 R$^{21}$ group, and said R$^{21}$ group is halo, and said halo is F), (b) R$^{10}$ is selected from the group consisting of phenyl and phenyl substituted with one or two independently selected —OR$^{15}$ groups, wherein R$^{15}$ is methyl, (d) R$^9$ is selected from the group consisting of imidazolyl and imidazolyl substituted with one or two independently selected methyl groups, and (e) G is N(R$^{14}$) (and in one example G is NH).

In another embodiment of this invention: (a) R$^6$ is alkyl (e.g., methyl), (b) R$^7$ is phenyl substituted with 1 to 3 independently selected R$^{21}$ groups, (c) R$^{10}$ is selected from the group consisting of aryl and aryl substituted with one or more independently selected R$^{21}$ groups, (d) R$^9$ is selected from the group consisting of heteroaryl and heteroaryl substituted with one or more independently selected R$^{21}$ groups, and (e) G is N(R$^{14}$) (and in one example G is NH).

In another embodiment of this invention: (a) R$^6$ is alkyl (e.g., methyl), (b) R$^7$ is phenyl substituted with 1 to 3 independently selected R$^{21}$ groups, (c) R$^{10}$ is selected from the group consisting of phenyl and phenyl substituted with one or more independently selected R$^{21}$ groups, (d) R$^9$ is selected from the group consisting of imidazolyl and imidazolyl substituted with one or more independently selected R$^{21}$ groups, and (e) G is N(R$^{14}$) (and in one example G is NH).

In another embodiment of this invention: (a) R$^6$ is alkyl (e.g., methyl), (b) R$^7$ is phenyl substituted with 1 to 3 independently selected R$^{21}$ halo groups, (c) R$^{10}$ is selected from the group consisting of phenyl and phenyl substituted with one or more independently selected —OR$^{15}$ groups, (d) R$^9$ is selected from the group consisting of imidazolyl and imidazolyl substituted with one or more independently selected alkyl groups, and (e) G is N(R$^{14}$) (and in one example G is NH).

In another embodiment of this invention: (a) R$^6$ is alkyl (e.g., methyl), (b) R$^7$ is phenyl substituted with 1 to 2 independently selected R$^{21}$ halo groups, (c) R$^{10}$ is selected from the group consisting of phenyl and phenyl substituted with one or two independently selected —OR$^{15}$ groups, wherein R$^{15}$ is alkyl, (d) R$^9$ is selected from the group consisting of imidazolyl and imidazolyl substituted with one or two independently selected alkyl groups, and (e) G is N(R$^{14}$) (and in one example G is NH).

In another embodiment of this invention: (a) R$^6$ is alkyl (e.g., methyl), (b) R$^7$ is phenyl substituted with 1 R$^{21}$ halo group, (c) R$^{10}$ is selected from the group consisting of phenyl and phenyl substituted with one or two independently selected —OR$^{15}$ groups, wherein R$^{15}$ is alkyl, (d) R$^9$ is selected from the group consisting of imidazolyl and imidazolyl substituted with one or two independently selected alkyl groups groups, and (e) G is $N(R^{14})$ (and in one example G is NH).

In another embodiment of this invention: (a) $R^6$ is alkyl (e.g., methyl), (b) $R^7$ is phenyl, substituted with 1 to 3 F (i.e., $R^7$ is phenyl substituted with 1 to 3 $R^{21}$ groups, and said $R^{21}$ groups are halo, and said halo is F), (c) $R^{10}$ is selected from the group consisting of phenyl and phenyl substituted with one or two independently selected $—OR^{15}$ groups, wherein $R^{15}$ is methyl, (d) $R^9$ is selected from the group consisting of imidazolyl and imidazolyl substituted with one or two independently selected methyl groups, and (e) G is $N(R^{14})$ (and in one example G is NH).

In another embodiment of this invention: (a) $R^6$ is alkyl (e.g., methyl), (b) $R^7$ is phenyl, substituted with 1 to 2 F (i.e., $R^7$ is phenyl substituted with 1 to 2 $R^{21}$ groups, and said $R^{21}$ groups are halo, and said halo is F), (c) $R^{10}$ is selected from the group consisting of phenyl and phenyl substituted with one or two independently selected $—OR^{15}$ groups, wherein $R^{15}$ is methyl, (d) $R^9$ is selected from the group consisting of imidazolyl and imidazolyl substituted with one or two independently selected methyl groups, and (e) G is $N(R^{14})$ (and in one example G is NH).

In another embodiment of this invention: (a) $R^6$ is alkyl (e.g., methyl), (b) $R^7$ is phenyl, substituted with 1 F (i.e., $R^7$ is phenyl substituted with 1 $R^{21}$ group, and said $R^{21}$ group is halo, and said halo is F), (b) $R^{10}$ is selected from the group consisting of phenyl and phenyl substituted with one or two independently selected $—OR^{15}$ groups, wherein $R^{15}$ is methyl, (d) $R^9$ is selected from the group consisting of imidazolyl and imidazolyl substituted with one or two independently selected methyl groups, and (e) G is $N(R^{14})$ (and in one example G is NH).

In another embodiment of this invention: (a) $R^6$ is alkyl (e.g., methyl), (b) $R^7$ is phenyl, (c) $R^{10}$ is selected from the group consisting of aryl and aryl substituted with one or more independently selected $R^{21}$ groups, (d) $R^9$ is selected from the group consisting of heteroaryl and heteroaryl substituted with one or more independently selected $R^{21}$ groups, and (e) G is $N(R^{14})$ (and in one example G is NH).

In another embodiment of this invention: (a) $R^6$ is alkyl (e.g., methyl), (b) $R^7$ is phenyl, (c) $R^{10}$ is selected from the group consisting of phenyl and phenyl substituted with one or more independently selected $R^{21}$ groups, (d) $R^9$ is selected from the group consisting of imidazolyl and imidazolyl substituted with one or more independently selected $R^{21}$ groups, and (e) G is $N(R^{14})$ (and in one example G is NH).

In another embodiment of this invention: (a) $R^6$ is alkyl (e.g., methyl), (b) $R^7$ is phenyl, (c) $R^{10}$ is selected from the group consisting of phenyl and phenyl substituted with one or more independently selected $—OR^{15}$ groups, (d) $R^9$ is selected from the group consisting of imidazolyl and imidazolyl substituted with one or more independently selected alkyl groups, and (e) G is $N(R^{14})$ (and in one example G is NH).

In another embodiment of this invention: (a) $R^6$ is alkyl (e.g., methyl), (b) $R^7$ is phenyl, (c) $R^{10}$ is selected from the group consisting of phenyl and phenyl substituted with one or two independently selected $—OR^{15}$ groups, wherein $R^{15}$ is alkyl, (d) $R^9$ is selected from the group consisting of imidazolyl and imidazolyl substituted with one or two independently selected alkyl groups, and (e) G is $N(R^{14})$ (and in one example G is NH).

In another embodiment of this invention: (a) $R^6$ is alkyl (e.g., methyl), (b) $R^7$ is phenyl, (c) $R^{10}$ is selected from the group consisting of phenyl and phenyl substituted with one or two independently selected $—OR^{15}$ groups, wherein $R^{15}$ is alkyl, (d) $R^9$ is selected from the group consisting of imidazolyl and imidazolyl substituted with one or two independently selected alkyl groups, and (e) G is $N(R^{14})$ (and in one example G is NH).

In another embodiment of this invention: (a) $R^6$ is alkyl (e.g., methyl), (b) $R^7$ is phenyl, (c) $R^{10}$ is selected from the group consisting of phenyl and phenyl substituted with one or two independently selected $—OR^{15}$ groups, wherein $R^{15}$ is methyl, (d) $R^9$ is selected from the group consisting of imidazolyl and imidazolyl substituted with one or two independently selected methyl groups, and (e) G is $N(R^{14})$ (and in one example G is NH).

In another embodiment of this invention: (a) $R^6$ is alkyl (e.g., methyl), (b) $R^7$ is phenyl, (c) $R^{10}$ is selected from the group consisting of phenyl and phenyl substituted with one or two independently selected $—OR^{15}$ groups, wherein $R^{15}$ is methyl, (d) $R^9$ is selected from the group consisting of imidazolyl and imidazolyl substituted with one or two independently selected methyl groups, and (e) G is $N(R^{14})$ (and in one example G is NH).

In another embodiment of this invention: (a) $R^6$ is alkyl (e.g., methyl), (b) $R^7$ is phenyl, (b) $R^{10}$ is selected from the group consisting of phenyl and phenyl substituted with one or two independently selected $—OR^{15}$ groups, wherein $R^{15}$ is methyl, (d) $R^9$ is selected from the group consisting of imidazolyl and imidazolyl substituted with one or two independently selected methyl groups, and (e) G is $N(R^{14})$ (and in one example G is NH).

Other embodiments of this invention are directed to the above embodiments (which are directed to the combination of $R^6$, and $R^7$, and $R^{10}$, and $R^9$, with G being O, C(O), $N(R^{14})$ (such as NH), or S) wherein ring B is as defined in any one of the embodiments directed to ring B above.

Other embodiments of this invention are directed to the above embodiments (which are directed to the combination of $R^6$, and $R^7$, and $R^{10}$, and $R^9$, with G being O, C(O), $N(R^{14})$ (such as NH), or S) wherein the optional bond in ring B is present.

Other embodiments of this invention are directed to the above embodiments (which are directed to the combination of $R^6$, and $R^7$, and $R^{10}$, and $R^9$, with G being O, C(O), $N(R^{14})$ (such as NH), or S) wherein the optional bond in ring B is present and U is N.

Other embodiments of this invention are directed to the above embodiments (which are directed to the combination of $R^6$, and $R^7$, and $R^{10}$, and $R^9$, with G being O, C(O), $N(R^{14})$ (such as NH), or S) wherein the optional bond in ring B is present, U is N, and ring B is a 5 membered ring.

Other embodiments of this invention are directed to the above embodiments (which are directed to the combination of $R^6$, and $R^7$, and $R^{10}$, and $R^9$, with G being O, C(O), $N(R^{14})$ (such as NH), or S) wherein the optional bond in ring B is present, U is N, and ring B is a 6 membered ring.

Other embodiments of this invention are directed to the above embodiments (which are directed to the combination of $R^6$, and $R^7$, and $R^{10}$, and $R^9$, with G being O, C(O), $N(R^{14})$ (such as NH), or S) wherein the optional bond in ring B is present, U is N, and ring B is a 7 membered ring.

Other embodiments of this invention are directed to the above embodiments (which are directed to the combination of $R^6$, and $R^7$, and $R^{10}$, and $R^9$, with G being O, C(O), $N(R^{14})$ (such as NH), or S) wherein the optional bond in ring B is present and U is $CR^5$.

Other embodiments of this invention are directed to the above embodiments (which are directed to the combination of $R^6$, and $R^7$, and $R^{10}$, and $R^9$, with G being O, C(O), $N(R^{14})$ (such as NH), or S) wherein the optional bond in ring B is present, U is $CR^5$, and ring B is a 5 membered ring.

Other embodiments of this invention are directed to the above embodiments (which are directed to the combination of $R^6$, and $R^7$, and $R^{10}$, and $R^9$, with G being O, C(O), $N(R^{14})$ (such as NH), or S) wherein the optional bond in ring B is present, U is $CR^5$, and ring B is a 6 membered ring.

Other embodiments of this invention are directed to the above embodiments (which are directed to the combination of $R^6$, and $R^7$, and $R^{10}$, and $R^9$, with G being O, C(O), $N(R^{14})$ (such as NH), or S) wherein the optional bond in ring B is present, U is $CR^5$, and ring B is a 7 membered ring.

Other embodiments of this invention are directed to the above embodiments (which are directed to the combination of $R^6$, and $R^7$, and $R^{10}$, and $R^9$, with G being O, C(O), $N(R^{14})$ (such as NH), or S) wherein the optional bond in ring B is present, U is $CR^5$ and $R^5$ is H.

Other embodiments of this invention are directed to the above embodiments (which are directed to the combination of $R^6$, and $R^7$, and $R^{10}$, and $R^9$, with G being O, C(O), $N(R^{14})$ (such as NH), or S) wherein the optional bond in ring B is present, U is $CR^5$ and $R^5$ is H, and ring B is a 5 membered ring.

Other embodiments of this invention are directed to the above embodiments (which are directed to the combination of $R^6$, and $R^7$, and $R^{10}$, and $R^9$, with G being O, C(O), $N(R^{14})$ (such as NH), or S) wherein the optional bond in ring B is present, U is $CR^5$ and $R^5$ is H, and ring B is a 6 membered ring.

Other embodiments of this invention are directed to the above embodiments (which are directed to the combination of $R^6$, and $R^7$, and $R^{10}$, and $R^9$, with G being O, C(O), $N(R^{14})$ (such as NH), or S) wherein the optional bond in ring B is present, U is $CR^5$ and $R^5$ is H, and ring B is a 7 membered ring.

Other embodiments of this invention are directed to any one of the embodiments above wherein ring B is substituted with 1 or two $R^{21}$ groups. In one example each $R^{21}$ group is the same or different alkyl group. In another example each $R^{21}$ is methyl. In another example ring B is substituted with two $R^{21}$ groups. In another example ring B is substituted with two $R^{21}$ groups and each group is the same or different alkyl group. In another example ring B is substituted with two $R^{21}$ groups and each group is methyl group. In another example ring B is substituted with one $R^{21}$ group. In another example ring B is substituted with one $R^{21}$ group and said $R^{21}$ group is alkyl. In another example ring B is substituted with one $R^{21}$ group and said $R^{21}$ group is alkyl and said alkyl group is methyl.

In another embodiment of this invention ring B is substituted with 1 or two $R^{21}$ groups.

In another embodiment of this invention ring B is substituted with 1 or 2 $R^{21}$ groups wherein each $R^{21}$ group is the same or different alkyl group.

In another embodiment of this invention ring B is substituted with 1 or 2 $R^{21}$ groups wherein each $R^{21}$ group is methyl.

In another embodiment of this invention ring B is substituted with two $R^{21}$ groups.

In another embodiment of this invention ring B is substituted with two $R^{21}$ groups wherein each $R^{21}$ group is the same or different alkyl group.

In another embodiment of this invention ring B is substituted with two $R^{21}$ groups and each $R^{21}$ group is methyl.

In another embodiment of this invention ring B is substituted with one $R^{21}$ group.

In another embodiment of this invention ring B is substituted with one $R^{21}$ group wherein said $R^{21}$ group is an alkyl group.

In another embodiment of this invention ring B is substituted with one $R^{21}$ group and said $R^{21}$ group is methyl.

In another embodiment of this invention, the compounds of formula (I) are selected from the group consisting of:

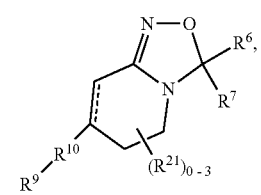

2A

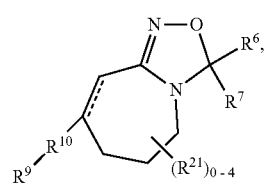

3A

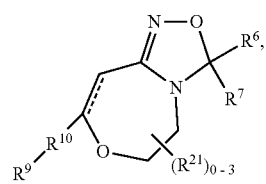

4A

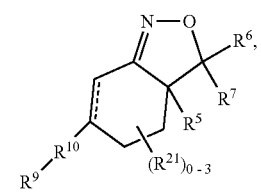

5A

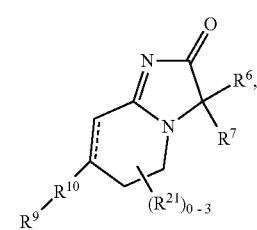

6A

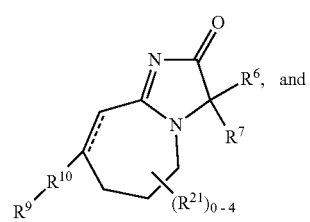

7A

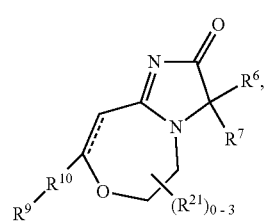

8A wherein $R^5$, $R^6$, $R^7$, $R^9$, $R^{10}$, and $R^{21}$ are as defined for formula (I) or any of the embodiments thereof. In one example of this embodiment there are 0 to 2 R$^{21}$ groups (i.e. there are no R$^{21}$ groups, or there is one R$^{21}$ group, or there are two independently selected R$^{21}$ groups) in ring B. In another example of this embodiment there are two independently selected R$^{21}$ groups in ring B. In another example of this embodiment there is one R$^{21}$ group in ring B. In one example of this embodiment there are 0 to 2 R$^{21}$ groups in ring B wherein said R$^{21}$ groups are the same or different alkyl groups (e.g. methyl). In another example of this embodiment there are two independently selected R$^{21}$ groups in ring B wherein each R$^{21}$ group is the same or different alkyl group (e.g., methyl). In another example of this embodiment there is one R$^{21}$ group and said R$^{21}$ group is alkyl (e.g. methyl). In another example of this embodiment there are no R$^{21}$ groups in ring B.

In another embodiment of this invention, the compounds of formula (I) are selected from the group consisting of:

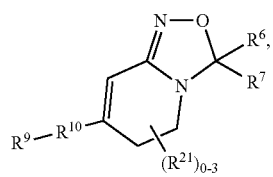
2B

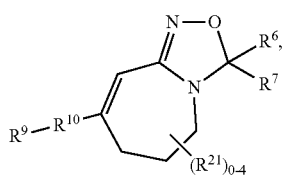
3B

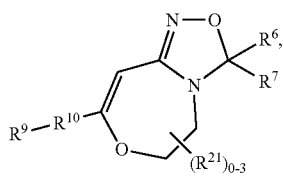
4B

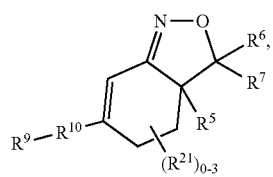
5B

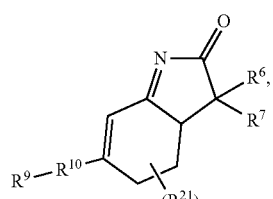
6B

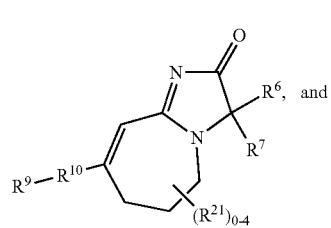
7B

-continued

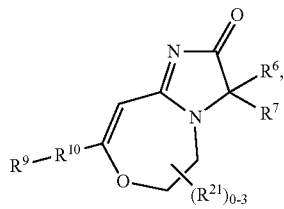
8B wherein R$^5$, R$^6$, R$^7$, R$^9$, R$^{10}$, and R$^{21}$ are as defined for formula (I) or any of the embodiments thereof. In one example of this embodiment there are 0 to 2 R$^{21}$ groups (i.e. there are no R$^{21}$ groups, or there is one R$^{21}$ group, or there are two independently selected R$^{21}$ groups) in ring B. In another example of this embodiment there are two independently selected R$^{21}$ groups in ring B. In another example of this embodiment there is one R$^{21}$ group in ring B. In one example of this embodiment there are 0 to 2 R$^{21}$ groups in ring B wherein said R$^{21}$ groups are the same or different alkyl groups (e.g. methyl). In another example of this embodiment there are two independently selected R$^{21}$ groups in ring B wherein each R$^{21}$ group is the same or different alkyl group (e.g., methyl). In another example of this embodiment there is one R$^{21}$ group and said R$^{21}$ group is alkyl (e.g. methyl). In another example of this embodiment there are no R$^{21}$ groups in ring B.

In another embodiment of this invention, the compounds of formula (I) are selected from the group consisting of:

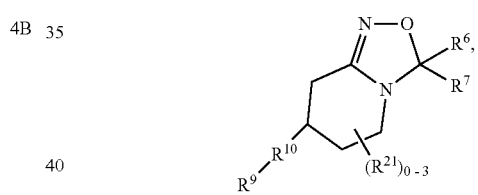
2C

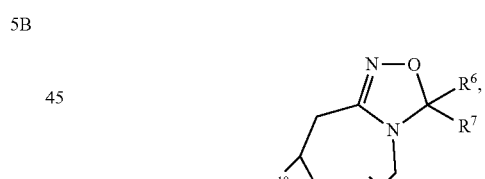
3C

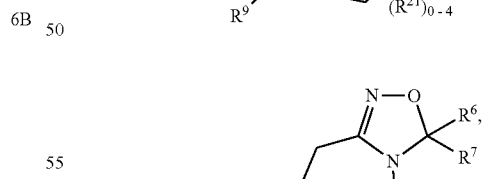
4C

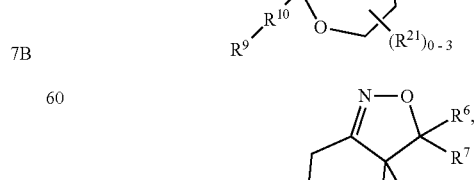
5C

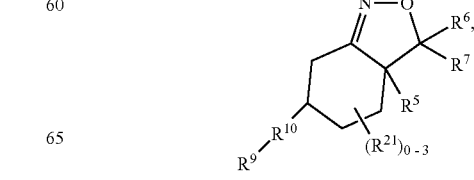

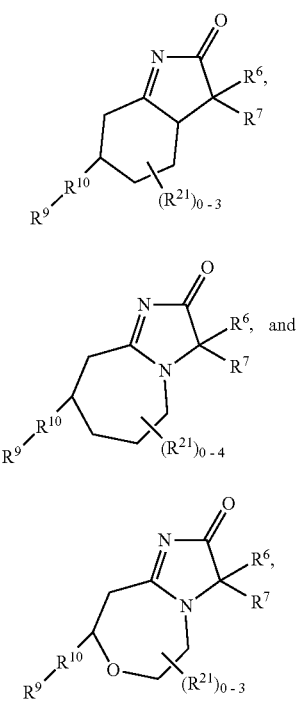

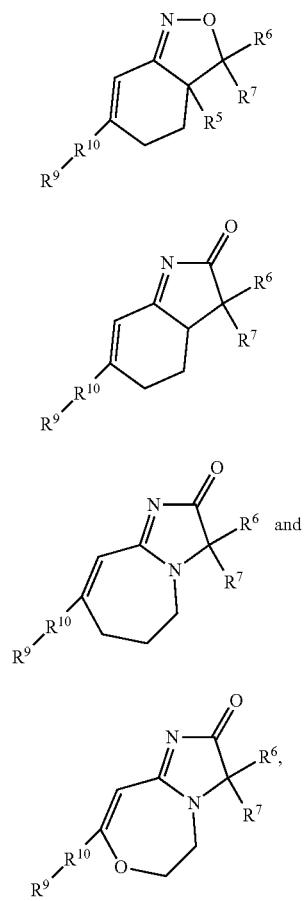

wherein $R^5$, $R^6$, $R^7$, $R^9$, $R^{10}$, and $R^{21}$ are as defined for formula (I) or any of the embodiments thereof. In one example of this embodiment there are 0 to 2 $R^{21}$ groups (i.e. there are no $R^{21}$ groups, or there is one $R^{21}$ group, or there are two independently selected $R^{21}$ groups) in ring B. In another example of this embodiment there are two independently selected $R^{21}$ groups in ring B. In another example of this embodiment there is one $R^{21}$ group in ring B. In one example of this embodiment there are 0 to 2 $R^{21}$ groups in ring B wherein said $R^{21}$ groups are the same or different alkyl groups (e.g. methyl). In another example of this embodiment there are two independently selected $R^{21}$ groups in ring B wherein each $R^{21}$ group is the same or different alkyl group (e.g., methyl). In another example of this embodiment there is one $R^{21}$ group and said $R^{21}$ group is alkyl (e.g. methyl). In another example of this embodiment there are no $R^{21}$ groups in ring B.

In another embodiment of this invention, the compounds of formula (I) are selected from the group consisting of:

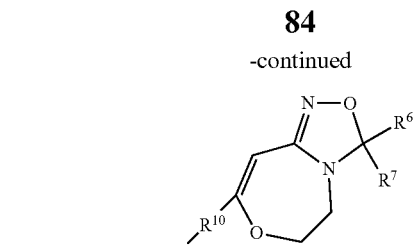

wherein $R^5$, $R^6$, $R^7$, $R^9$, and $R^{10}$, are as defined for formula (I) or any of the embodiments thereof.

In another embodiment of this invention, the compounds of formula (I) are selected from the group consisting of:

-continued

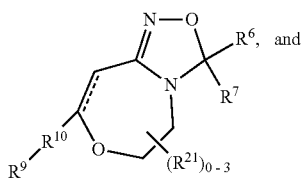
4E

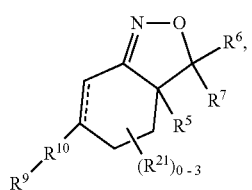
5E wherein $R^5$, $R^6$, $R^7$, $R^9$, $R^{10}$, and $R^{21}$ are as defined for formula (I) or any of the embodiments thereof. In one example of this embodiment there are 0 to 2 $R^{21}$ groups (i.e. there are no $R^{21}$ groups, or there is one $R^{21}$ group, or there are two independently selected $R^{21}$ groups) in ring B. In another example of this embodiment there are two independently selected $R^{21}$ groups in ring B. In another example of this embodiment there is one $R^{21}$ group in ring B. In one example of this embodiment there are 0 to 2 $R^{21}$ groups in ring B wherein said $R^{21}$ groups are the same or different alkyl groups (e.g. methyl). In another example of this embodiment there are two independently selected $R^{21}$ groups in ring B wherein each $R^{21}$ group is the same or different alkyl group (e.g., methyl). In another example of this embodiment there is one $R^{21}$ group and said $R^{21}$ group is alkyl (e.g. methyl). In another example of this embodiment there are no $R^{21}$ groups in ring B.

In another embodiment of this invention, the compounds of formula (I) are selected from the group consisting of:

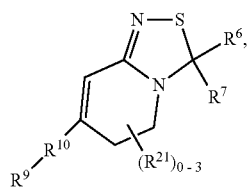
2F

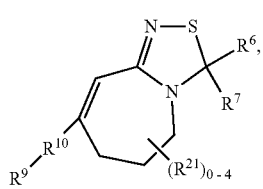
3F

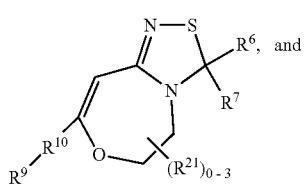
4F

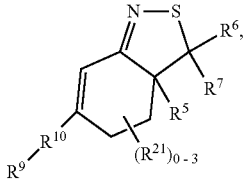
5F wherein $R^5$, $R^6$, $R^7$, $R^9$, $R^{10}$, and $R^{21}$ are as defined for formula (I) or any of the embodiments thereof. In one example of this embodiment there are 0 to 2 $R^{21}$ groups (i.e. there are no $R^{21}$ groups, or there is one $R^{21}$ group, or there are two independently selected $R^{21}$ groups) in ring B. In another example of this embodiment there are two independently selected $R^{21}$ groups in ring B. In another example of this embodiment there is one $R^{21}$ group in ring B. In one example of this embodiment there are 0 to 2 $R^{21}$ groups in ring B wherein said $R^{21}$ groups are the same or different alkyl groups (e.g. methyl). In another example of this embodiment there are two independently selected $R^{21}$ groups in ring B wherein each $R^{21}$ group is the same or different alkyl group (e.g., methyl). In another example of this embodiment there is one $R^{21}$ group and said $R^{21}$ group is alkyl (e.g. methyl). In another example of this embodiment there are no $R^{21}$ groups in ring B.

In another embodiment of this invention, the compounds of formula (I) are selected from the group consisting of:

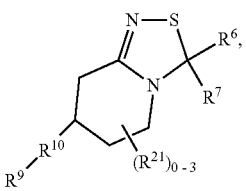
2G

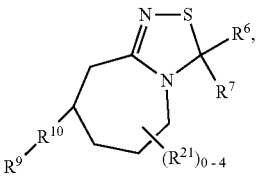
3G

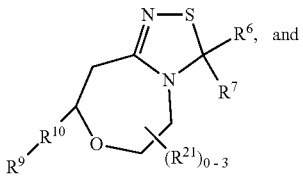
4G

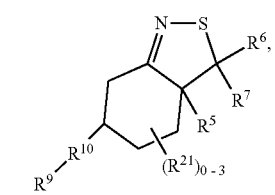
5G wherein $R^5$, $R^6$, $R^7$, $R^9$, $R^{10}$, and $R^{21}$ are as defined for formula (I) or any of the embodiments thereof. In one example of this embodiment there are 0 to 2 $R^{21}$ groups (i.e. there are no $R^{21}$ groups, or there is one $R^{21}$ group, or there are two independently selected $R^{21}$ groups) in ring B. In another example of this embodiment there are two independently selected $R^{21}$ groups in ring B. In another example of this embodiment there is one $R^{21}$ group in ring B. In one example of this embodiment there are 0 to 2 $R^{21}$ groups in ring B wherein said $R^{21}$ groups are the same or different alkyl groups (e.g. methyl). In another example of this embodiment there are two independently selected $R^{21}$ groups in ring B wherein each $R^{21}$ group is the same or different alkyl group (e.g., methyl). In another example of this embodiment there is one $R^{21}$ group and said $R^{21}$ group is alkyl (e.g. methyl). In another example of this embodiment there are no $R^{21}$ groups in ring B.

In another embodiment of this invention, the compounds of formula (I) are selected from the group consisting of:

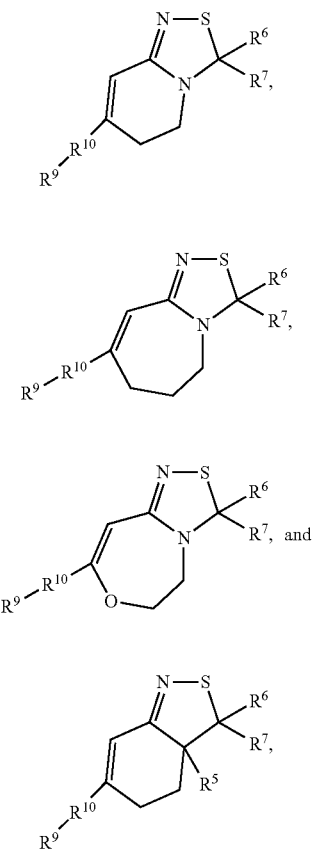

2H

3H

4H

5H wherein $R^5$, $R^6$, $R^7$, $R^9$, and $R^{10}$, are as defined for formula (I) or any of the embodiments thereof.

In another embodiment of this invention, the compounds of formula (I) are selected from the group consisting of:

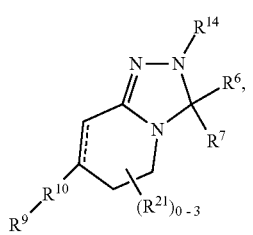

21

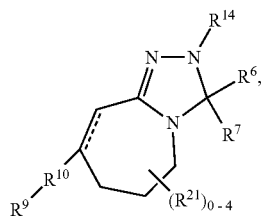

31

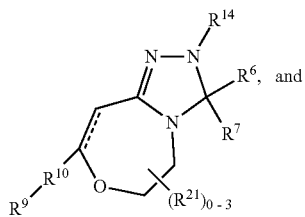

41

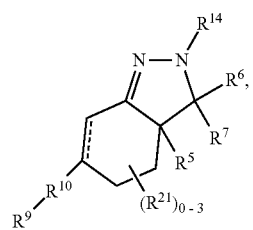

51 wherein $R^5$, $R^6$, $R^7$, $R^9$, $R^{10}$, $R^{14}$ and $R^{21}$ are as defined for formula (I) or any of the embodiments thereof. In one example of this embodiment there are 0 to 2 $R^{21}$ groups (i.e. there are no $R^{21}$ groups, or there is one $R^{21}$ group, or there are two independently selected $R^{21}$ groups) in ring B. In another example of this embodiment there are two independently selected $R^{21}$ groups in ring B. In another example of this embodiment there is one $R^{21}$ group in ring B. In one example of this embodiment there are 0 to 2 $R^{21}$ groups in ring B wherein said $R^{21}$ groups are the same or different alkyl groups (e.g. methyl). In another example of this embodiment there are two independently selected $R^{21}$ groups in ring B wherein each $R^{21}$ group is the same or different alkyl group (e.g., methyl). In another example of this embodiment there is one $R^{21}$ group and said $R^{21}$ group is alkyl (e.g. methyl). In another example of this embodiment there are no $R^{21}$ groups in ring B.

In another embodiment of this invention, the compounds of formula (I) are selected from the group consisting of:

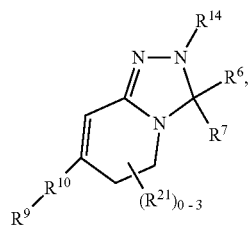

2J

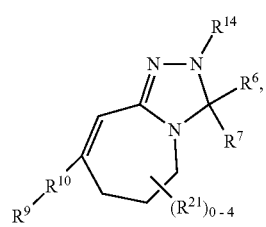

3J

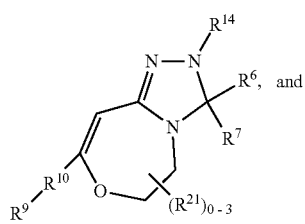

4J

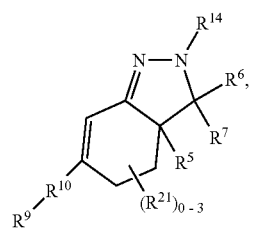

5J wherein $R^5$, $R^6$, $R^7$, $R^9$, $R^{10}$, $R^{14}$ and $R^{21}$ are as defined for formula (I) or any of the embodiments thereof. In one example of this embodiment there are 0 to 2 $R^{21}$ groups (i.e. there are no $R^{21}$ groups, or there is one $R^{21}$ group, or there are two independently selected $R^{21}$ groups) in ring B. In another example of this embodiment there are two independently selected $R^{21}$ groups in ring B. In another example of this embodiment there is one $R^{21}$ group in ring B. In one example of this embodiment there are 0 to 2 $R^{21}$ groups in ring B wherein said $R^{21}$ groups are the same or different alkyl groups (e.g. methyl). In another example of this embodiment there are two independently selected $R^{21}$ groups in ring B wherein each $R^{21}$ group is the same or different alkyl group (e.g., methyl). In another example of this embodiment there is one $R^{21}$ group and said $R^{21}$ group is alkyl (e.g. methyl). In another example of this embodiment there are no $R^{21}$ groups in ring B.

In another embodiment of this invention, the compounds of formula (I) are selected from the group consisting of:

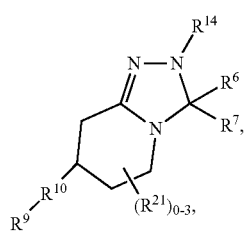 2K

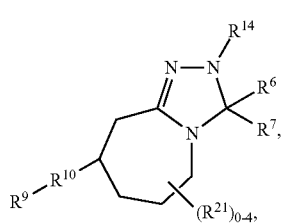 3K

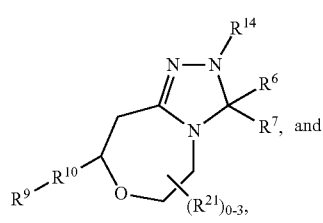 4K

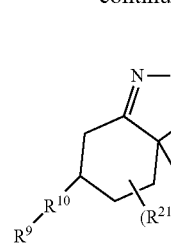 5K wherein $R^5$, $R^6$, $R^7$, $R^9$, $R^{10}$, $R^{14}$ and $R^{21}$ are as defined for formula (I) or any of the embodiments thereof. In one example of this embodiment there are 0 to 2 $R^{21}$ groups (i.e. there are no $R^{21}$ groups, or there is one $R^{21}$ group, or there are two independently selected $R^{21}$ groups) in ring B. In another example of this embodiment there are two independently selected $R^{21}$ groups in ring B. In another example of this embodiment there is one $R^{21}$ group in ring B. In one example of this embodiment there are 0 to 2 $R^{21}$ groups in ring B wherein said $R^{21}$ groups are the same or different alkyl groups (e.g. methyl). In another example of this embodiment there are two independently selected $R^{21}$ groups in ring B wherein each $R^{21}$ group is the same or different alkyl group (e.g., methyl). In another example of this embodiment there is one $R^{21}$ group and said $R^{21}$ group is alkyl (e.g. methyl). In another example of this embodiment there are no $R^{21}$ groups in ring B.

In another embodiment of this invention, the compounds of formula (I) are selected from the group consisting of:

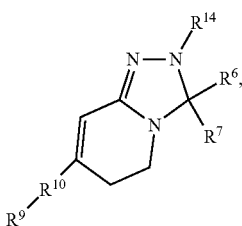 2L

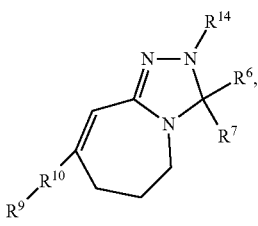 3L

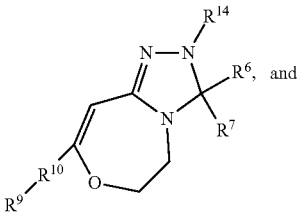 4L

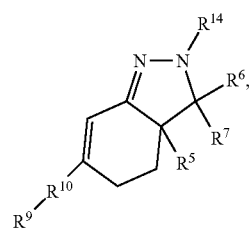 5L wherein $R^5$, $R^6$, $R^7$, $R^9$, $R^{10}$, and $R^{14}$ are as defined for formula (I) or any of the embodiments thereof.

In another embodiment of this invention, the compounds of formula (I) are selected from the group consisting of:

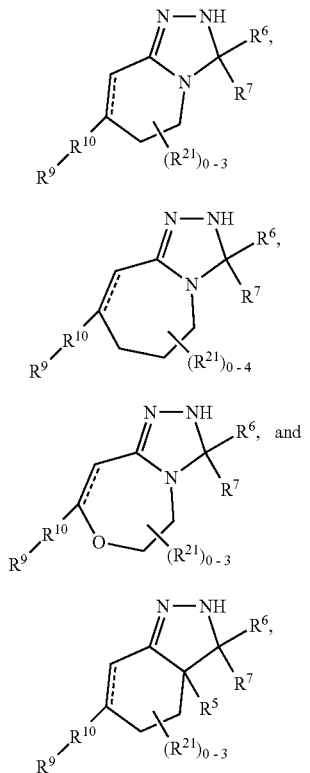

2M

3M

4M

5M wherein $R^5$, $R^6$, $R^7$, $R^9$, $R^{10}$, and $R^{21}$ are as defined for formula (I) or any of the embodiments thereof. In one example of this embodiment there are 0 to 2 $R^{21}$ groups (i.e. there are no $R^{21}$ groups, or there is one $R^{21}$ group, or there are two independently selected $R^{21}$ groups) in ring B. In another example of this embodiment there are two independently selected $R^{21}$ groups in ring B. In another example of this embodiment there is one $R^{21}$ group in ring B. In one example of this embodiment there are 0 to 2 $R^{21}$ groups in ring B wherein said $R^{21}$ groups are the same or different alkyl groups (e.g. methyl). In another example of this embodiment there are two independently selected $R^{21}$ groups in ring B wherein each $R^{21}$ group is the same or different alkyl group (e.g., methyl). In another example of this embodiment there is one $R^{21}$ group and said $R^{21}$ group is alkyl (e.g. methyl). In another example of this embodiment there are no $R^{21}$ groups in ring B.

In another embodiment of this invention, the compounds of formula (I) are selected from the group consisting of:

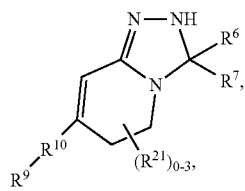

2N

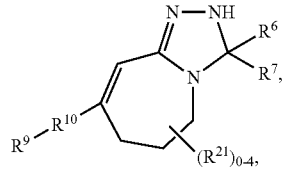

3N

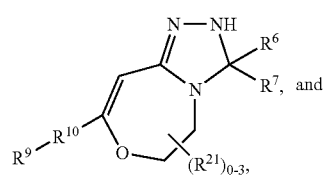

4N

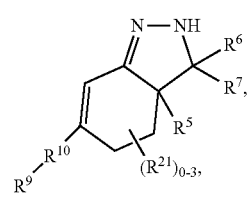

5N wherein $R^5$, $R^6$, $R^7$, $R^9$, $R^{10}$, and $R^{21}$ are as defined for formula (I) or any of the embodiments thereof. In one example of this embodiment there are 0 to 2 $R^{21}$ groups (i.e. there are no $R^{21}$ groups, or there is one $R^{21}$ group, or there are two independently selected $R^{21}$ groups) in ring B. In another example of this embodiment there are two independently selected $R^{21}$ groups in ring B. In another example of this embodiment there is one $R^{21}$ group in ring B. In one example of this embodiment there are 0 to 2 $R^{21}$ groups in ring B wherein said $R^{21}$ groups are the same or different alkyl groups (e.g. methyl). In another example of this embodiment there are two independently selected $R^{21}$ groups in ring B wherein each $R^{21}$ group is the same or different alkyl group (e.g., methyl). In another example of this embodiment there is one $R^{21}$ group and said $R^{21}$ group is alkyl (e.g. methyl). In another example of this embodiment there are no $R^{21}$ groups in ring B.

In another embodiment of this invention, the compounds of formula (I) are selected from the group consisting of:

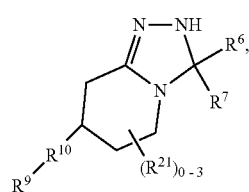

2O

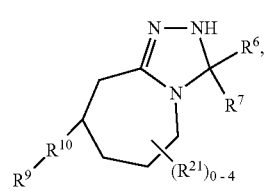

3O

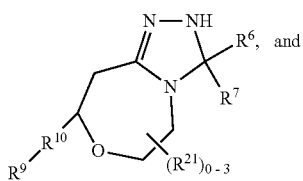

4O

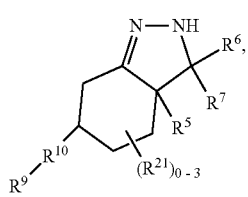

5O wherein $R^5$, $R^6$, $R^7$, $R^9$, $R^{10}$, and $R^{21}$ are as defined for formula (I) or any of the embodiments thereof. In one example of this embodiment there are 0 to 2 $R^{21}$ groups (i.e. there are no $R^{21}$ groups, or there is one $R^{21}$ group, or there are two independently selected $R^{21}$ groups) in ring B. In another example of this embodiment there are two independently selected $R^{21}$ groups in ring B. In another example of this embodiment there is one $R^{21}$ group in ring B. In one example of this embodiment there are 0 to 2 $R^{21}$ groups in ring B wherein said $R^{21}$ groups are the same or different alkyl groups (e.g. methyl). In another example of this embodiment there are two independently selected $R^{21}$ groups in ring B wherein each $R^{21}$ group is the same or different alkyl group (e.g., methyl). In another example of this embodiment there is one $R^{21}$ group and said $R^{21}$ group is alkyl (e.g. methyl). In another example of this embodiment there are no $R^{21}$ groups in ring B.

In another embodiment of this invention, the compounds of formula (I) are selected from the group consisting of:

2P

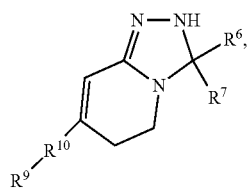

3P

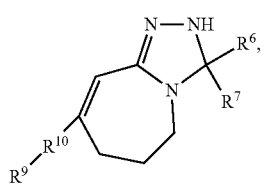

4P

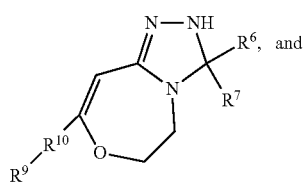

5P

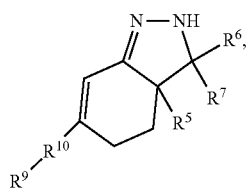

wherein $R^5$, $R^6$, $R^7$, $R^9$, and $R^{10}$ are as defined for formula (I) or any of the embodiments thereof.

In another embodiment of this invention the compound of formula (I) is a compound of formula 2A.

In another embodiment of this invention the compound of formula (I) is a compound of formula 3A.

In another embodiment of this invention the compound of formula (I) is a compound of formula 4A.

In another embodiment of this invention the compound of formula (I) is a compound of formula 5A.

In another embodiment of this invention the compound of formula (I) is a compound of formula 6A.

In another embodiment of this invention the compound of formula (I) is a compound of formula 7A.

In another embodiment of this invention the compound of formula (I) is a compound of formula 8A.

In another embodiment of this invention the compound of formula (I) is a compound of formula 9A:

9A

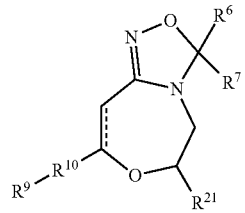

wherein in one example the ring B $R^{21}$ group is alkyl, and in another example the ring B $R^{21}$ group is methyl.

In another embodiment of this invention the compound of formula (I) is a compound of formula 9A:

9B

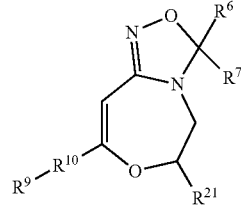

wherein in one example the ring B $R^{21}$ group is alkyl, and in another example the ring B $R^{21}$ group is methyl.

In another embodiment of this invention the compound of formula (I) is a compound of formula 9A:

9C

[Structure showing a 7-membered ring with N=O, N, O atoms and substituents R6, R7, R9, R10, R21]

wherein in one example the ring B R²¹ group is alkyl, and in another example the ring B R²¹ group is methyl.

In another embodiment of this invention the compound of formula (I) is a compound of formula 2E.
In another embodiment of this invention the compound of formula (I) is a compound of formula 3E.
In another embodiment of this invention the compound of formula (I) is a compound of formula 4E.
In another embodiment of this invention the compound of formula (I) is a compound of formula 5E.
In another embodiment of this invention the compound of formula (I) is a compound of formula 2F.
In another embodiment of this invention the compound of formula (I) is a compound of formula 3F.
In another embodiment of this invention the compound of formula (I) is a compound of formula 4F.
In another embodiment of this invention the compound of formula (I) is a compound of formula 5F.
In another embodiment of this invention the compound of formula (I) is a compound of formula 2G.
In another embodiment of this invention the compound of formula (I) is a compound of formula 3G.
In another embodiment of this invention the compound of formula (I) is a compound of formula 4G.
In another embodiment of this invention the compound of formula (I) is a compound of formula 5G.
In another embodiment of this invention the compound of formula (I) is a compound of formula 2H.
In another embodiment of this invention the compound of formula (I) is a compound of formula 3H.
In another embodiment of this invention the compound of formula (I) is a compound of formula 4H.
In another embodiment of this invention the compound of formula (I) is a compound of formula 5H.
In another embodiment of this invention the compound of formula (I) is a compound of formula 2I.
In another embodiment of this invention the compound of formula (I) is a compound of formula 3I.
In another embodiment of this invention the compound of formula (I) is a compound of formula 4I.
In another embodiment of this invention the compound of formula (I) is a compound of formula 5I.
In another embodiment of this invention the compound of formula (I) is a compound of formula 2J.
In another embodiment of this invention the compound of formula (I) is a compound of formula 3J.
In another embodiment of this invention the compound of formula (I) is a compound of formula 4J.
In another embodiment of this invention the compound of formula (I) is a compound of formula 5J.
In another embodiment of this invention the compound of formula (I) is a compound of formula 2K.
In another embodiment of this invention the compound of formula (I) is a compound of formula 3K.
In another embodiment of this invention the compound of formula (I) is a compound of formula 4K.
In another embodiment of this invention the compound of formula (I) is a compound of formula 5K.
In another embodiment of this invention the compound of formula (I) is a compound of formula 2L.
In another embodiment of this invention the compound of formula (I) is a compound of formula 3L.
In another embodiment of this invention the compound of formula (I) is a compound of formula 4L.
In another embodiment of this invention the compound of formula (I) is a compound of formula 5L.
In another embodiment of this invention the compound of formula (I) is a compound of formula 2M.
In another embodiment of this invention the compound of formula (I) is a compound of formula 3M.
In another embodiment of this invention the compound of formula (I) is a compound of formula 4M.
In another embodiment of this invention the compound of formula (I) is a compound of formula 5M.
In another embodiment of this invention the compound of formula (I) is a compound of formula 2N.
In another embodiment of this invention the compound of formula (I) is a compound of formula 3N.
In another embodiment of this invention the compound of formula (I) is a compound of formula 4N.
In another embodiment of this invention the compound of formula (I) is a compound of formula 5N.
In another embodiment of this invention the compound of formula (I) is a compound of formula 2O.
In another embodiment of this invention the compound of formula (I) is a compound of formula 3O.
In another embodiment of this invention the compound of formula (I) is a compound of formula 4O.
In another embodiment of this invention the compound of formula (I) is a compound of formula 5O.
In another embodiment of this invention the compound of formula (I) is a compound of formula 2P.
In another embodiment of this invention the compound of formula (I) is a compound of formula 3P.
In another embodiment of this invention the compound of formula (I) is a compound of formula 4P.
In another embodiment of this invention the compound of formula (I) is a compound of formula 5P.

In another embodiment of this invention, the compounds of formula (I) are selected from the group consisting of: 2A, 3A, 4A, 5A, 6A, 7A, 8A, 2B, 3B, 4B, 5B, 6B, 7B, 8B, 2C, 3C, 4C, 5C, 6C, 7C, 8C, 2D, 3D, 4D, 5D, 6D, 7D, 8D, 2E, 3E, 4E, 5E, 2F, 3F, 4F, 5F, 2G, 3G, 4G, 5G, 2H, 3H, 4H, 5H, 2I, 3I, 4I, 5I, 2J, 3J, 4J, 5J, 2K, 3K, 4K, 5K, 2L, 3L, 4LH, 5L, 2M, 3M, 4M, 5M, 2N, 3N, 4N, 5N, 2O, 3O, 4O, 5O, 2P, 3P, 4P, and 5P (as defined above including the examples thereof), wherein the —R¹⁰—R⁹ moiety is selected from the group consisting of:

[Two chemical structures: one with H₃CO- substituted phenyl attached to a methylimidazole, and one with F₃CO- substituted phenyl attached to a methylimidazole]

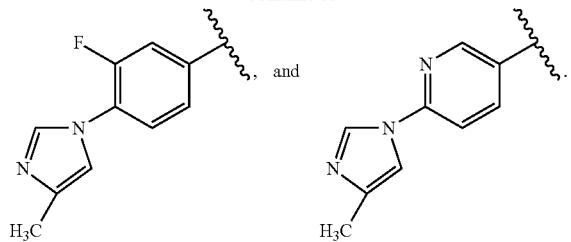

In another embodiment of this invention, the compounds of formula (I) are selected from the group consisting of: 2A, 3A, 4A, 5A, 6A, 7A, 8A, 2B, 3B, 4B, 5B, 6B, 7B, 8B, 2C, 3C, 4C, 5C, 6C, 7C, 8C, 2D, 3D, 4D, 5D, 6D, 7D, and 8D (as defined above including the examples thereof), wherein the —R$^{10}$—R$^9$ moiety is selected from the group consisting of:

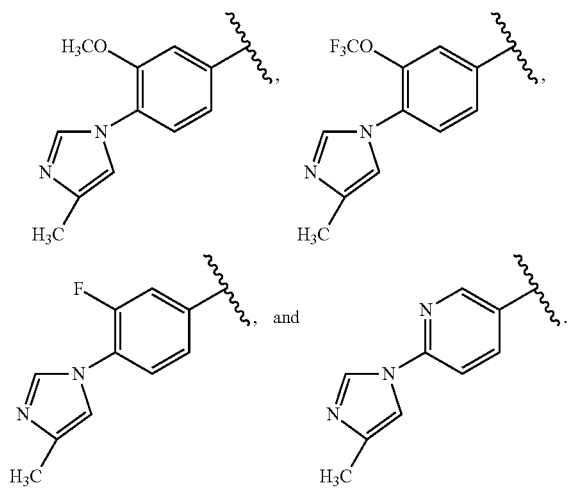

In another embodiment of this invention, the compounds of formula (I) are selected from the group consisting of: 2A, 3A, 4A, 5A, 6A, 7A, 8A, 2B, 3B, 4B, 5B, 6B, 7B, 8B, 2C, 3C, 4C, 5C, 6C, 7C, 8C, 2D, 3D, 4D, 5D, 6D, 7D, 8D, 2E, 3E, 4E, 5E, 2F, 3F, 4F, 5F, 2G, 3G, 4G, 5G, 2H, 3H, 4H, 5H, 2I, 3I, 4I, 5I, 2J, 3J, 4J, 5J, 2K, 3K, 4K, 5K, 2L, 3L, 4LH, 5L, 2M, 3M, 4M, 5M, 2N, 3N, 4N, 5N, 2O, 3O, 4O, 5O, 2P, 3P, 4P, and 5P (as defined above including the examples thereof), wherein the —R$^{10}$—R$^9$ moiety is selected from the group consisting of:

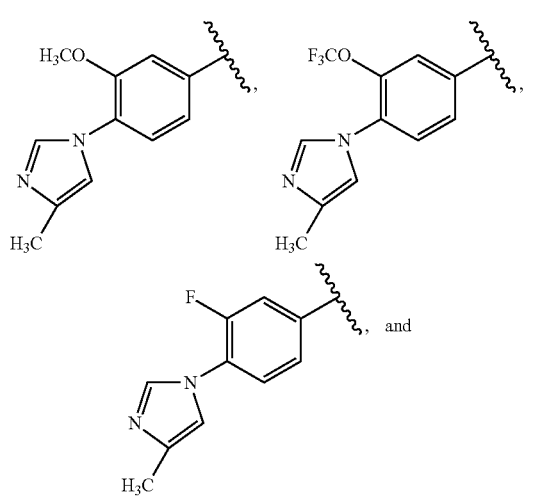

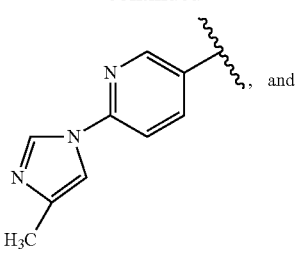

wherein R$^6$ is alkyl (e.g., methyl), and R$^7$ is substituted phenyl (e.g. fluoro substituted phenyl, such as, for example, p-F-phenyl).

In another embodiment of this invention, the compounds of formula (I) are selected from the group consisting of: 2A, 3A, 4A, 5A, 6A, 7A, 8A, 2B, 3B, 4B, 5B, 6B, 7B, 8B, 2C, 3C, 4C, 5C, 6C, 7C, 8C, 2D, 3D, 4D, 5D, 6D, 7D, and 8D (as defined above including the examples thereof), wherein the —R$^{10}$—R$^9$ moiety is selected from the group consisting of:

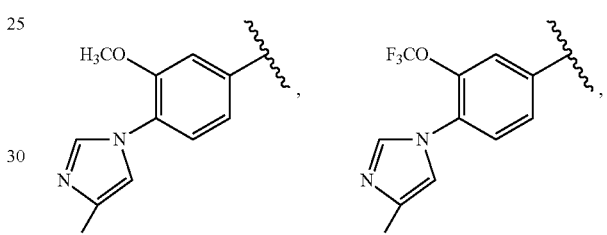

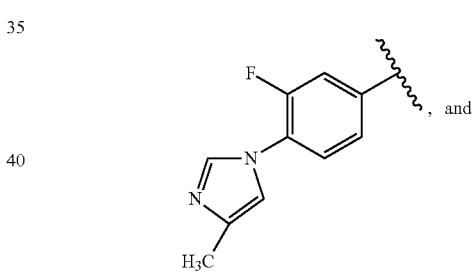

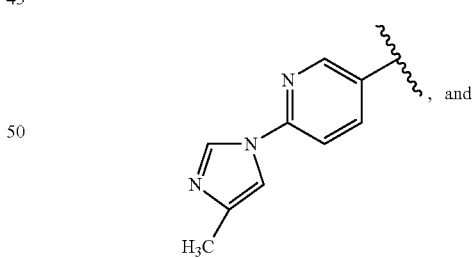

wherein R$^6$ is alkyl (e.g., methyl), and R$^7$ is substituted phenyl (e.g. fluoro substituted phenyl, such as, for example, p-F-phenyl).

In another embodiment of this invention, the compounds of formula (I) are selected from the group consisting of: 2A, 3A, 4A, 5A, 6A, 7A, 8A, 2B, 3B, 4B, 5B, 6B, 7B, 8B, 2C, 3C, 4C, 5C, 6C, 7C, 8C, 2D, 3D, 4D, 5D, 6D, 7D, 8D, 2E, 3E, 4E, 5E, 2F, 3F, 4F, 5F, 2G, 3G, 4G, 5G, 2H, 3H, 4H, 5H, 2I, 3I, 4I, 5I, 2J, 3J, 4J, 5J, 2K, 3K, 4K, 5K, 2L, 3L, 4LH, 5L, 2M, 3M, 4M, 5M, 2N, 3N, 4N, 5N, 2O, 3O, 4O, 5O, 2P, 3P, 4P, and 5P (as defined above including the examples thereof), wherein the —R¹⁰—R⁹ moiety is:

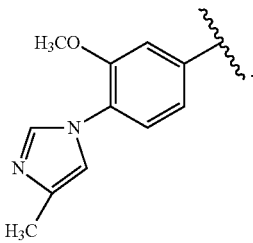

In another embodiment of this invention, the compounds of formula (I) are selected from the group consisting of: 2A, 3A, 4A, 5A, 6A, 7A, 8A, 2B, 3B, 4B, 5B, 6B, 7B, 8B, 2C, 3C, 4C, 5C, 6C, 7C, 8C, 2D, 3D, 4D, 5D, 6D, 7D, and 8D (as defined above including the examples thereof), wherein the —R¹⁰—R⁹ moiety is:

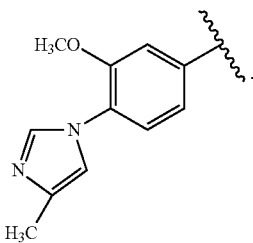

In another embodiment of this invention, the compounds of formula (I) are selected from the group consisting of: 2A, 3A, 4A, 5A, 6A, 7A, 8A, 2B, 3B, 4B, 5B, 6B, 7B, 8B, 2C, 3C, 4C, 5C, 6C, 7C, 8C, 2D, 3D, 4D, 5D, 6D, 7D, 8D, 2E, 3E, 4E, 5E, 2F, 3F, 4F, 5F, 2G, 3G, 4G, 5G, 2H, 3H, 4H, 5H, 2I, 3I, 4I, 5I, 2J, 3J, 4J, 5J, 2K, 3K, 4K, 5K, 2L, 3L, 4LH, 5L, 2M, 3M, 4M, 5M, 2N, 3N, 4N, 5N, 2O, 3O, 4O, 5O, 2P, 3P, 4P, and 5P (as defined above including the examples thereof), wherein the —R¹⁰—R⁹ moiety is:

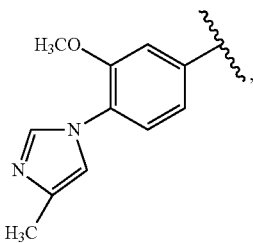

$R^6$ is alkyl (e.g., methyl), and $R^7$ is substituted phenyl (e.g. fluoro substituted phenyl, such as, for example, p-F-phenyl).

In another embodiment of this invention, the compounds of formula (I) are selected from the group consisting of: 2A, 3A, 4A, 5A, 6A, 7A, 8A, 2B, 3B, 4B, 5B, 6B, 7B, 8B, 2C, 3C, 4C, 5C, 6C, 7C, 8C, 2D, 3D, 4D, 5D, 6D, 7D, and 8D (as defined above including the examples thereof), wherein the —R¹⁰—R⁹ moiety is:

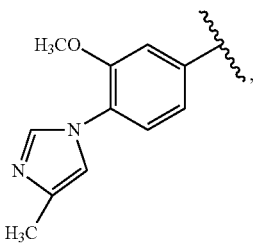

$R^6$ is alkyl (e.g., methyl), and $R^7$ is substituted phenyl (e.g. fluoro substituted phenyl, such as, for example, p-F-phenyl).

In one embodiment of this invention the compound of formula (I) is 2A, the —R¹⁰—R⁹ moiety is:

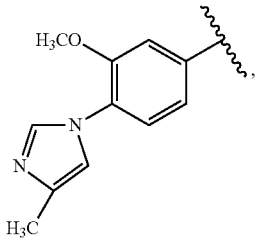

$R^6$ is alkyl (e.g., methyl), and $R^7$ is substituted phenyl (e.g. fluoro substituted phenyl, such as, for example, p-F-phenyl).

In one embodiment of this invention the compound of formula (I) is 3A, the —R¹⁰—R⁹ moiety is:

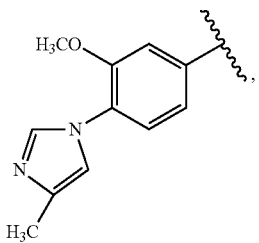

$R^6$ is alkyl (e.g., methyl), and $R^7$ is substituted phenyl (e.g. fluoro substituted phenyl, such as, for example, p-F-phenyl).

In one embodiment of this invention the compound of formula (I) is 4A, the —R¹⁰—R⁹ moiety is:

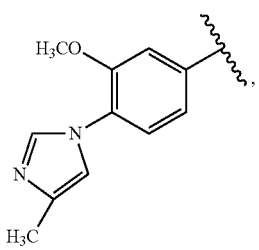

$R^6$ is alkyl (e.g., methyl), and $R^7$ is substituted phenyl (e.g. fluoro substituted phenyl, such as, for example, p-F-phenyl).

In one embodiment of this invention the compound of formula (I) is 5A, the —R¹⁰—R⁹ moiety is:

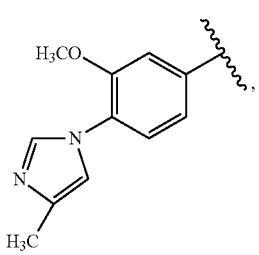

$R^6$ is alkyl (e.g., methyl), and $R^7$ is substituted phenyl (e.g. fluoro substituted phenyl, such as, for example, p-F-phenyl).

In one embodiment of this invention the compound of formula (I) is 6A, the —R¹⁰—R⁹ moiety is:

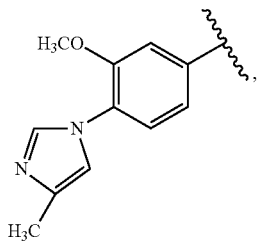 [SMILES: *c1ccc(-n2cnc(C)c2)c(OC)c1]

R⁶ is alkyl (e.g., methyl), and R⁷ is substituted phenyl (e.g. fluoro substituted phenyl, such as, for example, p-F-phenyl).

In one embodiment of this invention the compound of formula (I) is 7A, the —R¹⁰—R⁹ moiety is:

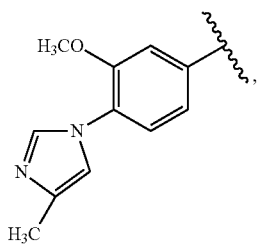 [SMILES: *c1ccc(-n2cnc(C)c2)c(OC)c1]

R⁶ is alkyl (e.g., methyl), and R⁷ is substituted phenyl (e.g. fluoro substituted phenyl, such as, for example, p-F-phenyl).

In one embodiment of this invention the compound of formula (I) is 8A, the —R¹⁰—R⁹ moiety is:

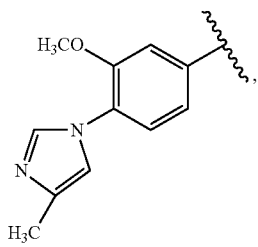 [SMILES: *c1ccc(-n2cnc(C)c2)c(OC)c1]

R⁶ is alkyl (e.g., methyl), and R⁷ is substituted phenyl (e.g. fluoro substituted phenyl, such as, for example, p-F-phenyl).

In one embodiment of this invention the compound of formula (I) is 2B, the —R¹⁰—R⁹ moiety is:

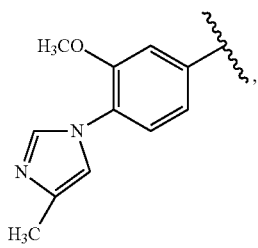 [SMILES: *c1ccc(-n2cnc(C)c2)c(OC)c1]

R⁶ is alkyl (e.g., methyl), and R⁷ is substituted phenyl (e.g. fluoro substituted phenyl, such as, for example, p-F-phenyl).

In one embodiment of this invention the compound of formula (I) is 3B, the —R¹⁰—R⁹ moiety is:

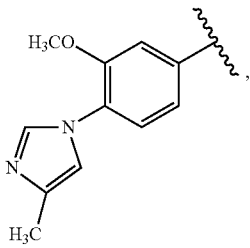 [SMILES: *c1ccc(-n2cnc(C)c2)c(OC)c1]

R⁶ is alkyl (e.g., methyl), and R⁷ is substituted phenyl (e.g. fluoro substituted phenyl, such as, for example, p-F-phenyl).

In one embodiment of this invention the compound of formula (I) is 4B, the —R¹⁰—R⁹ moiety is:

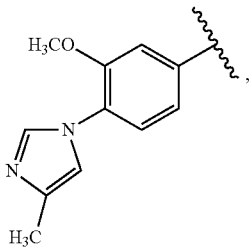 [SMILES: *c1ccc(-n2cnc(C)c2)c(OC)c1]

R⁶ is alkyl (e.g., methyl), and R⁷ is substituted phenyl (e.g. fluoro substituted phenyl, such as, for example, p-F-phenyl).

In one embodiment of this invention the compound of formula (I) is 5B, the —R¹⁰—R⁹ moiety is:

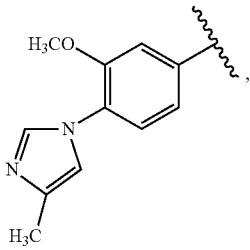 [SMILES: *c1ccc(-n2cnc(C)c2)c(OC)c1]

R⁶ is alkyl (e.g., methyl), and R⁷ is substituted phenyl (e.g. fluoro substituted phenyl, such as, for example, p-F-phenyl).

In one embodiment of this invention the compound of formula (I) is 6B, the —R¹⁰—R⁹ moiety is:

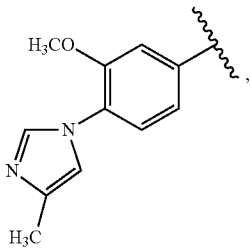 [SMILES: *c1ccc(-n2cnc(C)c2)c(OC)c1]

R⁶ is alkyl (e.g., methyl), and R⁷ is substituted phenyl (e.g. fluoro substituted phenyl, such as, for example, p-F-phenyl).

In one embodiment of this invention the compound of formula (I) is 7B, the —R¹⁰—R⁹ moiety is:

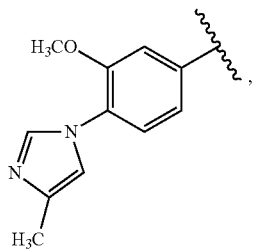 [SMILES: *c1ccc(-n2cnc(C)c2)c(OC)c1]

R⁶ is alkyl (e.g., methyl), and R⁷ is substituted phenyl (e.g. fluoro substituted phenyl, such as, for example, p-F-phenyl).

In one embodiment of this invention the compound of formula (I) is 8B, the —R¹⁰—R⁹ moiety is:

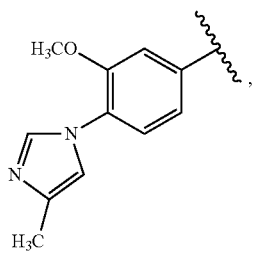 [SMILES: *c1ccc(-n2cnc(C)c2)c(OC)c1]

R⁶ is alkyl (e.g., methyl), and R⁷ is substituted phenyl (e.g. fluoro substituted phenyl, such as, for example, p-F-phenyl).

In one embodiment of this invention the compound of formula (I) is 2C, the —R¹⁰—R⁹ moiety is:

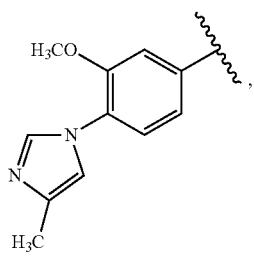

R⁶ is alkyl (e.g., methyl), and R⁷ is substituted phenyl (e.g. fluoro substituted phenyl, such as, for example, p-F-phenyl).

In one embodiment of this invention the compound of formula (I) is 3C, the —R¹⁰—R⁹ moiety is:

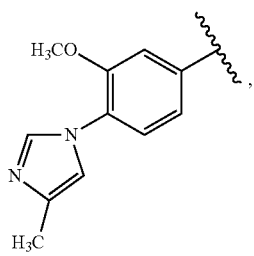 [SMILES: *c1ccc(-n2cnc(C)c2)c(OC)c1]

R⁶ is alkyl (e.g., methyl), and R⁷ is substituted phenyl (e.g. fluoro substituted phenyl, such as, for example, p-F-phenyl).

In one embodiment of this invention the compound of formula (I) is 4C, the —R¹⁰—R⁹ moiety is:

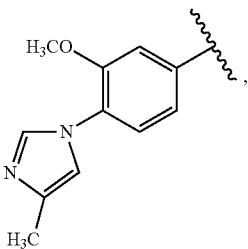 [SMILES: *c1ccc(-n2cnc(C)c2)c(OC)c1]

R⁶ is alkyl (e.g., methyl), and R⁷ is substituted phenyl (e.g. fluoro substituted phenyl, such as, for example, p-F-phenyl).

In one embodiment of this invention the compound of formula (I) is 5C, the —R¹⁰—R⁹ moiety is:

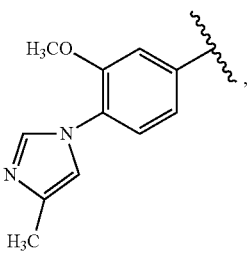 [SMILES: *c1ccc(-n2cnc(C)c2)c(OC)c1]

R⁶ is alkyl (e.g., methyl), and R⁷ is substituted phenyl (e.g. fluoro substituted phenyl, such as, for example, p-F-phenyl).

In one embodiment of this invention the compound of formula (I) is 6C, the —R¹⁰—R⁹ moiety is:

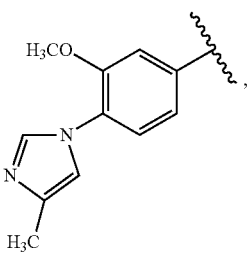 [SMILES: *c1ccc(-n2cnc(C)c2)c(OC)c1]

R⁶ is alkyl (e.g., methyl), and R⁷ is substituted phenyl (e.g. fluoro substituted phenyl, such as, for example, p-F-phenyl).

In one embodiment of this invention the compound of formula (I) is 7C, the —R¹⁰—R⁹ moiety is:

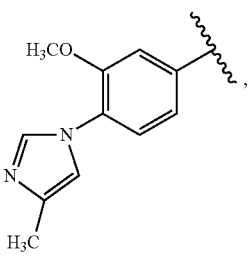 [SMILES: *c1ccc(-n2cnc(C)c2)c(OC)c1]

R⁶ is alkyl (e.g., methyl), and R⁷ is substituted phenyl (e.g. fluoro substituted phenyl, such as, for example, p-F-phenyl).

In one embodiment of this invention the compound of formula (I) is 8C, the —R$^{10}$—R$^9$ moiety is:

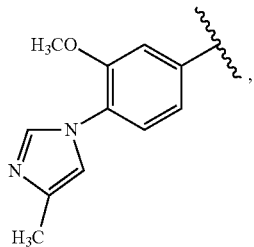 [SMILES: *c1ccc(-n2cnc(C)c2)c(OC)c1]

R$^6$ is alkyl (e.g., methyl), and R$^7$ is substituted phenyl (e.g. fluoro substituted phenyl, such as, for example, p-F-phenyl).

In one embodiment of this invention the compound of formula (I) is 2D, the —R$^{10}$—R$^9$ moiety is:

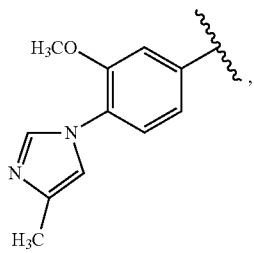

R$^6$ is alkyl (e.g., methyl), and R$^7$ is substituted phenyl (e.g. fluoro substituted phenyl, such as, for example, p-F-phenyl).

In one embodiment of this invention the compound of formula (I) is 3D, the —R$^{10}$—R$^9$ moiety is:

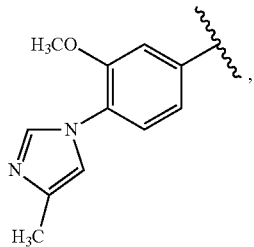

R$^6$ is alkyl (e.g., methyl), and R$^7$ is substituted phenyl (e.g. fluoro substituted phenyl, such as, for example, p-F-phenyl).

In one embodiment of this invention the compound of formula (I) is 4D, the —R$^{10}$—R$^9$ moiety is:

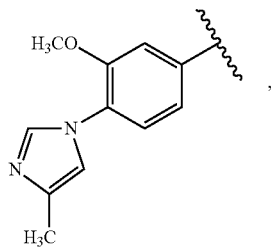

R$^6$ is alkyl (e.g., methyl), and R$^7$ is substituted phenyl (e.g. fluoro substituted phenyl, such as, for example, p-F-phenyl).

In one embodiment of this invention the compound of formula (I) is 5D, the —R$^{10}$—R$^9$ moiety is:

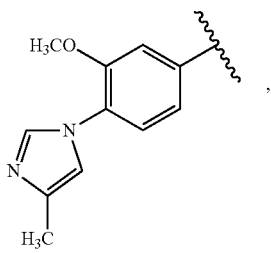 [SMILES: *c1ccc(-n2cnc(C)c2)c(OC)c1]

R$^6$ is alkyl (e.g., methyl), and R$^7$ is substituted phenyl (e.g. fluoro substituted phenyl, such as, for example, p-F-phenyl).

In one embodiment of this invention the compound of formula (I) is 6D, the —R$^{10}$—R$^9$ moiety is:

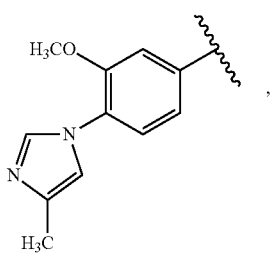 [SMILES: *c1ccc(-n2cnc(C)c2)c(OC)c1]

R$^6$ is alkyl (e.g., methyl), and R$^7$ is substituted phenyl (e.g. fluoro substituted phenyl, such as, for example, p-F-phenyl).

In one embodiment of this invention the compound of formula (I) is 7D, the —R$^{10}$—R$^9$ moiety is:

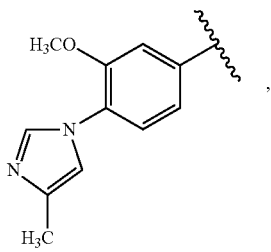 [SMILES: *c1ccc(-n2cnc(C)c2)c(OC)c1]

R$^6$ is alkyl (e.g., methyl), and R$^7$ is substituted phenyl (e.g. fluoro substituted phenyl, such as, for example, p-F-phenyl).

In one embodiment of this invention the compound of formula (I) is 8D, the —R$^{10}$—R$^9$ moiety is:

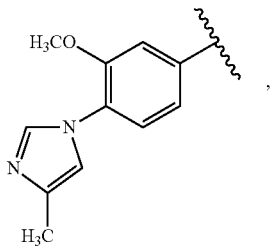 [SMILES: *c1ccc(-n2cnc(C)c2)c(OC)c1]

R$^6$ is alkyl (e.g., methyl), and R$^7$ is substituted phenyl (e.g. fluoro substituted phenyl, such as, for example, p-F-phenyl).

In another embodiment of this invention, the compounds of formula (I) are selected from the group consisting of: 2E, 3E, 4E, 5E, 2F, 3F, 4F, 5F, 2G, 3G, 4G, 5G, 2H, 3H, 4H, 5H, 2I, 3I, 4I, 5I, 2J, 3J, 4J, 5J, 2K, 3K, 4K, 5K, 2L, 3L, 4LH, 5L, 2M, 3M, 4M, 5M, 2N, 3N, 4N, 5N, 2O, 3O, 4O, 5O, 2P, 3P, 4P, and 5P, wherein the —$R^{10}$—$R^9$ moiety is selected from the group consisting of:

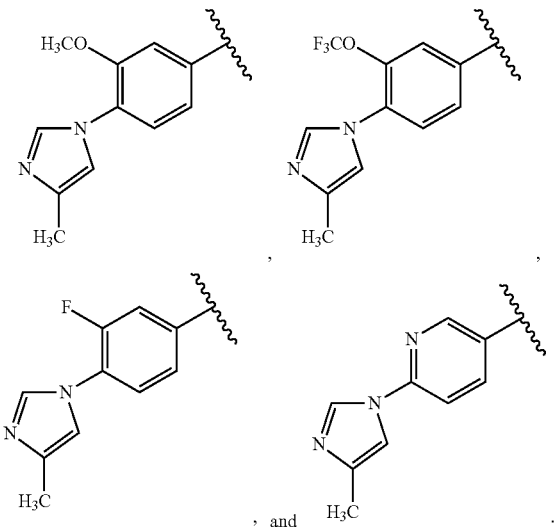

In another embodiment of this invention, the compounds of formula (I) are selected from the group consisting of: 2E, 3E, 4E, 5E, 2F, 3F, 4F, 5F, 2G, 3G, 4G, 5G, 2H, 3H, 4H, 5H, 2I, 3I, 4I, 5I, 2J, 3J, 4J, 5J, 2K, 3K, 4K, 5K, 2L, 3L, 4LH, 5L, 2M, 3M, 4M, 5M, 2N, 3N, 4N, 5N, 2O, 3O, 4O, 5O, 2P, 3P, 4P, and 5P, wherein the —$R^{10}$—$R^9$ moiety is selected from the group consisting of:

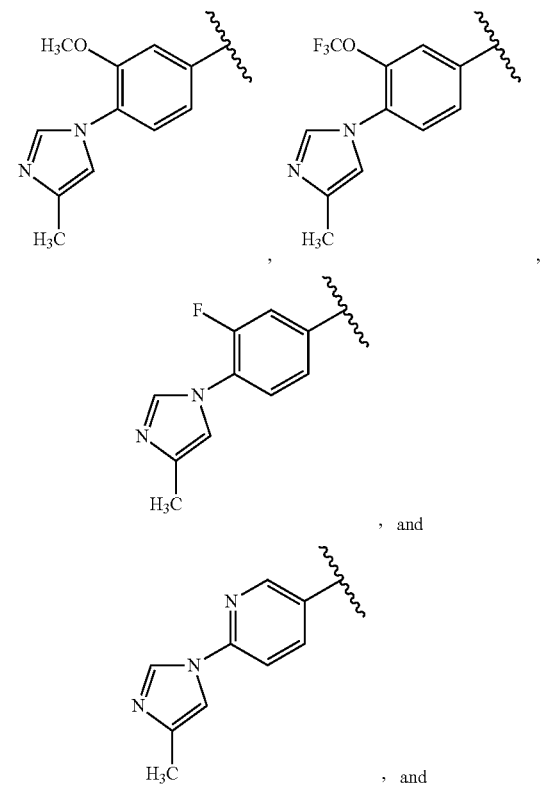

wherein $R^6$ is alkyl (e.g., methyl), and $R^7$ is substituted phenyl (e.g. fluoro substituted phenyl, such as, for example, p-F-phenyl).

In another embodiment of this invention, the compounds of formula (I) are selected from the group consisting of: 2E, 3E, 4E, 5E, 2F, 3F, 4F, 5F, 2G, 3G, 4G, 5G, 2H, 3H, 4H, 5H, 2I, 3I, 4I, 5I, 2J, 3J, 4J, 5J, 2K, 3K, 4K, 5K, 2L, 3L, 4LH, 5L, 2M, 3M, 4M, 5M, 2N, 3N, 4N, 5N, 2O, 3O, 4O, 5O, 2P, 3P, 4P, and 5P, wherein the —$R^{10}$—$R^9$ moiety is:

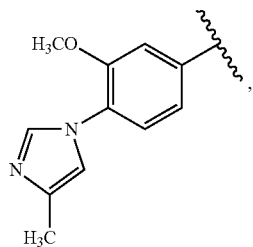 [SMILES: *c1ccc(-n2cnc(C)c2)c(OC)c1]

In another embodiment of this invention, the compounds of formula (I) are selected from the group consisting of: 2E, 3E, 4E, 5E, 2F, 3F, 4F, 5F, 2G, 3G, 4G, 5G, 2H, 3H, 4H, 5H, 2I, 3I, 4I, 5I, 2J, 3J, 4J, 5J, 2K, 3K, 4K, 5K, 2L, 3L, 4LH, 5L, 2M, 3M, 4M, 5M, 2N, 3N, 4N, 5N, 2O, 3O, 4O, 5O, 2P, 3P, 4P, and 5P, wherein the —$R^{10}$—$R^9$ moiety is:

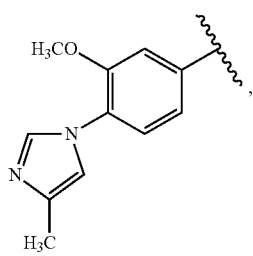 [SMILES: *c1ccc(-n2cnc(C)c2)c(OC)c1]

$R^6$ is alkyl (e.g., methyl), and $R^7$ is substituted phenyl (e.g. fluoro substituted phenyl, such as, for example, p-F-phenyl).

A representative compound of this invention is:

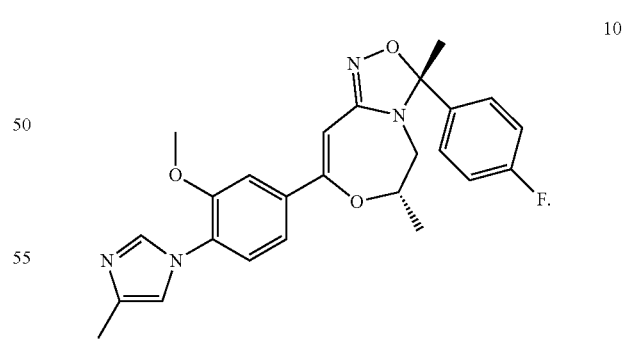

Thus, in the embodiments above directed to compounds 2A, 3A, 4A, 5A, 6A, 7A, 8A, 2B, 3B, 4B, 5B, 6B, 7B, 8B, 2C, 3C, 4C, 5C, 6C, 7C, 8C, 2D, 3D, 4D, 5D, 6D, 7D, and 8D,

can have the stereochemistry:

Also, in the embodiments above directed to compounds 2A, 3A, 4A, 5A, 6A, 7A, 8A, 2B, 3B, 4B, 5B, 6B, 7B, 8B, 2C, 3C, 4C, 5C, 6C, 7C, and 8C, the $R^{21}$ groups on ring B can have the stereochemistry:

Also, in the embodiments above directed to compounds 2E, 3E, 4E, 5E, 2F, 3F, 4F, 5F, 2G, 3G, 4G, 5G, 2H, 3H, 4H, 5H, 2I, 3I, 4I, 5I, 2J, 3J, 4J, 5J, 2K, 3K, 4K, 5K, 2L, 3L, 4L, 5L, 2M, 3M, 4M, 5M, 2N, 3N, 4N, 5N, 2O, 3O, 4O, 5O, 2P, 3P, 4P, and 5P,

can have the stereochemistry:

Also, in the embodiments above directed to compounds 2E, 3E, 4E, 5E, 2F, 3F, 4F, 5F, 2G, 3G, 4G, 5G, 2I, 3I, 4I, 5I, 2J, 3J, 4J, 5J, 2K, 3K, 4K, 5K, 2M, 3M, 4M, 5M, 2N, 3N, 4N, 5N, 2O, 3O, 4O, and 5O, the $R^{21}$ groups on ring B can have the stereochemistry:

In another embodiment of this invention $R^{21}$ is selected from the group consisting of: alkyl, —$OR^{15}$, —$C(O)OR^{15}$, —$C(O)NR^{15}R^{16}$, and alkyl substituted with 1 to 5 independently selected $R^{22}$ groups (e.g., halo, such as, for example, F, Cl, and Br).

In another embodiment of this invention $R^{21}$ is selected from the group consisting of: alkyl, —$OR^{15}$, —$C(O)OR^{15}$, —$C(O)NR^{15}R^{16}$, and alkyl substituted with 1 to 5 independently selected $R^{22}$ groups (e.g., halo, such as, for example, F, Cl, and Br, and wherein in one example the alkyl substituted $R^{21}$ group is —$CF_3$), wherein $R^{15}$ and $R^{16}$ are independently selected from the group consisting of: H, alkyl, $(R^{18})_n$-arylalkyl- (wherein, for example, n is 1, and $R^{18}$ is —$OR^{20}$, and $R^{20}$ is alkyl (e.g., methyl), cycloalkyl (e.g., cyclobutyl), and $(R^{18})_n$-alkyl (e.g, n is 1, $R^{18}$ is —$OR^{20}$, and $R^{20}$ is alkyl (e.g., methyl).

In another embodiment of this invention $R^{21}$ is selected from the group consisting of: (a) alkyl, —$OR^{15}$ (wherein $R^{15}$ is alkyl, e.g., methyl and ethyl), (b) —$C(O)OR^{15}$ (wherein $R^{15}$ is alkyl, e.g., methyl), (c) —$C(O)NR^{15}R^{16}$ (wherein $R^{15}$ and $R^{16}$ are independently selected from the group consisting of: H, alkyl, $(R^{18})_n$-arylalkyl- (wherein, for example, n is 1, and $R^{18}$ is —$OR^{20}$, and $R^{20}$ is alkyl (e.g., methyl), cycloalkyl (e.g., cyclobutyl), and $(R^{18})_n$-alkyl (e.g, n is 1, $R^{18}$ is —$OR^{20}$, and $R^{20}$ is alkyl (e.g., methyl), and in one example, only one of $R^{15}$ and $R^{16}$ is H), and (d) alkyl substituted with 1 to 5 independently selected $R^{22}$ groups (e.g., halo, such as, for example, F, Cl, and Br, and wherein in one example the alkyl substituted $R^{21}$ group is —$CF_3$).

Other embodiments of this invention are directed to compounds of formula (I) wherein $R^{14}$ is selected from the group consisting of: benzofusedcycloalkyl (i.e., fused benzocycloalkyl), fused benzoheterocycloalkyl, fused heteroarylcycloalkyl, fused heteroarylheterocycloalkyl, and wherein said $R^{14}$ groups are optionally substituted with 1-5 independently selected $R^{21}$ groups. In one example, the $R^{21}$ groups are halo (e.g., F).

Examples of the fused ring $R^6$ or $R^7$ groups include, but are not limited to:

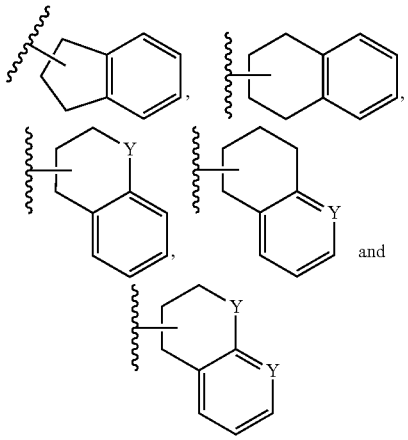

wherein each Y is independently selected from the group consisting of: —O—, —$NR^{14}$— and —$C(R^{21})_q$—, (wherein q is 0, 1 or 2 and each $R^{21}$ is independently selected), and wherein $R^{14}$ and $R^{21}$ are as defined for formula (I). Examples of these fused ring $R^6$ or $R^7$ groups include, for example:

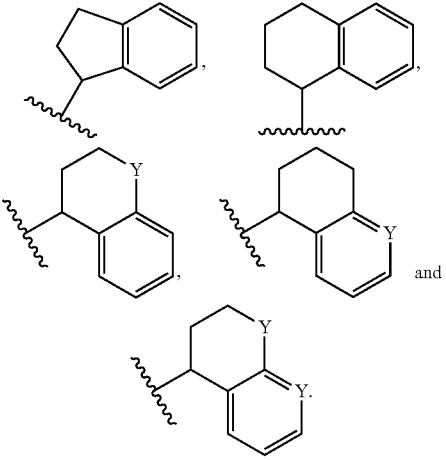

Compounds of formula (I) also include compounds wherein $R^6$ or $R^7$ is an alkyl group (e.g., methyl or ethyl) substituted with one $R^{21}$ group. Examples of such groups include alkyl (e.g., methyl or ethyl) substituted with the $R^{21}$ moiety aryl (e.g., phenyl or naphthyl). Examples of said $R^6$ or $R^7$ groups also include alkyl (e.g., methyl or ethyl) substituted with the $R^{21}$ moiety aryl (e.g., phenyl or naphthyl), which in turn is substituted with one or more (e.g., one or two) independently selected $R^{22}$ groups (e.g., $R^{22}$ is halo, such as, for example, F).

Examples of the substituted $R^6$ or $R^7$ alkyl groups include, but are not limited to:

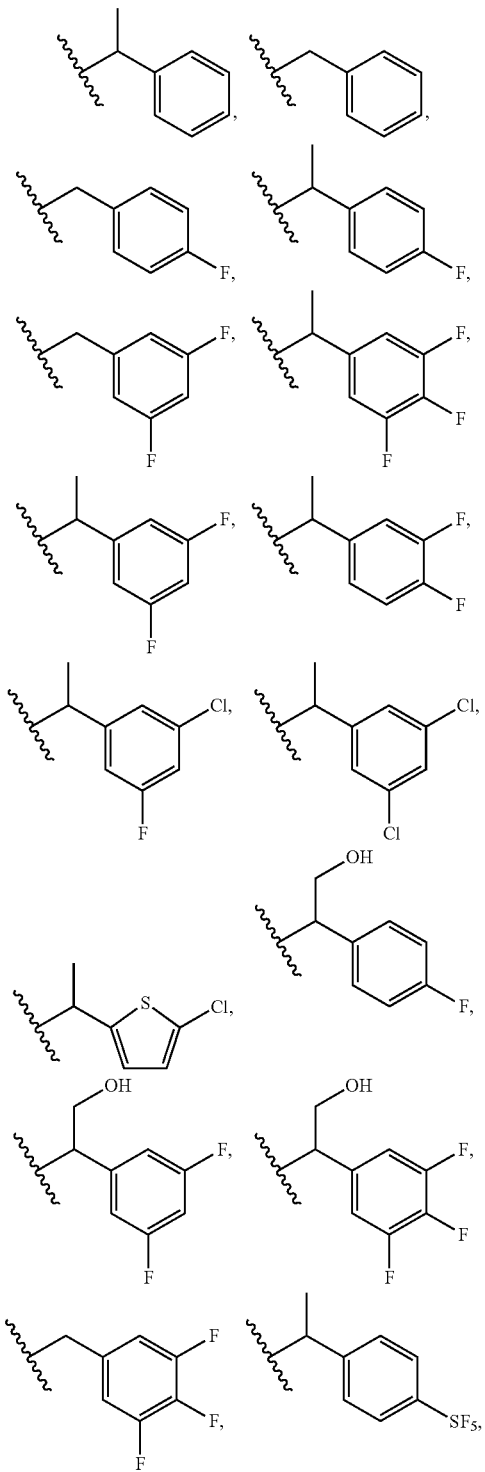

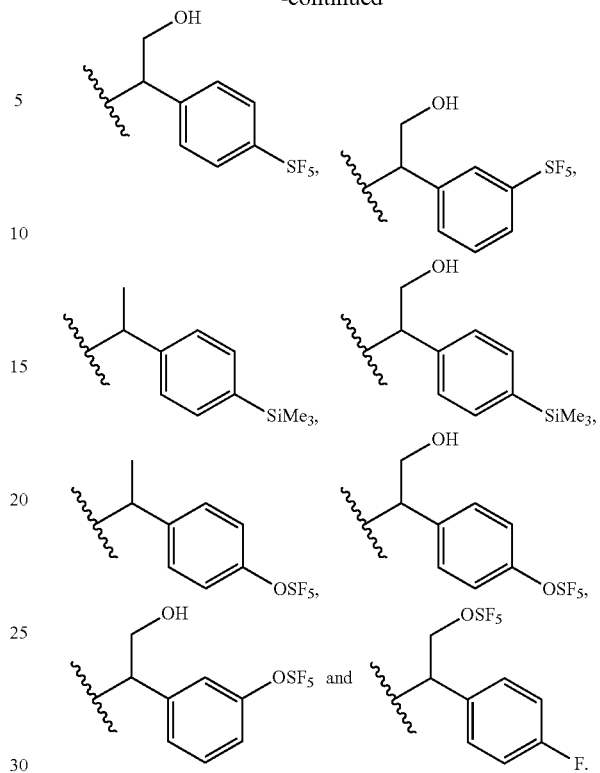

Other embodiments of this invention are directed to compounds of formula (I) wherein $R^6$ or $R^7$ is a cycloalkyl group (e.g., cyclopropyl or cyclobutyl) substituted with one $R^{21}$ group (e.g., aryl, such as, for example, phenyl), or a cycloalkyl group (e.g., cyclopentyl or cyclohexyl) substituted with one $R^{21}$ group (e.g., aryl, such as, for example, phenyl) which in turn is substituted with one or more (e.g., one or two) independently selected $R^{22}$ groups (e.g., halo, such as, for example, F). In one example the $R^{21}$ group is bound to the same carbon of the $R^6$ or $R^7$ group that binds the R $R^6$ or $R^7$ group to the rest of the molecule.

Examples of the cycloalkyl $R^6$ or $R^7$ groups include, but are not limited to:

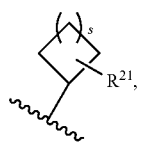

such as, for example,

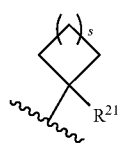

wherein s is 0 (i.e., the ring is cyclopropyl), or 1 (i.e., the ring is cyclobutyl). Examples of these $R^6$ or $R^7$ groups include, but are not limited to:

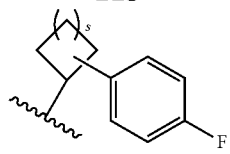

such as, for example,

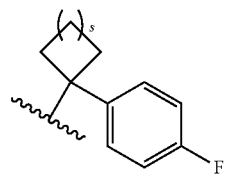

wherein s is 0 (i.e., the ring is cyclopropyl), or 1 (i.e., the ring is cyclobutyl).

Other embodiments of this invention are directed to compounds of formula (I) wherein $R^6$ or $R^7$ is

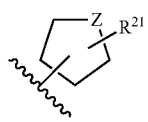

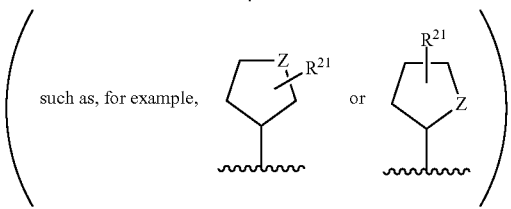

wherein Z is selected from the group consisting of: (1) —O—, (2) —NR$^{14}$—, (3) —C(R$^{21}$)$_q$— wherein q is 0, 1 or 2, and each R$^{21}$ is independently selected, (4) —C(R$^{21}$)$_q$—C(R$^{21}$)$_q$— wherein each q is independently 0, 1 or 2 and each R$^{21}$ is independently selected, (5) —(C(R$^{21}$)$_q$)$_q$—O—(C(R$^{21}$)$_q$)$_q$— wherein each q is independently 0, 1 or 2, and each R$^{21}$ is independently selected, and (6) —(C(R$^{21}$)$_q$)$_q$—N(R$^{14}$)—(C(R$^{21}$)$_q$)$_q$— wherein each q is independently 0, 1 or 2, and each R$^{21}$ is independently selected. Examples of R$^{21}$ include, but are not limited to, aryl (e.g., phenyl) and aryl (e.g., phenyl) substituted with one or more (e.g., one or two, or one) independently selected R$^{22}$ groups (e.g., halo, such as, for example, F). Examples of this R$^6$ or R$^7$ include, but are not limited to:

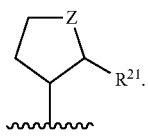

Thus, examples of this R$^6$ or R$^7$ group include, but are not limited to:

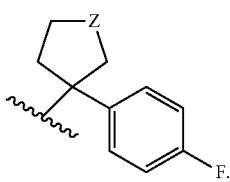

Examples of $R^6$ or $R^7$ also include, but are not limited to:

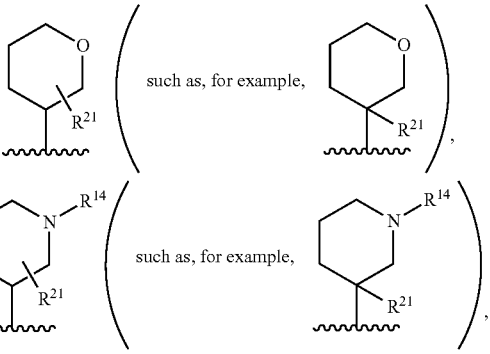

Examples of the $R^6$ or $R^7$ group

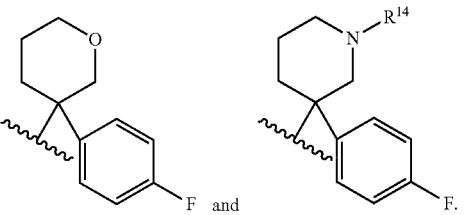

also include, but are not limited to:

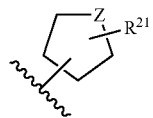

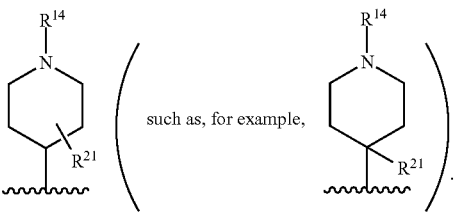

Examples of the $R^6$ or $R^7$ group

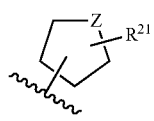

also include, but are not limited to:

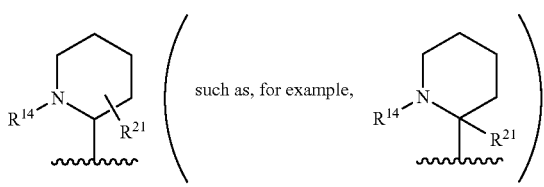

Examples of the $R^6$ or $R^7$ group

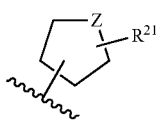

also include, but are not limited to:

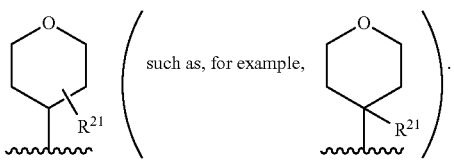

Examples of the $R^6$ or $R^7$ group

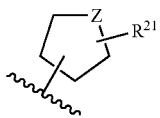

also include, but are not limited to:

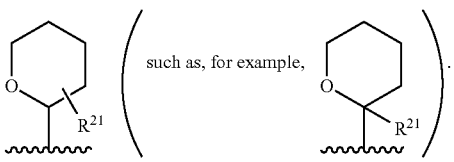

Other embodiments of this invention are directed to compounds of formula (I) wherein $R^{10}$ is aryl (e.g., phenyl) or aryl (e.g., phenyl) substituted with one or more (e.g., one or two, or one) $R^{21}$ groups (e.g., $-OR^{15}$, wherein, for example, $R^{15}$ is alkyl, such as, for example, methyl), and $R^9$ is heteroaryl (e.g., imidazolyl) or heteroaryl (e.g., imidazolyl) substituted with one or more (e.g., one or two, or one) $R^{21}$ groups (e.g., alkyl, such as, for example, methyl).

Thus, examples of the $-R^{10}-R^9$ moiety of the compounds of this invention include, but are not limited to:

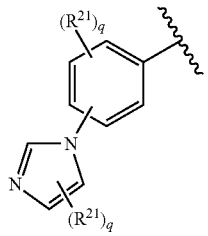

wherein q is 0, 1 or 2, such as, for example,

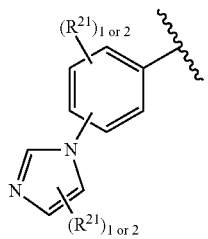

such as, for example,

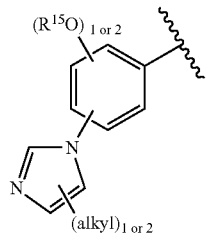

wherein $R^{15}$ is alkyl (e.g., methyl), such as, for example,

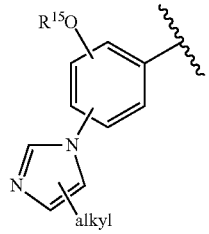

wherein $R^{15}$ is alkyl (e.g., methyl), such as, for example,

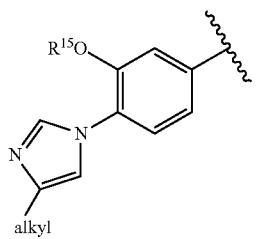

wherein $R^{15}$ is alkyl (e.g., methyl), such as, for example,

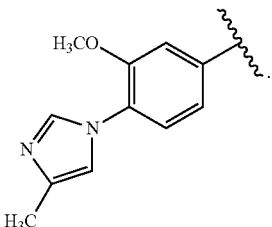

In another embodiment of the compounds of formula (I) $R^6$ or $R^7$ is benzofusedcycloalkyl.

In another embodiment of the compounds of formula (I) $R^6$ or $R^7$ is:

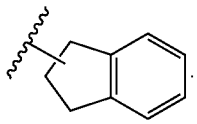

In another embodiment of the compounds of formula (I) $R^6$ or $R^7$ is:

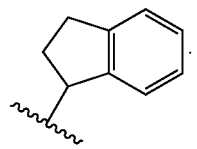

In another embodiment of the compounds of formula (I) $R^6$ or $R^7$ is:

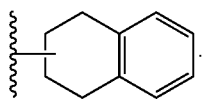

In another embodiment of the compounds of formula (I) $R^6$ or $R^7$ is:

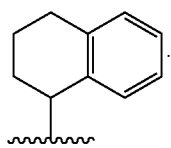 [SMILES: *C1CCCc2ccccc21]

In another embodiment of the compounds of formula (I) $R^6$ or $R^7$ is alkyl substituted with one $R^{21}$ group.

In another embodiment of the compounds of formula (I) $R^6$ or $R^7$ is alkyl substituted with one $R^{21}$ group, and said alkyl is

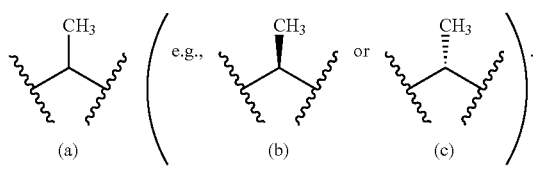

In another embodiment of the compounds of formula (I) $R^6$ or $R^7$ is alkyl (e.g., (a), (b) or (c) described above) substituted with one $R^{21}$ group wherein said $R^{21}$ group is aryl.

In another embodiment of the compounds of formula (I) $R^6$ or $R^7$ is alkyl (e.g., (a), (b) or (c) described above) substituted with one $R^{21}$ group wherein said $R^{21}$ group is phenyl.

In another embodiment of the compounds of formula (I) $R^6$ or $R^7$ is alkyl (e.g., (a), (b) or (c) described above) substituted with one $R^{21}$ group wherein said $R^{21}$ group is naphthyl.

In another embodiment of the compounds of formula (I) $R^6$ or $R^7$ is alkyl substituted with one $R^{21}$ group, and said $R^{21}$ group is substituted with two independently selected $R^{22}$ groups.

In another embodiment of the compounds of formula (I) $R^6$ or $R^7$ is alkyl substituted with one $R^{21}$ group, and said $R^{21}$ group is substituted with one $R^{22}$ group.

In another embodiment of the compounds of formula (I) $R^6$ or $R^7$ is alkyl substituted with one $R^{21}$ group, wherein said alkyl group is (a) (e.g., (b) or (c)), as described above, and said $R^{21}$ group is substituted with two independently selected $R^{22}$ groups.

In another embodiment of the compounds of formula (I) $R^6$ or $R^7$ is alkyl substituted with one $R^{21}$ group, wherein said alkyl group is (a) (e.g., (b) or (c)), as described above, and said $R^{21}$ group is substituted with one $R^{22}$ group.

In another embodiment of the compounds of formula (I) $R^6$ or $R^7$ is alkyl substituted with one $R^{21}$ group, wherein said $R^{21}$ group is aryl, and said $R^{21}$ group is substituted with two independently selected $R^{22}$ groups.

In another embodiment of the compounds of formula (I) $R^6$ or $R^7$ is alkyl substituted with one $R^{21}$ group, wherein said $R^{21}$ group is aryl, said alkyl group is (a) (e.g., (b) or (c)), as described above, and said $R^{21}$ group is substituted with two independently selected $R^{22}$ groups.

In another embodiment of the compounds of formula (I) $R^6$ or $R^7$ is alkyl substituted with one $R^{21}$ group, wherein said $R^{21}$ group is aryl, wherein said alkyl group is (a) (e.g., (b) or (c)), as described above, and said $R^{21}$ group is substituted with one $R^{22}$ group.

In another embodiment of the compounds of formula (I) $R^6$ or $R^7$ is alkyl substituted with one $R^{21}$ group, wherein said $R^{21}$ group is aryl, said alkyl group is (a) (e.g., (b) or (c)), as described above, and said $R^{21}$ group is substituted with two independently selected $R^{22}$ groups, and each $R^{22}$ is halo.

In another embodiment of the compounds of formula (I) $R^6$ or $R^7$ is alkyl substituted with one $R^{21}$ group, wherein said $R^{21}$ group is aryl, wherein said alkyl group is (a) (e.g., (b) or (c)), as described above, and said $R^{21}$ group is substituted with one $R^{22}$ group and said $R^{22}$ is halo.

In another embodiment of the compounds of formula (I) $R^6$ or $R^7$ is alkyl substituted with one $R^{21}$ group, wherein said $R^{21}$ group is aryl, said alkyl group is (a) (e.g., (b) or (c)), as described above, and said $R^{21}$ group is substituted with two independently selected $R^{22}$ groups, and each $R^{22}$ is F.

In another embodiment of the compounds of formula (I) $R^6$ or $R^7$ is alkyl substituted with one $R^{21}$ group, wherein said $R^{21}$ group is aryl, wherein said alkyl group is (a) (e.g., (b) or (c)), as described above, and said $R^{21}$ group is substituted with one $R^{22}$ group. and said $R^{22}$ is F.

In another embodiment of the compounds of formula (I) $R^6$ or $R^7$ is:

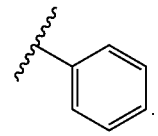 [SMILES: *c1ccccc1]

In another embodiment of the compounds of formula (I) $R^6$ or $R^7$ is:

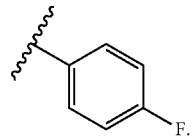 [SMILES: *c1ccc(F)cc1]

In another embodiment of the compounds of formula (I) $R^6$ or $R^7$ is:

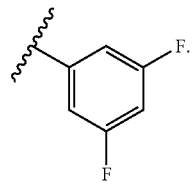 [SMILES: *c1cc(F)cc(F)c1]

In another embodiment of this invention $R^6$ or $R^7$ is:

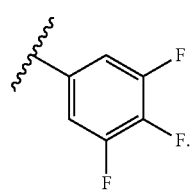 [SMILES: *c1cc(F)c(F)c(F)c1]

In another embodiment of this invention $R^6$ or $R^7$ is:

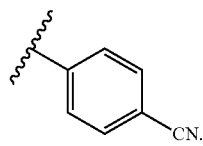 [SMILES: *c1ccc(C#N)cc1]

In another embodiment of this invention $R^6$ or $R^7$ is:

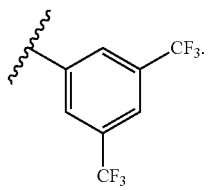 [SMILES: *c1cc(C(F)(F)F)cc(C(F)(F)F)c1]

In another embodiment of this invention $R^6$ or $R^7$ is:

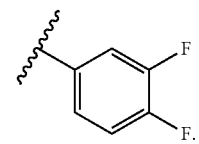 [SMILES: *c1ccc(F)c(F)c1]

In another embodiment of this invention $R^6$ or $R^7$ is:

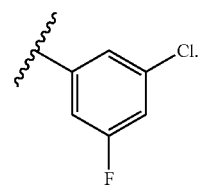 [SMILES: *c1cc(F)cc(Cl)c1]

In another embodiment of this invention $R^6$ or $R^7$ is:

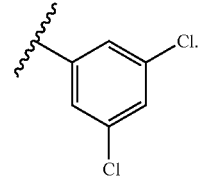 [SMILES: *c1cc(Cl)cc(Cl)c1]

In another embodiment of this invention $R^6$ or $R^7$ is:

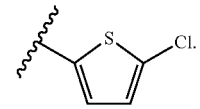

In another embodiment of this invention $R^6$ or $R^7$ is:

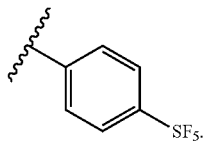

In another embodiment of this invention $R^6$ or $R^7$ is:

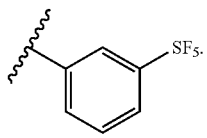

In another embodiment of this invention $R^6$ or $R^7$ is:

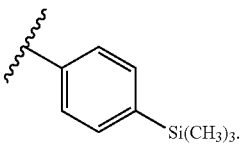

In another embodiment of this invention $R^6$ or $R^7$ is:

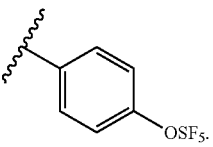

In another embodiment of this invention $R^6$ or $R^7$ is:

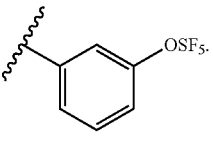

Examples of $R^{21}$ groups include —$OR^{15}$ wherein, for example, $R^{15}$ is alkyl (such as methyl or ethyl), or $R^{15}$ is cycloalkylalkyl (such as, for example, —$CH_2$-cyclopropyl), or $R^{15}$ is -alkyl-$(R^{18})_n$ (wherein, for example, said $R^{18}$ is —$OR^{20}$, and said $R^{20}$ is alkyl, and wherein examples of said -alkyl-$(R^{18})_n$ moiety is —$(CH_2)_2OCH_3$).

Examples of the $R^{21}$ moiety in the embodiments of this invention include, but are not limited to: (a) —$OR^{15}$, (b) —$OR^{15}$ wherein $R^{15}$ is alkyl, (c) —$OR^{15}$ wherein $R^{15}$ is alkyl and said alkyl is methyl or ethyl, (d) —$OR^{15}$ wherein $R^{15}$ is cycloalkylalkyl, (e) —$OR^{15}$ wherein $R^{15}$ is -alkyl-$(R^{18})_n$, (f) —$OR^{15}$ wherein $R^{15}$ is -alkyl-$(R^{18})_n$ and wherein said $R^{18}$ is —$OR^{20}$, (g) —$OR^{15}$ wherein $R^{15}$ is -alkyl-$(R^{18})_n$ and wherein said $R^{18}$ is —$OR^{20}$ and said $R^{20}$ is alkyl. Examples of the $R^{21}$ moiety include but are not limited to: —$OCH_3$, —$OCH_2CH_3$, —$O(CH_2)_2OCH_3$, and —$CH_2$-cyclopropyl.

Examples of $R^{21}$ also include —$C(O)OR^{15}$ wherein, for example, $R^{15}$ is alkyl, such as, for example, methyl).

Examples of $R^{21}$ also include —C(O)NR$^{15}$R$^{16}$, wherein, for example, one of $R^{15}$ or $R^{16}$ is H, and the other is selected from the group consisting of: $(R^{18})_n$-arylalkyl-, $(R^{18})_n$-alkyl-, and cycloalkyl. In one example of this —C(O)NR$^{15}$R$^{16}$ moiety the $R^{18}$ is —OR$^{20}$, n is 1, $R^{20}$ is alkyl, said cycloalkyl is cyclobutyl, and said arylalkyl- is benzyl.

Examples of $R^{21}$ also include halo (e.g., Br, Cl or F).

Examples of $R^{21}$ also include arylalkyl, such as, for example, benzyl.

In the embodiments below, Groups A, B and C are defined as follows:
(1) Group A: 2A, 3A, 4A, 5A, 6A, 7A, 8A, 2B, 3B, 4B, 5B, 6B, 7B, 8B, 2C, 3C, 4C, 5C, 6C, 7C, 8C, 2D, 3D, 4D, 5D, 6D, 7D, 8D, 2E, 3E, 4E, 5E, 2F, 3F, 4F, 5F, 2G, 3G, 4G, 5G, 2H, 3H, 4H, 5H, 2I, 3I, 4I, 5I, 2J, 3J, 4J, 5J, 2K, 3K, 4K, 5K, 2L, 3L, 4LH, 5L, 2M, 3M, 4M, 5M, 2N, 3N, 4N, 5N, 2O, 3O, 4O, 5O, 2P, 3P, 4P, 5P and Compounds 9, and 15 to 26;
(2) Group B: 2A, 3A, 4A, 5A, 6A, 7A, 8A, 2B, 3B, 4B, 5B, 6B, 7B, 8B, 2C, 3C, 4C, 5C, 6C, 7C, 8C, 2D, 3D, 4D, 5D, 6D, 7D, 8D, and Compounds 9, and 15 to 26; and
(3) Group C: 2E, 3E, 4E, 5E, 2F, 3F, 4F, 5F, 2G, 3G, 4G, 5G, 2H, 3H, 4H, 5H, 2I, 3I, 4I, 5I, 2J, 3J, 4J, 5J, 2K, 3K, 4K, 5K, 2L, 3L, 4LH, 5L, 2M, 3M, 4M, 5M, 2N, 3N, 4N, 5N, 2O, 3O, 4O, 5O, 2P, 3P, 4P, and 5P.

One embodiment of this invention is directed to a compound of formula (I).

Another embodiment of this invention is directed to a pharmaceutically acceptable salt of a compound of formula (I). And in one example the salt is a salt of a compound selected from the group consisting of Group A. And in another example the salt is a salt of a compound selected from the group consisting of Group B. And in another example the salt is a salt of a compound selected from the group consisting of Group C. And in another example the salt is a salt of a compound selected from the group consisting of Group B. And in another example the salt is a salt of a compound selected from the group consisting of compounds 9, and 15 to 26.

Another embodiment of this invention is directed to a pharmaceutically acceptable ester of a compound of formula (I). And in one example the ester is an ester of a compound selected from the group consisting of Group A. And in another example the ester is an ester of a compound selected from the group consisting of Group B. And in another example the ester is an ester of a compound selected from the group consisting of Group C. And in another example the ester is an ester of a compound selected from the group consisting of Group B. And in another example the ester is an ester of a compound selected from the group consisting of compounds 9, and 15 to 26.

Another embodiment of this invention is directed to a solvate of a compound of formula (I). And in one example the solvate is a solvate of a compound selected from the group consisting of Group A. And in another example the solvate is a solvate of a compound selected from the group consisting of Group B. And in another example the solvate is a solvate of a compound selected from the group consisting of Group C. And in another example the solvate is a solvate of a compound selected from the group consisting of Group B. And in another example the solvate is a solvate of a compound selected from the group consisting of compounds 9, and 15 to 26.

Another embodiment of this invention is directed to a compound of formula (I) in pure and isolated form. And in one example the compound of formula (I) is selected from the group consisting of compounds 9, and 15 to 26.

Another embodiment of this invention is directed to a compound of formula (I) in pure form. And in one example the compound of formula (I) is selected from the group consisting of compounds 9, and 15 to 26.

Another embodiment of this invention is directed to a compound of formula (I) in isolated form. And in one example the compound of formula (I) is selected from the group consisting of compounds 9, and 15 to 26.

Another embodiment of this invention is directed to a compound of formula (I) selected from the group consisting of compounds 9, and 15 to 26.

Another embodiment of this invention is directed to pharmaceutically acceptable salt of a compound of formula (I), said compound being selected from the group consisting of compounds 9, and 15 to 26.

Another embodiment of this invention is directed to a compound of formula (I) wherein said compound is compound 9.

Another embodiment of this invention is directed to a compound of formula (I) wherein said compound is compound 15.

Another embodiment of this invention is directed to a compound of formula (I) wherein said compound is compound 16.

Another embodiment of this invention is directed to a compound of formula (I) wherein said compound is compound 17.

Another embodiment of this invention is directed to a compound of formula (I) wherein said compound is compound 18.

Another embodiment of this invention is directed to a compound of formula (I) wherein said compound is compound 20.

Another embodiment of this invention is directed to a compound of formula (I) wherein said compound is compound 21.

Another embodiment of this invention is directed to a compound of formula (I) wherein said compound is compound 22.

Another embodiment of this invention is directed to a compound of formula (I) wherein said compound is compound 23.

Another embodiment of this invention is directed to a compound of formula (I) wherein said compound is compound 24.

Another embodiment of this invention is directed to a compound of formula (I) wherein said compound is compound 25.

Another embodiment of this invention is directed to a compound of formula (I) wherein said compound is compound 26.

Another embodiment of this invention is directed to a pharmaceutically acceptable salt of compound 9.

Another embodiment of this invention is directed to a pharmaceutically acceptable salt of compound 15.

Another embodiment of this invention is directed to a pharmaceutically acceptable salt of compound 16.

Another embodiment of this invention is directed to a pharmaceutically acceptable salt of compound 17.

Another embodiment of this invention is directed to a pharmaceutically acceptable salt of compound 18.

Another embodiment of this invention is directed to a pharmaceutically acceptable salt of compound 20.

Another embodiment of this invention is directed to a pharmaceutically acceptable salt of compound 21.

Another embodiment of this invention is directed to a pharmaceutically acceptable salt of compound 22.

Another embodiment of this invention is directed to a pharmaceutically acceptable salt of compound 23.

Another embodiment of this invention is directed to a pharmaceutically acceptable salt of compound 24.

Another embodiment of this invention is directed to a pharmaceutically acceptable salt of compound 25.

Another embodiment of this invention is directed to a pharmaceutically acceptable salt of compound 26.

Another embodiment of this invention is directed to a pharmaceutically acceptable ester of compound 9.

Another embodiment of this invention is directed to a pharmaceutically acceptable ester of compound 15.

Another embodiment of this invention is directed to a pharmaceutically acceptable ester of compound 16.

Another embodiment of this invention is directed to a pharmaceutically acceptable ester of compound 17.

Another embodiment of this invention is directed to a pharmaceutically acceptable ester of compound 18.

Another embodiment of this invention is directed to a pharmaceutically acceptable ester of compound 20.

Another embodiment of this invention is directed to a pharmaceutically acceptable salt of compound 21.

Another embodiment of this invention is directed to a pharmaceutically acceptable ester of compound 22.

Another embodiment of this invention is directed to a pharmaceutically acceptable ester of compound 23.

Another embodiment of this invention is directed to a pharmaceutically acceptable ester of compound 24.

Another embodiment of this invention is directed to a pharmaceutically acceptable ester of compound 25.

Another embodiment of this invention is directed to a pharmaceutically acceptable ester of compound 26.

Another embodiment of this invention is directed to a solvate of compound 9.

Another embodiment of this invention is directed to a solvate of compound 15.

Another embodiment of this invention is directed to a solvate of compound 16.

Another embodiment of this invention is directed to a solvate of compound 17.

Another embodiment of this invention is directed to a solvate of compound 18.

Another embodiment of this invention is directed to a solvate of compound 20.

Another embodiment of this invention is directed to a solvate of compound 21.

Another embodiment of this invention is directed to a solvate of compound 22.

Another embodiment of this invention is directed to a solvate of compound 23.

Another embodiment of this invention is directed to a solvate of compound 24.

Another embodiment of this invention is directed to a solvate of compound 25.

Another embodiment of this invention is directed to a solvate of compound 26.

Another embodiment of this invention is directed to a pharmaceutical composition comprising a therapeutically effective amount of at least one compound of Formula (I), or a pharmaceutically acceptable salt, solvate, or ester thereof, and at least one pharmaceutically acceptable carrier.

Another embodiment of this invention is directed to a pharmaceutical composition comprising an effective amount of one or more (e.g., one) compounds of formula (I) and a pharmaceutically acceptable carrier.

Another embodiment of this invention is directed to a pharmaceutical composition comprising an effective amount of a pharmaceutically acceptable salt of one or more (e.g., one) compounds of formula (I) and a pharmaceutically acceptable carrier.

Another embodiment of this invention is directed to a pharmaceutical composition comprising an effective amount of a pharmaceutically acceptable ester of one or more (e.g., one) compounds of formula (I) and a pharmaceutically acceptable carrier.

Another embodiment of this invention is directed to a pharmaceutical composition comprising an effective amount of a solvate of one or more (e.g., one) compounds of formula (I) and a pharmaceutically acceptable carrier.

Another embodiment of this invention is directed to a pharmaceutical composition comprising an effective amount of one or more (e.g., one) compounds of formula (I), and an effective amount of one or more (e.g., one) other pharmaceutically active ingredients (e.g., drugs), and a pharmaceutically acceptable carrier. Examples of the other pharmaceutically active ingredients include, but are not limited to drugs selected form the group consisting of: (a) drugs useful for the treatment of Alzheimer's disease, (b) drugs useful for inhibiting the deposition of amyloid protein (e.g., amyloid beta protein) in, on or around neurological tissue (e.g., the brain), (c) drugs useful for treating neurodegenerative diseases, and (d) drugs useful for inhibiting gamma-secretase.

Another embodiment of this invention is directed to a pharmaceutical composition comprising a therapeutically effective amount of at least one compound of Formula (I), or a pharmaceutically acceptable salt, solvate, or ester thereof, and at least one pharmaceutically acceptable carrier, and a therapeutically effective amount of one or more compounds selected from the group consisting of cholinesterase inhibitors, Aβ antibody inhibitors, gamma secretase inhibitors and beta secretase inhibitors.

Another embodiment of this invention is directed to a pharmaceutical composition comprising an effective amount of one or more (e.g., one) compounds of formula (I), and effective amount of one or more BACE inhibitors, and a pharmaceutically acceptable carrier.

Another embodiment of this invention is directed to a pharmaceutical composition comprising an effective amount of one or more (e.g., one) compounds of formula (I), and effective amount of one or more cholinesterase inhibitors (e.g., acetyl- and/or butyrylchlolinesterase inhibitors), and a pharmaceutically acceptable carrier.

Another embodiment of this invention is directed to a pharmaceutical composition comprising an effective amount of one or more (e.g., one) compounds of formula (I), and effective amount of one or more muscarinic antagonists (e.g., $m_1$ or $m_2$ antagonists), and a pharmaceutically acceptable carrier.

Another embodiment of this invention is directed to a pharmaceutical composition comprising an effective amount of one or more (e.g., one) compounds of formula I, and effective amount of Exelon (rivastigmine), and a pharmaceutically acceptable carrier.

Another embodiment of this invention is directed to a pharmaceutical composition comprising an effective amount of one or more (e.g., one) compounds of formula I, and effective amount of Cognex (tacrine), and a pharmaceutically acceptable carrier.

Another embodiment of this invention is directed to a pharmaceutical composition comprising an effective amount of one or more (e.g., one) compounds of formula I, and effective amount of a Tau kinase inhibitor, and a pharmaceutically acceptable carrier.

Another embodiment of this invention is directed to a pharmaceutical composition comprising an effective amount of one or more (e.g., one) compounds of formula I, and effective amount of one or more Tau kinase inhibitor (e.g., GSK3beta inhibitor, cdk5 inhibitor, ERK inhibitor), and a pharmaceutically acceptable carrier.

Another embodiment of this invention is directed to a pharmaceutical composition comprising an effective amount of one or more (e.g., one) compounds of formula I, and effective amount of one anti-Abeta vaccine (active immunization), and a pharmaceutically acceptable carrier.

Another embodiment of this invention is directed to a pharmaceutical composition comprising an effective amount of one or more (e.g., one) compounds of formula I, and effective amount of one or more APP ligands, and a pharmaceutically acceptable carrier.

Another embodiment of this invention is directed to a pharmaceutical composition comprising an effective amount of one or more (e.g., one) compounds of formula I, and effective amount of one or more agents that upregulate insulin degrading enzyme and/or neprilysin, and a pharmaceutically acceptable carrier.

Another embodiment of this invention is directed to a pharmaceutical composition comprising an effective amount of one or more (e.g., one) compounds of formula I, and effective amount of one or more cholesterol lowering agents (for example, statins such as Atorvastatin, Fluvastatin, Lovastatin, Mevastatin, Pitavastatin, Pravastatin, Rosuvastatin, Simvastatin, and cholesterol absorption inhibitor such as Ezetimibe), and a pharmaceutically acceptable carrier.

Another embodiment of this invention is directed to a pharmaceutical composition comprising an effective amount of one or more (e.g., one) compounds of formula I, and effective amount of one or more fibrates (for example, clofibrate, Clofibride, Etofibrate, Aluminium Clofibrate), and a pharmaceutically acceptable carrier Another embodiment of this invention is directed to a pharmaceutical composition comprising an effective amount of one or more (e.g., one) compounds of formula I, and effective amount of one or more LXR agonists, and a pharmaceutically acceptable carrier.

Another embodiment of this invention is directed to a pharmaceutical composition comprising an effective amount of one or more (e.g., one) compounds of formula I, and effective amount of one or more LRP mimics, and a pharmaceutically acceptable carrier.

Another embodiment of this invention is directed to a pharmaceutical composition comprising an effective amount of one or more (e.g., one) compounds of formula I, and effective amount of one or more 5-HT6 receptor antagonists, and a pharmaceutically acceptable carrier.

Another embodiment of this invention is directed to a pharmaceutical composition comprising an effective amount of one or more (e.g., one) compounds of formula I, and effective amount of one or more nicotinic receptor agonists, and a pharmaceutically acceptable carrier.

Another embodiment of this invention is directed to a pharmaceutical composition comprising an effective amount of one or more (e.g., one) compounds of formula I, and effective amount of one or more H3 receptor antagonists, and a pharmaceutically acceptable carrier.

Another embodiment of this invention is directed to a pharmaceutical composition comprising an effective amount of one or more (e.g., one) compounds of formula I, and effective amount of one or more histone deacetylase inhibitors, and a pharmaceutically acceptable carrier.

Another embodiment of this invention is directed to a pharmaceutical composition comprising an effective amount of one or more (e.g., one) compounds of formula I, and effective amount of one or more hsp90 inhibitors, and a pharmaceutically acceptable carrier.

Another embodiment of this invention is directed to a pharmaceutical composition comprising an effective amount of one or more (e.g., one) compounds of formula I, and effective amount of one or more m1 muscarinic receptor agonists, and a pharmaceutically acceptable carrier.

Another embodiment of this invention is directed to combinations, i.e., a pharmaceutical composition, comprising a pharmaceutically acceptable carrier, an effective (i.e., therapeutically effective) amount of one or more compounds of formula (I), in combination with an effective (i.e., therapeutically effective) amount of one or more compounds selected from the group consisting of cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), Aβ antibody inhibitors, gamma secretase inhibitors and beta secretase inhibitors.

Another embodiment of this invention is directed to a pharmaceutical composition comprising an effective amount of one or more (e.g., one) compounds of formula I, and effective amount of one or more 5-HT6 receptor antagonists mGluR1 or mGluR5 positive allosteric modulators or agonists, and a pharmaceutically acceptable carrier.

Another embodiment of this invention is directed to a pharmaceutical composition comprising an effective amount of one or more (e.g., one) compounds of formula I, and effective amount of one or more one mGluR2/3 antagonists, and a pharmaceutically acceptable carrier.

Another embodiment of this invention is directed to a pharmaceutical composition comprising an effective amount of one or more (e.g., one) compounds of formula I, and effective amount of one or more anti-inflammatory agents that can reduce neuroinflammation, and a pharmaceutically acceptable carrier.

Another embodiment of this invention is directed to a pharmaceutical composition comprising an effective amount of one or more (e.g., one) compounds of formula I, and effective amount of one or more Prostaglandin EP2 receptor antagonists, and a pharmaceutically acceptable carrier.

Another embodiment of this invention is directed to a pharmaceutical composition comprising an effective amount of one or more (e.g., one) compounds of formula I, and effective amount of one or more PAI-1 inhibitors, and a pharmaceutically acceptable carrier.

Another embodiment of this invention is directed to a pharmaceutical composition comprising an effective amount of one or more (e.g., one) compounds of formula I, and effective amount of one or more agents that can induce Abeta efflux such as gelsolin, and a pharmaceutically acceptable carrier.

Other embodiments of this invention are directed to any one of the above embodiments directed to pharmaceutical compositions wherein the compound of formula (I) is selected from the group consisting of Group A.

Other embodiments of this invention are directed to any one of the above embodiments directed to pharmaceutical compositions wherein the compound of formula (I) is selected from the group consisting of Group B.

Other embodiments of this invention are directed to any one of the above embodiments directed to pharmaceutical compositions wherein the compound of formula (I) is selected from the group consisting of Group C.

Other embodiments of this invention are directed to any one of the above embodiments directed to pharmaceutical compositions wherein the compound of formula (I) is selected from the group consisting of compounds 9, and 15 to 25.

The compounds of formula (I) can be useful as gamma secretase modulators and can be useful in the treatment and prevention of diseases such as, for example, central nervous system disorders (such as Alzheimers disease and Downs Syndrome), mild cognitive impairment, glaucoma, cerebral amyloid angiopathy, stroke, dementia, microgliosis, brain inflammation, and olfactory function loss.

Another embodiment of this invention is directed to a method of treating a central nervous system disorder comprising administering a therapeutically effective amount of at least one compound of Formula (I) to a patient in need of such treatment.

Another embodiment of this invention is directed to a method of treating a central nervous system disorder comprising administering a therapeutically effective amount of a pharmaceutical composition comprising a therapeutically effective amount of at least one compound of Formula (I), or a pharmaceutically acceptable salt, solvate, or ester thereof, and at least one pharmaceutically acceptable carrier.

Another embodiment of this invention is directed to a method of treating a central nervous system disorder comprising administering a therapeutically effective amount of a pharmaceutical composition comprising a therapeutically effective amount of at least one compound of Formula (I), or a pharmaceutically acceptable salt, solvate, or ester thereof, and at least one pharmaceutically acceptable carrier, and a therapeutically effective amount of one or more compounds selected from the group consisting of cholinesterase inhibitors, Aβ antibody inhibitors, gamma secretase inhibitors and beta secretase inhibitors.

Another embodiment of this invention is directed to a method for modulating (including inhibiting, antagonizing and the like) gamma-secretase comprising administering an effective amount of one or more (e.g., one) compounds of formula (I) to a patient in need of such treatment.

Another embodiment of this invention is directed to a method for modulating (including inhibiting, antagonizing and the like) gamma-secretase, comprising administering an effective amount of a compound of formula (I) to a patient in need of treatment.

Another embodiment of this invention is directed to a method of treating one or more neurodegenerative diseases, comprising administering an effective amount of one or more (e.g., one) compounds of formula (I) to a patient in need of treatment.

Another embodiment of this invention is directed to a method of treating one or more neurodegenerative diseases, comprising administering an effective amount of a compound of formula (I) to a patient in need of treatment.

Another embodiment of this invention is directed to a method of inhibiting the deposition of amyloid protein (e.g., amyloid beta protein) in, on or around neurological tissue (e.g., the brain), comprising administering an effective amount of one or more (e.g., one) compounds of formula (I) to a patient in need of treatment.

Another embodiment of this invention is directed to a method of inhibiting the deposition of amyloid protein (e.g., amyloid beta protein) in, on or around neurological tissue (e.g., the brain), comprising administering an effective amount of a compound of formula (I) to a patient in need of treatment.

Another embodiment of this invention is directed to a method of treating Alzheimer's disease, comprising administering an effective amount of one or more (e.g., one) compounds of formula (I) to a patient in need of treatment.

Another embodiment of this invention is directed to a method of treating Alzheimer's disease, comprising administering an effective amount of a compound of formula (I) to a patient in need of treatment.

Another embodiment of this invention is directed to a method of treating mild cognitive impairment, glaucoma, cerebral amyloid angiopathy, stroke, dementia, microgliosis, brain inflammation, or olfactory function loss, comprising administering an effective (i.e., therapeutically effective) amount of one or more (e.g., one) compounds of formula (I) to a patient in need of treatment.

Another embodiment of this invention is directed to a method of treating mild cognitive impairment, glaucoma, cerebral amyloid angiopathy, stroke, dementia, microgliosis, brain inflammation, or olfactory function loss, comprising administering an effective (i.e., therapeutically effective) amount of a compound of formula (I) to a patient in need of treatment.

Another embodiment of this invention is directed to a method of treating mild cognitive impairment, comprising administering an effective amount of one or more (e.g., one) compounds of formula (I) to a patient in need of treatment.

Another embodiment of this invention is directed to a method of treating glaucoma, comprising administering an effective amount of one or more (e.g., one) compounds of formula (I) to a patient in need of treatment.

Another embodiment of this invention is directed to a method of treating cerebral amyloid angiopathy, comprising administering an effective amount of one or more (e.g., one) compounds of formula (I) to a patient in need of treatment.

Another embodiment of this invention is directed to a method of treating stroke, comprising administering an effective amount of one or more (e.g., one) compounds of formula (I) to a patient in need of treatment.

Another embodiment of this invention is directed to a method of treating dementia, comprising administering an effective amount of one or more (e.g., one) compounds of formula (I) to a patient in need of treatment.

Another embodiment of this invention is directed to a method of treating microgliosis, comprising administering an effective amount of one or more (e.g., one) compounds of formula (I) to a patient in need of treatment.

Another embodiment of this invention is directed to a method of treating brain inflammation, comprising administering an effective amount of one or more (e.g., one) compounds of formula (I) to a patient in need of treatment.

Another embodiment of this invention is directed to a method of treating olfactory function loss, comprising administering an effective amount of one or more (e.g., one) compounds of formula (I) to a patient in need of treatment.

Another embodiment of this invention is directed to a method of treating Downs syndrome, comprising administering an effective amount of one or more (e.g., one) compounds of formula (I) to a patient in need of treatment.

Another embodiment of this invention is directed to a method of treating Downs syndrome, comprising administering an effective amount of a compound of formula (I) to a patient in need of treatment.

Other embodiments of this invention are directed to any one of the above embodiments directed to methods of treating wherein the compound of formula (I) is selected from the group consisting of Group A.

Other embodiments of this invention are directed to any one of the above embodiments directed to methods of treating wherein the compound of formula (I) is selected from the group consisting of Group B.

Other embodiments of this invention are directed to any one of the above embodiments directed to methods of treating wherein the compound of formula (I) is selected from the group consisting of Group C.

Other embodiments of this invention are directed to any one of the above embodiments directed to methods of treating wherein the compound of formula (I) is selected from the group consisting of compounds 9, and 15 to 25.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of an effective amount of one or more (e.g. one) compounds of formula (I) and the administration of an effective amount of one or more (e.g., one) other pharmaceutical active ingredients (e.g., drugs). The compounds of formula (I) and the other drugs can be administered separately (i.e., each is in its own separate dosage form), or the compounds of formula (I) can be combined with the other drugs in the same dosage form.

Thus, other embodiments of this invention are directed to any one of the methods of treatment, or methods of inhibiting, described herein, wherein an effective amount of the compound of formula (I) is used in combination with an effective amount of one or more other pharmaceutically active ingredients (e.g., drugs). The other pharmaceutically active ingredients (i.e., drugs) are selected from the group consisting of: BACE inhibitors (beta secretase inhibitors); muscarinic antagonists (e.g., $m_1$ agonists or $m_2$ antagonists); cholinesterase inhibitors (e.g., acetyl- and/or butyrylchlolinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Exelon (rivastigmine); Cognex (tacrine); Tau kinase inhibitors (e.g., GSK3beta inhibitors, cdk5 inhibitors, or ERK inhibitors); anti-Abeta vaccine; APP ligands; agents that upregulate insulin cholesterol lowering agents (for example, statins such as Atorvastatin, Fluvastatin, Lovastatin, Mevastatin, Pitavastatin, Pravastatin, Rosuvastatin, Simvastatin); cholesterol absorption inhibitors (such as Ezetimibe); fibrates (such as, for example, for example, clofibrate, Clofibride, Etofibrate, and Aluminium Clofibrate); LXR agonists; LRP mimics; nicotinic receptor agonists; H3 receptor antagonists; histone deacetylase inhibitors; hsp90 inhibitors; m1 muscarinic receptor agonists; 5-HT6 receptor antagonists; mGluR1; mGluR5; positive allosteric modulators or agonists; mGluR2/3 antagonists; anti-inflammatory agents that can reduce neuroinflammation; Prostaglandin EP2 receptor antagonists; PAI-1 inhibitors; and agents that can induce Abeta efflux such as gelsolin.

Another embodiment of this invention is directed to a method of treating Alzheimer's disease, comprising administering an effective amount of one or more (e.g., one) compounds of formula (I), in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective amount of a compound of formula (I), in combination with an effective amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective amount of one or more (e.g., one) compounds of formula (I), in combination with an effective amount of one or more compounds selected from the group consisting of Aβ antibody inhibitors, gamma secretase inhibitors and beta secretase inhibitors.

Another embodiment of this invention is directed to a method of treating Alzheimer's disease, comprising administering an effective amount of one or more (e.g., one) compounds of formula (I), in combination with an effective amount of one or more BACE inhibitors.

Another embodiment of this invention is directed to a method of treating Alzheimer's disease, comprising administering an effective amount of one or more compounds of formula I, in combination with an effective amount of Exelon (rivastigmine).

Another embodiment of this invention is directed to a method of treating Alzheimer's disease, comprising administering an effective amount of one or more compounds of formula I, in combination with an effective amount of Cognex (tacrine).

Another embodiment of this invention is directed to a method of treating Alzheimer's disease, comprising administering an effective amount of one or more compounds of formula I, in combination with an effective amount of a Tau kinase inhibitor.

Another embodiment of this invention is directed to a method of treating Alzheimer's disease, comprising administering an effective amount of one or more compounds of formula I, in combination with an effective amount of one or more Tau kinase inhibitor (e.g., GSK3beta inhibitor, cdk5 inhibitor, ERK inhibitor).

This invention also provides a method of treating Alzheimer's disease, comprising administering an effective amount of one or more compounds of formula I, in combination with an effective amount of one anti-Abeta vaccination (active immunization).

Another embodiment of this invention is directed to a method of treating Alzheimer's disease, comprising administering an effective amount of one or more compounds of formula I, in combination with an effective amount of one or more APP ligands.

Another embodiment of this invention is directed to a method of treating Alzheimer's disease, comprising administering an effective amount of one or more compounds of formula I, in combination with an effective amount of one or more agents that upregulate insulin degrading enzyme and/or neprilysin.

Another embodiment of this invention is directed to a method of treating Alzheimer's disease, comprising administering an effective amount of one or more compounds of formula I, in combination with an effective amount of one or more cholesterol lowering agents (for example, statins such as Atorvastatin, Fluvastatin, Lovastatin, Mevastatin, Pitavastatin, Pravastatin, Rosuvastatin, Simvastatin, and cholesterol absorption inhibitor such as Ezetimibe).

This invention also provides a method of treating Alzheimer's disease, comprising administering an effective amount of one or more compounds of formula I, in combination with an effective amount of one or more fibrates (for example, clofibrate, Clofibride, Etofibrate, Aluminium Clofibrate).

Another embodiment of this invention is directed to a method of treating Alzheimer's disease, comprising administering an effective amount of one or more compounds of formula I, in combination with an effective amount of one or more LXR agonists.

Another embodiment of this invention is directed to a method of treating Alzheimer's disease, comprising administering an effective amount of one or more compounds of formula I, in combination with an effective amount of one or more LRP mimics.

Another embodiment of this invention is directed to a method of treating Alzheimer's disease, comprising administering an effective amount of one or more compounds of formula I, in combination with an effective amount of one or more 5-HT6 receptor antagonists.

Another embodiment of this invention is directed to a method of treating Alzheimer's disease, comprising administering an effective amount of one or more compounds of formula I, in combination with an effective amount of one or more nicotinic receptor agonists.

Another embodiment of this invention is directed to a method of treating Alzheimer's disease, comprising administering an effective amount of one or more compounds of formula I, in combination with an effective amount of one or more H3 receptor antagonists.

This invention also provides a method of treating Alzheimer's disease, comprising administering an effective amount of one or more compounds of formula I, in combination with an effective amount of one or more histone deacetylase inhibitors.

Another embodiment of this invention is directed to a method of treating Alzheimer's disease, comprising administering an effective amount of one or more compounds of formula I, in combination with an effective amount of one or more hsp90 inhibitors.

Another embodiment of this invention is directed to a method of treating Alzheimer's disease, comprising administering an effective amount of one or more compounds of formula I, in combination with an effective amount of one or more m1 muscarinic receptor agonists.

Another embodiment of this invention is directed to a method of treating Alzheimer's disease, comprising administering an effective amount of one or more compounds of formula I, in combination with an effective amount of one or more 5-HT6 receptor antagonists mGluR1 or mGluR5 positive allosteric modulators or agonists Another embodiment of this invention is directed to a method of treating Alzheimer's disease, comprising administering an effective amount of one or more compounds of formula I, in combination with an effective amount of one or more mGluR2/3 antagonists.

Another embodiment of this invention is directed to a method of treating Alzheimer's disease, comprising administering an effective amount of one or more compounds of formula I, in combination with an effective amount of one or more anti-inflammatory agents that can reduce neuroinflammation.

Another embodiment of this invention is directed to a method of treating Alzheimer's disease, comprising administering an effective amount of one or more compounds of formula I, in combination with an effective amount of one or more Prostaglandin EP2 receptor antagonists.

Another embodiment of this invention is directed to a method of treating Alzheimer's disease, comprising administering an effective amount of one or more compounds of formula I, in combination with an effective amount of one or more PAI-1 inhibitors.

Another embodiment of this invention is directed to a method of treating Alzheimer's disease, comprising administering an effective amount of one or more compounds of formula I, in combination with an effective amount of one or more agents that can induce Abeta efflux such as gelsolin.

Another embodiment of this invention is directed to a method of treating Downs syndrome, comprising administering an effective amount of one or more (e.g., one) compounds of formula (I), in combination with an effective amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Downs syndrome, comprising administering an effective amount of a compound of formula (I), in combination with an effective amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Other embodiments of this invention are directed to any one of the above embodiments directed to combination therapies (i.e., the above methods of treating wherein compounds of formula (I) are used in combination with other pharmaceutically active ingredients, i.e., drugs) wherein the compound of formula (I) is selected from the group consisting of Group A.

Other embodiments of this invention are directed to any one of the above embodiments directed to combination therapies (i.e., the above methods of treating wherein compounds of formula (I) are used in combination with other pharmaceutically active ingredients, i.e., drugs) wherein the compound of formula (I) is selected from the group consisting of Group B.

Other embodiments of this invention are directed to any one of the above embodiments directed to combination therapies (i.e., the above methods of treating wherein compounds of formula (I) are used in combination with other pharmaceutically active ingredients, i.e., drugs) wherein the compound of formula (I) is selected from the group consisting of Group C.

Other embodiments of this invention are directed to any one of the above embodiments directed to combination therapies (i.e., the above methods of treating wherein compounds of formula (I) are used in combination with other pharmaceutically active ingredients, i.e., drugs) wherein the compound of formula (I) is selected from the group consisting of compounds 9, and 15 to 25.

This invention also provides a kit comprising, in separate containers, in a single package, pharmaceutical compositions for use in combination, wherein one container comprises an effective amount of a compound of formula (I) in a pharmaceutically acceptable carrier, and another container (i.e., a second container) comprises an effective amount of another pharmaceutically active ingredient (as described above), the combined quantities of the compound of formula (I) and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase, or (e) mild cognitive impairment, or (f) glaucoma, or (g) cerebral amyloid angiopathy, or (h) stroke, or (i) dementia, or (j) microgliosis, or (k) brain inflammation, or (l) olfactory function loss.

This invention also provides a kit comprising, in separate containers, in a single package, pharmaceutical compositions for use in combination, wherein one container comprises an effective amount of a compound of formula (I) in a pharmaceutically acceptable carrier, and another container (i.e., a second container) comprises an effective amount of another pharmaceutically active ingredient (as described above), the combined quantities of the compound of formula (I) and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

Other embodiments of this invention are directed to any one of the above embodiments directed to kits wherein the compound of formula (I) is selected from the group consisting of Group A.

Other embodiments of this invention are directed to any one of the above embodiments directed to kits wherein the compound of formula (I) is selected from the group consisting of Group B.

Other embodiments of this invention are directed to any one of the above embodiments directed to kits wherein the compound of formula (I) is selected from the group consisting of Group C.

Other embodiments of this invention are directed to any one of the above embodiments directed to kits wherein the compound of formula (I) is selected from the group consisting of compounds 9, and 15 to 26.

Examples of cholinesterase inhibitors are tacrine, donepezil, rivastigmine, galantamine, pyridostigmine and neostigmine, with tacrine, donepezil, rivastigmine and galantamine being preferred.

Examples of $m_1$ agonists are known in the art. Examples of $m_2$ antagonists are also known in the art; in particular, $m_2$ antagonists are disclosed in U.S. Pat. Nos. 5,883,096; 6,037,352; 5,889,006; 6,043,255; 5,952,349; 5,935,958; 6,066,636; 5,977,138; 6,294,554; 6,043,255; and 6,458,812; and in WO 03/031412, all of which are incorporated herein by reference.

Examples of BACE inhibitors include those described in: US2005/0119227 published Jun. 2, 2005 (see also WO2005/016876 published Feb. 24, 2005), US2005/0043290 published Feb. 24, 2005 (see also WO2005/014540 published Feb. 17, 2005), WO2005/058311 published Jun. 30, 2005 (see also US2007/0072852 published Mar. 29, 2007), US2006/0111370 published May 25, 2006 (see also WO2006/065277 published Jun. 22, 2006), U.S. application Ser. No. 11/710,582 filed Feb. 23, 2007, US2006/0040994 published Feb. 23, 2006 (see also WO2006/014762 published Feb. 9, 2006), WO2006/014944 published Feb. 9, 2006 (see also US2006/0040948 published Feb. 23, 2006), WO2006/138266 published Dec. 28, 2006 (see also US2007/0010667 published Jan. 11, 2007), WO2006/138265 published Dec. 28, 2006, WO2006/138230 published Dec. 28, 2006, WO2006/138195 published Dec. 28, 2006 (see also US2006/0281729 published Dec. 14, 2006), WO2006/138264 published Dec. 28, 2006 (see also US2007/0060575 published Mar. 15, 2007), WO2006/138192 published Dec. 28, 2006 (see also US2006/0281730 published Dec. 14, 2006), WO2006/138217 published Dec. 28, 2006 (see also US2006/0287294 published Dec. 21, 2006), US2007/0099898 published May 3, 200 (see also WO2007/050721 published May 3, 2007), WO2007/053506 published May 10, 2007 (see also US2007/099875 published May 3, 2007), U.S. application Ser. No. 11/759,336 filed Jun. 7, 2007, U.S. Application Ser. No. 60/874,362 filed Dec. 12, 2006, and U.S. Application Ser. No. 60/874,419 filed Dec. 12, 2006, the disclosures of each being incorporated herein by reference thereto.

It is noted that the carbons of formula (I) and other formulas herein may be replaced with 1 to 3 silicon atoms so long as all valency requirements are satisfied.

As used above, and throughout this disclosure, the following terms, unless otherwise indicated, shall be understood to have the following meanings:

"Patient" includes both human and animals.

"Mammal" means humans and other mammalian animals.

"One or more" means that there is at least one and there can be more than one, and examples include 1, 2 or 3, or 1 and 2, or 1.

"At least one" means there is at least one and there can be more than one, and examples include 1, 2 or 3, or 1 and 2, or 1.

"An effective amount" as used to describe the amount of a compound of formula (I) in a pharmaceutical composition, or to describe the amount of a compound of formula (I) used in a method of treatment, or to describe the amount of a pharmaceutical composition used in a method of treatment, or to describe the amount of other pharmaceutic ingredients (i.e., drugs) used in a pharmaceutical compositions or methods of treatment, means a therapeutically effective amount.

"Bn" means benzyl.

"Et" means ethyl.

"i-pr" means isopropyl.

"Me" means methyl.

"Pr" means propyl.

"t-Bu" means tert-butyl.

"TBDMSCl" means tert-butyldimethylsilyl chloride.

"DMAP" means 4-(dimethylamino)pyridine.

"Carbocyclic" means a non-aromatic saturated or unsaturated mono- or multicyclic ring system comprising about 3 to about 10 carbon atoms, preferably about 5 to about 10 carbon atoms. Carbocyclic rings include cycloalkyl rings and cycloalkenyl rings as defined below. Thus, examples of carbocyclic rings include bicyclic rings, such as, for example, norbornyl, adamantly, norbornenyl, and

bicyclo[3.3.1]nonane

The carbocyclic rings are optionally substituted with one or more independently selected "ring system substituents" as defined below.

"Fused benzocycloalkyl ring" means a phenyl ring fused to a cycloalkyl ring (as cycloalkyl is defined below), such as, for example,

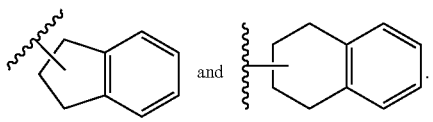

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, oxime (e.g., =N—OH), —NH(alkyl), —NH(cycloalkyl), —N(alkyl)$_2$, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl. aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine. "Halo" refers to fluoro, chloro, bromo or iodo.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, =O, =N—OY$_1$, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), oxime (e.g., =N—OH), Y$_1$Y$_2$N—, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

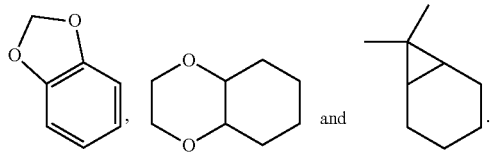

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" or "heterocycloalkyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" also includes rings wherein =O replaces two available hydrogens on the same carbon atom on a ring system (i.e., heterocyclyl includes rings having a carbonyl in the ring). An example of such moiety is pyrrolidone:

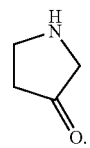

"Heterocyclylalkyl" (or "heterocycloalkylalkyl") means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" (or "heterocycloalkenyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" also includes rings wherein =O replaces two available hydrogens on the same carbon atom on a ring system (i.e., heterocyclyl includes rings having a carbonyl in the ring). An example of such moiety is pyrrolidinone:

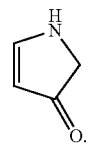

"Heterocyclenylalkyl" (or "heterocycloalkenylalkyl") means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

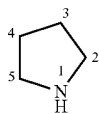

there is no —OH attached directly to carbons marked 2 and 5.

It should also be noted that tautomeric forms such as, for example, the moieties:

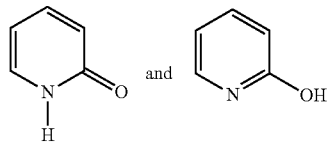 [SMILES: O=c1cccc[nH]1 ; Oc1ccccn1]

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-(C1-C2)alkyl and piperidino-, pyrrolidino- or morpholino$(C_2-C_3)$ alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyloxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(O($C_1-C_6$)alkyl)$_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —C(OH)C(O)OY$^1$ wherein Y$^1$ is H, $(C_1-C_6)$alkyl or benzyl, —C(OY$^2$)Y$^3$ wherein Y$^2$ is $(C_1-C_4)$ alkyl and Y$^3$ is $(C_1-C_6)$alkyl, carboxy$(C_1-C_6)$alkyl, amino $(C_1-C_4)$alkyl or mono-N— or di-N,N—$(C_1-C_6)$alkylaminoalkyl, —C(Y$^4$)Y$^5$ wherein Y$^4$ is H or methyl and Y$^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formula (I), and salts, solvates, esters and prodrugs thereof, may exist in their tautomeric form (for example, as an amide, enol, keto or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$ and $^{123}I$, respectively.

Certain isotopically-labelled compounds of Formula (I) (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Certain isotopically-labelled compounds of Formula (I) can be useful for medical imaging purposes. E.g., those labeled with positron-emitting isotopes like $^{11}C$ or $^{18}F$ can be useful for application in Positron Emission Tomography (PET) and those labeled with gamma ray emitting isotopes like $^{123}I$ can be useful for application in Single photon emission computed tomography (SPECT). Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Additionally, isotopic substitution at a site where epimerization occurs may slow or reduce the epimerization process and thereby retain the more active or efficacious form of the compound for a longer period of time. Isotopically labeled compounds of Formula (I), in particular those containing isotopes with longer half lives (T½>1 day), can generally be prepared by following procedures analogous to those disclosed in the Schemes and/or in the Examples herein below, by substituting an appropriate isotopically labeled reagent for a non-isotopically labeled reagent.

Polymorphic forms of the compounds of Formula (I), and of the salts, solvates, esters and prodrugs of the compounds of Formula (I), are intended to be included in the present invention.

The compounds according to the invention can have pharmacological properties; in particular, the compounds of Formula (I) can be modulators of gamma secretase (including inhibitors, antagonists and the like).

More specifically, the compounds of Formula (I) can be useful in the treatment of a variety of disorders of the central nervous system including, for example, including, but not limited to, Alzheimer's disease, AIDS-related dementia, Parkinson's disease, amyotrophic lateral sclerosis, retinitis pigmentosa, spinal muscular atrophy and cerebellar degeneration and the like.

Another aspect of this invention is a method of treating a mammal (e.g., human) having a disease or condition of the central nervous system by administering a therapeutically effective amount of at least one compound of Formula (I), or a pharmaceutically acceptable salt, solvate, ester or prodrug of said compound to the mammal.

A preferred dosage is about 0.001 to 500 mg/kg of body weight/day of the compound of Formula (I). An especially preferred dosage is about 0.01 to 25 mg/kg of body weight/day of a compound of Formula I, or a pharmaceutically acceptable salt or solvate of said compound.

The compounds of this invention may also be useful in combination (administered together or sequentially) with one or more additional agents listed above.

The compounds of this invention may also be useful in combination (administered together or sequentially) with one or more compounds selected from the group consisting of Aβ antibody inhibitors, gamma secretase inhibitors and beta secretase inhibitors.

If formulated as a fixed dose, such combination products employ the compounds of this invention within the dosage range described herein and the other pharmaceutically active agent or treatment within its dosage range.

Accordingly, in an aspect, this invention includes combinations comprising an amount of at least one compound of Formula (I), or a pharmaceutically acceptable salt, solvate, ester or prodrug thereof, and an amount of one or more additional agents listed above wherein the amounts of the compounds/treatments result in desired therapeutic effect.

The pharmacological properties of the compounds of this invention may be confirmed by a number of pharmacological assays. Certain assays are exemplified later in this document.

This invention is also directed to pharmaceutical compositions which comprise at least one compound of Formula (I), or a pharmaceutically acceptable salt, solvate, ester or prodrug of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Formula (I), or a pharmaceutically acceptable salt, solvate, ester or prodrug of said compound and a pharmaceutically acceptable carrier, vehicle or diluent.

Yet another aspect of this invention is a kit comprising an amount of at least one compound of Formula (I), or a pharmaceutically acceptable salt, solvate, ester or prodrug of said compound and an amount of at least one additional agent listed above, wherein the amounts of the two or more ingredients result in desired therapeutic effect.

The invention disclosed herein is exemplified by the following illustrative schemes and examples which should not be construed to limit the scope of the disclosure. Alternative

Example 1

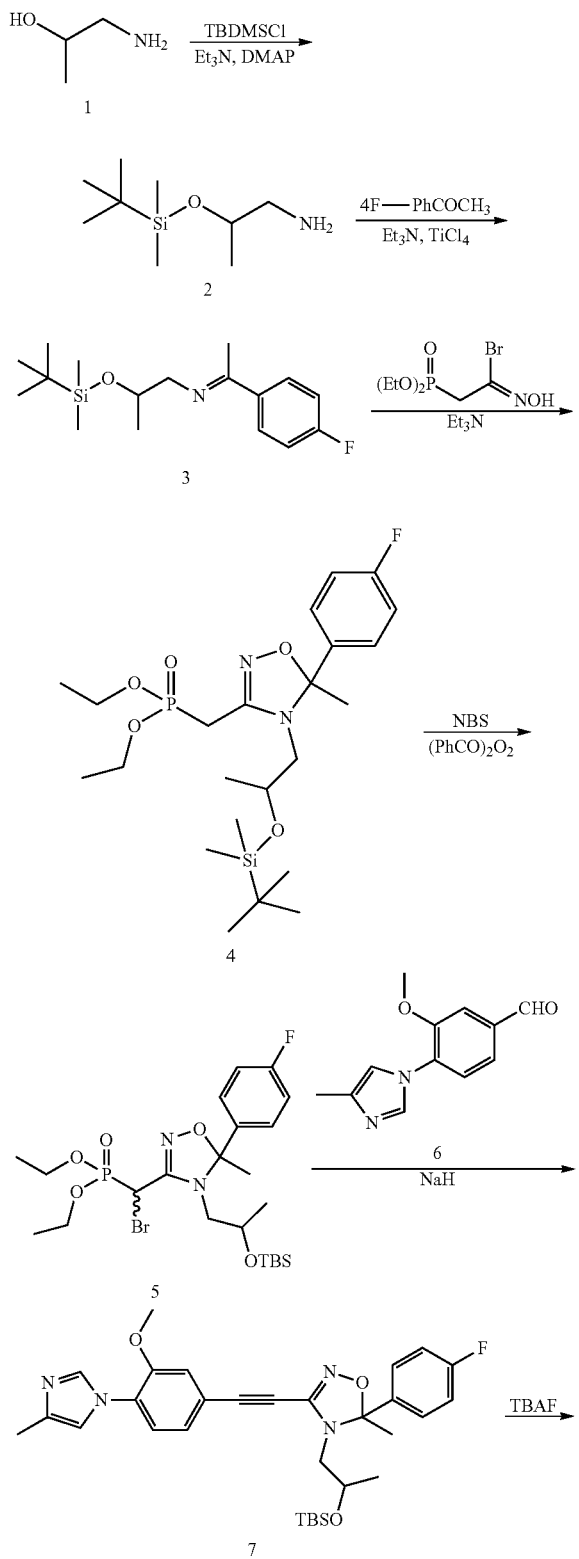

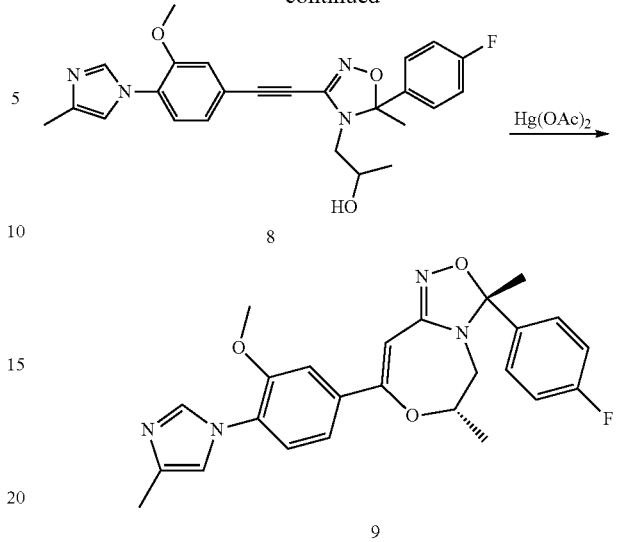

Step 1

TBDMSCl (10.5 g, 70 mmol) was added to a solution of 1 (5.0 g, 67 mmol), triethylamine (9 ml, 67 mmol) and DMAP (500 mg, 4.1 mmol) in methylene chloride (80 mL), and the reaction solution was stirred at room temperature for 12 hours. Water was added and the layers were separated. The aqueous phase was extracted with ethyl acetate, the organic phase was dried over anhydrous sodium sulfate and concentrated under reduced pressure to obtain 10.6 g of product 2.

Step 2

Triethylamine (34 g, 336 mmol) was added to a solution of 2 (10.0 g, 52.8 mmol) and 4'-fluoro acetophenone (6.64 g, 48.0 mmol) in a mixture of DMF (48 mL) and DCM (13 mL). The reaction solution was cooled to 0° C. and a solution of titanium(IV) chloride (8.7 g, 45.6 mmol) in DCM (5 mL) was added dropwise over 30 minute period. The resulting solution was stirred at 40° C. for one hour, then at room temperature for 12 hours. Diluted with ether, clarified by filtration and the filtrate was washed with cold water, brine and dried over anhydrous sodium sulfate. The solvent was removed under reduced pressure to give 14.3 g of product 3.

Step 3

A solution of N-Bromosuccinamide (3.6 g, 20.5 mmol) in DMF (20 mL) was added dropwise to a solution of diethyl 2-(hydroxyimino)-ethylphsphonate (4.0 g, 20.5 mmol) [Bioorganic & Medicinal Chemistry Letters, 15(1), 231-234; 2005] in DMF (50 mL) at −20° C. over 15 minutes. The reaction solution was stirred at −20° C. for 30 minutes, then allowed to slowly warm to 0° C. and kept at that temperature for two hours. A mixture of 3 (6.3 g 20.5 mmol) and triethylamine (2.1 g, 20.5 mmol) in DCM (25 mL) was slowly added and the reaction solution was stirred at room temperature for 12 hours. The solvent was removed at reduced pressure and the residue was dissolved in ethyl acetate. The organic phase was washed with brine, dried over anhydrous sodium sulfate and concentrated at reduced pressure. The residue was purified by column chromatography using Silica Gel (hexane: ethyl acetate=100:0 to 0:100) to obtain 1.53 g of product 4.

Step 4

NBS (383 mg, 2.2 mmol) was added to a solution of 4 (760 mg, 2.0 mmol) in CCl4 (15 mL), and the reaction solution was stirred at room temperature for one hour. A catalytic amount of benzoyl peroxide (48 mg, 0.2 mmol) was added and the reaction solution was stirred at 60° C. for 12 hours. The reaction solution was clarified by filtration and the filtrate was concentrated under reduced pressure. The residue was diluted with ethyl acetate, washed with saturated solution of sodium thiosulfate, and brine. The organic phase was dried over anhydrous sodium sulfate and concentrated under reduced pressure to obtain 955 mg of product 5 as a 1:1 mixture, which was used as is in the next reaction.

Step 5

To a solution of 5 (860 mg, 1.5 mmol) and 6 (318 mg, 1.5 mmol) [US 2007/0219181 A1, page 62] in THF (20 mL) at room temperature was added sodium hydride (90 mg, 2.3 mmol, 60%) all at once, and the reaction solution was stirred at room temperature for 12 hours. The reaction solution was quenched with water, and extracted with ethyl acetate. The organic phase was dried over anhydrous sodium sulfate and concentrated under reduced pressure. The residue was dissolved in DMF (10 mL) and treated with sodium hydride (90 mg, 2.3 mmol, 60%). The reaction solution was stirred at room temperature for one hour before it was quenched with water. The layers ware separated and the organic layer was washed with water, dried over anhydrous sodium sulfate and concentrated. The residue was purified by column chromatography using Silica Gel (hexane:triethylamine=99:1) to obtain 426 mg of products 7.

Step 6

Tetrabutylammonium fluoride (2.5 mL, 1M THF) was added to ice-cold solution of 7 (400 mg, 0.71 mmol) in THF (10 mL), and the reaction solution was stirred at 0° C. for 12 hours. The reaction solution was concentrated under reduced pressure, and the residue was diluted with ethyl acetate. The organic phase was washed with 0.5 N HCl, dried over anhydrous magnesium sulfate and concentrated at reduced pressure. The residue was purified by column chromatography using Silica Gel (hexane:ethyl acetate=100:0 to 0:100) to obtain 141 mg of product 8.

Step 7

To a solution of 8 (32 mg, 0.07 mmol) in CHCl3 (2 mL) wad added mercury(II) trifluoroatetae (31 mg, 0.07 mmol) and the reaction mixture stirred at room temperature for 12 hours. The crude was purified by column chromatography using Silica Gel (methanol:ethyl acetae=10:90) to obtain 10 mg of product 9.

Compound 9:

$^1$H-NMR (CDCl$_3$) δ (ppm): 7.73 (s, 1H), 7.53 (m, 2H), 7.28 (m, 3H), 7.11 (m, 2H), 6.93 (s, 1H), 5.93 (s, 1H), 4.55 (m, 1H), 3.85 (s, 3H), 3.13 (m, 2H), 2.30 (s, 3H), 1.90 (s, 3H), 1.45 (d, 3H, J=6.4 Hz). MS (ES-LCMS, M+1) 449.

Example 2

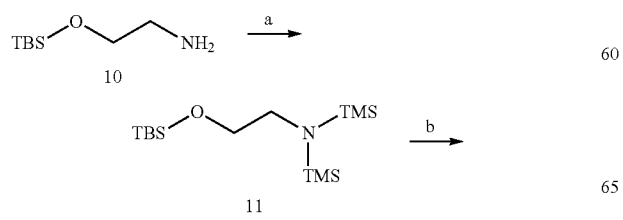

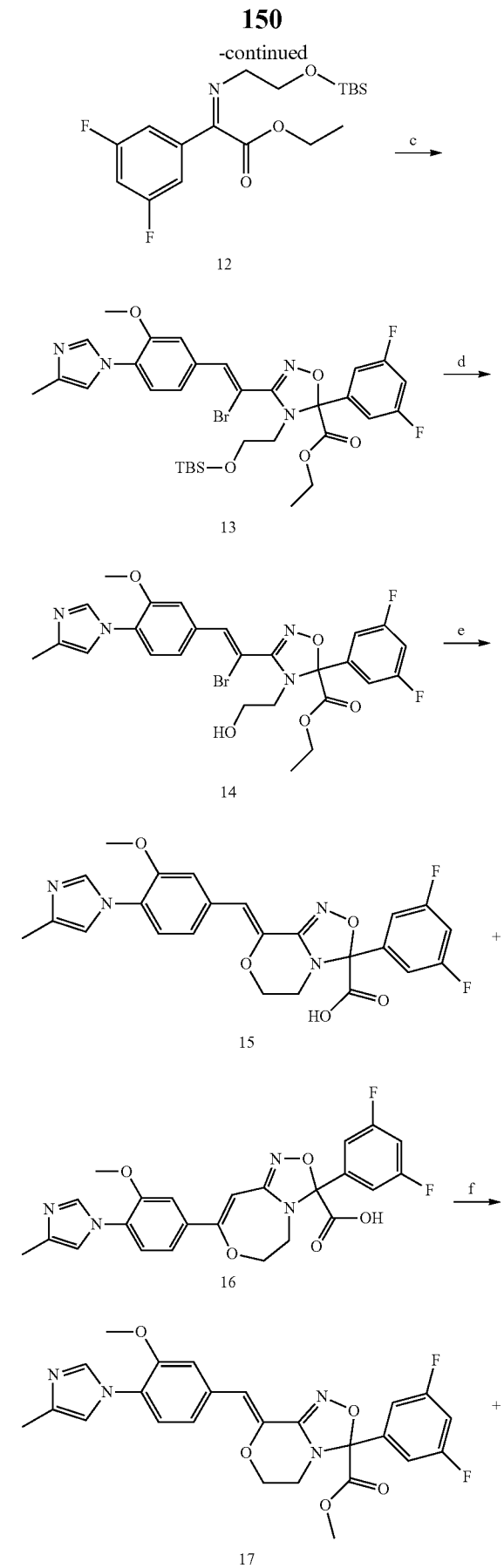

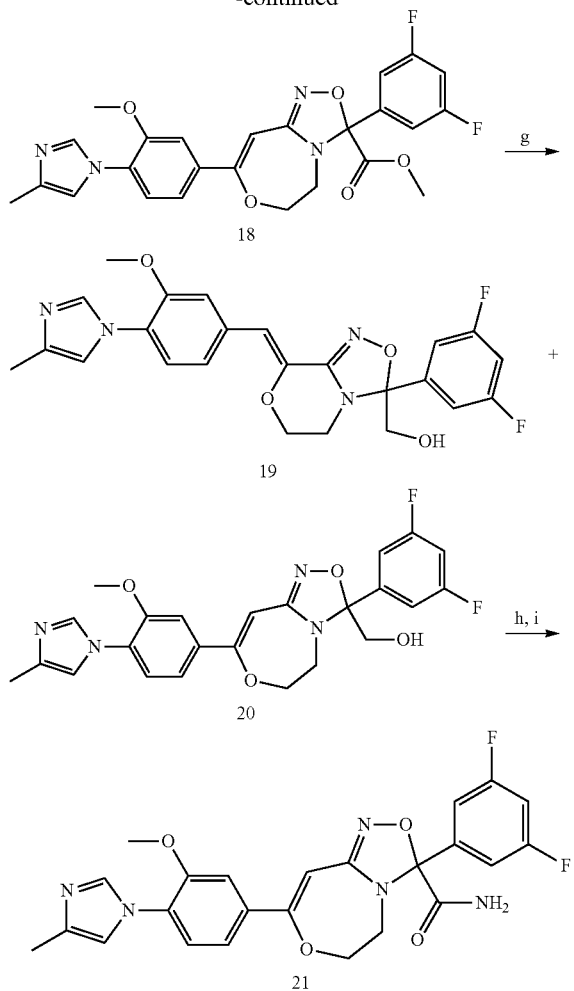

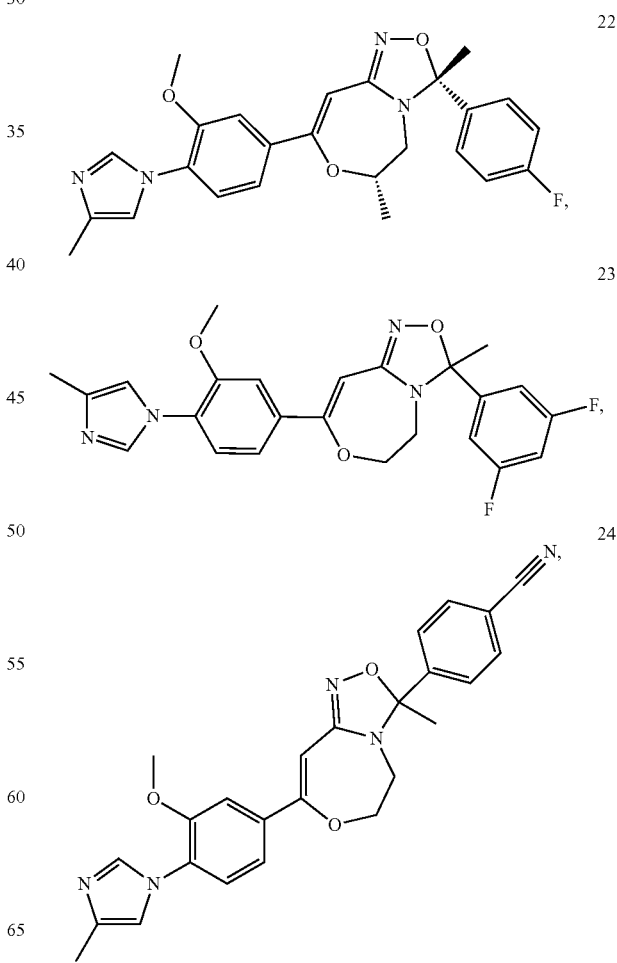

mmol) at 0° C. After stirring at 0° C. for 45 minutes, additional NaH (0.012 g, 0.304 mmol) was added, and the mixture was stirred at 0° C. for additional 1.5 h. THF was removed, the residue was dissolved in DMF, filtered, and purified by reverse-phase HPLC to give 0.1 g of compound 15 and 16 MH+: 483.3, total yield for 15 and 16: 68%.

Step f

To the solution of 15 and 16 (0.092 g, 0.19 mmol) in 5 ml of toluene/MeOH (4:1) was added TMSCHN₂ (0.2 ml, 0.38 mmol). After stirring at r.t. for 24 h, the solvent was removed; the residue was purified by Isco using 5% of MeOH/CH₂Cl₂ to give 0.075 g of 17 and 18, yield: 80%, followed by reverse-phase HPLC to give 0.033 g of 17 and 0.027 g of 18 MH+: 497.3.

Step g

To the solution of 18 (0.026 g, 0.052 mmol) in 3 ml of EtOH/MeOH (1:1) was added NaBH₄ (0.008 g, 0.21 mmol). After stirring at r.t. for 1 h, the solvent was removed; the residue was purified by Isco using 5% of MeOH/CH₂Cl₂ to give 0.02 g of 20, yield: 82%, MH+: 469.3.

Step h and Step i

To the solution of 14 (0.10 g, 0.17 mmol) in 4 ml of anhydrous THF/DMF (1:1) was added LHMDS (0.42, 0.42 mmol) at 0° C. After stirring at 0° C. for 0.5 h, additional LHMDS (0.10 ml, 0.10 mmol) was added, and the mixture was stirred at 0° C. for additional 1.5 h. THF was removed, the residue was extracted with 10% of MeOH/CH₂Cl₂ and NH₄Cl aqueous solution, dried over Na₂SO₄, filtered. The filtrate was concentrated and treated with TMSCHN₂ in step g (the same as step d) to give 0.008 g of 21, MH+: 482.3.

Following procedures similar to those of Examples 1 and 2, the following compounds were prepared:

Step a

To the solution of 10 (15 g, 85.5 mmol) in 300 ml of anhydrous CH₂Cl₂ at 0° C. was slowly added Et₃N (26 ml, 188.2 mmol). The cooling bath was removed, TMSCl (24 ml, 188.2 mmol) was slowly added to the mixture. After stirring at r.t. for 24 h, additional Et₃N (12 ml, 85.5 mmol) and TMSCl (11 ml, 85.5 mmol) were added. The mixture was stirred at r.t. for another 24 h. The solvent was removed, the product was dissolved in 500 ml of ether, filtered through the celite, and concentrated to give 22.5 g of 11, yield: 82%.

Step b

To the solution of 11 (22.5 g, 70.4 mmol) and ethyl 3,5-difluorobenzoylformate (11.5 g, 53.7 mmol) in 180 ml of anhydrous 1,2-dichloroethane was added TMSTf (0.5 ml, 2.69 mmol) at r.t. After stirring at 85° C. for 24 h, the solvent was removed, the product was dissolved in 500 ml of ether, washed with H₂O (2×200 ml), and brine, dried over Na₂SO₄, filtered and concentrated to give 22 g of 12, yield: 100%.

Step c 57 g of the title compound 13 was obtained from 12 (12 g) in the same manner as in Example 1, steps 3 and 4.

Step d

To the solution of 13 (3.6 g, 5.10 mmol) in 50 ml of MeOH was added 1-choloethyl chloroformate (0.83 ml, 7.65 mmol). After stirring at r.t. for 0.5 h, the solvent was removed, the product was purified by Isco using 5% of MeOH/CH₂Cl₂ to give 2.8 g of 14, yield: 93%. MH+: 591.04.

Step e

To the solution of 14 (0.18 g, 0.304 mmol) in 4 ml of anhydrous THF/DMF (1:1) was added NaH (0.026 g, 0.638

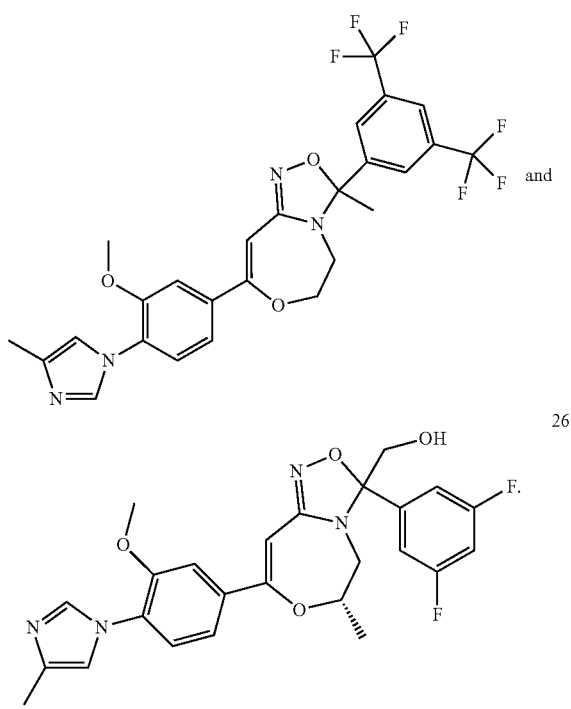

Example 3

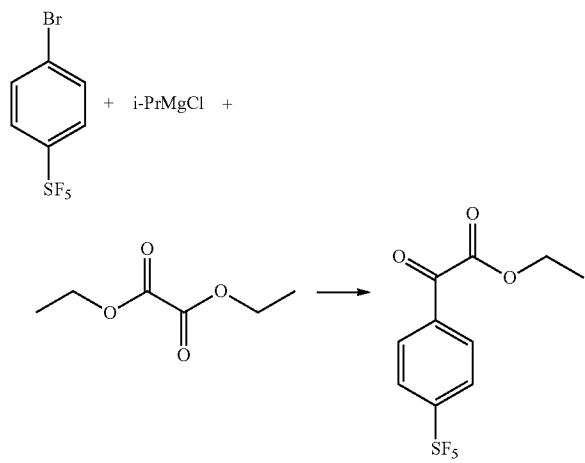

4-bromophenyl sulfur pentabromide (5.2 g, 18.4 mmole) was dissolved in 50 ml THF and the reaction was cooled to −40° C. Isopropylmagnesium chloride lithium chloride complex (1.3M in THF, 14.1 ml) was added and the reaction was stirred for two hours with bath temperature rising to 0° C. This solution was then cannulated to Diethyl oxalate (2.68 g, 18.4 mmole) in 50 ml THF at −78° C. The reaction was stirred for three hours with temperature slowly rising to room temperature. 200 ml water and 200 ml EtOAc were added. The organic layer was washed with water (2×200 ml), dried over $Na_2SO_4$ and concentrated. The residue was purified by column (EtOAc/hexane from 0/100 to 25/75 in 45 minutes). Yield: 2.0 g. $^1H$ NMR ($CDCl_3$ 400 MHz): 8.16 (d, J=8.8 Hz, 2H), 7.91 (d, J=8.8 Hz, 2H), 4.47 (q, J=7.3 Hz, 2H), 1.44 (t, J=7.3 Hz, 3H).

Following a similar procedure the following compound is prepared:

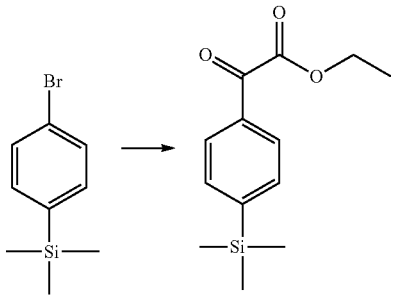

Following these procedures and techniques well known in the art, compounds having —$SF_5$, —$OSF_5$ or —$Si(R^{15})_3$ are prepared.

Assay:

Secretase Reaction and Aβ Analysis in Whole Cells: HEK293 cells overexpressing APP with Swedish and London mutations were treated with the specified compounds for 5 hour at 37° C. in 100 ml of DMEM medium containing 10% fetal bovine serum. At the end of the incubation, total Aβ, Aβ40 and Aβ42 were measured using electrochemiluminescence (ECL) based sandwich immunoassays. Total Aβ was determined using a pair of antibodies TAG-W02 and biotin-4G8, Aβ40 was identified with antibody pairs TAG-G2-10 and biotin-4G8, while Aβ42 was identified with TAG-G2-11 and biotin-4G8. The ECL signal was measured using Sector Imager 2400 (Meso Scale Discovery).

MS Analysis of Aβ Profile: Aβ profile in conditioned media was determined using surface enhanced laser desorption/ionization (SELDI) mass spectrometry. Conditioned media was incubated with antibody W02 coated PS20 ProteinChip array. Mass spectra of Aβ captured on the array were read on SELDI ProteinChip Reader (Bio-Rad) according to manufacture's instructions.

CSF Aβ Analysis: Aβ in rat CSF was determined using MSD technology as described above. Aβ40 was measured using antibody pair Tag-G2-10 and biotin-4G8, while Aβ42 was measured using Tag-anti Aβ42 (Meso Scale Discovery) and biotin-4G8. The ECL signal was measured using Sector Imager 2400 (Meso Scale Discovery).

Matrix-assisted laser desorption/ionization mass spectrometric (MALDI MS) analysis of Aβ is performed on a Voyager-DE STR mass spectrometer (ABI, Framingham, Mass.). The instrument is equipped with a pulsed nitrogen laser (337 nm). Mass spectra are acquired in the linear mode with an acceleration voltage of 20 kV. Each spectrum presented in this work represents an average of 256 laser shots. To prepare the sample-matrix solution, 1 μL of immunoprecipitated Aβ sample is mixed with 3 μL of saturated α-cyano-4-hydroxy-cinnamic acid solution in 0.1% TFA/acetonitrile. The sample-matrix solution is then applied to the sample plate and dried at ambient temperature prior to mass spectrometric analysis. All the spectra are externally calibrated with a mixture of bovine insulin and ACTH (18-39 clip).

Compounds 15 to 26 had an Aβ42 $IC_{50}$ within the range of about 51 to about 13932 nM.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound of the formula (I):

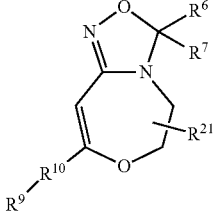

or a pharmaceutically acceptable salt thereof, wherein:

$R^6$ and $R^7$ are each independently selected from the group consisting of: H, —C(O)$R^{15}$, —C(O)O$R^{15}$, —C(O)N($R^{15}$)($R^{16}$), —C(=NO$R^{15}$)$R^{16}$, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclyalkyl-, benzofusedcycloalkyl, fused benzoheterocycloalkyl, fused heteroarylcycloalkyl, fused heteroarylheterocycloalkyl; and wherein each of said $R^6$ and $R^7$ alkyl-, alkenyl-, alkynyl-, aryl-, arylalkyl-, alkylaryl-, cycloalkyl-, cycloalkylalkyl-, heteroaryl-, heteroarylalkyl-, heterocyclyl-, heterocyclyalkyl-, benzofusedcycloalkyl, fused benzoheterocycloalkyl, fused heteroarylcycloalkyl, and fused heteroarylheterocycloalkyl group is optionally substituted with 1-5 independently selected $R^{21}$ substituents;

the $R^9$—$R^{10}$ moiety is selected from the group consisting of

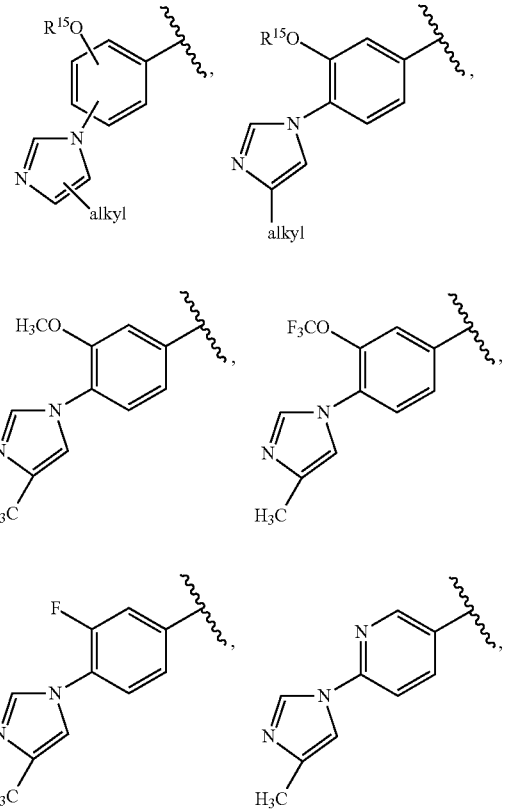

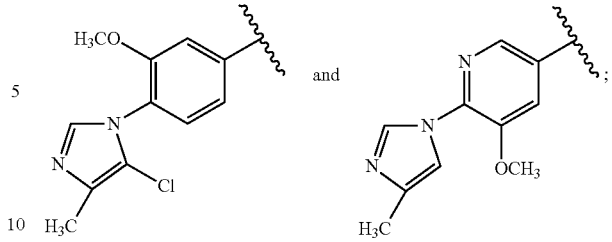

each $R^{15A}$ is independently selected from the group consisting of alkyl, alkenyl, alkynyl, cycloalkyl, cycloalkylalkyl, heterocyclyl, heterocyclylalkyl, aryl, arylalkyl, heteroaryl, heteroarylalkyl, arylcycloalkyl, arylheterocyclyl, $(R^{18})_{1-5}$-alkyl, $(R^{18})_{1-5}$-cycloalkyl, $(R^{18})_{1-5}$-cycloalkylalkyl, $(R^{18})_{1-5}$-heterocyclyl, $(R^{18})_{1-5}$-heterocyclylalkyl, $(R^{18})_{1-5}$-aryl, $(R^{18})_{1-5}$-arylalkyl, $(R^{18})_{1-5}$-heteroaryl and $(R^{18})_{1-5}$-heteroarylalkyl; and wherein each $R^{18}$ in each group can be on any substitutable atom;

each $R^{16A}$ is independently selected from the group consisting of alkyl, alkenyl, alkynyl, cycloalkyl, cycloalkylalkyl, heterocyclyl, heterocyclylalkyl, aryl, arylalkyl, heteroaryl, heteroarylalkyl, arylcycloalkyl, arylheterocyclyl, $(R^{18})_{1-5}$-alkyl, $(R^{18})_{1-5}$-cycloalkyl, $(R^{18})_{1-5}$-cycloalkylalkyl, $(R^{18})_{1-5}$-heterocyclyl, $(R^{18})_{1-5}$-heterocyclylalkyl, $(R^{18})_{1-5}$-aryl, $(R^{18})_{1-5}$-arylalkyl, $(R^{18})_{1-5}$-heteroaryl and $(R^{18})_{1-5}$-heteroarylalkyl; and wherein each $R^{18}$ in each group can be on any substitutable atom;

$R^{15}$, $R^{16}$ and $R^{17}$ are independently selected from the group consisting of H, alkyl, alkenyl, alkynyl, cycloalkyl, cycloalkylalkyl, heterocyclyl, heterocyclylalkyl, aryl, arylalkyl, heteroaryl, heteroarylalkyl, arylcycloalkyl, arylheterocyclyl, $(R^{18})_{1-5}$-alkyl, $(R^{18})_{1-5}$-cycloalkyl, $(R^{18})_{1-5}$-cycloalkylalkyl, $(R^{18})_{1-5}$-heterocyclyl, $(R^{18})_{1-5}$-heterocyclylalkyl, $(R^{18})_{1-5}$-aryl, $(R^{18})_{1-5}$-arylalkyl, $(R^{18})_{1-5}$-heteroaryl and $(R^{18})_{1-5}$-heteroarylalkyl; and wherein each $R^{18}$ in each group can be on any substitutable atom;

each $R^{18}$ is independently selected from the group consisting of alkyl, alkenyl, alkynyl, aryl, arylalkyl, arylalkenyl, arylalkynyl, —NO$_2$, halo, heteroaryl, HO-alkyoxyalkyl, —CF$_3$, —CN, alkyl-CN, —C(O)$R^{19}$, —C(O)OH, —C(O)O$R^{19}$, —C(O)NH$R^{20}$, —C(O)NH$_2$, —C(O)NH$_2$, —C(O)N(alkyl)$_2$, —C(O)N(alkyl)(aryl), —C(O)N(alkyl)(heteroaryl), —S$R^{19}$, —S(O)$_2R^{20}$, —S(O)NH$_2$, —S(O)NH(alkyl), —S(O)N(alkyl)(alkyl), —S(O)NH(aryl), —S(O)$_2$NH$_2$, —S(O)$_2$NH$R^{19}$, —S(O)$_2$NH(heterocyclyl), —S(O)$_2$N(alkyl)$_2$, —S(O)$_2$N(alkyl)(aryl), —OCF$_3$, —OH, —O$R^{20}$, —O-heterocyclyl, —O-cycloalkylalkyl, —O-heterocyclylalkyl, —NH$_2$, —NH$R^{20}$, —N(alkyl)$_2$, —N(arylalkyl)$_2$, —N(arylalkyl)-(heteroarylalkyl), —NHC(O)$R^{20}$, —NHC(O)NH$_2$, —NHC(O)NH(alkyl), —NHC(O)N(alkyl)(alkyl), —N(alkyl)C(O)NH(alkyl), —N(alkyl)C(O)N(alkyl)(alkyl), —NHS(O)$_2R^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl);

or, two $R^{18}$ moieties on adjacent carbons can be taken together with the atoms to which they are bound to form:

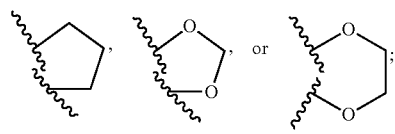

R$^{19}$ is selected from the group consisting of: alkyl, cycloalkyl, aryl, arylalkyl and heteroarylalkyl;

R$^{20}$ is selected from the group consisting of: alkyl, cycloalkyl, aryl, halo substituted aryl, arylalkyl, heteroaryl and heteroarylalkyl;

each R$^{21}$ is independently selected from the group consisting of alkyl, alkenyl, alkynyl, cycloalkyl, cycloalkylalkyl, cycloalkenyl, heterocycloalkyl, heterocycloalkylalkyl, aryl, arylalkyl, heteroaryl, heteroarylalkyl, halo, —CN, —OR$^{15}$, —C(O)R$^{15}$, —C(O)OR$^{15}$, —C(O)N(R$^{15}$)(R$^{16}$), —SF$_5$, —OSF$_5$, —Si(R$^{15A}$)$_3$, wherein each R$^{15A}$ is independently selected, —SR$^{15}$, —S(O)N(R$^{15}$)(R$^{16}$), —CH(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —CH$_2$—N(R$^{15}$)C(O)N(R$^{16}$)(R$^{17}$), —CH$_2$—R$^{15}$, —CH$_2$N(R$^{15}$)(R$^{16}$), —N(R$^{15}$)S(O)R$^{16A}$, —N(R$^{15}$)S(O)$_2$R$^{16A}$, —CH$_2$—N(R$^{15}$)S(O)$_2$R$^{16A}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —S(O)R$^{15A}$, —N$_3$, —NO$_2$ and —S(O)$_2$R$^{15A}$; and, optionally, each of said alkyl, cycloalkenyl, cycloalkyl, cycloalkylalkyl, heterocycloalkyl, heterocycloalkylalkyl, aryl, arylalkyl, heteroaryl, heteroarylalkyl, alkenyl and alkynyl R$^{21}$ groups are substituted with 1 to 5 independently selected R$^{22}$ groups; and each R$^{22}$ is independently selected from the group consisting of: alkyl, cycloalkyl, cycloalkenyl, heterocycloalkyl, aryl, heteroaryl, halo, —CF$_3$, —CN, —OR$^{15}$, —C(O)R$^{15}$, —C(O)OR$^{15}$, -alkyl-C(O)OR$^{15}$, C(O)N(R$^{15}$)(R$^{16}$), —SF$_5$, —OSF$_5$, —Si(R$^{15A}$)$_3$ wherein each R$^{15A}$ is independently selected, —SR$^{15}$, —S(O)N(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —N(R$^{15}$)S(O)R$^{16A}$, —N(R$^{15}$)S(O)$_2$R$^{16A}$, —CH$_2$—N(R$^{15}$)S(O)$_2$R$^{16A}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$, —CH$_2$—N(R$^{15}$)C(O)OR$^{16}$, —N$_3$, =NOR$^{15}$, —NO$_2$, —S(O)R$^{15A}$ and —S(O)$_2$R$^{15A}$.

2. The compound of claim 1 or a pharmaceutically acceptable salt thereof, wherein R$^6$ is alkyl, and R$^7$ is a substituted aryl group.

3. The compound of claim 1 or a pharmaceutically acceptable salt thereof, wherein R$^7$ is:

phenyl, or phenyl substituted with one or more independently selected R$^{21}$ groups, or phenyl substituted with 1 to 3 independently selected R$^{21}$ groups, or phenyl substituted with 1 to 3 R$^{21}$ groups, wherein each R$^{21}$ group is the same or different halo, or phenyl substituted with 1 to 3 F, or phenyl substituted with one —CN group, or phenyl substituted with one or two —CF$_3$ groups, or phenyl substituted with R$^{21}$ groups, wherein the R$^{21}$ group is selected from the group consisting of: —SF$_5$, —OSF$_5$ and —Si(R$^{15A}$)$_3$, and wherein each R$^{15A}$ is independently selected, or phenyl substituted with R$^{21}$ groups wherein the R$^{21}$ group is selected from the group consisting of: —SF$_5$, —OSF$_5$ and —Si(R$^{15A}$)$_3$, and wherein each R$^{15A}$ is the same or different alkyl group, or or phenyl substituted with R$^{21}$ groups wherein the R$^{21}$ group is selected from the group consisting of: —SF$_5$, —OSF$_5$ and —Si(CH$_3$)$_3$.

4. The compound of claim 1 or a pharmaceutically acceptable salt thereof, wherein R$^7$ is selected from the group consisting of:

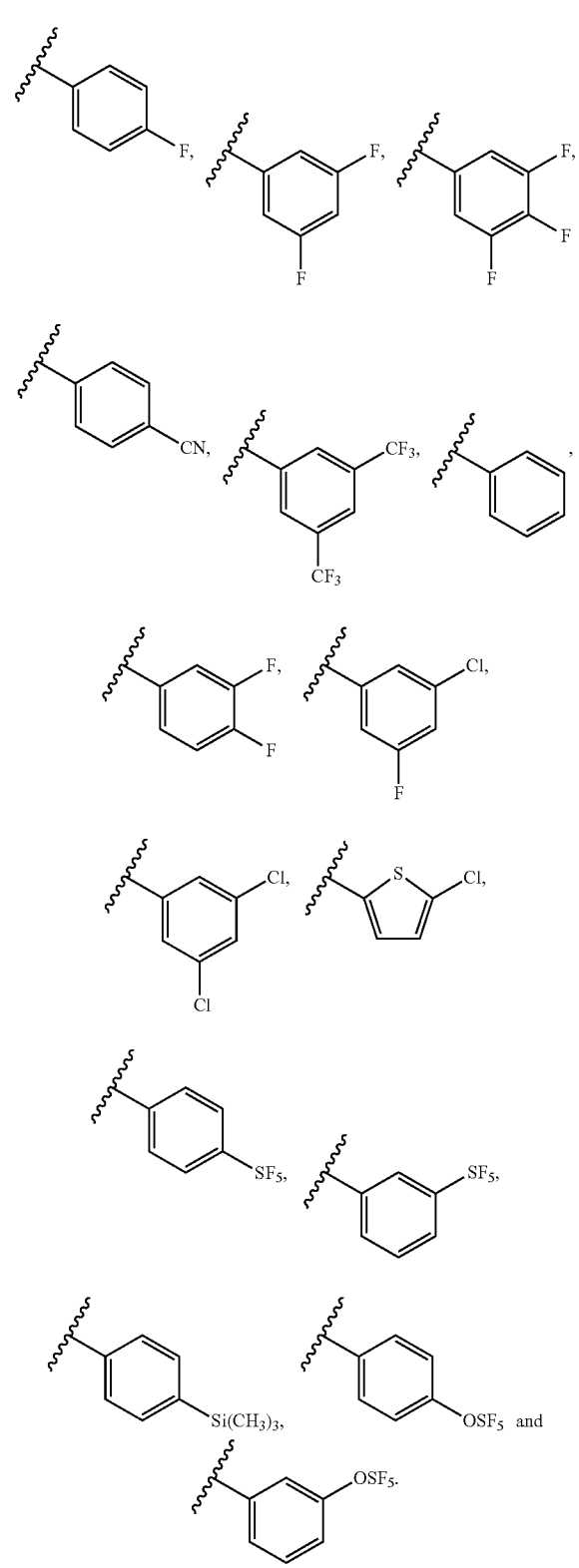

5. The compound of claim 3 or a pharmaceutically acceptable salt thereof, wherein R$^6$ is alkyl.

6. The compound of claim 1 selected from the group consisting of: compounds
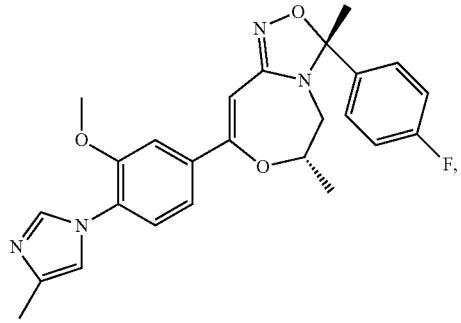
14
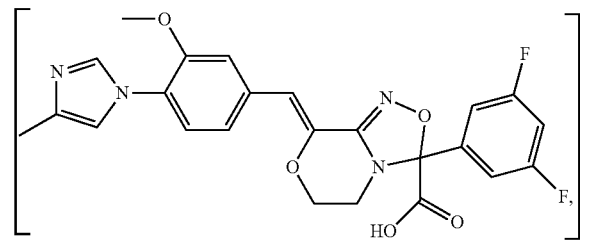
15
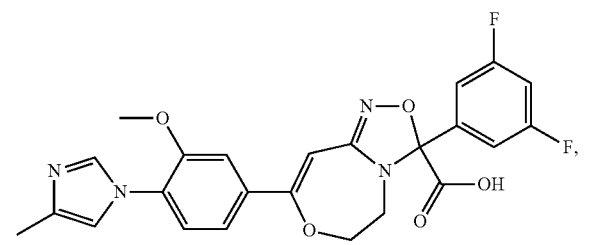
16
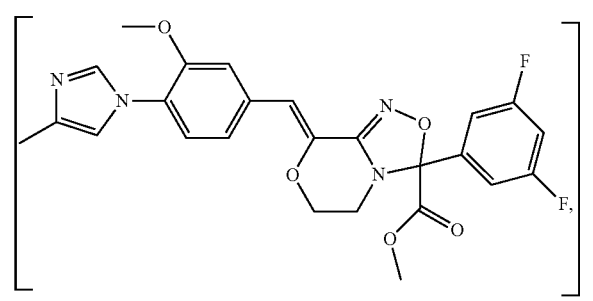
17
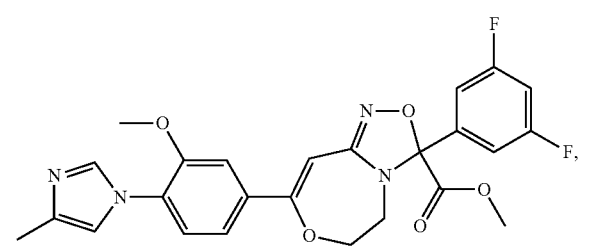
18
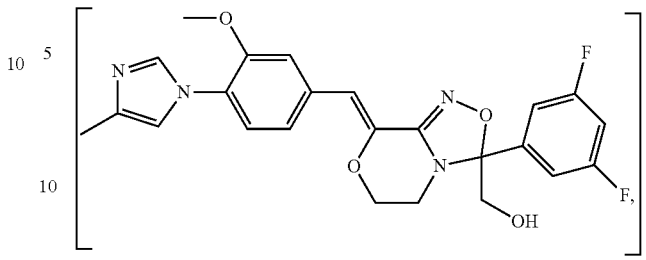
19
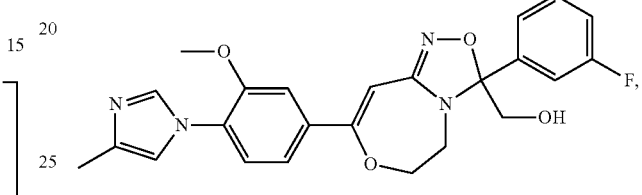
20
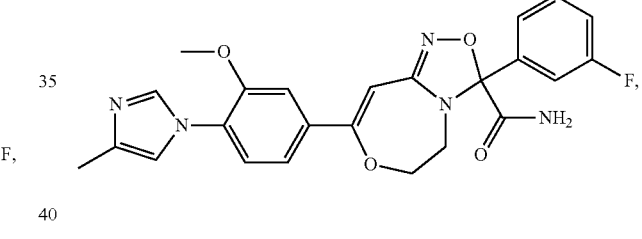
21
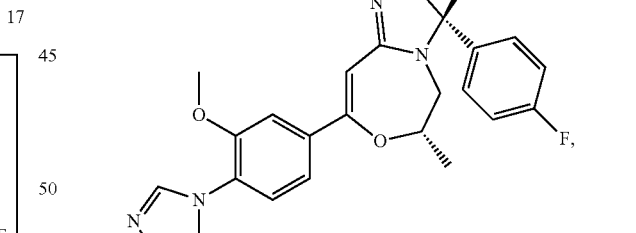
22
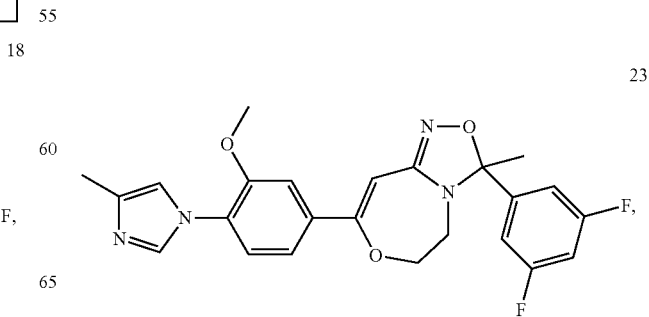
23

-continued

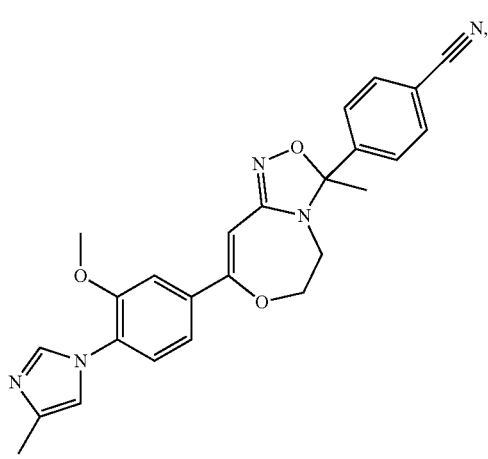

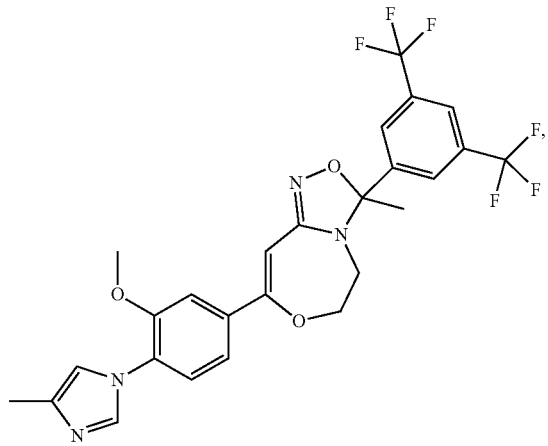

and

-continued

26 or a pharmaceutically acceptable salt thereof.

7. A pharmaceutical composition comprising a therapeutically effective amount of a compound of claim 1 or a pharmaceutically acceptable salt thereof, and a pharmaceutically acceptable carrier.

8. A method for treating Alzheimer's disease, the method comprising administering an effective amount of one or more compounds of claim 1 or a pharmaceutically acceptable salt thereof to a patient in need of treatment.

9. A method for treating Alzheimer's disease, the method comprising administering an effective amount of one or more compounds of claim 6 or a pharmaceutically acceptable salt thereof to a patient in need of treatment.

10. The compound of claim 1 or a pharmaceutically acceptable salt thereof, wherein the $R^9$—$R^{10}$ moiety is

* * * * *